United States Patent
Wishka et al.

(10) Patent No.: US 6,562,816 B2
(45) Date of Patent: May 13, 2003

(54) SUBSTITUTED-HETEROARYL-7-AZA[2.2.1] BICYCLOHEPTANES FOR THE TREATMENT OF DISEASE

(75) Inventors: Donn G. Wishka, Kalamazoo, MI (US); Jason K. Myers, Kalamazoo, MI (US); Bruce N. Rogers, Portage, MI (US); Eric Jon Jacobsen, Richland, MI (US); David W. Piotrowski, Portage, MI (US); Jeffrey W. Corbett, Portage, MI (US); Alice L. Bodnar, Kalamazoo, MI (US); Vincent E. Groppi, Jr., Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/218,772

(22) Filed: Aug. 14, 2002

(65) Prior Publication Data

US 2003/0069290 A1 Apr. 10, 2003

Related U.S. Application Data

(60) Provisional application No. 60/314,768, filed on Aug. 24, 2001, provisional application No. 60/314,851, filed on Aug. 24, 2001, provisional application No. 60/314,772, filed on Aug. 24, 2001, provisional application No. 60/314,773, filed on Aug. 24, 2001, and provisional application No. 60/388,712, filed on Jun. 14, 2002.

(51) Int. Cl.[7] .................... A61K 31/5377; A61P 25/28; C07D 487/06

(52) U.S. Cl. .................... 514/233.2; 514/413; 544/143; 546/167; 546/200; 546/269.7; 546/270.4; 546/271.4; 546/276.7; 548/131; 548/136; 548/142; 548/143; 548/214; 548/225; 548/227; 548/228; 548/229; 548/181; 548/236; 548/248; 548/312.1; 548/453

(58) Field of Search .................. 544/143; 546/276.7; 548/181, 236, 248, 453; 514/233.2

(56) References Cited

U.S. PATENT DOCUMENTS

| | | |
|---|---|---|
| 4,605,652 A | 8/1986 | Welstead et al. |
| 4,835,162 A | 5/1989 | Abood |
| 4,921,982 A | 5/1990 | Cohen et al. |
| 4,988,691 A | 1/1991 | Benelli et al. |
| 5,039,680 A | 8/1991 | Amperato et al. |
| 5,057,519 A | 10/1991 | Suberg |
| 5,106,843 A | 4/1992 | Ward et al. |
| 5,364,863 A | 11/1994 | Cohen |
| 5,510,478 A | 4/1996 | Sabb |
| 5,561,149 A | 10/1996 | Azria et al. |
| 5,624,941 A | 4/1997 | Barth et al. |
| 5,712,270 A | 1/1998 | Sabb |
| 5,977,144 A | 11/1999 | Meyer et al. |
| 6,054,464 A | 4/2000 | Macor et al. |
| 6,060,473 A * | 5/2000 | Shene et al. ............. 546/276.7 |
| 6,117,889 A | 9/2000 | Shen et al. |
| 6,255,490 B1 | 7/2001 | Shen et al. |

FOREIGN PATENT DOCUMENTS

| | | | |
|---|---|---|---|
| DE | 3810552 | 3/1988 | ......... C07D/451/12 |
| EP | 0955301 A2 | 11/1999 | ......... C07D/487/08 |
| WO | WO 92/15579 | 9/1992 | ......... C07D/451/00 |
| WO | WO 95/01793 | 1/1995 | ......... A61K/31/435 |
| WO | WO 97/30998 | 8/1997 | ......... C07D/453/02 |
| WO | WO 99/47490 | 9/1999 | ......... C07C/229/50 |
| WO | WO 00/73431 A2 | 12/2000 | ........... C12N/15/00 |
| WO | WO 01/29034 | 4/2001 | ......... C07D/453/02 |
| WO | WO 01/36417 A1 | 5/2001 | ......... C07D/451/04 |
| WO | WO 01/60821 | 8/2001 | ......... C07D/453/02 |
| WO | WO 01/76576 | 10/2001 | .......... A61K/31/00 |
| WO | WO 02/16358 A2 | 2/2002 | ......... C07D/453/02 |

OTHER PUBLICATIONS

Cooper and Millar, *J. Neurochem*, 1997, 68(5), pp. 2140–2151.

Eisele et al., *Chimaeric nicotinic–serotonergic receptor combines distinct ligand binding and channel specificities*, Nature, 366(6454), pp. 479–483, 1993.

Andrew G. Horti, et al., *Radiosynthesis and Preliminar Evaluation of 5-[123 / 125I]Iodo3-(2(S)-azetidinylmethoxy)pyridine: A Radioligand for Nicotinci Acetylcholine Receptors*, Nuclear Medicine & Biology, vol. 26, pp. 175–182, 1999.

Kem, William R. *Behavioral Brain Research*. "The brain α7 nicotinic receptor may be an important therapeutic target for the treatment of Alzheimer's disease: studies with DMXBA (GTS–21)." 113 (2000) 169–181.

Macor, JE. *Bioorganic & Medicinal Chemistry Letters*. "The 5–HT₃ Antagonist Tropisetron ( ICS 205–930) is a Potent and Selective α7 Nicotinic Receptor Partial Agonist." 11 (2001) 319–321.

* cited by examiner

Primary Examiner—Robert W. Ramsuer
(74) Attorney, Agent, or Firm—Mary J. Hosley

(57) ABSTRACT

The invention provides compounds of Formula I: compounds of the Formula I:

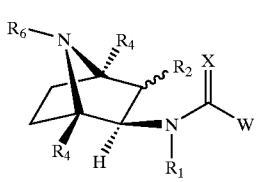

Formula I wherein $R_1$, $R_2$, $R_4$, $R_6$, X, and W are defined herein. These compounds may be in the form of pharmaceutical salts or compositions, may be in pure enantiomeric form or racemic mixtures, and are useful in pharmaceuticals used to treat diseases or conditions in which α7 is known to be involved.

32 Claims, No Drawings

SUBSTITUTED-HETEROARYL-7-AZA[2.2.1] BICYCLOHEPTANES FOR THE TREATMENT OF DISEASE

CROSS-REFERENCE TO RELATED APPLICATIONS

This application claims the benefit of U.S. provisional application Ser. No. 60/314,768 filed on Aug. 24, 2001, under 35 USC 119(e)(i) and U.S. provisional application Ser. No. 60/314,851 filed on Aug. 24, 2001 under 35 USC 119(e)(i), U.S. provisional application Ser. No. 60/314,772 filed on Aug. 24, 2001 under 35 USC 119(e)(i), U.S. provisional application Ser. No. 60/314,773 filed on Aug. 24, 2001, under 35 USC 119(e)(i), and U.S. provisional No. 60/388,712 filed Jun. 14, 2002, which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, *J. Neurochem.*, 1997, 68 (5):2140–51). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., *Nature*, 366(6454), p 479–83, 1993), and the pore forming C-terminal domain of the 5-HT₃ receptor expressed well in *Xenopus oocytes* while retaining nicotinic agonist sensitivity. Eisele et al. used the N-terminus of the avian (chick) form of the α7 nAChR receptor and the C-terminus of the mouse form of the 5-HT₃ gene. However, under physiological conditions the α7 nAChR is a calcium channel while the 5-HT₃R is a sodium and potassium channel. Indeed, Eisele et al. teaches that the chicken α7 nAChR/ mouse 5-HT₃R behaves quite differently than the native α7 nAChR with the pore element not conducting calcium but actually being blocked by calcium ions. WO 00/73431 A2 reports on assay conditions under which the 5-HT₃R can be made to conduct calcium. This assay may be used to screen for agonist activity at this receptor.

U.S. Pat. No. 6,255,490 B1 discloses 7-azabicyclo[2.2.1]-heptane and -heptene derivatives as cholinergic receptor ligands.

U.S. Pat. No. 6,117,889 discloses discloses 7-azabicyclo[2.2.1]-heptane and -heptene derivatives as analgesics and anti-inflammatory agents.

U.S. Pat. No. 6,060,473 discloses 7-azabicyclo[2.2.1]-heptane and -heptene derivatives as cholinergic receptor ligands.

U.S. Pat. No. 6,054,464 discloses azabicyclic esters of carbamic acids useful in therapy, especially in the treatment or prophylaxis of psychotic disorders and intellectual impairment disorders, as well as intermediates and use of intermediates in synthesis.

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the α4β2 or other receptor subtypes.

U.S. Pat. No. 5,712,270 discloses a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to 5HT$_{1A}$ receptors and dopamine D₂ receptors, making them useful as antipsychotic agents.

U.S. Pat. No. 5,624,941 discloses pyrazole derivatives useful in pharmaceuticals in which cannabis is known to be involved.

U.S. Pat. No. 5,561,149 discloses the use of a mono or bicyclic carbocyclic, or heterocyclic carboxylic, acid ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,510,478 discloses a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to 5HT$_{1A}$ receptors and dopamine D₂ receptors, making them useful as antipsychotic agents.

U.S. Pat. No. 5,364,863 discloses bicyclic carboxylic esters and amides, their pharmaceutical formulations, and a method for their use in treating migraine, emesis, gastrointestinal disorders, schizophrenia, or anxiety in mammals.

U.S. Pat. No. 5,106,843 discloses heterocyclic compounds useful as 5-HT₃ antagonists.

U.S. Pat. No. 5,057,519 discloses 5-HT₃ antagonists as being useful in reducing opiate tolerance.

U.S. Pat. No. 5,039,680 discloses 5-HT$_3$ antagonists in preventing or reducing dependency on dependency-inducing agents.

U.S. Pat. No. 4,988,691 discloses isoxazole-containing compounds exhibiting anti-serotonin activity.

U.S. Pat. No. 4,921,982 discloses 5-halo-2,3-dihydro-2, 2-dimethylbenzofuran-7-carboxylic acids which are useful as intermediates for 5-HT$_3$ antagonists.

U.S. Pat. No. 4,835,162 discloses agonists and antagonists to nicotine as smoking deterrents.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

WO 01/60821 discloses novel biarylcarboxamides.

WO 01/36417 A1 discloses novel N-azabicyclo-amide derivatives and use in therapy, especially in the treatment of prophylaxis of psychotic disorders and intellectual impairment disorders.

WO 01/29304 discloses quinuclidine acrylamides.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 97/30998 discloses azabicyclic esters of carbamic acids useful in therapy.

WO 95/01793 discloses 5-HT$_3$ antagonists as topical medicaments for treatment of peripheral disorders associated with pain.

WO 92/15579 discloses multicyclic tertiary amine polyaromatic squalene synthase inhibitors and method of treatment for lowering serum cholesterol levels using the compounds.

DE 3810552 A1 discloses esters and amides of indolyl-, benzo[b]thiophenyl-, benzo[b]furancarboxylic acids or 4-amino-2 methoxy-benzoic acids with N-heterocyclic or N-heterobicyclic alcohols or amines. The compounds disclosed have activity against pain especially migraine, as an anti-arrhythmic for gastrointestinal disturbances, stomach disturbances, gastritis ulcer, gall bladder, spastic colon, Crohn's disease, ulcerative colitis, carcinoid syndrome, diarrhea of various types. The compounds are also disclosed as speeding stomach emptying, controlling gastro duodenal and gastro esophageal reflux, disturbances of esophageal motility, hiatal hernia, cardiac insufficiency, hypotonic stomach, paralytic ileus, manic depressive psychosis and other psychoses. The compounds are also disclosed as useful for stress related diseases, senility, and enhancement of nasal absorption of other agents, e.g., in the treatment of emesis.

In *Bioorg. & Med. Chem. Lett.* 11 (2001) 319–321, the 5-HT$_3$ antagonist tropisetron (ICS 205-930) is discussed as a potent and selective α7 Nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

SUMMARY OF THE INVENTION

In general, the invention includes a compound of the formula A—L—B or a pharmaceutically acceptable salt thereof, wherein A includes a 7-azabicyclo[2.2.1]heptane ring having 1S, 2R, and 4R stereochemistry; B is a heteroaryl; and L is a linking moiety including an amide, a thioamide, an acrylamide, an acrylthioamide, a propiolamide, or a propiolthioamide substituent having the linking moiety bonded to the C-2 carbon of the heptane ring in an exo orientation.

The present invention discloses compounds of the Formula I:

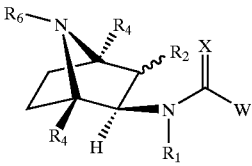

Formula I wherein the stereochemistry of the of the 7-azabicyclo [2.2.1]heptane ring is 1S, 4R and the nitrogen substituent at the C-2 carbon has the exo orientation and is R;

X is O or S;

R$_1$ is H, alkyl, halogenated alkyl, cycloalkyl, or aryl;

R$_2$ is H, alkyl, halogenated alkyl, substituted alkyl, cycloalkyl, or aryl;

W is —Q, —C=C—Q, or —C≡C—Q;

Q is a cyclic heteroaromatic moiety where the heteroatoms can be from 1–3 atoms selected from oxygen, sulfur, or nitrogen of the following structures:

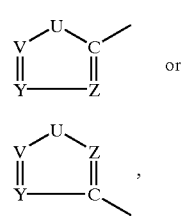

wherein U is —O—, —S—, or —N(R$_3$)—;

V and Y are independently selected from =N—, and =C(R$_5$)—;

Z is =N—, or =CH—;

R$_3$ is H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, R$_7$, R$_9$, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—R$_7$, —C(O)—R$_9$, or —C(O)-aryl;

Each R$_4$ is independently H, alkyl, or substituted alkyl;

Each R$_5$ is independently H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —OR$_8$, —SR$_8$, —N(R$_8$)$_2$, —C(O)R$_8$, —C(S)R$_8$, —C(O)OR$_8$, —C(O)N(R$_8$)$_2$, —NR$_8$C(O)R$_8$, —S(O)$_2$N(R$_8$)$_2$, —OS(O)$_2$R$_8$, —S(O)$_2$R$_8$, —S(O)R$_8$, —NR$_8$S(O)$_2$R$_8$, —N(R$_8$)C(O)N(R$_8$)$_2$, —CN, —NO$_2$, R$_7$, or R$_9$;

$R_6$ is H, alkyl, an amino protecting group, or an alkyl group having 1–3 substituents selected from F, Cl, Br, I, —OH, —CN, —NH$_2$, —NH(alkyl), or —N(alkyl)$_2$;

$R_7$ is 5-membered heteroaromatic mono-cyclic moieties containing within the ring 1–3 heteroatoms independently selected from the group consisting of =N—, —N(R$_{20}$)—, —O—, and —S—, and having 0–1 substituent selected from $R_{17}$ and further having 0–3 substituents independently selected from F, Cl, Br, or I, or $R_7$ is 9-membered fused-ring moieties having a 6-membered ring fused to a 5-membered ring including the formula

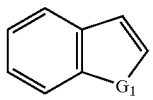

wherein $G_1$ is O, S or NR$_{20}$,

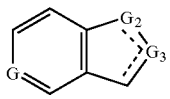

wherein G is C(R$_{14}$) or N, and each $G_2$ and $G_3$ is independently selected from C(R$_{14}$)$_2$, C(R$_{14}$), O, S, N, and N(R$_{20}$), provided that both $G_2$ and $G_3$ are not simultaneously O or S, or

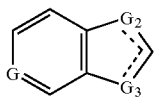

wherein G is C(R$_{14}$) or N, and each $G_2$ and $G_3$ is independently selected from C(R$_{14}$)$_2$, C(R$_{14}$), O, S, N, and N(R$_{20}$), each 9-membered bicyclic ring having 0–1 substituent selected from $R_{17}$ and 0–3 substituents independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl optionally substituted with 1–4 substituents independently selected from F, Cl, Br, I, $R_{13}$, and $R_{15}$, or naphthyl optionally substituted with 1–4 substituents independently selected from F, Cl, Br, I, $R_{13}$, and $R_{15}$;

$R_9$ is 6-membered heteroaromatic mono-cyclic moieties containing within the ring 1–3 heteroatoms selected from =N— and having 0–1 substituent selected from $R_{17}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{17}$ and 0–3 substituent(s) independently selected from F, Cl, Br, or I, wherein the $R_9$ moiety attaches to other substituents as defined in formula I at any position on either ring as valency allows;

Each $R_{10}$ is independently H, alkyl, cycloalkyl, heterocycloalkyl, $R_7$, $R_9$, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, or phenyl optionally substituted with 1–4 substituents independently selected from F, Cl, Br, I, $R_{13}$, and $R_{15}$;

Each $R_{11}$ is independently H, alkyl, cycloalkyl, heterocycloalkyl, halogenated alkyl, halogenated cycloalkyl, or halogenated heterocycloalkyl;

$R_{12}$ is alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —S(O)$_2$R$_{11}$, —S(O)R$_{11}$, —OS(O)$_2$R$_{11}$, —N(R$_{11}$)$_2$, —C(O)R$_{11}$, —C(S)R$_{11}$, —C(O)OR$_{11}$, —NO$_2$, —C(O)N(R$_{11}$)$_2$, —CN, —NR$_{11}$C(O)R$_{11}$, —NR$_{11}$C(O)N(R$_{11}$)$_2$, —S(O)$_2$N(R$_{11}$)$_2$, or —NR$_{11}$S(O)$_2$R$_{11}$;

$R_{13}$ is —OR$_{11}$, —SR$_{11}$, —SOR$_{11}$, —SO$_2$R$_{11}$, —OSO$_2$R$_{11}$, —N(R$_{11}$)$_2$, —C(O)R$_{11}$, —C(O)OR$_{11}$, —C(S)R$_{11}$, —C(O)N(R$_{11}$)$_2$, —NO$_2$—CN, —CF$_3$, —NR$_{11}$C(O)R$_{11}$, —NR$_{11}$C(O)N(R$_{11}$)$_2$, —S(O)$_2$N(R$_{11}$)$_2$, or —NR$_{11}$S(O)$_2$R$_{11}$;

$R_{14}$ is H or $R_{19}$;

$R_{15}$ is $R_7$, $R_9$, $R_{19}$, or lactam heterocycloalkyl;

Each $R_{16}$ is independently H, alkyl, cycloalkyl, halogenated alkyl, or halogenated cycloalkyl;

$R_{17}$ is alkyl, cycloalkyl, or heterocycloalkyl, each optionally substituted with 1–4 substituents independently selected from F, Cl, Br, I, —NO$_2$, —CN, —OR$_{16}$, —SR$_{16}$, —S(O)$_2$R$_{16}$, —S(O)R$_{16}$, —OS(O)$_2$R$_{16}$, —N(R$_{16}$)$_2$, —C(O)R$_{16}$, —C(S)R$_{16}$, —C(O)OR$_{16}$, —C(O)N(R$_{16}$)$_2$, —NR$_{16}$C(O)R$_{16}$, —NR$_{16}$C(O)N(R$_{16}$)$_2$, —S(O)$_2$N(R$_{16}$)$_2$, and —NR$_{16}$S(O)$_2$R$_{16}$, and the cycloalkyl and heterocycloalkyl also being further optionally substituted with =O or =S;

$R_{19}$ is alkyl, cycloalkyl, heterocycloalkyl, phenyl, or naphthyl, each optionally substituted with 1–4 substituents independently selected from F, Cl, Br, I, —CN, —NO$_2$, —OR$_{16}$, —SR$_{16}$, —S(O)$_2$R$_{16}$, —S(O)R$_{16}$, —OS(O)$_2$R$_{16}$, —N(R$_{16}$)$_2$, —C(O)R$_{16}$, —C(S)R$_{16}$, —C(O)OR$_{16}$, —C(O)N(R$_{16}$)$_2$, —NR$_{16}$C(O)R$_{16}$, —NR$_{16}$C(O)N(R$_{16}$)$_2$, —S(O)$_2$N(R$_{16}$)$_2$, or —NR$_{16}$S(O)$_2$R$_{16}$, and the cycloalkyl and heterocycloalkyl also being further optionally substituted with =O or =S;

$R_{20}$ is H, alkyl, halogenated alkyl, substituted alkyl, cycloalkyl, halogenated cycloalkyl, substituted cycloalkyl, phenyl, —SO$_2$R$_8$, or phenyl having 1 substituent selected from $R_{12}$ and further having 0–3 substituents independently selected from F, Cl, Br, or I;

or pharmaceutical composition, pharmaceutically acceptable salt, racemic mixture, or pure enantiomer thereof.

In another aspect, the invention includes a compound of formula A—L—B or a pharmaceutically acceptable salt thereof, wherein A includes a 7-azabicyclo[2.2.1]heptane ring having 1S, 2R, and 4R stereochemistry; B is a heteroaryl; and L is a linking moiety including an amide, a thioamide, an acrylamide, an acrylthioamide, a propiolamide, or a propiolthioamide having the linking moiety bonded to the C-2 carbon of the heptane ring in an exo orientation.

In another aspect, the invention includes methods of treating a mammal suffering from schizophrenia or psychosis by administering compounds of formula A—L—B or Formula I in conjunction with antipsychotic drugs (also called antipsychotic agents). The compounds of formula A—L—B or Formula I and the antipsychotic drugs can be administered simultaneously or at separate intervals. When administered simultaneously the compounds of the present invention and the antipsychotic drugs can be incorporated into a single pharmaceutical composition. Alternatively, two separate compositions, i.e., one containing compounds of present invention and the other containing antipsychotic drugs, can be administered simultaneously.

The present invention also includes the compounds of the present invention, pharmaceutical compositions containing the active compounds, and methods to treat the identified diseases.

Embodiments of the invention may include one or more or combination of the following.

The compound of Formula I, where X is O.

The compound of Formula I, where X is S.

The compound of Formula I, where W is any one or more or combination of Q, —C=C—Q, or —C≡C—Q, optionally substituted as the definition of Q allows.

The compound of Formula I, where Q is either (a) or (b) or both (a) and (b), each optionally substituted on a carbon atom where substitution is allowed with any one of the following: F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —OR$_8$, —SR$_8$, —N(R$_8$)$_2$, —C(O)R$_8$, —C(S)R$_8$, —C(O)OR$_8$, —C(O)N(R$_8$)$_2$, —NR$_8$C(O)R$_8$, —S(O)$_2$N(R$_8$)$_2$, —OS(O)$_2$R$_8$, —S(O)$_2$R$_8$, —S(O)R$_8$, —NR$_8$S(O)$_2$R$_8$, —N(R$_8$)C(O)N(R$_8$)$_2$, —CN, —NO$_2$, R$_7$, or R$_9$. One of ordinary skill in the art can identify where substitution is allowed by comparing moieties with (a) or (b).

The compound of Formula I, where Q is either (a) or (b) or both (a) and (b), each optionally substituted on a nitrogen atom where substitution is allowed with any one of the following: alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, R$_7$, R$_9$, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—R$_7$, —C(O)—R$_9$, or —C(O)-aryl. One of ordinary skill in the art can identify where substitution is allowed by comparing moieties with (a) or (b).

Another group of compounds of Formula I includes compounds where R$_3$ includes any one of the following: H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, R$_7$, R$_9$, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—R$_7$, —C(O)—R$_9$, or —C(O)-aryl. Another group of compounds of Formula I includes compounds wherein R$_3$ is H.

Another group of compounds of Formula I includes compounds where each R$_5$ is independently any one of the following: H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —OR$_8$, —SR$_8$, —NR$_8$R$_8$, —C(O)R$_8$, —C(S)R$_8$, —C(O)OR$_8$, —C(O)NR$_8$R$_8$, —NR$_8$C(O)R$_8$, —S(O)$_2$NR$_8$R$_8$, —OS(O)$_2$R$_8$, —S(O)$_2$R$_8$, —S(O)R$_8$, —NR$_8$S(O)$_2$R$_8$, —N(R$_8$)C(O)NR$_8$R$_8$, —CN, —NO$_2$, R$_7$, or R$_9$. Another group of compounds of Formula I includes compounds wherein each R$_5$ is H.

Another group of compounds of Formula I includes compounds wherein both V and Y are =C(R$_5$)— and Z is =CH—, and wherein only one =C(R$_5$)— can be =CH—. Another group of compounds of Formula I includes compounds wherein U is —O—, Y is =C(R$_5$)—, Z is =C(H)—, and V is other than =N—. Another group of compounds of Formula I includes compounds where W is Q and Q is (b), V and Y are C(R$_5$), Z is =N—, and U is N(R$_3$), wherein R$_3$ is other than phenyl, substituted phenyl, or benzyl substituted on the phenyl of the benzyl with —CH$_3$. Benzyl is an allowed substituent where substituted alkyl is allowed.

Another aspect of the invention includes a compound of formula A—L—B or a pharmaceutically acceptable salt thereof, wherein A includes a 7-azabicyclo[2.2.1]heptane ring having 1S, 2R, and 4R stereochemistry; B is a heteroaryl; and L is a linking moiety including an amide, a thioamide, an acrylamide, an acrylthioamide, a propiolamide, or a propiolthioamide having the linking moiety bonded to the C-2 carbon of the heptane ring in an exo orientation. Heteroaryl is 5-membered heteroaromatic mono-cyclic moieties containing within the ring 1–3 heteroatoms independently selected from nitrogen, oxygen, or sulfur, optionally substituted with up to 4 substitutents where valency allows with substituents independently being F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —OR$_8$, —SR$_8$, —N(R$_8$)$_2$, —C(O)R$_8$, C(O)-aryl, —C(S)R$_8$, —C(O)OR$_8$, —C(O)N(R$_8$)$_2$, —NR$_8$C(O)R$_8$, —S(O)$_2$N(R$_8$)$_2$, —OS(O)$_2$R$_8$, —S(O)$_2$R$_8$, —S(O)R$_8$, —NR$_8$S(O)$_2$R$_8$, —N(R$_8$)C(O)N(R$_8$)$_2$, —CN, —NO$_2$, R$_7$, or R$_9$.

The compound of Formula I, where R$_1$ is H, alkyl, or cycloalkyl, and where R$_2$ is H, alkyl, substituted alkyl, cycloalkyl, halogenated alkyl, or aryl.

The compound of Formula I, where (a) is any one or more or combination of the following: thiophen-2-yl, furan-2-yl, 1,3-thiazol-5-yl, or 1,3-oxazol-2-yl, 1,3-thiazole-2-yl, 1,3,4-oxadiazol-2-yl, 1,3-oxazole-5-yl, 1H-pyrrole-2-yl, or 1,2,4-oxadiazole-5-yl, any of which is optionally substituted on carbon (e.g., V or Y is independently CR$_5$), with H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —OR$_8$, —SR$_8$, —N(R$_8$)$_2$, —C(O)R$_8$, —C(S)R$_8$, —C(O)OR$_8$, —C(O)N(R$_8$)$_2$, —NR$_8$C(O)R$_8$, —S(O)$_2$N(R$_8$)$_2$, —OS(O)$_2$R$_8$, —S(O)$_2$R$_8$, —S(O)R$_8$, —NR$_8$S(O)$_2$R$_8$, —N(R$_8$)C(O)N(R$_8$)$_2$, —CN, —NO$_2$, R$_7$, or R$_9$; and further optionally substituted on nitrogen (e.g., when U is N—R$_3$), with alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, R$_7$, R$_9$, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—$R_7$, —C(O)—$R_9$, or —C(O)-aryl.

The compound of Formula I, where each $R_4$ is independently H, lower alkyl, or substituted lower alkyl.

The compound of Formula I, where $R_6$ is an amino protecting group.

The compound of Formula I, where $R_6$ is H, or lower alkyl optionally substituted with up to 3 substituents independently selected from F, Cl, Br, I, —OH, —CN, —$NH_2$, —NH(alkyl), or —N(alkyl)$_2$.

The compound of Formula I, where $R_1$ is H or lower alkyl, and where $R_2$ is H or lower alkyl.

The compound of Formula I, where at least one $R_4$ is H and one $R_4$ is H or lower alkyl optionally substituted with 1 substituent selected from —CN, —$NO_2$, —$OR_{10}$, —$SR_{10}$, —$S(O)R_{10}$, —$S(O)_2R_{10}$, —$OS(O)_2R_{10}$, —$NR_{10}R_{10}$, —$C(O)R_{10}$, —$C(O)OR_{10}$, —$C(S)R_{10}$, —$C(O)NR_{10}R_{10}$, —$NR_{10}C(O)R_{10}$, —$NR_{10}C(O)NR_{10}R_{10}$, —$S(O)_2NR_{10}R_{10}$, —$NR_{10}S(O)_2R_{10}$, or phenyl optionally substituted with up to 4 substitutents independently selected from F, Cl, Br, I, $R_{13}$, and $R_{15}$, provided that when said lower alkyl is optionally substituted, said lower alkyl can be further optionally substituted with up to 3 substituents independently selected from F, Cl, Br, and I, and further provided that $R_{10}$ is H, lower alkyl, or halogenated lower alkyl. This allows the lower alkyl of $R_4$ to be substituted with one substituent selected from —CN, —$NO_2$, —$OR_{10}$, —$SR_{10}$, —$S(O)R_{10}$, —$S(O)_2$, $R_{10}$, —$OS(O)_2R_{10}$, —$NR_{10}R_{10}$, —$C(O)R_{10}$, —$C(O)OR_{10}$, —$C(S)R_{10}$, —$C(O)NR_{10}R_{10}$, —$NR_{10}C(O)R_{10}$, —$NR_{10}C(O)NR_{10}R_{10}$, —$S(O)_2NR_{10}R_{10}$, —$NR_{10}S(O)_2R_{10}$, or phenyl optionally substituted with up to 4 substitutents independently selected from F, Cl, Br, I, $R_{13}$, and $R_{15}$, and further optionally substituted with up to 3 substituents independently selected from F, Cl, Br, and I on any carbon with sufficient valency for said substitution. This further provides that $R_{10}$ is H, lower alkyl or halogenated lower alkyl for the following optional substituents on $R_4$: —$OR_{10}$, —$SR_{10}$, —$S(O)R_{10}$, —$S(O)_2R_{10}$, —$OS(O)_2R_{10}$, —$NR_{10}R_{10}$, —$C(O)R_{10}$, —$C(O)OR_{10}$, —$C(O)R_{10}$, —$C(O)NR_{10}R_{10}$, —$NR_{10}C(O)R_{10}$, —$NR_{10}C(O)NR_{10}R_{10}$, —$S(O)_2NR_{10}R_{10}$, —$NR_{10}S(O)_2R_{10}$.

The compound of Formula I, where $R_1$, $R_2$, and each $R_4$ are H.

The compound of Formula I or formula A—L—B, where the compound is any one or more or combination of the following as the free base, or a pharmaceutically acceptable salt thereof:

N-[(1S,2R,4R)-7-azabicyclo[2.2.1]hept-2-yl]-5-bromo-2-thiophenecarboxamide;

(+/−) exo-N-[7-azabicyclo[2.2.1]hept-2-yl]-5-bromo-2-thiophenecarboxamide;

N-[(1S,2R,4R)-7-azabicyclo[2.2.1]hept-2-yl]-5-(methylthio)thiophene-2-carboxamide;

N-[(1S,2R,4R)-7-azabicyclo[2.2.1]hept-2-yl]-5-phenylthiophene-2-carboxamide;

N-[(1S,2R,4R)-7-azabicyclo[2.2.1]hept-2-yl]-5-(2-chlorophenyl)thiophene-2-carboxamide;

N-[(1S,2R,4R)-7-azabicyclo[2.2.1]hept-2-yl]-5-[(4-chlorophenyl)thio]thiophene-2-carboxamide;

N-[(1S,2R,4R)-7-azabicyclo[2.2.1]hept-2-yl]-5-methylthiophene-2-carboxamide;

N-[(1S,2R,4R)-7-azabicyclo[2.2.1]hept-2-yl]-5-pyridin-2-ylthiophene-2-carboxamide;

N-[(1S,2R,4R)-7-azabicyclo[2.2.1]hept-2-yl]-5-(3-nitrophenyl)-2-furamide;

N-[(1S,2R,4R)-7-azabicyclo[2.2.1]hept-2-yl]-5-(4-nitrophenyl)-2-furamide;

N-[(1S,2R,4R)-7-azabicyclo[2.2.1]hept-2-yl]-5-(4-chlorophenyl)-2-furamide;

N-[(1S,2R,4R)-7-azabicyclo[2.2.1]hept-2-yl]-5-chlorothiophene-2-carboxamide;

N-[(1S,2R,4R)-7-azabicyclo[2.2.1]hept-2-yl]-5-(2-nitrophenyl)-2-furamide;

N-[(1S,2R,4R)-7-azabicyclo[2.2.1]hept-2-yl]-5-(4-aminophenyl)-2-furamide;

N-[(1S,2R,4R)-7-azabicyclo[2.2.1]hept-2-yl]-5-(2-fluorophenyl)-2-furamide;

N-[(1S,2R,4R)-7-azabicyclo[2.2.1]hept-2-yl]-5-(3-fluorophenyl)-2-furamide;

N-[(1S,2R,4R)-7-azabicyclo[2.2.1]hept-2-yl]-5-(4-fluorophenyl)-2-furamide;

N-[(1S,2R,4R)-7-azabicyclo[2.2.1]hept-2-yl]-5-(4-methylphenyl)-2-furamide;

N-[(1S,2R,4R)-7-azabicyclo[2.2.1]hept-2-yl]-5-bromo-2-furamide;

N-[(1S,2R,4R)-7-azabicyclo[2.2.1]hept-2-yl]-2-phenyl-1,3-thiazole-5-carboxamide;

N-[(1S,2R,4R)-7-azabicyclo[2.2.1]hept-2-yl]-2-(2-fluorophenyl)-1,3-thiazole-5-carboxamide;

N-[(1S,2R,4R)-7-azabicyclo[2.2.1]hept-2-yl]-5-phenyl-2-furamide; or

N-[(1S,2R,4R)-7-azabicyclo[2.2.1]hept-2-yl]-5-phenyl-1,3-oxazole-2-carboxamide.

The compound of Formula I or formula A—L—B, where the compound is any one or more or combination of the following as the free base, or a pharmaceutically acceptable salt thereof: N-[(1S,2R,4R)-7-azabicyclo[2.2.1]hept-2-yl]-5-(4-chlorophenyl)-thiophene-2-carboxamide;

N-[(1S,2R,4R)-7-azabicyclo[2.2.1]hept-2-yl]-5-(3-chlorophenyl)-thiophene-2-carboxamide;

N-[(1S,2R,4R)-7-azabicyclo[2.2.1]hept-2-yl]-2,3'-bithiophene-5-carboxamide;

N-[(1S,2R,4R)-7-azabicyclo[2.2.1]hept-2-yl]-5-(2-nitrophenyl)-thiophene-2-carboxamide;

N-[(1S,2R,4R)-7-azabicyclo[2.2.1]hept-2-yl]-5-(3-nitrophenyl)-thiophene-2-carboxamide;

N-[(1S,2R,4R)-7-azabicyclo[2.2.1]hept-2-yl]-4-phenyl-thiophene-2-carboxamide;

N-[(1S,2R,4R)-7-azabicyclo[2.2.1]hept-2-yl]-5-(3-benzyloxyphenyl)-thiophene-2-carboxamide;

N-[(1S,2R,4R)-7-azabicyclo[2.2.1]hept-2-yl]-5-(4-benzyloxyphenyl)-thiophene-2-carboxamide;

N-[(1S,2R,4R)-7-azabicyclo[2.2.1]hept-2-yl]-5-(3-fluoro-4-benzyloxyphenyl)-thiophene-2-carboxamide;

5-(2-aminophenyl)-N-[(1S,2R,4R)-7-azabicyclo[2.2.1]hept-2-yl]-thiophene-2-carboxamide;

N-[(1S,2R,4R)-7-azabicyclo[2.2.1]hept-2-yl]-5-pyridin-3-yl-thiophene-2-carboxamide;

N-[(1S,2R,4R)-7-azabicyclo[2.2.1]hept-2-yl]-5'-methyl-2,2'-bithiophene-5-carboxamide;

N-[(1S,2R,4R)-7-azabicyclo[2.2.1]hept-2-yl]-5'-chloro-2,2'-bithiophene-5-carboxamide;

N-[(1S,2R,4R)-7-azabicyclo[2.2.1]hept-2-yl]-5-nitro-thiophene-2-carboxamide;

5-(aminomethyl)-N-[(1S,2R,4R)-7-azabicyclo[2.2.1]hept-2-yl]-thiophene-2-carboxamide;

N-[(1S,2R,4R)-7-azabicyclo[2.2.1]hept-2-yl]-5-cyano-thiophene-2-carboxamide;

N-[(1S,2R,4R)-7-azabicyclo[2.2.1]hept-2-yl]-5-methoxy-thiophene-2-carboxamide;

N-[(1S,2R,4R)-7-azabicyclo[2.2.1]hept-2-yl]-[2,2]bithiophene-5-carboxamide;

N-[(1S,2R,4R)-7-azabicyclo[2.2.1]hept-2-yl]-5-acetyl-thiophene-2-carboxamide;

N-[(1S,2R,4R)-7-azabicyclo[2.2.1]hept-2-yl]-5-(phenylsulfanyl)-thiophene-2-carboxamide;

N-[(1S,2R,4R)-7-azabicyclo[2.2.1]hept-2-yl]-5-phenyl-thiophene-2-carbothioamide;

N-[(1S,2R,4R)-7-azabicyclo[2.2.1]hept-2-yl]-5-(2-acetamidophenyl)-thiophene-2-carboxamide;

N-[(1S,2R,4R)-7-azabicyclo[2.2.1]hept-2-yl]-5-(3-acetamidophenyl)-thiophene-2-carboxamide;

N-[(1S,2R,4R)-7-azabicyclo[2.2.1]hept-2-yl]-5-(4-acetamidophenyl)-thiophene-2-carboxamide;

N-[(1S,2R,4R)-7-azabicyclo[2.2.1]hept-2-yl]-5-(2-trifluoroacetamidophenyl)-thiophene-2-carboxamide;

N-[(1S,2R,4R)-7-azabicyclo[2.2.1]hept-2-yl]-5-(3-trifluoroacetamidophenyl)-thiophene-2-carboxamide;

N-[(1S,2R,4R)-7-azabicyclo[2.2.1]hept-2-yl]-5-(4-trifluoroacetamidophenyl)-thiophene-2-carboxamide;

N-[(1S,2R,4R)-7-azabicyclo[2.2.1]hept-2-yl]-5-(2-methanesulfonylaminophenyl)-thiophene-2-carboxamide;

N-[(1S,2R,4R)-7-azabicyclo[2.2.1]hept-2-yl]-5-(3-methanesulfonylarminophenyl)-thiophene-2-carboxamide;

N-[(1S,2R,4R)-7-azabicyclo[2.2.1]hept-2-yl]-5-(4-methanesulfonylaminophenyl)-thiophene-2-carboxamide;

N-[(1S,2R,4R)-7-azabicyclo[2.2.1]hept-2-yl]-5-(2-trifluoromethanesulfonylaminophenyl)-thiophene-2-carboxamide;

N-[(1S,2R,4R)-7-azabicyclo[2.2.1]hept-2-yl]-5-(3-trifluoromethanesulfonylaminophenyl)-thiophene-2-carboxamide;

N-[(1S,2R,4R)-7-azabicyclo[2.2.1]hept-2-yl]-5-(4-trifluoromethanesulfonylaminophenyl)-thiophene-2-carboxamide;

N-[(1S,2R,4R)-7-azabicyclo[2.2.1]hept-2-yl]-5-(2-difluoroacetamidophenyl)-thiophene-2-carboxamide;

N-[(1S,2R,4R)-7-azabicyclo[2.2.1]hept-2-yl]-5-(3-difluoroacetamidophenyl)-thiophene-2-carboxamide;

N-[(1S,2R,4R)-7-azabicyclo[2.2.1]hept-2-yl]-5-(4-difluoroacetamidophenyl)-thiophene-2-carboxamide;

N-[(1S,2R,4R)-7-azabicyclo[2.2.1]hept-2-yl]-5-(2-carbamoylphenyl)-thiophene-2-carboxamide;

N-[(1S,2R,4R)-7-azabicyclo[2.2.1]hept-2-yl]-5-(3-carbamoylphenyl)-thiophene-2-carboxamide;

-[(1S,2R,4R)-7-azabicyclo[2.2.1]hept-2-yl]-5-(4-carbamoylphenyl)-thiophene-2-carboxamide;

N-[(1S,2R,4R)-7-azabicyclo[2.2.1]hept-2-yl]-5-(2-sulfamoylphenyl)-thiophene-2-carboxamide;

N-[(1S,2R,4R)-7-azabicyclo[2.2.1]hept-2-yl]-5-(3-sulfamoylphenyl)-thiophene-2-carboxamide;

N-[(1S,2R,4R)-7-azabicyclo[2.2.1]hept-2-yl]-5-(4-sulfamoylphenyl)-thiophene-2-carboxamide;

N-[(1S,2R,4R)-7-azabicyclo[2.2.1]hept-2-yl]-5-(2-acetamidophenylsulfanyl)-thiophene-2-carboxamide;

N-[(1S,2R,4R)-7-azabicyclo[2.2.1]hept-2-yl]-5-(3-acetamidophenylsulfanyl)-thiophene-2-carboxamide;

N-[(1S,2R,4R)-7-azabicyclo[2.2.1]hept-2-yl]-5-(4-acetamidophenylsulfanyl)-thiophene-2-carboxamide;

N-[(1S,2R,4R)-7-azabicyclo[2.2.1]hept-2-yl]-5-(2-trifluoroacetamidophenylsulfanyl)-thiophene-2-carboxamide;

N-[(1S,2R,4R)-7-azabicyclo[2.2.1]hept-2-yl]-5-(3-trifluoroacetamidophenylsulfanyl)-thiophene-2-carboxamide;

N-[(1S,2R,4R)-7-azabicyclo[2.2.1]hept-2-yl]-5-(4-trifluoroacetamidophenylsulfanyl)-thiophene-2-carboxamide;

N-[(1S,2R,4R)-7-azabicyclo[2.2.1]hept-2-yl]-5-(2-methanesulfonylaminophenylsulfanyl)-thiophene-2-carboxamide;

N-[(1S,2R,4R)-7-azabicyclo[2.2.1]hept-2-yl]-5-(3-methanesulfonylaminophenylsulfanyl)-thiophene-2-carboxamide;

N-[(1S,2R,4R)-7-azabicyclo[2.2.1]hept-2-yl]-5-(4-methanesulfonylaminophenylsulfanyl)-thiophene-2-carboxamide;

N-[(1S,2R,4R)-7-azabicyclo[2.2.1]hept-2-yl]-5-(2-trifluoromethanesulfonylaminophenylsulfanyl)-thiophene-2-carboxamide;

N-[(1S,2R,4R)-7-azabicyclo[2.2.1]hept-2-yl]-5-(3-trifluoromethanesulfonylaminophenylsulfanyl)-thiophene-2-carboxamide;

N-[(1S,2R,4R)-7-azabicyclo[2.2.1]hept-2-yl]-5-(4-trifluoromethanesulfonylaminophenylsulfanyl)-thiophene-2-carboxamide;

N-[(1S,2R,4R)-7-azabicyclo[2.2.1]hept-2-yl]-5-(2-difluoroacetamidophenylsulfanyl)-thiophene-2-carboxamide;

N-[(1S,2R,4R)-7-azabicyclo[2.2.1]hept-2-yl]-5-(3-difluoroacetamidophenylsulfanyl)-thiophene-2-carboxamide;

N-[(1S,2R,4R)-7-azabicyclo[2.2.1]hept-2-yl]-5-(4-difluoroacetamidophenylsulfanyl)-thiophene-2-carboxamide;

N-[(1S,2R,4R)-7-azabicyclo[2.2.1]hept-2-yl]-5-(2-carbamoylphenylsulfanyl)-thiophene-2-carboxamide;

N-[(1S,2R,4R)-7-azabicyclo[2.2.1]hept-2-yl]-5-(3-carbamoylphenylsulfanyl)-thiophene-2-carboxamide;

N-[(1S,2R,4R)-7-azabicyclo[2.2.1]hept-2-yl]-5-(4-carbamoylphenylsulfanyl)-thiophene-2-carboxamide;

N-[(1S,2R,4R)-7-azabicyclo[2.2.1]hept-2-yl]-5-(2-sulfamoylphenylsulfanyl)-thiophene-2-carboxamide;

N-[(1S,2R,4R)-7-azabicyclo[2.2.1]hept-2-yl]-5-(3-sulfamoylphenylsulfanyl)-thiophene-2-carboxamide;

N-[(1S,2R,4R)-7-azabicyclo[2.2.1]hept-2-yl]-5-(4-sulfamoylphenylsulfanyl)-thiophene-2-carboxamide;

N-[(1S,2R,4R)-7-azabicyclo[2.2.1]hept-2-yl]-5-(2-hydroxyphenylsulfanyl)-thiophene-2-carboxamide;

N-[(1S,2R,4R)-7-azabicyclo[2.2.1]hept-2-yl]-5-(3-hydroxyphenylsulfanyl)-thiophene-2-carboxamide;

N-[(1S,2R,4R)-7-azabicyclo[2.2.1]hept-2-yl]-5-(4-hydroxyphenylsulfanyl)-thiophene-2-carboxamide;

N-[(1S,2R,4R)-7-azabicyclo[2.2.1]hept-2-yl]-5-(2-aminophenylsulfanyl)-thiophene-2-carboxamide;

N-[(1S,2R,4R)-7-azabicyclo[2.2.1]hept-2-yl]-5-(3-aminophenylsulfanyl)-thiophene-2-carboxamide;

N-[(1S,2R,4R)-7-azabicyclo[2.2.1]hept-2-yl]-5-(4-aminophenylsulfanyl)-thiophene-2-carboxamide;
N-[(1S,2R,4R)-7-azabicyclo[2.2.1]hept-2-yl]-5-(2-acetamidophenoxy)-thiophene-2-carboxamide;
N-[(1S,2R,4R)-7-azabicyclo[2.2.1]hept-2-yl]-5-(3-acetamidophenoxy)-thiophene-2-carboxamide;
N-[(1S,2R,4R)-7-azabicyclo[2.2.1]hept-2-yl]-5-(4-acetamidophenoxy)-thiophene-2-carboxamide;
N-[(1S,2R,4R)-7-azabicyclo[2.2.1]hept-2-yl]-5-(2-trifluoroacetamidophenoxy)-thiophene-2-carboxaminde;
N-[(1S,2R,4R)-7-azabicyclo[2.2.1]hept-2-yl]-5-(3-trifluoroacetamidophenoxy)-thiophene-2-carboxamide;
N-[(1S,2R,4R)-7-azabicyclo[2.2.1]hept-2-yl]-5-(4-trifluoroacetamidophenoxy)-thiophene-2-carboxamide;
N-[(1S,2R,4R)-7-azabicyclo[2.2.1]hept-2-yl]-5-(2-methanesulfonylaminophenoxy)-thiophene-2-carboxamide;
N-[(1S,2R,4R)-7-azabicyclo[2.2.1]hept-2-yl]-5-(3-methanesulfonylaminophenoxy)-thiophene-2-carboxamide;
N-[(1S,2R,4R)-7-azabicyclo[2.2.1]hept-2-yl]-5-(4-methanesulfonylaminophenoxy)-thiophene-2-carboxamide;
N-[(1S,2R,4R)-7-azabicyclo[2.2.1]hept-2-yl]-5-(2-trifluoromethanesulfonylaminophenoxy)-thiophene-2-carboxamide;
N-[(1S,2R,4R)-7-azabicyclo[2.2.1]hept-2-yl]-5-(3-trifluoromethanesulfonylaminophenoxy)-thiophene-2-carboxamide;
N-[(1S,2R,4R)-7-azabicyclo[2.2.1]hept-2-yl]-5-(4-trifluoromethanesulfonylaminophenoxy)-thiophene-2-carboxamide;
N-[(1S,2R,4R)-7-azabicyclo[2.2.1]hept-2-yl]-5-(2-difluoroacetamidophenoxy)-thiophene-2-carboxamide;
N-[(1S,2R,4R)-7-azabicyclo[2.2.1]hept-2-yl]-5-(3-difluoroacetamidophenoxy)-thiophene-2-carboxamide;
N-[(1S,2R,4R)-7-azabicyclo[2.2.1]hept-2-yl]-5-(4-difluoroacetamidophenoxy)-thiophene-2-carboxamide;
N-[(1S,2R,4R)-7-azabicyclo[2.2.1]hept-2-yl]-5-(2-carbamoylphenoxy)-thiophene-2-carboxamide;
N-[(1S,2R,4R)-7-azabicyclo[2.2.1]hept-2-yl]-5-(3-carbamoylphenoxy)-thiophene-2-carboxamide;
N-[(1S,2R,4R)-7-azabicyclo[2.2.1]hept-2-yl]-5-(4-carbamoylphenoxy)-thiophene-2-carboxamide;
N-[(1S,2R,4R)-7-azabicyclo[2.2.1]hept-2-yl]-5-(2-sulfamoylphenoxy)-thiophene-2-carboxamide;
N-[(1S,2R,4R)-7-azabicyclo[2.2.1]hept-2-yl]-5-(3-sulfamoylphenoxy)-thiophene-2-carboxamide;
N-[(1S,2R,4R)-7-azabicyclo[2.2.1]hept-2-yl]-5-(4-sulfamoylphenoxy)-thiophene-2-carboxamide;
N-[(1S,2R,4R)-7-azabicyclo[2.2.1]hept-2-yl]-5-(2-hydroxyphenoxy)-thiophene-2-carboxamide;
N-[(1S,2R,4R)-7-azabicyclo[2.2.1]hept-2-yl]-5-(3-hydroxyphenoxy)-thiophene-2-carboxamide;
N-[(1S,2R,4R)-7-azabicyclo[2.2.1]hept-2-yl]-5-(4-hydroxyphenoxy)-thiophene-2-carboxamide;
N-[(1S,2R,4R)-7-azabicyclo[2.2.1]hept-2-yl]-5-(2-aminophenoxy)-thiophene-2-carboxamide;
N-[(1S,2R,4R)-7-azabicyclo[2.2.1]hept-2-yl]-5-(3-aminophenoxy)-thiophene-2-carboxamide;
N-[(1S,2R,4R)-7-azabicyclo[2.2.1]hept-2-yl]-5-(4-aminophenoxy)-thiophene-2-carboxamide;
N-[(1S,2R,4R)-7-azabicyclo[2.2.1]hept-2-yl]-5-(2-chlorophenoxy)-thiophene-2-carboxamide;
N-[(1S,2R,4R)-7-azabicyclo[2.2.1]hept-2-yl]-5-(3-chlorophenoxy)-thiophene-2-carboxamide;
N-[(1S,2R,4R)-7-azabicyclo[2.2.1]hept-2-yl]-5-(4-chlorophenoxy)-thiophene-2-carboxamide;
N-[(1S,2R,4R)-7-azabicyclo[2.2.1]hept-2-yl]-5-(2-cyanophenoxy)-thiophene-2-carboxamide;
N-[(1S,2R,4R)-7-azabicyclo[2.2.1]hept-2-yl]-5-(3-cyanophenoxy)-thiophene-2-carboxamide;
N-[(1S,2R,4R)-7-azabicyclo[2.2.1]hept-2-yl]-5-(4-cyanophenoxy)-thiophene-2-carboxamide;
N-[(1S,2R,4R)-7-azabicyclo[2.2.1]hept-2-yl]-5-(2-methoxyphenyl)-thiophene-2-carboxamide;
N-[(1S,2R,4R)-7-azabicyclo[2.2.1]hept-2-yl]-5-(3-methoxyphenyl)-thiophene-2-carboxamide;
N-[(1S,2R,4R)-7-azabicyclo[2.2.1]hept-2-yl]-5-(4-methoxyphenyl)-thiophene-2-carboxamide;
N-[(1S,2R,4R)-7-azabicyclo[2.2.1]hept-2-yl]-5-(2-methylphenyl)-thiophene-2-carboxamide;
N-[(1S,2R,4R)-7-azabicyclo[2.2.1]hept-2-yl]-5-(3-methylphenyl)-thiophene-2-carboxamide;
N-[(1S,2R,4R)-7-azabicyclo[2.2.1]hept-2-yl]-5-(4-methylphenyl)-thiophene-2-carboxamide;
N-[(1S,2R,4R)-7-azabicyclo[2.2.1]hept-2-yl]-5-(2-trifluoromethylphenyl)-thiophene-2-carboxamide;
N-[(1S,2R,4R)-7-azabicyclo[2.2.1]hept-2-yl]-5-(3-trifluoromethylphenyl)-thiophene-2-carboxamide;
N-[(1S,2R,4R)-7-azabicyclo[2.2.1]hept-2-yl]-5-(4-trifluoromethylphenyl)-thiophene-2-carboxamide;
N-[(1S,2R,4R)-7-azabicyclo[2.2.1]hept-2-yl]-5-(2-acetylphenyl)-thiophene-2-carboxamide;
N-[(1S,2R,4R)-7-azabicyclo[2.2.1]hept-2-yl]-5-(3-acetylphenyl)-thiophene-2-carboxamide;
N-[(1S,2R,4R)-7-azabicyclo[2.2.1]hept-2-yl]-5-(4-acetylphenyl)-thiophene-2-carboxamide;
N-[(1S,2R,4R)-7-azabicyclo[2.2.1]hept-2-yl]-5-(2-cyanophenyl)-thiophene-2-carboxamide;
N-[(1S,2R,4R)-7-azabicyclo[2.2.1]hept-2-yl]-5-(3-cyanophenyl)-thiophene-2-carboxamide;
N-[(1S,2R,4R)-7-azabicyclo[2.2.1]hept-2-yl]-5-(4-cyanophenyl)-thiophene-2-carboxamide;
N-[(1S,2R,4R)-7-azabicyclo[2.2.1]hept-2-yl]-5-(2-morpholin-4-yl-phenyl)-thiophene-2-carboxamide;
N-[(1S,2R,4R)-7-azabicyclo[2.2.1]hept-2-yl]-5-(3-morpholin-4-yl-phenyl)-thiophene-2-carboxamide;
N-[(1S,2R,4R)-7-azabicyclo[2.2.1]hept-2-yl]-5-(4-morpholin-4-yl-phenyl)-thiophene-2-carboxamide;
N-[(1S,2R,4R)-7-azabicyclo[2.2.1]hept-2-yl]-5-(2-methoxyphenoxy)-thiophene-2-carboxamide;
N-[(1S,2R,4R)-7-azabicyclo[2.2.1]hept-2-yl]-5-(3-methoxyphenoxy)-thiophene-2-carboxamide; N-[(1S,2R,4R)-7-azabicyclo[2.2.1]hept-2-yl]-5-(4-methoxyphenoxy)-thiophene-2-carboxamide;
N-[(1S,2R,4R)-7-azabicyclo[2.2.1]hept-2-yl]-5-(2-methylphenoxy)-thiophene-2-carboxamide;
N-[(1S,2R,4R)-7-azabicyclo[2.2.1]hept-2-yl]-5-(3-methylphenoxy)-thiophene-2-carboxamide;
N-[(1S,2R,4R)-7-azabicyclo[2.2.1]hept-2-yl]-5-(4-methylphenoxy)-thiophene-2-carboxamide;

N-[(1S,2R,4R)-7-azabicyclo[2.2.1]hept-2-yl]-5-(2-trifluoromethylphenoxy)-thiophene-2-carboxamide;
N-[(1S,2R,4R)-7-azabicyclo[2.2.1]hept-2-yl]-5-(3-trifluoromethylphenoxy)-thiophene-2-carboxamide;
N-[(1S,2R,4R)-7-azabicyclo[2.2.1]hept-2-yl]-5-(4-trifluoromethylphenoxy)-thiophene-2-carboxamide;
N-[(1S,2R,4R)-7-azabicyclo[2.2.1]hept-2-yl]-5-(2-acetylphenoxy)-thiophene-2-carboxamide;
N-[(1S,2R,4R)-7-azabicyclo[2.2.1]hept-2-yl]-5-(3-acetylphenoxy)-thiophene-2-carboxamide;
N-[(1S,2R,4R)-7-azabicyclo[2.2.1]hept-2-yl]-5-(4-acetylphenoxy)-thiophene-2-carboxamide;
N-[(1S,2R,4R)-7-azabicyclo[2.2.1]hept-2-yl]-5-(2-cyanophenoxy)-thiophene-2-carboxamide;
N-[(1S,2R,4R)-7-azabicyclo[2.2.1]hept-2-yl]-5-(3-cyanophenoxy)-thiophene-2-carboxamide;
N-[(1S,2R,4R)-7-azabicyclo[2.2.1]hept-2-yl]-5-(4-cyanophenoxy)-thiophene-2-carboxamide;
N-[(1S,2R,4R)-7-azabicyclo[2.2.1]hept-2-yl]-5-(2-morpholin-4-yl-phenoxy)-thiophene-2-carboxamide;
N-[(1S,2R,4R)-7-azabicyclo[2.2.1]hept-2-yl]-5-(3-morpholin-4-yl-phenoxy)-thiophene-2-carboxamide;
N-[(1S,2R,4R)-7-azabicyclo[2.2.1]hept-2-yl]-5-(4-morpholin-4-yl-phenoxy)-thiophene-2-carboxamide;
N-[(1S,2R,4R)-7-azabicyclo[2.2.1]hept-2-yl]-5-(2-methoxyphenylsulfanyl)-thiophene-2-carboxamide;
N-[(1S,2R,4R)-7-azabicyclo[2.2.1]hept-2-yl]-5-(3-methoxyphenylsulfanyl)-thiophene-2-carboxamide;
N-[(1S,2R,4R)-7-azabicyclo[2.2.1]hept-2-yl]-5-(4-methoxyphenylsulfanyl)-thiophene-2-carboxamide;
N-[(1S,2R,4R)-7-azabicyclo[2.2.1]hept-2-yl]-5-(2-methylphenylsulfanyl)-thiophene-2-carboxamide;
N-[(1S,2R,4R)-7-azabicyclo[2.2.1]hept-2-yl]-5-(3-methylphenylsulfanyl)-thiophene-2-carboxamide;
N-[(1S,2R,4R)-7-azabicyclo[2.2.1]hept-2-yl]-5-(4-methylphenylsulfanyl)-thiophene-2-carboxamide;
N-[(1S,2R,4R)-7-azabicyclo[2.2.1]hept-2-yl]-5-(2-trifluoromethylphenylsulfanyl)-thiophene-2-carboxamide;
N-[(1S,2R,4R)-7-azabicyclo[2.2.1]hept-2-yl]-5-(3-trifluoromethylphenylsulfanyl)-thiophene-2-carboxamide;
N-[(1S,2R,4R)-7-azabicyclo[2.2.1]hept-2-yl]-5-(4-trifluoromethylphenylsulfanyl)-thiophene-2-carboxamide;
N-[(1S,2R,4R)-7-azabicyclo[2.2.1]hept-2-yl]-5-(2-acetylphenylsulfanyl)-thiophene-2-carboxamide;
N-[(1S,2R,4R)-7-azabicyclo[2.2.1]hept-2-yl]-5-(3-acetylphenylsulfanyl)-thiophene-2-carboxamide;
N-[(1S,2R,4R)-7-azabicyclo[2.2.1]hept-2-yl]-5-(4-acetylphenylsulfanyl)-thiophene-2-carboxamide;
N-[(1S,2R,4R)-7-azabicyclo[2.2.1]hept-2-yl]-5-(2-cyanophenylsulfanyl)-thiophene-2-carboxamide;
N-[(1S,2R,4R)-7-azabicyclo[2.2.1]hept-2-yl]-5-(3-cyanophenylsulfanyl)-thiophene-2-carboxamide;
N-[(1S,2R,4R)-7-azabicyclo[2.2.1]hept-2-yl]-5-(4-cyanophenylsulfanyl)-thiophene-2-carboxamide;
N-[(1S,2R,4R)-7-azabicyclo[2.2.1]hept-2-yl]-5-(2-morpholin-4-yl-phenylsulfanyl)-thiophene-2-carboxamide;
N-[(1S,2R,4R)-7-azabicyclo[2.2.1]hept-2-yl]-5-(3-morpholin-4-yl-phenylsulfanyl)-thiophene-2-carboxamide;
N-[(1S,2R,4R)-7-azabicyclo[2.2.1]hept-2-yl]-5-(4-morpholin4-yl-phenylsulfanyl)-thiophene-2-carboxamide;
N-[(1S,2R,4R)-7-azabicyclo[2.2.1]hept-2-yl]-5-(pyridin-4-yl)-thiophene-2-carboxamide;
N-[(1S,2R,4R)-7-azabicyclo[2.2.1]hept-2-yl]-5-(2-methylpyridin-4-yl)-thiophene-2-carboxamide;
N-[(1S,2R,4R)-7-azabicyclo[2.2.1]hept-2-yl]-5-(6-methylpyridin-3-yl)-thiophene-2-carboxamide;
N-[(1S,2R,4R)-7-azabicyclo[2.2.1]hept-2-yl]-5-(5-methylpyridin-2-yl)-thiophene-2-carboxamide;
N-[(1S,2R,4R)-7-azabicyclo[2.2.1]hept-2-yl]-5-(2-methoxypyridin-4-yl)-thiophene-2-carboxamide;
N-[(1S,2R,4R)-7-azabicyclo[2.2.1]hept-2-yl]-5-(6-methoxypyridin-3-yl)-thiophene-2-carboxamide;
N-[(1S,2R,4R)-7-azabicyclo[2.2.1]hept-2-yl]-5-(5-methoxypyridin-2-yl)-thiophene-2-carboxamide;
N-[(1S,2R,4R)-7-azabicyclo[2.2.1]hept-2-yl]-5-(2-chloropyridin-4-yl)-thiophene-2-carboxamide;
N-[(11S,2R,4R)-7-azabicyclo[2.2.1]hept-2-yl]-5-(6-chloropyridin-3-yl)-thiophene-2-carboxamide;
N-[(1S,2R,4R)-7-azabicyclo[2.2.1]hept-2-yl]-5-(5-chloropyridin-2-yl)-thiophene-2-carboxamide;
N-[(1S,2R,4R)-7-azabicyclo[2.2.1]hept-2-yl]-5-(5-chloropyridin-3-yl)-thiophene-2-carboxamide;
N-[(1S,2R,4R)-7-azabicyclo[2.2.1]hept-2-yl]-5-(6-chloropyridin-2-yl)-thiophene-2-carboxamide;
N-[(1S,2R,4R)-7-azabicyclo[2.2.1]hept-2-yl]-5-(4-chloropyridin-2-yl)-thiophene-2-carboxamide;
N-[(1S,2R,4R)-7-azabicyclo[2.2.1]hept-2-yl]-5-(pyridin-4-yloxy)-thiophene-2-carboxamide;
N-[(1S,2R,4R)-7-azabicyclo[2.2.1]hept-2-yl]-5-(pyridin-3-yloxy)-thiophene-2-carboxamide;
N-[(1S,2R,4R)-7-azabicyclo[2.2.1]hept-2-yl]-5-(pyridin-2-yloxy)-thiophene-2-carboxamide;
N-[(1S,2R,4R)-7-azabicyclo[2.2.1]hept-2-yl]-5-(2-methylpyridin-4-yloxy)-thiophene-2-carboxamide;
N-[(1S,2R,4R)-7-azabicyclo[2.2.1]hept-2-yl]-5-(6-methylpyridin-3-yloxy)-thiophene-2-carboxamide;
N-[(1S,2R,4R)-7-azabicyclo[2.2.1]hept-2-yl]-5-(5-methylpyridin-2-yloxy)-thiophene-2-carboxamide;
N-[(1S,2R,4R)-7-azabicyclo[2.2.1]hept-2-yl]-5-(2-methoxypyridin-4-yloxy)-thiophene-2-carboxamide;
N-[(1S,2R,4R)-7-azabicyclo[2.2.1]hept-2-yl]-5-(6-methoxypyridin-3-yloxy)-thiophene-2-carboxamide;
N-[(1S,2R,4R)-7-azabicyclo[2.2.1]hept-2-yl]-5-(5-methoxypyridin-2-yloxy)-thiophene-2-carboxamide;
N-[(1S,2R,4R)-7-azabicyclo[2.2.1]hept-2-yl]-5-(2-chloropyridin-4-yloxy)-thiophene-2-carboxamide;
N-[(1S,2R,4R)-7-azabicyclo[2.2.1]hept-2-yl]-5-(6-chloropyridin-3-yloxy)-thiophene-2-carboxamide;
N-[(1S,2R,4R)-7-azabicyclo[2.2.1]hept-2-yl]-5-(5-chloropyridin-2-yloxy)-thiophene-2-carboxamide;
N-[(1S,2R,4R)-7-azabicyclo[2.2.1]hept-2-yl]-5-(2-chloropyridin-4-yloxy)-thiophene-2-carboxamide;
N-[(1S,2R,4R)-7-azabicyclo[2.2.1]hept-2-yl]-5-(6-chloropyridin-3-yloxy)-thiophene-2-carboxamide;
N-[(1S,2R,4R)-7-azabicyclo[2.2.1]hept-2-yl]-5-(5-chloropyridin-2-yloxy)-thiophene-2-carboxamide;
N-[(1S,2R,4R)-7-azabicyclo[2.2.1]hept-2-yl]-5-(5-chloropyridin-3-yloxy)-thiophene-2-carboxamide;
N-[(1S,2R,4R)-7-azabicyclo[2.2.1]hept-2-yl]-5-(6-chloropyridin-2-yloxy)-thiophene-2-carboxamide;

N-[(1S,2R,4R)-7-azabicyclo[2.2.1]hept-2-yl]-5-(4-chloropyridin-2-yloxy)-thiophene-2-carboxamide;
N-[(1S,2R,4R)-7-azabicyclo[2.2.1]hept-2-yl]-5-(pyridin-4-ylsulfanyl)-thiophene-2-carboxamide;
N-[(1S,2R,4R)-7-azabicyclo[2.2.1]hept-2-yl]-5-(pyridin-3-ylsulfanyl)-thiophene-2-carboxamide;
N-[(1S,2R,4R)-7-azabicyclo[2.2.1]hept-2-yl]-5-(pyridin-2-ylsulfanyl)-thiophene-2-carboxamide;
N-[(1S,2R,4R)-7-azabicyclo[2.2.1]hept-2-yl]-5-(2-methylpyridin-4-ylsulfanyl)-thiophene-2-carboxamide;
N-[(1S,2R,4R)-7-azabicyclo[2.2.1]hept-2-yl]-5-(6-methylpyridin-3-ylsulfanyl)-thiophene-2-carboxamide;
N-[(1S,2R,4R)-7-azabicyclo[2.2.1]hept-2-yl]-5-(5-methylpyridin-2-ylsulfanyl)-thiophene-2-carboxamide;
N-[(1S,2R,4R)-7-azabicyclo[2.2.1]hept-2-yl]-5-(2-methoxypyridin-4-ylsulfanyl)-thiophene-2-carboxamide;
N-[(1S,2R,4R)-7-azabicyclo[2.2.1]hept-2-yl]-5-(6-methoxypyridin-3-ylsulfanyl)-thiophene-2-carboxamide;
N-[(1S,2R,4R)-7-azabicyclo[2.2.1]hept-2-yl]-5-(5-methoxypyridin-2-ylsulfanyl)-thiophene-2-carboxamide;
N-[(1S,2R,4R)-7-azabicyclo[2.2.1]hept-2-yl]-5-(2-chloropyridin-4-ylsulfanyl)-thiophene-2-carboxamide;
N-[(1S,2R,4R)-7-azabicyclo[2.2.1]hept-2-yl]-5-(6-chloropyridin-3-ylsulfanyl)-thiophene-2-carboxamide;
N-[(1S,2R,4R)-7-azabicyclo[2.2.1]hept-2-yl]-5-(5-chloropyridin-2-ylsulfanyl)-thiophene-2-carboxamide;
N-[(1S,2R,4R)-7-azabicyclo[2.2.1]hept-2-yl]-5-(2-chloropyridin-4-ylsulfanyl)-thiophene-2-carboxamide;
N-[(1S,2R,4R)-7-azabicyclo[2.2.1]hept-2-yl]-5-(6-chloropyridin-3-ylsulfanyl)-thiophene-2-carboxamide;
N-[(1S,2R,4R)-7-azabicyclo[2.2.1]hept-2-yl]-5-(5-chloropyridin-2-ylsulfanyl)-thiophene-2-carboxamide;
N-[(1S,2R,4R)-7-azabicyclo[2.2.1]hept-2-yl]-5-(5-chloropyridin-3-ylsulfanyl)-thiophene-2-carboxamide;
N-[(1S,2R,4R)-7-azabicyclo[2.2.1]hept-2-yl]-5-(6-chloropyridin-2-ylsulfanyl)-thiophene-2-carboxamide;
N-[(1S,2R,4R)-7-azabicyclo[2.2.1]hept-2-yl]-5-(4-chloropyridin-2-ylsulfanyl)-thiophene-2-carboxamide;
N-[(1S,2R,4R)-7-azabicyclo[2.2.1]hept-2-yl]-5-(thiophen-4-yl)-thiophene-2-carboxamide;
N-[(1S,2R,4R)-7-azabicyclo[2.2.1]hept-2-yl]-5-(5-methylthiophen-2-yl)-thiophene-2-carboxamide;
N-[(1S,2R,4R)-7-azabicyclo[2.2.1]hept-2-yl]-5-(5-methoxythiophen-2-yl)-thiophene-2-carboxamide;
N-[(1S,2R,4R)-7-azabicyclo[2.2.1]hept-2-yl]-5-(5-chlorothiophen-2-yl)-thiophene-2-carboxamide;
N-[(1S,2R,4R)-7-azabicyclo[2.2.1]hept-2-yl]-5-(2-methyl-5-trifluoromethyl-2H-pyrazole-3-yl)-thiophene-2-carboxamide;
N-[(1S,2R,4R)-7-azabicyclo[2.2.1]hept-2-yl]-5-(2-methylthiazol-4-yl)-thiophene-2-carboxamide;
N-[(1S,2R,4R)-7-azabicyclo[2.2.1]hept-2-yl]-5-[2-(3-chlorophenyl)-vinyl]-thiophene-2-carboxamide;
N-[(1S,2R,4R)-7-azabicyclo[2.2.1]hept-2-yl]-5-(2,4-difluorophenyl-sulfanyl)-thiophene-2-carboxamide;
N-[(1S,2R,4R)-7-azabicyclo[2.2.1]hept-2-yl]-5-(3-chlorophenyl-sulfanyl)-thiophene-2-carboxamide;
N-[(1S,2R,4R)-7-azabicyclo[2.2.1]hept-2-yl]-5-(3-chloro-4-fluoro-phenylsulfanyl)-thiophene-2-carboxamide;
N-[(1S,2R,4R)-7-azabicyclo[2.2.1]hept-2-yl]-5-(2,3-dichlorophenyl-sulfanyl)-thiophene-2-carboxamide;
N-[(1S,2R,4R)-7-azabicyclo[2.2.1]hept-2-yl]-5-(2,4,5-trichlorophenyl-sulfanyl)-thiophene-2-carboxamide;
N-[(1S,2R,4R)-7-azabicyclo[2.2.1]hept-2-yl]-5-(3,4-dichlorophenyl-sulfanyl)-thiophene-2-carboxamide;
N-[(1S,2R,4R)-7-azabicyclo[2.2.1]hept-2-yl]-5-phenoxy-thiophene-2-carboxamide;
N-[(1S,2R,4R)-7-azabicyclo[2.2.1]hept-2-yl]-5-(2-hydroxyphenyl)-thiophene-2-25carboxamide;
N-[(1S,2R,4R)-7-azabicyclo[2.2.1]hept-2-yl]-5-(3-hydroxyphenyl)-thiophene-2-carboxamide;
N-[(1S,2R,4R)-7-azabicyclo[2.2.1]hept-2-yl]-5-(3-fluoro-4-hydroxyphenyl)-thiophene-2-carboxamide;
N-[(1S,2R,4R)-7-azabicyclo[2.2.1]hept-2-yl]-5-(furan-4-yl)-thiophene-2-carboxamide;
N-[(1S,2R,4R)-7-azabicyclo[2.2.1]hept-2-yl]-5-(5-methylfuran-2-yl)-thiophene-2-carboxamide;
N-[(1S,2R,4R)-7-azabicyclo[2.2.1]hept-2-yl]-5-(5-methoxyfuran-2-yl)-thiophene-2-carboxamide;
N-[(1S,2R,4R)-7-azabicyclo[2.2.1]hept-2-yl]-5-(5-chlorofuran-2-yl)-thiophene-2-carboxamide;
N-[(1S,2R,4R)-7-azabicyclo[2.2.1]hept-2-yl]-5-(oxazol-2-yl)-thiophene-2-carboxamide;
N-[(1S,2R,4R)-7-azabicyclo[2.2.1]hept-2-yl]-5-(5-methyloxazol-2-yl)-thiophene-2-carboxamide;
N-[(1S,2R,4R)-7-azabicyclo[2.2.1]hept-2-yl]-5-(5-methoxyoxazol-2-yl)-thiophene-2-carboxamide;
N-[(1S,2R,4R)-7-azabicyclo[2.2.1]hept-2-yl]-5-(5-chlorooxazol-2-yl)-thiophene-2-carboxamide;
N-[(1S,2R,4R)-7-azabicyclo[2.2.1]hept-2-yl]-5-(oxazol-5-yl)-thiophene-2-carboxamide;
N-[(1S,2R,4R)-7-azabicyclo[2.2.1]hept-2-yl]-5-(2-methyloxazol-5-yl)-thiophene-2-carboxamide;
N-[(1S,2R,4R)-7-azabicyclo[2.2.1]hept-2-yl]-5-(2-methoxyoxazol-5-yl)-thiophene-2-carboxamide;
N-[(1S,2R,4R)-7-azabicyclo[2.2.1]hept-2-yl]-5-(2-chlorooxazol-5-yl)-thiophene-2-carboxamide;
N-[(1S,2R,4R)-7-azabicyclo[2.2.1]hept-2-yl]-5-(thiazol-2-yl)-thiophene-2-carboxamide;
N-[(1S,2R,4R)-7-azabicyclo[2.2.1]hept-2-yl]-5-(5-methylthiazol-2-yl)-thiophene-2-carboxamide;
N-[(1S,2R,4R)-7-azabicyclo[2.2.1]hept-2-yl]-5-(5-methoxythiazol-2-yl)-thiophene-2-carboxamide;
N-[(1S,2R,4R)-7-azabicyclo[2.2.1]hept-2-yl]-5-(5-chlorothiazol-2-yl)-thiophene-2-carboxamide;
N-[(1S,2R,4R)-7-azabicyclo[2.2.1]hept-2-yl]-5-(thiazol-5-yl)-thiophene-2-carboxamide;
N-[(1S,2R,4R)-7-azabicyclo[2.2.1]hept-2-yl]-5-(2-methylthiazol-5-yl)-thiophene-2-carboxamide;
N-[(1S,2R,4R)-7-azabicyclo[2.2.1]hept-2-yl]-5-(2-methoxythiazol-5-yl)-thiophene-2-carboxamide;
N-[(1S,2R,4R)-7-azabicyclo[2.2.1]hept-2-yl]-5-(2-chlorothiazol-5-yl)-thiophene-2-carboxamide;
N-[(1S,2R,4R)-7-azabicyclo[2.2.1]hept-2-yl]-5-(4-methylthiazol-2-yl)-thiophene-2-carboxamide;
N-[(1S,2R,4R)-7-azabicyclo[2.2.1]hept-2-yl]-5-(4-methoxythiazol-2-yl)-thiophene-2-carboxamide;
N-[(1S,2R,4R)-7-azabicyclo[2.2.1]hept-2-yl]-5-(4-chlorothiazol-2-yl)-thiophene-2-carboxamide;

N-[(1S,2R,4R)-7-azabicyclo[2.2.1]hept-2-yl]-5-(4-methyloxazol-2-yl)-thiophene-2-carboxamide;
N-[(1S,2R,4R)-7-azabicyclo[2.2.1]hept-2-yl]-5-(4-methoxyoxazol-2-yl)-thiophene-2-carboxamide;
N-[(1S,2R,4R)-7-azabicyclo[2.2.1]hept-2-yl]-5-(4-chlorooxazol-2-yl)-thiophene-2-carboxamide;
N-[(1S,2R,4R)-7-azabicyclo[2.2.1]hept-2-yl]-5-([1,3,4]thiadiazol-2-yl)-thiophene-2-carboxamide;
N-[(1S,2R,4R)-7-azabicyclo[2.2.1]hept-2-yl]-5-(5-methyl[1,3,4]thiadiazol-2-yl)-thiophene-2-carboxamide;
N-[(1S,2R,4R)-7-azabicyclo[2.2.1]hept-2-yl]-5-(5-methoxy[1,3,4]thiadiazol-2-yl)-thiophene-2-carboxamide;
N-[(1S,2R,4R)-7-azabicyclo[2.2.1]hept-2-yl]-5-(5-chloro[1,3,4]thiadiazol-2-yl)-thiophene-2-carboxamide;
N-[(1S,2R,4R)-7-azabicyclo[2.2.1]hept-2-yl]-5-([1,3,4]oxadiazol-2-yl)-thiophene-2-carboxamide;
N-[(1S,2R,4R)-7-azabicyclo[2.2.1]hept-2-yl]-5-(5-methyl[1,3,4]oxadiazol-2-yl)-thiophene-2-carboxamide;
N-[(1S,2R,4R)-7-azabicyclo[2.2.1]hept-2-yl]-5-(5-methoxy[1,3,4]oxadiazol-2-yl)-thiophene-2-carboxamide;
N-[(1S,2R,4R)-7-azabicyclo[2.2.1]hept-2-yl]-5-(5-chloro[1,3,4]oxadiazol-2-yl)-thiophene-2-carboxamide;
N-[(1S,2R,4R)-7-azabicyclo[2.2.1]hept-2-yl]-5-(thiophen-4-yloxy)-thiophene-2-carboxamide;
N-[(1S,2R,4R)-7-azabicyclo[2.2.1]hept-2-yl]-5-(5-methylthiophen-2-yloxy)-thiophene-2-carboxamide;
N-[(1S,2R,4R)-7-azabicyclo[2.2.1]hept-2-yl]-5-(5-methoxythiophen-2-yloxy)-thiophene-2-carboxamide;
N-[(1S,2R,4R)-7-azabicyclo[2.2.1]hept-2-yl]-5-(5-chlorothiophen-2-yloxy)-thiophene-2-carboxamide;
N-[(1S,2R,4R)-7-azabicyclo[2.2.1]hept-2-yl]-5-(furan-4-yloxy)-thiophene- 2-carboxamide;
N-[(1S,2R,4R)-7-azabicyclo[2.2.1]hept-2-yl]-5-(5-methylfuran-2-yloxy)-thiophene-2-carboxamide;
N-[(1S,2R,4R)-7-azabicyclo[2.2.1]hept-2-yl]-5-(5-methoxyfuran-2-yloxy)-thiophene-2-carboxamide;
N-[(1S,2R,4R)-7-azabicyclo[2.2.1]hept-2-yl]-5-(5-chlorofuran-2-yloxy)-thiophene-2-carboxamide;
N-[(1S,2R,4R)-7-azabicyclo[2.2.1]hept-2-yl]-5-(oxazol-2-yloxy)-thiophene-2-carboxamide;
N-[(1S,2R,4R)-7-azabicyclo[2.2.1]hept-2-yl]-5-(5-methyloxazol-2-yloxy)-thiophene-2-carboxamide;
N-[(1S,2R,4R)-7-azabicyclo[2.2.1]hept-2-yl]-5-(5-methoxyoxazol-2-yloxy)-thiophene-2-carboxamide;
N-[(1S,2R,4R)-7-azabicyclo[2.2.1]hept-2-yl]-5-(5-chlorooxazol-2-yloxy)-thiophene-2-carboxamide;
N-[(1S,2R,4R)-7-azabicyclo[2.2.1]hept-2-yl]-5-(oxazol-5-yloxy)-thiophene-2-carboxamide;
N-[(1S,2R,4R)-7-azabicyclo[2.2.1]hept-2-yl]-5-(2-methyloxazol-5-yloxy)-thiophene-2-carboxamide;
N-[(1S,2R,4R)-7-azabicyclo[2.2.1]hept-2-yl]-5-(2-methoxyoxazol-
N-[(1S,2R,4R)-7-azabicyclo[2.2.1]hept-2-yl]-5-(2-chlorooxazol-5-yloxy)-thiophene-2-carboxamide;
N-[(1S,2R,4R)-7-azabicyclo[2.2.1]hept-2-yl]-5-(thiazol-2-yloxy)-thiophene-2-carboxamide;
N-[(1S,2R,4R)-7-azabicyclo[2.2.1]hept-2-yl]-5-(5-methylthiazol-2-yloxy)-thiophene-2-carboxamide;
N-[(1S,2R,4R)-7-azabicyclo[2.2.1]hept-2-yl]-5-(5-methoxythiazol-2-yloxy)-thiophene-2-carboxamide;
N-[(1S,2R,4R)-7-azabicyclo[2.2.1]hept-2-yl]-5-(5-chlorothiazol-2-yloxy)-thiophene-2-carboxamide;
N-[(1S,2R,4R)-7-azabicyclo[2.2.1]hept-2-yl]-5-(thiazol-5-yloxy)-thiophene-2-carboxamide;
N-[(1S,2R,4R)-7-azabicyclo[2.2.1]hept-2-yl]-5-(2-methylthiazol-5-yloxy)-thiophene-2-carboxamide;
N-[(1S,2R,4R)-7-azabicyclo[2.2.1]hept-2-yl]-5-(2-methoxythiazol-5-yloxy)-thiophene-2-carboxamide;
N-[(1S,2R,4R)-7-azabicyclo[2.2.1]hept-2-yl]-5-(2-chlorothiazol-5-yloxy)-thiophene-2-carboxamide;
N-[(1S,2R,4R)-7-azabicyclo[2.2.1]hept-2-yl]-5-(4-methylthiazol-2-yloxy)-thiophene-2-carboxamide;
N-[(1S,2R,4R)-7-azabicyclo[2.2.1]hept-2-yl]-5-(4-methoxythiazol-2-yloxy)-thiophene-2-carboxamide;
N-[(1S,2R,4R)-7-azabicyclo[2.2.1]hept-2-yl]-5-(4-chlorothiazol-2-yloxy)-thiophene-2-carboxamide;
N-[(1S,2R,4R)-7-azabicyclo[2.2.1]hept-2-yl]-5-(4-methyloxazol-2-yloxy)-thiophene-2-carboxamide;
N-[(1S,2R,4R)-7-azabicyclo[2.2.1]hept-2-yl]-5-(4-methoxyoxazol-2-yloxy)-thiophene-2-carboxamide;
N-[(1S,2R,4R)-7-azabicyclo[2.2.1]hept-2-yl]-5-(4-chlorooxazol-2-yloxy)-thiophene-2-carboxamide;
N-[(1S,2R,4R)-7-azabicyclo[2.2.1]hept-2-yl]-5-([1,3,4]thiadiazol-2-yloxy)-thiophene-2-carboxamide;
N-[(1S,2R,4R)-7-azabicyclo[2.2.1]hept-2-yl]-5-(5-methyl[1,3,4]thiadiazol-2-yloxy)-thiophene-2-carboxamide;
N-[(1S,2R,4R)-7-azabicyclo[2.2.1]hept-2-yl]-5-(5-methoxy[1,3,4]thiadiazol-2-yloxy)-thiophene-2-carboxamide;
N-[(1S,2R,4R)-7-azabicyclo[2.2.1]hept-2-yl]-5-(5-chloro[1,3,4]thiadiazol-2-yloxy)-thiophene-2-carboxamide;
N-[(1S,2R,4R)-7-azabicyclo[2.2.1]hept-2-yl]-5-([1,3,4]oxadiazol-2-yloxy)-thiophene-2-carboxamide;
N-[(1S,2R,4R)-7-azabicyclo[2.2.1]hept-2-yl]-5-(5-methyl[1,3,4]oxadiazol-2-yloxy)-thiophene-2-carboxamide;
N-[(1S,2R,4R)-7-azabicyclo[2.2.1]hept-2-yl]-5-(5-methoxy[1,3,4]oxadiazol-2-yloxy)-thiophene-2-carboxamide;
N-[(1S,2R,4R)-7-azabicyclo[2.2.1]hept-2-yl]-5-(5-chloro[1,3,4]oxadiazol-2-yloxy)-thiophene-2-carboxamide;
N-[(1S,2R,4R)-7-azabicyclo[2.2.1]hept-2-yl]-5-(thiophen-4-ylsulfanyl)-thiophene-2-carboxamide;
N-[(1S,2R,4R)-7-azabicyclo[2.2.1]hept-2-yl]-5-(5-methylthiophen-2-ylsulfanyl)-thiophene-2-carboxamide;
N-[(1S,2R,4R)-7-azabicyclo[2.2.1]hept-2-yl]-5-(5-methoxythiophen-2-ylsulfanyl)-thiophene-2-carboxamide;
N-[(1S,2R,4R)-7-azabicyclo[2.2.1]hept-2-yl]-5-(5-chlorothiophen-2-ylsulfanyl)-thiophene-2-carboxamide;
N-[(1S,2R,4R)-7-azabicyclo[2.2.1]hept-2-yl]-5-(furan-4-ylsulfanyl)-thiophene-2-carboxamide;
N-[(1S,2R,4R)-7-azabicyclo[2.2.1]hept-2-yl]-5-(5-methylfuran-2-ylsulfanyl)-thiophene-2-carboxamide;
N-[(1S,2R,4R)-7-azabicyclo[2.2.1]hept-2-yl]-5-(5-methoxyfuran-2-ylsulfanyl)-thiophene-2-carboxamide;
N-[(1S,2R,4R)-7-azabicyclo[2.2.1]hept-2-yl]-5-(5-chlorofuran-2-ylsulfanyl)-thiophene-2-carboxamide;

N-[(1S,2R,4R)-7-azabicyclo[2.2.1]hept-2-yl]-5-(oxazol-2-ylsulfanyl)-thiophene-2-carboxamide;
N-[(1S,2R,4R)-7-azabicyclo[2.2.1]hept-2-yl]-5-(5-methyloxazol-2-ylsulfanyl)-thiophene-2-carboxamide;
N-[(1S,2R,4R)-7-azabicyclo[2.2.1]hept-2-yl]-5-(5-methoxyoxazol-2-ylsulfanyl)-thiophene-2-carboxamide;
N-[(1S,2R,4R)-7-azabicyclo[2.2.1]hept-2-yl]-5-(5-chlorooxazol-2-ylsulfanyl)-thiophene-2-carboxamide;
N-[(1S,2R,4R)-7-azabicyclo[2.2.1]hept-2-yl]-5-(oxazol-5-ylsulfanyl)-thiophene-2-carboxamide;
N-[(1S,2R,4R)-7-azabicyclo[2.2.1]hept-2-yl]-5-(2-methyloxazol-5-ylsulfanyl)-thiophene-2-carboxamide;
N-[(1S,2R,4R)-7-azabicyclo[2.2.1]hept-2-yl]-5-(2-methoxyoxazol-5-ylsulfanyl)-thiophene-2-carboxamide;
N-[(1S,2R,4R)-7-azabicyclo[2.2.1]hept-2-yl]-5-(2-chlorooxazol-5-ylsulfanyl)-thiophene-2-carboxamide;
N-[(1S,2R,4R)-7-azabicyclo[2.2.1]hept-2-yl]-5-(thiazol-2-ylsulfanyl)-thiophene-2-carboxamide;
N-[(1S,2R,4R)-7-azabicyclo[2.2.1]hept-2-yl]-5-(5-methylthiazol-2-ylsulfanyl)-thiophene-2-carboxamide;
N-[(1S,2R,4R)-7-azabicyclo[2.2.1]hept-2-yl]-5-(5-methoxythiazol-2-ylsulfanyl)-thiophene-2-carboxamide;
N-[(1S,2R,4R)-7-azabicyclo[2.2.1]hept-2-yl]-5-(5-chlorothiazol-2-ylsulfanyl)-thiophene-2-carboxamide;
N-[(1S,2R,4R)-7-azabicyclo[2.2.1]hept-2-yl]-5-(thiazol-5-ylsulfanyl)-thiophene-2-carboxamide;
N-[(1S,2R,4R)-7-azabicyclo[2.2.1]hept-2-yl]-5-(2-methylthiazol-5-ylsulfanyl)-thiophene-2-carboxamide;
N-[(1S,2R,4R)-7-azabicyclo[2.2.1]hept-2-yl]-5-(2-methoxythiazol-5-ylsulfanyl)-thiophene-2-carboxamide;
N-[(1S,2R,4R)-7-azabicyclo[2.2.1]hept-2-yl]-5-(2-chlorothiazol-5-ylsulfanyl)-thiophene-2-carboxamide;
N-[(1S,2R,4R)-7-azabicyclo[2.2.1]hept-2-yl]-5-(4-methylthiazol-2-ylsulfanyl)-thiophene-2-carboxamide;
N-[(1S,2R,4R)-7-azabicyclo[2.2.1]hept-2-yl]-5-(4-methoxythiazol-2-ylsulfanyl)-thiophene-2-carboxamide;
N-[(1S,2R,4R)-7-azabicyclo[2.2.1]hept-2-yl]-5-(4-chlorothiazol-2-ylsulfanyl)-thiophene-2-carboxamide;
N-[(1S,2R,4R)-7-azabicyclo[2.2.1]hept-2-yl]-5-(4-methyloxazol-2-ylsulfanyl)-thiophene-2-carboxamide;
N-[(1S,2R,4R)-7-azabicyclo[2.2.1]hept-2-yl]-5-(4-methoxyoxazol-2-ylsulfanyl)-thiophene-2-carboxamide;
N-[(1S,2R,4R)-7-azabicyclo[2.2.1]hept-2-yl]-5-(4-chlorooxazol-2-ylsulfanyl)-thiophene-2-carboxamide;
N-[(1S,2R,4R)-7-azabicyclo[2.2.1]hept-2-yl]-5-([1,3,4]thiadiazol-2-ylsulfanyl)-thiophene-2-carboxamide;
N-[(1S,2R,4R)-7-azabicyclo[2.2.1]hept-2-yl]-5-(5-methyl[1,3,4]thiadiazol-2-ylsulfanyl)-thiophene-2-carboxamide;
N-[(1S,2R,4R)-7-azabicyclo[2.2.1]hept-2-yl]-5-(5-methoxy[1,3,4]thiadiazol-2-ylsulfanyl)-thiophene-2-carboxamide;
N-[(1S,2R,4R)-7-azabicyclo[2.2.1]hept-2-yl]-5-(5-chloro[1,3,4]thiadiazol-2-ylsulfanyl)-thiophene-2-carboxamide;
N-[(1S,2R,4R)-7-azabicyclo[2.2.1]hept-2-yl]-5-([1,3,4]oxadiazol-2-ylsulfanyl)-thiophene-2-carboxamide;
N-[(1S,2R,4R)-7-azabicyclo[2.2.1]hept-2-yl]-5-(5-methyl[1,3,4]oxadiazol-2-ylsulfanyl)-thiophene-2-carboxamide;
N-[(1S,2R,4R)-7-azabicyclo[2.2.1]hept-2-yl]-5-(5-methoxy[1,3,4]oxadiazol-2-ylsulfanyl)-thiophene-2-carboxamide;
N-[(1S,2R,4R)-7-azabicyclo[2.2.1]hept-2-yl]-5-(5-chloro[1,3,4]oxadiazol-2-ylsulfanyl)-thiophene-2-carboxamide;
N-[(1S,2R,4R)-7-azabicyclo[2.2.1]hept-2-yl]-5-(pyrrole-2-yl)-thiophene-2-carboxamide;
N-[(1S,2R,4R)-7-azabicyclo[2.2.1]hept-2-yl]-5-(isothiazol-3-yl)-thiophene-2-carboxamide;
N-[(1S,2R,4R)-7-azabicyclo[2.2.1]hept-2-yl]-5-(isoxazol-3-yl)-thiophene-2-carboxamide;
N-[(1S,2R,4R)-7-azabicyclo[2.2.1]hept-2-yl]-5-(3H-imidazol-4-yl)-thiophene-2-carboxamide;
N-[(1S,2R,4R)-7-azabicyclo[2.2.1]hept-2-yl]-4-(4-hydroxyphenylsulfanyl)-thiophene-2-carboxamide;
N-[(1S,2R,4R)-7-azabicyclo[2.2.1]hept-2-yl]-4-(3-acetamidophenylsulfanyl)-thiophene-2-carboxamide;
N-[(1S,2R,4R)-7-azabicyclo[2.2.1]hept-2-yl]-4-(2-methanesulfonylaminophenyl)-thiophene-2-carboxamide;
N-[(1S,2R,4R)-7-azabicyclo[2.2.1]hept-2-yl]-4-(pyridin-2-yloxy)-thiophene-2-carboxamide;
N-[(1S,2R,4R)-7-azabicyclo[2.2.1]hept-2-yl]-4-(2-methylpyridin-4-yloxy)-thiophene-2-carboxamide;
N-[(1S,2R,4R)-7-azabicyclo[2.2.1]hept-2-yl]-4-(4-trifluoromethylphenyl)-thiophene-2-carboxamide;
N-[(1S,2R,4R)-7-azabicyclo[2.2.1]hept-2-yl]-4-(2-acetylphenyl)-thiophene-2-carboxamide;
N-[(1S,2R,4R)-7-azabicyclo[2.2.1]hept-2-yl]-4-chloro-5-phenyl-thiophene-2-carboxamide;
N-[(1S,2R,4R)-7-azabicyclo[2.2.1]hept-2-yl]-4-methyl-5-phenyl-thiophene-2-carboxamide;
N-[(1S,2R,4R)-7-azabicyclo[2.2.1]hept-2-yl]-4-cyano-5-phenyl-thiophene-2-carboxamide;
N-[(1S,2R,4R)-7-azabicyclo[2.2.1]hept-2-yl]-4-methoxy-5-phenyl-thiophene-2-carboxamide;
N-[(1S,2R,4R)-7-azabicyclo[2.2.1]hept-2-yl]-5-chloro-4-phenyl-thiophene-2-carboxamide;
N-[(1S,2R,4R)-7-azabicyclo[2.2.1]hept-2-yl]-5-methyl-4-phenyl-thiophene-2-carboxamide;
N-[(1S,2R,4R)-7-azabicyclo[2.2.1]hept-2-yl]-5-cyano-4-phenyl-thiophene-2-carboxamide;
N-[(1S,2R,4R)-7-azabicyclo[2.2.1]hept-2-yl]-5-methoxy-4-phenyl-thiophene-2-carboxamide;
N-[(1S,2R,4R)-7-azabicyclo[2.2.1]hept-2-yl]-4-chloro-5-bromo-thiophene-2-carboxamide;
N-[(1S,2R,4R)-7-azabicyclo[2.2.1]hept-2-yl]-4-chloro-5-methylsulfanyl-thiophene-2-carboxamide;
N-[(1S,2R,4R)-7-azabicyclo[2.2.1]hept-2-yl]-4-chloro-5-methyl-thiophene-2-carboxamide;
N-[(1S,2R,4R)-7-azabicyclo[2.2.1]hept-2-yl]-4-chloro-5-cyano-thiophene-2-carboxamide;
N-[(1S,2R,4R)-7-azabicyclo[2.2.1]hept-2-yl]-5-chloro-4-bromo-thiophene-2-carboxamide;
N-[(1S,2R,4R)-7-azabicyclo[2.2.1]hept-2-yl]-5-chloro-4-methylsulfanyl-thiophene-2-carboxamide;
N-[(1S,2R,4R)-7-azabicyclo[2.2.1]hept-2-yl]-5-chloro-4-methyl-thiophene-2-carboxamide;

N-[(1S,2R,4R)-7-azabicyclo[2.2.1]hept-2-yl]-5-chloro-4-cyano-thiophene-2-carboxamide;
N-[(1S,2R,4R)-7-azabicyclo[2.2.1]hept-2-yl]-5-(acetylamino)-furan-2-carboxamide;
N-[(1S,2R,4R)-7-azabicyclo[2.2.1]hept-2-yl]-5-trifluoromethyl-furan-2-carboxamide;
N-[(1S,2R,4R)-7-azabicyclo[2.2.1]hept-2-yl]-5-(2-bromophenyl)-furan-2-carboxamide;
N-[(1S,2R,4R)-7-azabicyclo[2.2.1]hept-2-yl]-5-(3-bromophenyl)-furan-2-carboxamide;
N-[(1S,2R,4R)-7-azabicyclo[2.2.1]hept-2-yl]-5-(2,3-dichlorophenyl)-furan-2-carboxamide;
N-[(1S,2R,4R)-7-azabicyclo[2.2.1]hept-2-yl]-5-(2,4-dichlorophenyl)-furan-2-carboxamide;
N-[(1S,2R,4R)-7-azabicyclo[2.2.1]hept-2-yl]-5-(2,5-dichlorophenyl)-furan-2-carboxamide;
N-[(1S,2R,4R)-7-azabicyclo[2.2.1]hept-2-yl]-5-(2,6-dichlorophenyl)-furan-2-carboxamide;
N-[(1S,2R,4R)-7-azabicyclo[2.2.1]hept-2-yl]-5-(3,4-dichlorophenyl)-furan-2-carboxamide;
N-[(1S,2R,4R)-7-azabicyclo[2.2.1]hept-2-yl]-5-(3,5-dichlorophenyl)-furan-2-carboxamide;
N-[(1S,2R,4R)-7-azabicyclo[2.2.1]hept-2-yl]-5-(4-amino-2-fluorophenyl)-furan-2-carboxamide;
N-[(1S,2R,4R)-7-azabicyclo[2.2.1]hept-2-yl]-5-(3-amino-2-fluorophenyl)-furan-2-carboxamide;
N-[(1S,2R,4R)-7-azabicyclo[2.2.1]hept-2-yl]-5-(4-amino-2-chlorophenyl)-furan-2-carboxamide;
N-[(1S,2R,4R)-7-azabicyclo[2.2.1]hept-2-yl]-5-(3-amino-2-chlorophenyl)-furan-2-carboxamide;
N-[(1S,2R,4R)-7-azabicyclo[2.2.1]hept-2-yl]-5-(3-aminophenyl)-furan-2-carboxamide;
N-[(1S,2R,4R)-7-azabicyclo[2.2.1]hept-2-yl]-5-(2-cyanophenyl)-furan-2-carboxamide;
N-[(1S,2R,4R)-7-azabicyclo[2.2.1]hept-2-yl]-5-(3-cyanophenyl)-furan-2-carboxamide;
N-[(1S,2R,4R)-7-azabicyclo[2.2.1]hept-2-yl]-5-(2-hydroxyphenyl)-furan-2-carboxamide;
N-[(1S,2R,4R)-7-azabicyclo[2.2.1]hept-2-yl]-5-(3-hydroxyphenyl)-furan-2-carboxamide;
N-[(1S,2R,4R)-7-azabicyclo[2.2.1]hept-2-yl]-5-(4-hydroxyphenyl)-furan-2-carboxamide;
N-[(1S,2R,4R)-7-azabicyclo[2.2.1]hept-2-yl]-5-(2-fluoro-4-methylphenyl)-furan-2-carboxamide;
N-[(1S,2R,4R)-7-azabicyclo[2.2.1]hept-2-yl]-5-(2-fluoro-3-methoxyphenyl)-furan-2-carboxamide;
N-[(1S,2R,4R)-7-azabicyclo[2.2.1]hept-2-yl]-5-(2-fluoro-4-methoxyphenyl)-furan-2-carboxamide;
N-[(1S,2R,4R)-7-azabicyclo[2.2.1]hept-2-yl]-5-(2-[(methylsulfonyl)amino]phenyl)-furan-2-carboxamide;
N-[(1S,2R,4R)-7-azabicyclo[2.2.1]hept-2-yl]-5-(3-[(methylsulfonyl)amino]phenyl)-furan-2-carboxamide;
N-[(1S,2R,4R)-7-azabicyclo[2.2.1]hept-2-yl]-5-(4-[(methylsulfonyl)amino]phenyl)-furan-2-carboxamide;
N-[(1S,2R,4R)-7-azabicyclo[2.2.1]hept-2-yl]-5-(2-([(trifluoromethyl)sulfonyl]amino)phenyl)-furan-2-carboxamide;
N-[(1S,2R,4R)-7-azabicyclo[2.2.1]hept-2-yl]-5-(3-([(trifluoromethyl)sulfonyl]amino)phenyl)-furan-2-carboxamide;
N-[(1S,2R,4R)-7-azabicyclo[2.2.1]hept-2-yl]-5-(4-([(trifluoromethyl)sulfonyl]amino)phenyl)-furan-2-carboxamide;
N-[(1S,2R,4R)-7-azabicyclo[2.2.1]hept-2-yl]-5-(2-[(phenylsulfonyl)amino]phenyl)-furan-2-carboxamide;
N-[(1S,2R,4R)-7-azabicyclo[2.2.1]hept-2-yl]-5-(3-[(phenylsulfonyl)amino]phenyl)-furan-2-carboxamide;
N-[(1S,2R,4R)-7-azabicyclo[2.2.1]hept-2-yl]-5-(4-[(phenylsulfonyl)amino]phenyl)-furan-2-carboxamide;
N-[(1S,2R,4R)-7-azabicyclo[2.2.1]hept-2-yl]-5-(2-[(methylamino)carbonyl]phenyl)-furan-2-carboxamide;
N-[(1S,2R,4R)-7-azabicyclo[2.2.1]hept-2-yl]-5-(3-[(methylamino)carbonyl]phenyl)-furan-2-carboxamide;
N-[(1S,2R,4R)-7-azabicyclo[2.2.1]hept-2-yl]-5-(4-[(methylamino)carbonyl]phenyl)-furan-2-carboxamide;
N-[(1S,2R,4R)-7-azabicyclo[2.2.1]hept-2-yl]-5-(2-[(methylamino)sulfonyl]phenyl)-furan-2-carboxamide;
N-[(1S,2R,4R)-7-azabicyclo[2.2.1]hept-2-yl]-5-(3-[(methylamino)sulfonyl]phenyl)-furan-2-carboxamide;
N-[(1S,2R,4R)-7-azabicyclo[2.2.1]hept-2-yl]-5-(4-[(methylamino)sulfonyl]phenyl)-furan-2-carboxamide;
N-[(1S,2R,4R)-7-azabicyclo[2.2.1]hept-2-yl]-5-[2-(methylamino)phenyl]-furan-2-carboxamide;
N-[(1S,2R,4R)-7-azabicyclo[2.2.1]hept-2-yl]-5-[3-(methylamino)phenyl]-furan-2-carboxamide;
N-[(1S,2R,4R)-7-azabicyclo[2.2.1]hept-2-yl]-5-[4-(methylamino)phenyl]-furan-2-carboxamide;
N-[(1S,2R,4R)-7-azabicyclo[2.2.1]hept-2-yl]-5-[2-(ethylamino)phenyl]-furan-2-carboxamide;
N-[(1S,2R,4R)-7-azabicyclo[2.2.1]hept-2-yl]-5-[3-(ethylamino)phenyl]-furan-2-carboxamide;
N-[(1S,2R,4R)-7-azabicyclo[2.2.1]hept-2-yl]-5-[4-(ethylamino)phenyl]-furan-2-carboxamide;
N-[(1S,2R,4R)-7-azabicyclo[2.2.1]hept-2-yl]-5-(2-acetylphenyl)-furan-2-carboxamide;
N-[(1S,2R,4R)-7-azabicyclo[2.2.1]hept-2-yl]-5-(3-acetylphenyl)-furan-2-carboxamide;
N-[(1S,2R,4R)-7-azabicyclo[2.2.1]hept-2-yl]-5-(4-acetylphenyl)-furan-2-carboxamide;
N-[(1S,2R,4R)-7-azabicyclo[2.2.1]hept-2-yl]-5-[2-(methylthio)phenyl]-furan-2-carboxamide;
N-[(1S,2R,4R)-7-azabicyclo[2.2.1]hept-2-yl]-5-[3-(methylthio)phenyl]-furan-2-carboxamide;
N-[(1S,2R,4R)-7-azabicyclo[2.2.1]hept-2-yl]-5-[4-(methylthio)phenyl]-furan-2-carboxamide;
N-[(1S,2R,4R)-7-azabicyclo[2.2.1]hept-2-yl]-5-[2-(phenylthio)phenyl]-furan-2-carboxamide;
N-[(1S,2R,4R)-7-azabicyclo[2.2.1]hept-2-yl]-5-[3-(phenylthio)phenyl]-furan-2-carboxamide;
N-[(1S,2R,4R)-7-azabicyclo[2.2.1]hept-2-yl]-5-[4-(phenylthio)phenyl]-furan-2-carboxamide;
N-[(1S,2R,4R)-7-azabicyclo[2.2.1]hept-2-yl]-5-(2-phenoxyphenyl)-furan-2-carboxamide;
N-[(1S,2R,4R)-7-azabicyclo[2.2.1]hept-2-yl]-5-(3-phenoxyphenyl)-furan-2-carboxamide;
N-[(1S,2R,4R)-7-azabicyclo[2.2.1]hept-2-yl]-5-(4-phenoxyphenyl)-furan-2-carboxamide;
N-[(1S,2R,4R)-7-azabicyclo[2.2.1]hept-2-yl]-5-(2-anilinophenyl)-furan-2-carboxamide;
N-[(1S,2R,4R)-7-azabicyclo[2.2.1]hept-2-yl]-5-(3-anilinophenyl)-furan-2-carboxamide;
N-[(1S,2R,4R)-7-azabicyclo[2.2.1]hept-2-yl]-5-(4-anilinophenyl)-furan-2-carboxamide;

N-[(1S,2R,4R)-7-azabicyclo[2.2.1]hept-2-yl]-5-(phenylthio)-furan-2-carboxamide;
N-[(1S,2R,4R)-7-azabicyclo[2.2.1]hept-2-yl]-5-[(2-fluorophenyl)thio]-furan-2-carboxamide;
N-[(1S,2R,4R)-7-azabicyclo[2.2.1]hept-2-yl]-5-[(3-fluorophenyl)thio]-furan-2-carboxamide;
N-[(1S,2R,4R)-7-azabicyclo[2.2.1]hept-2-yl]-5-[(4-fluorophenyl)thio]-furan-2-carboxamide;
N-[(1S,2R,4R)-7-azabicyclo[2.2.1]hept-2-yl]-5-[(2-chlorophenyl)thio]-furan-2-carboxamide;
N-[(1S,2R,4R)-7-azabicyclo[2.2.1]hept-2-yl]-5-[(3-chlorophenyl)thio]-furan-2-carboxamide;
N-[(1S,2R,4R)-7-azabicyclo[2.2.1]hept-2-yl]-5-[(4-chlorophenyl)thio]-furan-2-carboxamide;
N-[(1S,2R,4R)-7-azabicyclo[2.2.1]hept-2-yl]-5-(2-fluorophenoxy)-furan-2-carboxamide;
N-[(1S,2R,4R)-7-azabicyclo[2.2.1]hept-2-yl]-5-(3-fluorophenoxy)-furan-2-carboxamide;
N-[(1S,2R,4R)-7-azabicyclo[2.2.1]hept-2-yl]-5-(4-fluorophenoxy)-furan-2-carboxamide;
N-[(1S,2R,4R)-7-azabicyclo[2.2.1]hept-2-yl]-5-(2-chlorophenoxy)-furan-2-carboxamide;
N-[(1S,2R,4R)-7-azabicyclo[2.2.1]hept-2-yl]-5-(3-chlorophenoxy)-furan-2-carboxamide;
N-[(1S,2R,4R)-7-azabicyclo[2.2.1]hept-2-yl]-5-(4-chlorophenoxy)-furan-2-carboxamide;
N-[(1S,2R,4R)-7-azabicyclo[2.2.1]hept-2-yl]-5-pyridin-2-yl-furan-2-carboxamide;
N-[(1S,2R,4R)-7-azabicyclo[2.2.1hept-2-yl]-5-pyridin-3-yl-furan-2-carboxamide;
N-[(1S,2R,4R)-7-azabicyclo[2.2.1]hept-2-yl]-5-pyridin-4-yl-furan-2-carboxamide;
N-[(1S,2R,4R)-7-azabicyclo[2.2.1]hept-2-yl]-5-(3-fluoropyridin-2-yl)-furan-2-carboxamide;
N-[(1S,2R,4R)-7-azabicyclo[2.2.1]hept-2-yl]-5-(4-fluoropyridin-2-yl)-furan-2-carboxamide;
N-[(1S,2R,4R)-7-azabicyclo[2.2.1]hept-2-yl]-5-(5-fluoropyridin-2-yl)-furan-2-carboxamide;
N-[(1S,2R,4R)-7-azabicyclo[2.2.1]hept-2-yl]-5-(6-fluoropyridin-2-yl)-furan-2-carboxamide;
N-[(1S,2R,4R)-7-azabicyclo[2.2.1]hept-2-yl]-5-(2-fluoropyridin-3-yl)-furan-2-carboxamide;
N-[(1S,2R,4R)-7-azabicyclo[2.2.1]hept-2-yl]-5-(4-fluoropyridin-3-yl)-furan-2-carboxamide;
N-[(1S,2R,4R)-7-azabicyclo[2.2.1]hept-2-yl]-5-(5-fluoropyridin-3-yl)-furan-2-carboxamide;
N-[(1S,2R,4R)-7-azabicyclo[2.2.1]hept-2-yl]-5-(6-fluoropyridin-3-yl)-furan-2-carboxamide;
N-[(1S,2R,4R)-7-azabicyclo[2.2.1]hept-2-yl]-5-(2-fluoropyridin-4-yl)-furan-2-carboxamide;
N-[(1S,2R,4R)-7-azabicyclo[2.2.1]hept-2-yl]-5-(3-fluoropyridin-4-yl)-furan-2-carboxamide;
N-[(1S,2R,4R)-7-azabicyclo[2.2.1]hept-2-yl]-5-(3-chloropyridin-2-yl)-furan-2-carboxamide;
N-[(1S,2R,4R)-7-azabicyclo[2.2.1]hept-2-yl]-5-(4-chloropyridin-2-yl)-furan-2-carboxamide;
N-[(1S,2R,4R)-7-azabicyclo[2.2.1]hept-2-yl]-5-(5-chloropyridin-2-yl)-furan-2-carboxamide;
N-[(1S,2R,4R)-7-azabicyclo[2.2.1]hept-2-yl]-5-(6-chloropyridin-2-yl)-furan-2-carboxamide;
N-[(1S,2R,4R)-7-azabicyclo[2.2.1]hept-2-yl]-5-(2-chloropyridin-3-yl)-furan-2-carboxamide;
N-[(1S,2R,4R)-7-azabicyclo[2.2.1]hept-2-yl]-5-(4-chloropyridin-3-yl)-furan-2-carboxamide;
N-[(1S,2R,4R)-7-azabicyclo[2.2.1]hept-2-yl]-5-(5-chloropyridin-3-yl)-furan-2-carboxamide;
N-[(1S,2R,4R)-7-azabicyclo[2.2.1]hept-2-yl]-5-(6-chloropyridin-3-yl)-furan-2-carboxamide;
N-[(1S,2R,4R)-7-azabicyclo[2.2.1]hept-2-yl]-5-(2-chloropyridin-4-yl)-furan-2-carboxamide;
N-[(1S,2R,4R)-7-azabicyclo[2.2.1]hept-2-yl]-5-(3-chloropyridin-4-yl)-furan-2-carboxamide;
N-[(1S,2R,4R)-7-azabicyclo[2.2.1]hept-2-yl]-5-(2-piperidin-1-ylphenyl)-furan-2-carboxamide;
N-[(1S,2R,4R)-7-azabicyclo[2.2.1]hept-2-yl]-5-(3-piperidin-1-ylphenyl)-furan-2-carboxamide;
N-[(1S,2R,4R)-7-azabicyclo[2.2.1]hept-2-yl]-5-(4-piperidin-1-ylphenyl)-furan-2-carboxamide;
N-[(1S,2R,4R)-7-azabicyclo[2.2.1]hept-2-yl]-5-(2-morpholin-4-ylphenyl)-furan-2-carboxamide;
N-[(1S,2R,4R)-7-azabicyclo[2.2.1]hept-2-yl]-5-(3-morpholin-4-ylphenyl)-furan-2-carboxamide;
N-[(1S,2R,4R)-7-azabicyclo[2.2.1]hept-2-yl]-5-(4-morpholin-4-ylphenyl)-furan-2-carboxamide;
N-[(1S,2R,4R)-7-azabicyclo[2.2.1]hept-2-yl]-5-(2-pyrrolidin-1-ylphenyl)-furan-2-carboxamide;
N-[(1S,2R,4R)-7-azabicyclo[2.2.1]hept-2-yl]-5-(3-pyrrolidin-1-ylphenyl)-furan-2-carboxamide;
N-[(1S,2R,4R)-7-azabicyclo[2.2.1]hept-2-yl]-5-(4-pyrrolidin-1-ylphenyl)-furan-2-carboxamide;
N-[(1S,2R,4R)-7-azabicyclo[2.2.1]hept-2-yl]-5-[2-(1H-pyrrol-2-yl)phenyl]-furan-2-carboxamide;
N-[(1S,2R,4R)-7-azabicyclo[2.2.1]hept-2-yl]-5-[3-(1H-pyrrol-2-yl)phenyl]-furan-2-carboxamide;
N-[(1S,2R,4R)-7-azabicyclo[2.2.1]hept-2-yl]-5-[4-(1H-pyrrol-2-yl)phenyl]-furan-2-carboxamide;
N-[(1S,2R,4R)-7-azabicyclo[2.2.1]hept-2-yl]-5-[2-(2-furyl)phenyl]-furan-2-carboxamide;
N-[(1S,2R,4R)-7-azabicyclo[2.2.1]hept-2-yl]-5-[2-(3-furyl)phenyl]-furan-2-carboxamide;
N-[(1S,2R,4R)-7-azabicyclo[2.2.1]hept-2-yl]-5-[2-(5-methyl-2-furyl)phenyl]-furan-2-carboxamide;
N-[(1S 2R,4R)-7-azabicyclo[2.2.1]hept-2-yl]-5-[3-(2-furyl)phenyl]-furan-2-carboxamide;
N-[(1S,2R,4R)-7-azabicyclo[2.2.1]hept-2-yl]-5-[3-(3-furyl)phenyl]-furan-2-carboxamide;
N-[(1S,2R,4R)-7-azabicyclo[2.2.1]hept-2-yl]-5-[3-(5-methyl-2-furyl)phenyl]-furan-2-carboxamide;
N-[(1S,2R,4R)-7-azabicyclo[2.2.1]hept-2-yl]-5-[4-(2-furyl)phenyl]-furan-2-carboxamide;
N-[(1S,2R,4R)-7-azabicyclo[2.2.1]hept-2-yl]-5-[4-(3-furyl)phenyl]-furan-2-carboxamide;
N-[(1S,2R,4R)-7-azabicyclo[2.2.1]hept-2-yl]-5-[4-(5-methyl-2-furyl)phenyl]-furan-2-carboxamide;
N-[(1S,2R,4R)-7-azabicyclo[2.2.1]hept-2-yl]-5-[2-(1,3-thiazol-2-yl)phenyl]-furan-2-carboxamide;
N-[(1S,2R,4R)-7-azabicyclo[2.2.1]hept-2-yl]-5-[3-(1,3-thiazol-2-yl)phenyl]-furan-2-carboxamide;
N-[(1S,2R,4R)-7-azabicyclo[2.2.1]hept-2-yl]-5-[4-(1,3-thiazol-2-yl)phenyl]-furan-2-carboxamide;
N-[(1S,2R,4R)-7-azabicyclo[2.2.1]hept-2-yl]-5-[2-(1,3-oxazol-2-yl)phenyl]-furan-2-carboxamide;
N-[(1S,2R,4R)-7-azabicyclo[2.2.1]hept-2-yl]-5-[3-(1,3-oxazol-2-yl)phenyl]-furan-2-carboxamide;

N-[(1S,2R,4R)-7-azabicyclo[2.2.1]hept-2-yl]-5-[4-(1,3-oxazol-2-yl)phenyl]-furan-2-carboxamide;
N-[(1S,2R,4R)-7-azabicyclo[2.2.1]hept-2-yl]-5-(2-isothiazol-5-ylphenyl)-furan-2-carboxamide;
N-[(1S,2R,4R)-7-azabicyclo[2.2.1]hept-2-yl]-5-(3-isothiazol-5-ylphenyl)-furan-2-carboxamide;
N-[(1S,2R,4R)-7-azabicyclo[2.2.1]hept-2-yl]-5-(4-isothiazol-5-ylphenyl)-furan-2-carboxamide;
N-[(1S,2R,4R)-7-azabicyclo[2.2.1]hept-2-yl]-5-[4-(1H-indol-2-yl)phenyl]-furan-2-carboxamide;
N-[(1S,2R,4R)-7-azabicyclo[2.2.1]hept-2-yl]-5-[4-(1H-indol-3-yl)phenyl]-furan-2-carboxamide;
N-[(1S,2R,4R)-7-azabicyclo[2.2.1]hept-2-yl]-5-(1H-indol-5-yl)-furan-2-carboxamide;
N-[(1S,2R,4R)-7-azabicyclo[2.2.1]hept-2-yl]-5-(1H-indol-6-yl)-furan-2-carboxamide;
N-[(1S,2R,4R)-7-azabicyclo[2.2.1]hept-2-yl]-5-(2-chlorophenyl)-furan-2-carboxamide;
N-[(1S,2R,4R)-7-azabicyclo[2.2.1]hept-2-yl]-5-(3-chlorophenyl)-furan-2-carboxamide;
N[(1S,2R,4R)-7-azabicyclo[2.2.1]hept-2-yl]-5-(4-bromophenyl)-furan-2-carboxamide;
N-[(1S,2R,4R)-7-azabicyclo[2.2.1]hept-2-yl]-5-[2-(trifluoromethyl)-phenyl]-furan-2-carboxamide;
N-[(1S,2R,4R)-7-azabicyclo[2.2.1]hept-2-yl]-5-[3-(trifluoromethyl)-phenyl]-furan-2-carboxamide;
N-[(1S,2R,4R)-7-azabicyclo[2.2.1]hept-2-yl]-5-(2,4-difluorophenyl)-furan-2-carboxamide;
N-[(1S,2R,4R)-7-azabicyclo[2.2.1]hept-2-yl]-5-(2,5-difluorophenyl)-furan-2-carboxamide;
N-[(1S,2R,4R)-7-azabicyclo[2.2.1]hept-2-yl]-5-(2-methoxyphenyl)-furan-2-carboxamide;
N-[(1S,2R,4R)-7-azabicyclo[2.2.1]hept-2-yl]-5-(3-methoxyphenyl)-furan-2-carboxamide;
N-[(1S,2R,4R)-7-azabicyclo[2.2.1]hept-2-yl]-5-[3-(trifluoromethoxy)phenyl]-furan-2-carboxamide;
N-[(1S,2R,4R)-7-azabicyclo[2.2.1]hept-2-yl]-5-[2-chloro-5-(trifluoromethyl)phenyl]-furan-2-carboxamide;
N-[(1S,2R,4R)-7-azabicyclo[2.2.1]hept-2-yl]-5-(4-fluoro-3-methylphenyl)-furan-2-carboxamide;
N-[(1S,2R,4R)-7-azabicyclo[2.2.1]hept-2-yl]-5-(4-cyanophenyl)-furan-2-carboxamide;
N-[(1S,2R,4R)-7-azabicyclo[2.2.1]hept-2-yl]-5-thien-2-yl-furan-2-carboxamide;
N-[(1S,2R,4R)-7-azabicyclo[2.2.1]hept-2-yl]-5-thien-3-yl-furan-2-carboxamide;
N-[(1S,2R,4R)-7-azabicyclo[2.2.1]hept-2-yl]-5-nitro-furan-2-carboxamide;
N-[(1S,2R,4R)-7-azabicyclo(2.2.1]hept-2-yl]-4,5-dimethyl-furan-2-carboxamide;
N-[(1S,2R,4R)-7-azabicyclo[2.2.1]hept-2-yl]-5-(4-chloro-2-nitrophenyl)-furan-2-carboxamide;
N-[(1S,2R,4R)-7-azabicyclo[2.2.1]hept-2-yl]-5-(4-methyl-2-nitrophenyl)-furan-2-carboxamide;
N-[(1S,2R,4R)-7-azabicyclo[2.2.1]hept-2-yl]-5-(2,3-difluorophenyl)-furan-2-carboxamide;
N-[(1S,2R,4R)-7-azabicyclo[2.2.1]hept-2-yl]-5-(3,4-difluorophenyl)-furan-2-carboxamide;
N-[(1S,2R,4R)-7-azabicyclo[2.2.1]hept-2-yl]-5-(3,5-difluorophenyl)-furan-2-carboxamide;
N-[(1S,2R,4R)-7-azabicyclo[2.2.1]hept-2-yl]-5-(4-methoxy-phenyl)-furan-2-carboxamide;
N-[(1S,2R,4R)-7-azabicyclo[2.2.1]hept-2-yl]-5-(2-methylphenyl)-furan-2-carboxamide;
N-[(1S,2R,4R)-7-azabicyclo[2.2.1]hept-2-yl]-5-(3-methylphenyl)-furan-2-carboxamide;
N-[(1S,2R,4R)-7-azabicyclo[2.2.1]hept-2-yl]-5-[2-(trifluoromethoxy)phenyl]-furan-2-carboxamide;
N-[(1S,2R,4R)-7-azabicyclo[2.2.1]hept-2-yl]-5-[4-(trifluoromethoxy)phenyl]-furan-2-carboxamide;
N-[(1S,2R,4R)-7-azabicyclo[2.2.1]hept-2-yl]-5-(4-tert-butylphenyl)-furan-2-carboxamide;
N-[(1S,2R,4R)-7-azabicyclo[2.2.1]hept-2-yl]-5-(1-benzothien-2-yl)-furan-2-carboxamide;
N-[(1S,2R,4R)-7-azabicyclo[2.2.1]hept-2-yl]-5-quinolin-3-yl-furan-2-carboxamide;
N-[(1S,2R,4R)-7-azabicyclo[2.2.1]hept-2-yl]-5-(4-ethylphenyl)-furan-2-carboxamide;
N-[(1S,2R,4R)-7-azabicyclo[2.2.1]hept-2-yl]-5-(4-isopropylphenyl)-furan-2-carboxamide;
N-[(1S,2R,4R)-7-azabicyclo[2.2.1]hept-2-yl]-5-(3-fluoro-4-methoxyphenyl)-furan-2-carboxamide;
N-[(1S,2R,4R)-7-azabicyclo[2.2.1]hept-2-yl]-5-(1-benzofuran-2-yl)-furan-2-carboxamide;
5-(2-aminophenyl)—N-[(1S,2R,4R)-7-azabicyclo[2.2.1]hept-2-yl]-furan-2-carboxamide;
5-(2-amino-4-methylphenyl)—N-[(1S,2R,4R)-7-azabicyclo[2.2.1]hept-2-yl]-furan-2-carboxamide;
N-[(1S,2R,4R)-7-azabicyclo[2.2.1]hept-2-yl]-5-(phenylethynyl)-furan-2-carboxamide;
N-[(1S,2R,4R)-7-azabicyclo[2.2.1]hept-2-yl]-5-phenoxy-furan-2-carboxamide;
N-[(1S,2R,4R)-7-azabicyclo[2.2.1]hept-2-yl]-5-(methylthio)-1,3-thiazole-2-carboxamide;
N-[(1S,2R,4R)-7-azabicyclo[2.2.1]hept-2-yl]-5-chloro-1,3-thiazole-2-carboxamide;
N-[(1S,2R,4R)-7-azabicyclo[2.2.1]hept-2-yl]-5-bromo-1,3-thiazole-2-carboxamide;
N-[(1S,2R,4R)-7-azabicyclo[2.2.1]hept-2-yl]-5-(phenylthio)-1,3-thiazole-2-carboxamide;
N-[(1S,2R,4R)-7-azabicyclo[2.2.1]hept-2-yl]-5-[(2-fluorophenyl)thio]-1,3-thiazole-2-carboxamide;
N-[(1S,2R,4R)-7-azabicyclo[2.2.1]hept-2-yl]-5-[(3-fluorophenyl)thio]-1,3-thiazole-2-carboxamide;
N-[(1S,2R,4R)-7-azabicyclo[2.2.1]hept-2-yl]-5-[(4-fluorophenyl)thio]-1,3-thiazole-2-carboxamide;
N-[(1S,2R,4R)-7-azabicyclo[2.2.1]hept-2-yl]-5-[(2-chlorophenyl)thio]-1,3-thiazole-2-carboxamide;
N-[(1S,2R,4R)-7-azabicyclo[2.2.1]hept-2-yl]-5-[(3-chlorophenyl)thio]-1,3-thiazole-2-carboxamide;
N-[(1S,2R,4R)-7-azabicyclo[2.2.1]hept-2-yl]-5-[(4-chlorophenyl)thio]-1,3-thiazole-2-carboxamide;
N-[(1S,2R,4R)-7-azabicyclo[2.2.1]hept-2-yl]-5-phenoxy-1,3-thiazole-2-carboxamide;
N-[(1S,2R,4R)-7-azabicyclo[2.2.1]hept-2-yl]-5-(2-fluorophenoxy)-1,3-thiazole-2-carboxamide;
N-[(1S,2R,4R)-7-azabicyclo[2.2.1]hept-2-yl]-5-(3-fluorophenoxy)-1,3-thiazole-2-carboxamide;
N-[(1S,2R,4R)-7-azabicyclo[2.2.1]hept-2-yl]-5-(4-fluorophenoxy)-1,3-thiazole-2-carboxamide;
N-[(1S,2R,4R)-7-azabicyclo[2.2.1]hept-2-yl]-5-(2-chlorophenoxy)-1,3-thiazole-2-carboxamide;
N-[(1S,2R,4R)-7-azabicyclo[2.2.1]hept-2-yl]-5-(3-chlorophenoxy)-1,3-thiazole-2-carboxamide;

N-[(1S,2R,4R)-7-azabicyclo[2.2.1]hept-2-yl]-5-(4-chlorophenoxy)-1,3-thiazole-2-carboxamide;

N-[(3R)-1-azabicyclo[2.2.2]oct-3-yl)]-5-thien-3-yl-1,3-thiazole-2-carboxamide;

N-[(1S,2R,4R)-7-azabicyclo[2.2.1]hept-2-yl]-5-(2,4-difluorophenyl)-1,3-thiazole-2-carboxamide;

N-[(1S,2R,4R)-7-azabicyclo[2.2.1]hept-2-yl]-5-(3,5-difluorophenyl)-1,3-thiazole-2-carboxamide;

N-[(1S,2R,4R)-7-azabicyclo[2.2.1]hept-2-yl]-5-(2,4-dichlorophenyl)-1,3-thiazole-2-carboxamide;

N-[(1S,2R,4R)-7-azabicyclo[2.2.1]hept-2-yl]-5-(3,5-dichlorophenyl)-1,3-thiazole-2-carboxamide;

N-[(1S,2R,4R)-7-azabicyclo[2.2.1]hept-2-yl]-5-(2-bromophenyl)-1,3-thiazole-2-carboxamide;

N-[(1S,2R,4R)-7-azabicyclo[2.2.1]hept-2-yl]-5-(3-bromophenyl)-1,3-thiazole-2-carboxamide;

N-[(1S,2R,4R)-7-azabicyclo[2.2.1]hept-2-yl]-5-(2-cyanophenyl)-1,3-thiazole-2-carboxamide;

N-[(1S,2R,4R)-7-azabicyclo[2.2.1]hept-2-yl]-5-(3-cyanophenyl)-1,3-thiazole-2-carboxamide;

N-[(1S,2R,4R)-7-azabicyclo[2.2.1]hept-2-yl]-5-(4-cyanophenyl)-1,3-thiazole-2-carboxamide;

N-[(1S,2R,4R)-7-azabicyclo[2.2.1]hept-2-yl]-5-(2-hydroxyphenyl)-1,3-thiazole-2-carboxamide;

N-[(1S,2R,4R)-7-azabicyclo[2.2.1]hept-2-yl]-5-(3-hydroxyphenyl)-1,3-thiazol-2-carboxamide;

N-[(1S,2R,4R)-7-azabicyclo[2.2.1]hept-2-yl]-5-(4-hydroxyphenyl)-1,3-thiazole-2-carboxamide;

N-[(1S,2R,4R)-7-azabicyclo[2.2.1]hept-2-yl]-5-(2-nitrophenyl)-1,3-thiazole-2-carboxamide;

N-[(1S,2R,4R)-7-azabicyclo[2.2.1]hept-2-yl]-5-(4-nitrophenyl)-1,3-thiazole-2-carboxamide;

N-[(1S,2R,4R)-7-azabicyclo[2.2.1]hept-2-yl]-5-(2-methylphenyl)-1,3-thiazole-2-carboxamide;

N-[(1S,2R,4R)-7-azabicyclo[2.2.1]hept-2-yl]-5-(3-methylphenyl)-1,3-thiazole-2-carboxamide;

N-[(1S,2R,4R)-7-azabicyclo[2.2.1]hept-2-yl]-5-(4-methylphenyl)-1,3-thiazole-2-carboxamide;

N-[(1S,2R,4R)-7-azabicyclo[2.2.1]hept-2-yl]-5-(2-aminophenyl)-1,3-thiazole-2-carboxamide;

N-[(1S,2R,4R)-7-azabicyclo[2.2.1]hept-2-yl]-5-(3-aminophenyl)-1,3-thiazole-2-carboxamide;

N-[(1S,2R,4R)-7-azabicyclo[2.2.1]hept-2-yl]-5-(4-aminophenyl)-1,3-thiazole-2-carboxamide;

N-[(1S,2R,4R)-7-azabicyclo[2.2.1]hept-2-yl]-5-[(2-(acetylamino)phenyl]-1,3-thiazole-2-carboxamide;

N-[(1S,2R,4R)-7-azabicyclo[2.2.1]hept-2-yl]-5-[3-(acetylamino)phenyl]-1,3-thiazole-2-carboxamide;

N-[(1S,2R,4R)-7-azabicyclo[2.2.1]hept-2-yl]-5-[4-(acetylamino)phenyl]-1,3-thiazole-2-carboxamide;

N-[(1S,2R,4R)-7-azabicyclo[2.2.1]hept-2-yl]-5-(pyridin-2-yl)-1,3-thiazole-2-carboxamaide;

N-[(1S,2R,4R)-7-azabicyclo[2.2.1]hept-2-yl]-5-(pyridin-3-yl)-1,3-thiazole-2-carboxamide;

N-[(1S,2R,4R)-7-azabicyclo[2.2.1]hept-2-yl]-5-(pyridin-4-yl)-1,3-thiazole-2-carboxamide;

N-[(1S,2R,4R)-7-azabicyclo[2.2.1]hept-2-yl]-5-(3-fluoropyridin-2-yl)-1,3-thiazole-2-carboxamide;

N-[(1S,2R,4R)-7-azabicyclo[2.2.1]hept-2-yl]-5-(4-fluoropyridin-2-yl)-1,3-thiazole-2-carboxamide;

N-[(1S,2R,4R)-7-azabicyclo[2.2.1]hept-2-yl]-5-(5-fluoropyridin-2-yl)-1,3-thiazole-2-carboxamide;

N-[(1S,2R,4R)-7-azabicyclo[2.2.1]hept-2-yl]-5-(6-fluoropyridin-2-yl)-1,3-thiazole-2-carboxamide;

N-[(1S,2R,4R)-7-azabicyclo[2.2.1]hept-2-yl]-5-(2-fluoropyridin-3-yl)-1,3-thiazole-2-carboxamide;

N-[(1S,2R,4R)-7-azabicyclo[2.2.1]hept-2-yl]-5-(4-fluoropyridin-3-yl)-1,3-thiazole-2-carboxamide;

N-[(1S,2R,4R)-7-azabicyclo[2.2.1]hept-2-yl]-5-(5-fluoropyridin-3-yl)-1,3-thiazole-2-carboxamide;

N-[(1S,2R,4R)-7-azabicyclo[2.2.1]hept-2-yl]-5-(6-fluoropyridin-3-yl)-1,3-thiazole-2-carboxamide;

N-[(1S,2R,4R)-7-azabicyclo[2.2.1]hept-2-yl]-5-(2-fluoropyridin-4-yl)-1,3-thiazole-2-carboxamide;

N-[(1S,2R,4R)-7-azabicyclo[2.2.1]hept-2-yl]-5-[(2-methoxyphenyl)thio]-1,3-thiazole-2-carboxamide;

N-[(1S,2R,4R)-7-azabicyclo[2.2.1]hept-2-yl]-5-[(3-methoxyphenyl)thio]-1,3-thiazole-2-carboxamide;

N-[(1S,2R,4R)-7-azabicyclo[2.2.1]hept-2-yl]-5-[(4-methoxyphenyl)thio]-1,3-thiazole-2-carboxamide;

N-[(1S,2R,4R)-7-azabicyclo[2.2.1]hept-2-yl]-5-[(2-methylphenyl)thio]-1,3-thiazole-2-carboxamide;

N-[(1S,2R,4R)-7-azabicyclo[2.2.1]hept-2-yl]-5-[(3-methylphenyl)thio]-1,3-thiazole-2-carboxamide;

N-[(1S,2R,4R)-7-azabicyclo[2.2.1]hept-2-yl]-5-[(4-methylphenyl)thio]-1,3-thiazole-2-carboxamide;

N-[(1S,2R,4R)-7-azabicyclo[2.2.1]hept-2-yl]-5-([4-(acetylamino)phenyl]thio)-1,3-thiazole-2-carboxamide;

N-[(1S,2R,4R)-7-azabicyclo[2.2.1]hept-2-yl]-5-[(4-aminophenyl)thio]-1,3-thiazole-2-carboxamide;

N-[(1S,2R,4R)-7-azabicyclo[2.2.1]hept-2-yl]-5-[(4-hydroxyphenyl)thio]-1,3-thiazole-2-carboxamide;

N-[(1S,2R,4R)-7-azabicyclo[2.2.1]hept-2-yl]-5-(2-methylphenoxy)-1,3-thiazole-2-carboxamide;

N-[(1S,2R,4R)-7-azabicyclo[2.2.1]hept-2-yl]-5-(3-methylphenoxy)-1,3-thiazole-2-carboxamide;

N-[(1S,2R,4R)-7-azabicyclo[2.2.1]hept-2-yl]-5-(4-methylphenoxy)-1,3-thiazole-2-carboxamide;

N-[(1S,2R,4R)-7-azabicyclo[2.2.1]hept-2-yl]-5-(2-methoxyphenoxy)-1,3-thiazole-2-carboxamide;

N-[(1S,2R,4R)-7-azabicyclo[2.2.1]hept-2-yl]-5-(3-methoxyphenoxy)-1,3-thiazole-2-carboxamide;

N-[(1S,2R,4R)-7-azabicyclo[2.2.1]hept-2-yl]-5-(4-methoxyphenoxy)-1,3-thiazole-2-carboxamide;

N-[(1S,2R,4R)-7-azabicyclo[2.2.1]hept-2-yl]-5-(4-hydroxyphenoxy)-1,3-thiazole-2-carboxamide;

N-[(1S,2R,4R)-7-azabicyclo[2.2.1]hept-2-yl]-5-(4-aminophenoxy)-1,3-thiazole-2-carboxamide;

N-[(1S,2R,4R)-7-azabicyclo[2.2.1]hept-2-yl]-5-[4-(acetylamino)phenoxy]-1,3-thiazole-2-carboxamide;

N-[(1S,2R,4R)-7-azabicyclo[2.2.1]hept-2-yl]-5-(2-fluorophenyl)-4-methyl-1,3-thiazole-2-carboxamide;

N-[(1S,2R,4R)-7-azabicyclo[2.2.1]hept-2-yl]-5-(3-fluorophenyl)-4-methyl-1,3-thiazole-2-carboxamide;

N-[(1S,2R,4R)-7-azabicyclo[2.2.1]hept-2-yl]-5-(2-chlorophenyl)-4-methyl-1,3-thiazole-2-carboxamide;

N-[(1S,2R,4R)-7-azabicyclo[2.2.1]hept-2-yl]-5-(3-chlorophenyl)-4-methyl-1,3-thiazole-2-carboxamide;

N-[(1S,2R,4R)-7-azabicyclo[2.2.1]hept-2-yl]-5-(2-methoxyphenyl)-4-methyl-1,3-thiazole-2-carboxamide;

N-[(1S,2R,4R)-7-azabicyclo[2.2.1]hept-2-yl]-5-(3-methoxyphenyl)-4-methyl-1,3-thiazole-2-carboxamide;

N-[(1S,2R,4R)-7-azabicyclo[2.2.1]hept-2-yl]-4-methyl-5-thien-2-yl-1,3-thiazole-2-carboxamide, N-[(1S,2R,4R)-7-azabicyclo[2.2.1]hept-2-yl]-4-methyl-5-phenyl-1,3-thiazole-2-carboxamide;

N-[(1S,2R,4R)-7-azabicyclo[2.2.1]hept-2-yl]-5-phenyl-1,3-thiazole-2-carboxamide;

N-[(1S,2R,4R)-7-azabicyclo[2.2.1]hept-2-yl]-5-(4-bromophenyl)-1,3-thiazole-2-carboxamide;

N-[(1S,2R,4R)-7-azabicyclo[2.2.1]hept-2-yl]-5-(3-nitrophenyl)-1,3-thiazole-2-carboxamide;

N-[(1S,2R,4R)-7-azabicyclo[2.2.1]hept-2-yl]-5-(3-methoxyphenyl)-1,3-thiazole-2-carboxamide;

N-[(1S,2R,4R)-7-azabicyclo[2.2.1]hept-2-yl]-5-(2-chlorophenyl)-1,3-thiazole-2-carboxamide;

N-[(1S,2R,4R)-7-azabicyclo[2.2.1]hept-2-yl]-5-(4-fluorophenyl)-1,3-thiazole-2-carboxamide;

N-[(1S,2R,4R)-7-azabicyclo[2.2.1]hept-2-yl]-5-(2-methoxyphenyl)-1,3-thiazole-2-carboxamide;

N-[(1S,2R,4R)-7-azabicyclo[2.2.1]hept-2-yl]-5-(4-chlorophenyl)-1,3-thiazole-2-carboxamide;

N-[(1S,2R,4R)-7-azabicyclo[2.2.1]hept-2-yl]-5-methyl-1,3-thiazole-2-carboxamide;

N-[(1S,2R,4R)-7-azabicyclo[2.2.1]hept-2-yl]-5-(3-chlorophenyl)-1,3-thiazole-2-carboxamide;

N-[(1S,2R,4R)-7-azabicyclo[2.2.1]hept-2-yl]-5-(2-fluorophenyl)-1,3-thiazole-2-carboxamide;

N-[(1S,2R,4R)-7-azabicyclo[2.2.1]hept-2-yl]-5-(3-fluorophenyl)-1,3-thiazole-2-carboxamide;

N-[(1S,2R,4R)-7-azabicyclo[2.2.1]hept-2-yl]-5-thien-2-yl-1,3-thiazole-2-carboxamide;

N-[(1S,2R,4R)-7-azabicyclo[2.2.1]hept-2-yl]-2-(phenylsulfanyl)-1,3-thiazole-5-carboxamide;

N-[(1S,2R,4R)-7-azabicyclo[2.2.1]hept-2-yl]-2-[(4-chlorophenyl)-sulfanyl]-1,3-thiazole-5-carboxamide;

N-[(1S,2R,4R)-7-azabicyclo[2.2.1]hept-2-yl]-2-phenoxy-1,3-thiazole-5-carboxamide;

N-[(1S,2R,4R)-7-azabicyclo[2.2.1]hept-2-yl]-2-[(4-fluorophenyl)-sulfanyl]-1,3-thiazole-5-carboxamide;

N-[(1S,2R,4R)-7-azabicyclo[2.2.1]hept-2-yl]-2-(methylsulfanyl)-1,3-thiazole-5-carboxamide;

N-[(1S,2R,4R)-7-azabicyclo[2.2.1]hept-2-yl]-2-(4-chlorophenoxy)-1,3-thiazole-5-carboxamide;

N-[(1S,2R,4R)-7-azabicyclo[2.2.1]hept-2-yl]-2,4-dimethyl-1,3-thiazole-5-carboxamide;

N-[(1S,2R,4R)-7-azabicyclo[2.2.1]hept-2-yl]-2-(3-fluorophenyl)-1,3-thiazole-5-carboxamide;

N-[(1S,2R,4R)-7-azabicyclo[2.2.1]hept-2-yl]-2-(4-fluorophenyl)-1,3-thiazole-5-carboxamide;

N-[(1S,2R,4R)-7-azabicyclo[2.2.1]hept-2-yl]-2-(2-hydroxyphenyl)-1,3-thiazole-5-carboxamide;

N-[(1S,2R,4R)-7-azabicyclo[2.2.1]hept-2-yl]-2-(4-methylphenyl)-1,3-thiazole-5-carboxamide;

N-[(1S,2R,4R)-7-azabicyclo[2.2.1]hept-2-yl]-2-[4-(benzyloxy)phenyl]-1,3-thiazole-5-carboxamide;

N-[(1S,2R,4R)-7-azabicyclo[2.2.1]hept-2-yl]-4-methyl-2-phenyl-1,3-thiazole-5-carboxamide;

N-[(1S,2R,4R)-7-azabicyclo[2.2.1]hept-2-yl]-2-(4-chlorophenyl)-4-methyl-1,3-thiazole-5-carboxamide;

N-[(1S,2R,4R)-7-azabicyclo[2.2.1]hept-2-yl]-4-methyl-2-pyridin-2-yl-1,3-thiazole-5-carboxamide;

N-[(1S,2R,4R)-7-azabicyclo[2.2.1]hept-2-yl]-4-methyl-2-pyridin-4-yl-1,3-thiazole-5-carboxamide;

N-[(1S,2R,4R)-7-azabicyclo[2.2.1]hept-2-yl]-2-(methylamino)-1,3-thiazole-5-carboxamide;

N-[(1S,2R,4R)-7-azabicyclo[2.2.1]hept-2-yl]-2-(2,3-difluorophenyl)-1,3-thiazole-5-carboxamide;

N-[(1S,2R,4R)-7-azabicyclo[2.2.1]hept-2-yl]-2-(2,4-difluorophenyl)-1,3-thiazole-5-carboxamide;

N-[(1S,2R,4R)-7-azabicyclo[2.2.1]hept-2-yl]-2-(2,5-difluorophenyl)-1,3-thiazole-5-carboxamide;

N-[(1S,2R,4R)-7-azabicyclo[2.2.1]hept-2-yl]-2-(2,6-difluorophenyl)-1,3-thiazole-5-carboxamide;

N-[(1S,2R,4R)-7-azabicyclo[2.2.1]hept-2-yl]-2-(3,4-difluorophenyl)-1,3-thiazole-5-carboxamide;

N-[(1S,2R,4R)-7-azabicyclo[2.2.1]hept-2-yl]-2-(3,5-difluorophenyl)-1,3-thiazole-5-carboxamide;

N-[(1S,2R,4R)-7-azabicyclo[2.2.1]hept-2-yl]-2-(2-chlorophenyl)-1,3-thiazole-5-carboxamide;

N-[(1S,2R,4R)-7-azabicyclo[2.2.1]hept-2-yl]-2-(3-chlorophenyl)-1,3-thiazole-5-carboxamide;

N-[(1S,2R,4R)-7-azabicyclo[2.2.1]hept-2-yl]-2-(4-chlorophenyl)-1,3-thiazole-5-carboxamide;

N-[(1S,2R,4R)-7-azabicyclo[2.2.1]hept-2-yl]-2-(2-bromophenyl)-1,3-thiazole-5-carboxamide;

N-[(1S,2R,4R)-7-azabicyclo[2.2.1]hept-2-yl]-2-(3-bromophenyl)-1,3-thiazole-5-carboxamide;

N-[(1S,2R,4R)-7-azabicyclo[2.2.1]hept-2-yl]-2-(4-bromophenyl)-1,3-thiazole-5-carboxamide;

N-[(1S,2R,4R)-7-azabicyclo[2.2.1]hept-2-yl]-2-(2-cyanophenyl)-1,3-thiazole-5-carboxamide;

N-[(1S,2R,4R)-7-azabicyclo[2.2.1]hept-2-yl]-2-(3-cyanophenyl)-1,3-thiazole-5-carboxamide;

N-[(1S,2R,4R)-7-azabicyclo[2.2.1]hept-2-yl]-2-(4-cyanophenyl)-1,3-thiazole-5-carboxamide;

N-[(1S,2R,4R)-7-azabicyclo[2.2.1]hept-2-yl]-2-(2-nitrophenyl)-1,3-thiazole-5-carboxamide;

N-[(1S,2R,4R)-7-azabicyclo[2.2.1]hept-2-yl]-2-(3-nitrophenyl)-1,3-thiazole-5-carboxamide;

N-[(1S,2R,4R)-7-azabicyclo[2.2.1]hept-2-yl]-2-(4-nitrophenyl)-1,3-thiazole-5-carboxamide;

N-[(1S,2R,4R)-7-azabicyclo[2.2.1]hept-2-yl]-2-(2-methylphenyl)-1,3-thiazole-5-carboxamide;

N-[(1S,2R,4R)-7-azabicyclo[2.2.1]hept-2-yl]-2-(3-methylphenyl)-1,3-thiazole-5-carboxamide;

N-[(1S,2R,4R)-7-azabicyclo[2.2.1]hept-2-yl]-2-(2-aminophenyl)-1,3-thiazole-5-carboxamide;

N-[(1S,2R,4R)-7-azabicyclo[2.2.1]hept-2-yl]-2-(3-aminophenyl)-1,3-thiazole-5-carboxamide;

N-[(1S,2R,4R)-7-azabicyclo[2.2.1]hept-2-yl]-2-(4-aminophenyl)-1,3-thiazole-5-carboxamide;

N-[(1S,2R,4R)-7-azabicyclo[2.2.1]hept-2-yl]-2-[2-(methylamino)phenyl]-1,3-thiazole-5-carboxamide;

N-[(1S,2R,4R)-7-azabicyclo[2.2.1]hept-2-yl]-2-[3-(methylamino)phenyl]-1,3-thiazole-5-carboxamide;

N-[(1S,2R,4R)-7-azabicyclo[2.2.1]hept-2-yl]-2-[4-(methylamino)phenyl]-1,3-thiazole-5-carboxamide;

N-[(1S,2R,4R)-7-azabicyclo[2.2.1]hept-2-yl]-2-[2-(acetylamino)phenyl]-1,3-thiazole-5-carboxamide;

N-[(1S,2R,4R)-7-azabicyclo[2.2.1]hept-2-yl]-2-[3-(acetylamino)phenyl]-1,3-thiazole-5-carboxamide;

N-[(1S,2R,4R)-7-azabicyclo[2.2.1]hept-2-yl]-2-[4-(acetylamino)phenyl]-1,3-thiazole-5-carboxamide;

N-[(1S,2R,4R)-7-azabicyclo[2.2.1]hept-2-yl]-2-(2-[(trifluoroacetyl)amino]phenyl)-1,3-thiazole-5-carboxamide;

N-[(1S,2R,4R)-7-azabicyclo[2.2.1]hept-2-yl]-2-(3-[(trifluoroacetyl)amino]phenyl)-1,3-thiazole-5-carboxamide;
N-[(1S,2R,4R)-7-azabicyclo[2.2.1]hept-2-yl]-2-(4-[(trifluoroacetyl)amino]phenyl)-1,3-thiazole-5-carboxamide;
N-[(1S,2R,4R)-7-azabicyclo[2.2.1]hept-2-yl]-2-(2-[(methylsulfonyl)amino]phenyl)-1,3-thiazole-5-carboxamide;
N-[(1S,2R,4R)-7-azabicyclo[2.2.1]hept-2-yl]-2-(3-[(methylsulfonyl)amino]phenyl)-1,3-thiazole-5-carboxamide;
N-[(1S,2R,4R)-7-azabicyclo[2.2.1]hept-2-yl]-2-(4-[(methylsulfonyl)amino]phenyl)-1,3-thiazole-5-carboxamide;
N-[(1S,2R,4R)-7-azabicyclo[2.2.1]hept-2-yl]-2-(3-hydroxyphenyl)-1,3-thiazole-5-carboxamide;
N-[(1S,2R,4R)-7-azabicyclo[2.2.1]hept-2-yl]-2-(4-hydroxyphenyl)-1,3-thiazole-5-carboxamide;
N-[(1S,2R,4R)-7-azabicyclo[2.2.1]hept-2-yl]-2-(2-methoxyphenyl)-1,3-thiazole-5-carboxamide;
N-[(1S,2R,4R)-7-azabicyclo[2.2.1]hept-2-yl]-2-(3-methoxyphenyl)-1,3-thiazole-5-carboxamide;
N-[(1S,2R,4R)-7-azabicyclo[2.2.1]hept-2-yl]-2-(4-methoxyphenyl)-1,3-thiazole-5-carboxamide;
N-[(1S,2R,4R)-7-azabicyclo[2.2.1]hept-2-yl]-2-[2-(trifluoromethoxy)phenyl]-1,3-thiazole-5-carboxamide;
N-[(1S,2R,4R)-7-azabicyclo[2.2.1]hept-2-yl]-2-[3-(trifluoromethoxy)phenyl]-1,3-thiazole-5-carboxamide;
N-[(1S,2R,4R)-7-azabicyclo[2.2.1]hept-2-yl]-2-[4-(trifluoromethoxy)phenyl]-1,3-thiazole-5-carboxamide;
N-[(1S,2R,4R)-7-azabicyclo[2.2.1]hept-2-yl]-2-pyridin-2-yl-1,3-thiazole-5-carboxamide;
N-[(1S,2R,4R)-7-azabicyclo[2.2.1]hept-2-yl]-2-pyridin-3-yl-1,3-thiazole-5-carboxamide;
N-[(1S,2R,4R)-7-azabicyclo[2.2.1]hept-2-yl]-2-pyridin-4-yl-1,3-thiazole-5-carboxamide;
N-[(1S,2R,4R)-7-azabicyclo[2.2.1]hept-2-yl]-2-(6-fluoropyridin-2-yl)-1,3-thiazole-5-carboxamide;
N-[(1S,2R,4R)-7-azabicyclo[2.2.1]hept-2-yl]-2-(5-fluoropyridin-2-yl)-1,3-thiazole-5-carboxamide;
N-[(1S,2R,4R)-7-azabicyclo[2.2.1]hept-2-yl]-2-(4-fluoropyridin-2-yl)-1,3-thiazole-5-carboxamide;
N-[(1S,2R,4R)-7-azabicyclo[2.2.1]hept-2-yl]-2-(3-fluoropyridin-2-yl)-1,3-thiazole-5-carboxamide;
N-[(1S,2R,4R)-7-azabicyclo[2.2.1]hept-2-yl]-2-(2-fluoropyridin-2-yl)-1,3-thiazole-5-carboxamide;
N-[(1S,2R,4R)-7-azabicyclo[2.2.1]hept-2-yl]-2-(6-fluoropyridin-3-yl)-1,3-thiazole-5-carboxamide;
N-[(1S,2R,4R)-7-azabicyclo[2.2.1]hept-2-yl]-2-(5-fluoropyridin-3-yl)-1,3-thiazole-5-carboxamide;
N-[(1S,2R,4R)-7-azabicyclo[2.2.1]hept-2-yl]-2-(4-fluoropyridin-3-yl)-1,3-thiazole-5-carboxamide;
N-[(1S,2R,4R)-7-azabicyclo[2.2.1]hept-2-yl]-2-(2-fluoropyridin-3-yl)-1,3-thiazole-5-carboxamide;
N-[(1S,2R,4R)-7-azabicyclo[2.2.1]hept-2-yl]-2-(2-fluoropyridin-4-yl)-1,3-thiazole-5-carboxamide;
N-[(1S,2R,4R)-7-azabicyclo[2.2.1]hept-2-yl]-2-(3-fluoropyridin-4-yl)-1,3-thiazole-5-carboxamide;
N-[(1S,2R,4R)-7-azabicyclo[2.2.1]hept-2-yl]-5-(phenylsulfanyl)-1,3,4-thiadiazole-2-carboxamide;
N-[(1S,2R,4R)-7-azabicyclo[2.2.1]hept-2-yl]-5-phenoxy-1,3,4-thiadiazole-2-carboxamide;
N-[(1S,2R,4R)-7-azabicyclo[2.2.1]hept-2-yl]-5-[(4-chlorophenyl)-sulfanyl]-1,3,4-thiadiazole-2-carboxamide;
N-[(1S,2R,4R)-7-azabicyclo[2.2.1]hept-2-yl]-5-(4-fluorophenoxy)-1,3,4-thiadiazole-2-carboxamide;
N-[(1S,2R,4R)-7-azabicyclo[2.2.1]hept-2-yl]-5-(4-chlorophenoxy)-1,3,4-thiadiazole-2-carboxamide;
N-[(1S,2R,4R)-7-azabicyclo[2.2.1]hept-2-yl]-5-[(3-fluorophenyl)-sulfanyl]-1,3,4-thiadiazole-2-carboxamide;
N-[(1S,2R,4R)-7-azabicyclo[2.2.1]hept-2-yl]-5-[(2-chlorophenyl)-sulfanyl]-1,3,4-thiadiazole-2-carboxamide;
N-[(1S,2R,4R)-7-azabicyclo[2.2.1]hept-2-yl]-5-[(4-fluorophenyl)-sulfanyl]-1,3,4-thiadiazole-2-carboxamide;
N-[(1S,2R,4R)-7-azabicyclo[2.2.1]hept-2-yl]-5-[(3-chlorophenyl)-sulfanyl]-1,3,4-thiadiazole-2-carboxamide;
N-[(1S,2R,4R)-7-azabicyclo[2.2.1]hept-2-yl]-5-phenyl-1,3,4-oxadiazole-2-carboxamide;
N-[(1S,2R,4R)-7-azabicyclo[2.2.1]hept-2-yl]-5-(methylthio)-1,3,4-oxadiazole-2-carboxamide;
N-[(1S,2R,4R)-7-azabicyclo[2.2.1]hept-2-yl]-5-(3-chlorophenyl)-1,3-oxazole-2-carboxamide;
N-[(1S,2R,4R)-7-azabicyclo[2.2.1]hept-2-yl]-5-(3-methoxyphenyl)-1,3-oxazole-2-carboxamide;
N-[(1S,2R,4R)-7-azabicyclo[2.2.1]hept-2-yl]-5-(3-nitrophenyl)-1,3-oxazole-2-carboxamide;
N-[(1S,2R,4R)-7-azabicyclo[2.2.1]hept-2-yl]-5-(4-methoxyphenyl)-1,3-oxazole-2-carboxamide;
N-[(1S,2R,4R)-7-azabicyclo[2.2.1]hept-2-yl]-5-(2-nitrophenyl)-1,3-oxazole-2-carboxamide;
N-[(1S,2R,4R)-7-azabicyclo[2.2.1]hept-2-yl]-5-(2-methoxyphenyl)-1,3-oxazole-2-carboxamide;
N-[(1S,2R,4R)-7-azabicyclo[2.2.1]hept-2-yl]-5-(4-fluorophenyl)-1,3-oxazole-2carboxamide;
N-[(1S,2R,4R)-7-azabicyclo[2.2.1]hept-2-yl]-5-(2-chlorophenyl)-1,3-oxazole-2-carboxamide;
N-[(1S,2R,4R)-7-azabicyclo[2.2.1]hept-2-yl]-5-(3-cyanophenyl)-1,3-oxazole-2-carboxamide;
N-[(1S,2R,4R)-7-azabicyclo[2.2.1]hept-2-yl]-5-(4-bromophenyl)-1,3-oxazole-2-carboxamide;
N-[(1S,2R,4R)-7-azabicyclo[2.2.1]hept-2-yl]-5-phenylsulfanyl-1,3-oxazole-2-carboxamide;
N-[(1S,2R,4R)-7-azabicyclo[2.2.1]hept-2-yl]-5-(2-fluorophenylsulfanyl)-1,3-oxazole-2-carboxamide;
N-[(1S,2R,4R)-7-azabicyclo[2.2.1]hept-2-yl]-5-(3-fluorophenylsulfanyl)-1,3-oxazole-2-carboxamide;
N-[(1S,2R,4R)-7-azabicyclo[2.2.1]hept-2-yl]-5-(4-fluorophenylsulfanyl)-1,3-oxazole-2-carboxamide;
N-[(1S,2R,4R)-7-azabicyclo[2.2.1]hept-2-yl]-5-(3,4-difluorophenylsulfanyl)-1,3-oxazole-2-carboxamide;
N-[(1S,2R,4R)-7-azabicyclo[2.2.1]hept-2-yl]-5-(2,4-difluorophenylsulfanyl)-1,3-oxazole-2-carboxamide;
N-[(1S,2R,4R)-7-azabicyclo[2.2.1]hept-2-yl]-5-(3,5-difluorophenylsulfanyl)-1,3-oxazole-2-carboxamaide;
N-[(1S,2R,4R)-7-azabicyclo[2.2.1]hept-2-yl]-5-(2-chlorophenylsulfanyl)-1,3-oxazole-2-carboxamide;

N-[(1S,2R,4R)-7-azabicyclo[2.2.1]hept-2-yl]-5-(3-chlorophenylsulfanyl)-1,3-oxazole-2-carboxamide;
N-[(1S,2R,4R)-7-azabicyclo[2.2.1]hept-2-yl]-5-(4-chlorophenylsulfanyl)-1,3-oxazole-2-carboxamide;
N-[(1S,2R,4R)-7-azabicyclo[2.2.1]hept-2-yl]-5-(3,4-dichlorophenylsulfanyl)-1,3-oxazole-2-carboxamide;
N-[(1S,2R,4R)-7-azabicyclo[2.2.1]hept-2-yl]-5-(2,4-dichlorophenysulfanyl)-1,3-oxazole-2-carboxamide;
N-[(1S,2R,4R)-7-azabicyclo[2.2.1]hept-2-yl]-5-(3,5-dichlorophenylsulfanyl)-1,3-oxazole-2-carboxamide;
N-[(1S,2R,4R)-7-azabicyclo[2.2.1]hept-2-yl]-5-(2-fluorophenyl)-1,3-oxazole-2-carboxamide;
N-[(1S,2R,4R)-7-azabicyclo[2.2.1]hept-2-yl]-5-(3-fluorophenyl)-1,3-oxazole-2-carboxamide;
N-[(1S,2R,4R)-7-azabicyclo[2.2.1]hept-2-yl]-5-(3,4-difluorophenyl)-1,3-oxazole-2-carboxamide;
N-[(1S,2R,4R)-7-azabicyclo[2.2.1]hept-2-yl]-5-(2,4-difluorophenyl)-1,3-oxazole-2-carboxamide;
N-[(1S,2R,4R)-7-azabicyclo[2.2.1]hept-2-yl]-5-(3,5-difluorophenyl)-1,3-oxazole-2-carboxamide;
N-[(1S,2R,4R)-7-azabicyclo[2.2.1]hept-2-yl]-5-(4-chlorophenyl)-1,3-oxazole-2-carboxamide;
N-[(1S,2R,4R)-7-azabicyclo[2.2.1]hept-2-yl]-5-(3,4-dichlorophenyl)-1,3-oxazole-2-carboxamide;
N-[(1S,2R,4R)-7-azabicyclo[2.2.1]hept-2-yl]-5-(2,4-dichlorophenyl)-1,3-oxazole-2-carboxamide;
N-[(1S,2R,4R)-7-azabicyclo[2.2.1]hept-2-yl]-5-(3,5-dichlorophenyl)-1,3-oxazole-2-carboxamide;
N-[(1S,2R,4R)-7-azabicyclo[2.2.1]hept-2-yl]-5-(2-bromophenyl)-1,3-oxazole-2-carboxamide;
N-[(1S,2R,4R)-7-azabicyclo[2.2.1]hept-2-yl]-5-(3-bromophenyl)-1,3-oxazole-2-carboxamide;
N-[(1S,2R,4R)-7-azabicyclo[2.2.1]hept-2-yl]-5-(2-cyanophenyl)-1,3-oxazole-2-carboxamide;
N-[(1S,2R,4R)-7-azabicyclo[2.2.1]hept-2-yl]-5-(4-cyanophenyl)-1,3-oxazole-2-carboxamide;
N-[(1S,2R,4R)-7-azabicyclo[2.2.1]hept-2-yl]-5-(2-hydroxyphenyl)-1,3-oxazole-2-carboxamide;
N-[(1S,2R,4R)-7-azabicyclo[2.2.1]hept-2-yl]-5-(3-hydroxyphenyl)-1,3-oxazole-2-carboxamide;
N-[(1S,2R,4R)-7-azabicyclo[2.2.1]hept-2-yl]-5-(4-hydroxyphenyl)-1,3-oxazole-2-carboxamide;
N-[(1S,2R,4R)-7-azabicyclo[2.2.1]hept-2-yl]-5-(4-nitrophenyl)-1,3-oxazole-2-carboxamide;
N-[(1S,2R,4R)-7-azabicyclo[2.2.1]hept-2-yl]-5-(2-methylphenyl)-1,3-oxazole-2-carboxamide;
N-[(1S,2R,4R)-7-azabicyclo[2.2.1]hept-2-yl]-5-(3-methylphenyl)-1,3-oxazole-2-carboxamide;
N-[(1S,2R,4R)-7-azabicyclo[2.2.1]hept-2-yl]-5-(4-methylphenyl)-1,3-oxazole-2-carboxamide;
N-[(1S,2R,4R)-7-azabicyclo[2.2.1]hept-2-yl]-5-(2-methylaminophenyl)-1,3-oxazole-2-carboxamide;
N-[(1S,2R,4R)-7-azabicyclo[2.2.1]hept-2-yl]-5-(3-methylaminophenyl)-1,3-oxazole-2-carboxamide;
N-[(1S,2R,4R)-7-azabicyclo[2.2.1]hept-2-yl]-5-(4-methylaminophenyl)-1,3-oxazole-2-carboxamide;
N-[(1S,2R,4R)-7-azabicyclo[2.2.1]hept-2-yl]-5-(2-aminophenyl)-1,3-oxazole-2-carboxamide;
N-[(1S,2R,4R)-7-azabicyclo[2.2.1]hept-2-yl]-5-(3-aminophenyl)-1,3-oxazole-2-carboxamide;
N-[(1S,2R,4R)-7-azabicyclo[2.2.1]hept-2-yl]-5-(4-aminophenyl)-1,3-oxazole-2-carboxamide;
N-[(1S,2R,4R)-7-azabicyclo[2.2.1]hept-2-yl]-5-[2-(acetylamino)phenyl]-1,3-oxazole-2-carboxamide;
N-[(1S,2R,4R)-7-azabicyclo[2.2.1]hept-2-yl]-5-[3-(acetylamino)phenyl]-1,3-oxazole-2-carboxamide;
N-[(1S,2R,4R)-7-azabicyclo[2.2.1]hept-2-yl]-5-[4-(acetylamino)phenyl]-1,3-oxazole-2-carboxamide;
N-[(1S,2R,4R)-7-azabicyclo[2.2.1]hept-2-yl]-5-(pyridin-2-yl)-1,3-oxazole-2-carboxamide;
N-[(1S,2R,4R)-7-azabicyclo[2.2.1]hept-2-yl]-5-(pyridin-3-yl)-1,3-oxazole-2-carboxamide;
N-[(1S,2R,4R)-7-azabicyclo[2.2.1]hept-2-yl]-5-(pyridin-4-yl)-1,3-oxazole-2-carboxamide;
N-[(1S,2R,4R)-7-azabicyclo[2.2.1]hept-2-yl]-5-(3-fluoropyridin-2-yl)-1,3-oxazole-2-carboxamide;
N-[(1S,2R,4R)-7-azabicyclo[2.2.1]hept-2-yl]-5-(4-fluoropyridin-2-yl)-1,3-oxazole-2-carboxamide;
N-[(1S,2R,4R)-7-azabicyclo[2.2.1]hept-2-yl]-5-(5-fluoropyridin-2-yl)-1,3-oxazole-2-carboxamide;
N-[(1S,2R,4R)-7-azabicyclo[2.2.1]hept-2-yl]-5-(6-fluoropyridin-2-yl)-1,3-oxazole-2-carboxamide;
N-[(1S,2R,4R)-7-azabicyclo[2.2.1]hept-2-yl]-5-(2-fluoropyridin-3-yl)-1,3-oxazole-2-carboxamide;
N-[(1S,2R,4R)-7-azabicyclo[2.2.1]hept-2-yl]-5-(4-fluoropyridin-3-yl)-1,3-oxazole-2-carboxamide;
N-[(1S,2R,4R)-7-azabicyclo[2.2.1]hept-2-yl]-5-(5-fluoropyridin-3-yl)-1,3-oxazole-2-carboxamide;
N-[(1S,2R,4R)-7-azabicyclo[2.2.1]hept-2-yl]-5-(6-fluoropyridin-3-yl)-1,3-oxazole-2-carboxamide;
N-[(1S,2R,4R)-7-azabicyclo[2.2.1]hept-2-yl]-5-(2-fluoropyridin-4-yl)-1,3-oxazole-2-carboxamide;
N-[(1S,2R,4R)-7-azabicyclo[2.2.1]hept-2-yl]-5-(2-fluoropyridin-3-yl)-1,3-oxazole-2-carboxamide;
N-[(1S,2R,4R)-7-azabicyclo[2.2.1]hept-2-yl]-5-phenoxy-1,3-oxazole-2-carboxamide;
N-[(1S,2R,4R)-7-azabicyclo[2.2.1]hept-2-yl]-5-(2-fluorophenoxy)-1,3-oxazole-2-carboxamide;
N-[(1S,2R,4R)-7-azabicyclo[2.2.1]hept-2-yl]-5-(3-fluorophenoxy)-1,3-oxazole-2-carboxamide;
N-[(1S,2R,4R)-7-azabicyclo[2.2.1]hept-2-yl]-5-(4-fluorophenoxy)-1,3-oxazole-2-carboxamide;
N-[(1S,2R,4R)-7-azabicyclo[2.2.1]hept-2-yl]-5-(3,4-difluorophenoxy)-1,3-oxazole-2-carboxamide;
N-[(1S,2R,4R)-7-azabicyclo[2.2.1]hept-2-yl]-5-(2,4-difluorophenoxy)-1,3-oxazole-2-carboxamide;
N-[(1S,2R,4R)-7-azabicyclo[2.2.1]hept-2-yl]-5-(3,5-difluorophenoxy)-1,3-oxazole-2-carboxamide;
N-[(1S,2R,4R)-7-azabicyclo[2.2.1]hept-2-y]-5-(2-chlorophenoxy)-1,3-oxazole-2-carboxamide;
N-[(1S,2R,4R)-7-azabicyclo[2.2.1]hept-2-yl]-5-(3-chlorophenoxy)-1,3-oxazole-2-carboxamide;
N-[(1S,2R,4R)-7-azabicyclo[2.2.1]hept-2-yl]-5-(4-chlorophenoxy)-1,3-oxazole-2-carboxamide;
N-[(1S,2R,4R)-7-azabicyclo[2.2.1]hept-2-yl]-5-(3,4-dichlorophenoxy)-1,3-oxazole-2-carboxamide;
N-[(1S,2R,4R)-7-azabicyclo[2.2.1]hept-2-yl]-5-(2,4-dichlorophenoxy)-1,3-oxazole-2-carboxamide;
N-[(1S,2R,4R)-7-azabicyclo[2.2.1]hept-2-yl]-5-(3,5-dichlorophenoxy)-1,3-oxazole-2-carboxamide;
N-[(1S,2R,4R)-7-azabicyclo[2.2.1]hept-2-yl]-2-phenyl-1,3-oxazole-5-carboxamide;
N-[(1S,2R,4R)-7-azabicyclo[2.2.1]hept-2-yl]-1-methyl-5-phenyl-1H-pyrrole-2-carboxamide;

N-[(1S,2R,4R)-7-azabicyclo[2.2.1]hept-2-yl]-5-bromo-1-methyl-1H-pyrrole-2-carboxamide;
N-[(1S,2R,4R)-7-azabicyclo[2.2.1]hept-2-yl]-5-[2-(methylthio)phenyl]-1-methyl-1H-pyrrole-2-carboxamide;
N-[(1S,2R,4R)-7-azabicyclo[2.2.1]hept-2-yl]-5-[4-(methylthio)phenyl]-1-methyl-1H-pyrrole-2-carboxamide;
N-[(1S,2R,4R)-7-azabicyclo[2.2.1]hept-2-yl]-5-phenyl-1H-pyrrole-2-carboxamide;
N-[(1S,2R,4R)-7-azabicyclo[2.2.1]hept-2-yl]-5-(2-fluorophenyl)-1-methyl-1H-pyrrole-2-carboxamide;
N-[(1S,2R,4R)-7-azabicyclo[2.2.1]hept-2-yl]-5-(3-fluorophenyl)-1-methyl-1H-pyrrole-2-carboxamide;
N-[(1S,2R,4R)-7-azabicyclo[2.2.1]hept-2-yl]-5-(4-fluorophenyl)-1-methyl-1H-pyrrole-2-carboxamide;
N-[(1S,2R,4R)-7-azabicyclo[2.2.1]hept-2-yl]-5-(2,3-difluorophenyl)-1-methyl-1H-pyrrole-2-carboxamide;
N-[(1S,2R,4R)-7-azabicyclo[2.2.1]hept-2-yl]-5-(2,4-difluorophenyl)-1-methyl-1H-pyrrole-2-carboxamide;
N-[(1S,2R,4R)-7-azabicyclo[2.2.1]hept-2-yl]-5-(2,6-difluorophenyl)-1-methyl-1H-pyrrole-2-carboxamide;
N-[(1S,2R,4R)-7-azabicyclo[2.2.1]hept-2-yl]-5-(3,4-difluorophenyl)-1-methyl-1H-pyrrole-2-carboxamide;
N-[(1S,2R,4R)-7-azabicyclo[2.2.1]hept-2-yl]-5-(3,5-difluorophenyl)-1-methyl-1H-pyrrole-2-carboxamide;
N-[(1S,2R,4R)-7-azabicyclo[2.2.1]hept-2-yl]-5-(2,4,6-trifluorophenyl)-1-methyl-1H-pyrrole-2-carboxamide;
N-[(1S,2R,4R)-7-azabicyclo[2.2.1]hept-2-yl]-5-(2-chlorophenyl)-1-methyl-1H-pyrrole-2-carboxamide;
N-[(1S,2R,4R)-7-azabicyclo[2.2.1]hept-2-yl]-5-(3-chlorophenyl)-1-methyl-1H-pyrrole-2-carboxamide;
N-[(1S,2R,4R)-7-azabicyclo[2.2.1]hept-2-yl]-5-(4-chlorophenyl)-1-methyl-1H-pyrrole-2-carboxamide;
N-[(1S,2R,4R)-7-azabicyclo[2.2.1]hept-2-yl]-5-(2,4-dichlorophenyl)-1-methyl-1H-pyrrole-2-carboxamide;
N-[(1S,2R,4R)-7-azabicyclo[2.2.1]hept-2-yl]-5-(3,4-dichlorophenyl)-1-methyl-1H-pyrrole-2-carboxamide;
N-[(1S,2R,4R)-7-azabicyclo[2.2.1]hept-2-yl]-5-(3,5-dichlorophenyl)-1-methyl-1H-pyrrole-2-carboxamide;
N-[(1S,2R,4R)-7-azabicyclo[2.2.1]hept-2-yl]-5-(2-bromophenyl)-1-methyl-1H-pyrrole-2-carboxamide;
N-[(1S,2R,4R)-7-azabicyclo[2.2.1]hept-2-yl]-5-(3-bromophenyl)-1-methyl-1H-pyrrole-2-carboxamide;
N-[(1S,2R,4R)-7-azabicyclo[2.2.1]hept-2-yl]-5-(4-bromophenyl)-1-methyl-1H-pyrrole-2-carboxamide;
N-[(1S,2R,4R)-7-azabicyclo[2.2.1]hept-2-yl]-5-(2-hydroxyphenyl)-1-methyl-1H-pyrrole-2-carboxamide;
N-[(1S,2R,4R)-7-azabicyclo[2.2.1]hept-2-yl]-5-(3-hydroxyphenyl)-1-methyl-1H-pyrrole-2-carboxamide;
N-[(1S,2R,4R)-7-azabicyclo[2.2.1]hept-2-yl]-5-(4-hydroxyphenyl)-1-methyl-1H-pyrrole-2-carboxamide;
N-[(1S,2R,4R)-7-azabicyclo[2.2.1]hept-2-yl]-5-(2-methoxyphenyl)-1-methyl-1H-pyrrole-2-carboxamide;
N-[(1S,2R,4R)-7-azabicyclo[2.2.1]hept-2-yl]-5-(3-methoxyphenyl)-1-methyl-1H-pyrrole-2-carboxamide;
N-[(1S,2R,4R)-7-azabicyclo[2.2.1]hept-2-yl]-5-(4-methoxyphenyl)-1-methyl-1H-pyrrole-2-carboxamide;
N-[(1S,2R,4R)-7-azabicyclo[2.2.1]hept-2-yl]-5-(2-methylphenyl)-1-methyl-1H-pyrrole-2-carboxamide;
N-[(1S,2R,4R)-7-azabicyclo[2.2.1]hept-2-yl]-5-(3-methylphenyl)-1-methyl-1H-pyrrole-2-carboxamide;
N-[(1S,2R,4R)-7-azabicyclo[2.2.1]hept-2-yl]-5-(4-methylphenyl)-1-methyl-1H-pyrrole-2-carboxamide;
N-[(1S,2R,4R)-7-azabicyclo[2.2.1]hept-2-yl]-5-(2-methylaminophenyl)-1-methyl-1H-pyrrole-2-carboxamide;
N-[(1S,2R,4R)-7-azabicyclo[2.2.1]hept-2-yl]-5-(3-methylaminophenyl)-1-methyl-1H-pyrrole-2-carboxamide;
N-[(1S,2R,4R)-7-azabicyclo[2.2.1]hept-2-yl]-5-(4-methylaminophenyl)-1-methyl-1H-pyrrole-2-carboxamide;
N-[(1S,2R,4R)-7-azabicyclo[2.2.1]hept-2-yl]-5-(2-nitrophenyl)-1-methyl-1H-pyrrole-2-carboxamide;
N-[(1S,2R,4R)-7-azabicyclo[2.2.1]hept-2-yl]-5-(3-nitrophenyl)-1-methyl-1H-pyrrole-2-carboxamide;
N-[(1S,2R,4R)-7-azabicyclo[2.2.1]hept-2-yl]-5-(4-nitrophenyl)-1-methyl-1H-pyrrole-2-carboxamide;
N-[(1S,2R,4R)-7-azabicyclo[2.2.1]hept-2-yl]-5-(2-aminophenyl)-1-methyl-1H-pyrrole-2-carboxamide;
N-[(1S,2R,4R)-7-azabicyclo[2.2.1]hept-2-yl]-5-(3-aminophenyl)-1-methyl-1H-pyrrole-2-carboxamide;
N-[(1S,2R,4R)-7-azabicyclo[2.2.1]hept-2-yl]-5-(4-aminophenyl)-1-methyl-1H-pyrrole-2-carboxamide;
N-[(1S,2R,4R)-7-azabicyclo[2.2.1]hept-2-yl]-5-[2-(acetylamino)phenyl]-1-methyl-1H-pyrrole-2-carboxamide;
N-[(1S,2R,4R)-7-azabicyclo[2.2.1]hept-2-yl]-5-[3-(acetylamino)phenyl]-1-methyl-1H-pyrrole-2-carboxamide;
N-[(1S,2R,4R)-7-azabicyclo[2.2.1]hept-2-yl]-5-[4-(acetylamino)phenyl]-1-methyl-1H-pyrrole-2-carboxamide;
N-[(1S,2R,4R)-7-azabicyclo[2.2.1]hept-2-yl]-5-(pyrid-2-yl)-1-methyl-1H-pyrrole-2-carboxamide;
N-[(1S,2R,4R)-7-azabicyclo[2.2.1]hept-2-yl]-5-(pyrid-3-yl)-1-methyl-1H-pyrrole-2-carboxamide;
N-[(1S,2R,4R)-7-azabicyclo[2.2.1]hept-2-yl]-5-(pyridin-4-yl)-1-methyl-1H-pyrrole-2-carboxamide;
N-[(1S,2R,4R)-7-azabicyclo[2.2.1]hept-2-yl]-5-(3-fluoropyrid-2-yl)-1-methyl-1H-pyrrole-2-carboxamide;
N-[(1S,2R,4R)-7-azabicyclo[2.2.1]hept-2-yl]-5-(4-fluoropyrid-2-yl)-1-methyl-1H-pyrrole-2-carboxamide;
N-[(1S,2R,4R)-7-azabicyclo[2.2.1]hept-2-yl]-5-(5-fluoropyrid-2-yl)-1-methyl-1H-pyrrole-2-carboxamide;
N-[(1S,2R,4R)-7-azabicyclo[2.2.1]hept-2-yl]-5-(6-fluoropyrid-2-yl)-1-methyl-1H-pyrrole-2-carboxamide;
N-[(1S,2R,4R)-7-azabicyclo[2.2.1]hept-2-yl]-5-(2-fluoropyrid-3-yl)-1-methyl-1H-pyrrole-2-carboxamide;
N-[(1S,2R,4R)-7-azabicyclo[2.2.1]hept-2-yl]-5-(4-fluoropyrid-3-yl)-1-methyl-1H-pyrrole-2-carboxamide;
N-[(1S,2R,4R)-7-azabicyclo[2.2.1]hept-2-yl]-5-(5-fluoropyrid-3-yl)-1-methyl-1H-pyrrole-2-carboxamide;
N-[(1S,2R,4R)-7-azabicyclo[2.2.1]hept-2-yl]-5-(6-fluoropyrid-3-yl)-1-methyl-1H-pyrrole-2-carboxamide;
N-[(1S,2R,4R)-7-azabicyclo[2.2.1]hept-2-yl]-5-(2-fluoropyrid-4-yl)-1-methyl-1H-pyrrole-2-carboxamide;

N-[(1S,2R,4R)-7-azabicyclo[2.2.1]hept-2-yl]-5-(3-fluoropyrid-4-yl)-1-methyl-1H-pyrrole-2-carboxamide;

N-[(1S,2R,4R)-7-azabicyclo[2.2.1]hept-2-yl]-5-(2-cyanophenyl)-1-methyl-1H-pyrrole-2-carboxamide;

N-[(1S,2R,4R)-7-azabicyclo[2.2.1]hept-2-yl]-5-(3-cyanophenyl)-1-methyl-1H-pyrrole-2-carboxamide;

N-[(1S,2R,4R)-7-azabicyclo[2.2.1]hept-2-yl]-5-(4-cyanophenyl)-1-methyl-1H-pyrrole-2-carboxamide;

N-[(1S,2R,4R)-7-azabicyclo[2.2.1]hept-2-yl]-5-(2-fluorophenyl)-1H-pyrrole-2-carboxamide;

N-[(1S,2R,4R)-7-azabicyclo[2.2.1]hept-2-yl]-5-(3-fluorophenyl)-1H-pyrrole-2-carboxamide;

N-[(1S,2R,4R)-7-azabicyclo[2.2.1]hept-2-yl]-5-(4-fluorophenyl)-1H-pyrrole-2-carboxamide;

N-[(1S,2R,4R)-7-azabicyclo[2.2.1]hept-2-yl]-5-(3,5-difluorophenyl)-1H-pyrrole-2-carboxamide;

N-[(1S,2R,4R)-7-azabicyclo[2.2.1]hept-2-yl]-5-(3,4-difluorophenyl)-1H-pyrrole-2-carboxamide;

N-[(1S,2R,4R)-7-azabicyclo[2.2.1]hept-2-yl]-5-(2,4-difluorophenyl)-1H-pyrrole-2-carboxamide;

N-[(1S,2R,4R)-7-azabicyclo[2.2.1]hept-2-yl]-5-(2-chlorophenyl)-1H-pyrrole-2-carboxamide;

N-[(1S,2R,4R)-7-azabicyclo[2.2.1]hept-2-yl]-5-(3-chlorophenyl)-1H-pyrrole-2-carboxamide;

N-[(1S,2R,4R)-7-azabicyclo[2.2.1]hept-2-yl]-5-(4-chlorophenyl)-1H-pyrrole-2-carboxamide;

N-[(1S,2R,4R)-7-azabicyclo[2.2.1]hept-2-yl]-5-(3,5-dichlorophenyl)-1H-pyrrole-2-carboxamide;

N-[(1S,2R,4R)-7-azabicyclo[2.2.1]hept-2-yl]-5-(3,4-dichlorophenyl)-1H-pyrrole-2-carboxamide;

N-[(1S,2R,4R)-7-azabicyclo[2.2.1]hept-2-yl]-5-(2,4-dichlorophenyl)-1H-pyrrole-2-carboxamide;

N-[(1S,2R,4R)-7-azabicyclo[2.2.1]hept-2-yl]-5-(2-bromophenyl)-1H-pyrrole-2-carboxamide;

N-[(1S,2R,4R)-7-azabicyclo[2.2.1]hept-2-yl]-5-(3-bromophenyl)-1H-pyrrole-2-carboxamide;

N-[(1S,2R,4R)-7-azabicyclo[2.2.1]hept-2-yl]-5-(4-bromophenyl)-1H-pyrrole-2-carboxamide;

N-[(1S,2R,4R)-7-azabicyclo[2.2.1]hept-2-yl]-5-(2-hydroxyphenyl)-1H-pyrrole-2-carboxamide;

N-[(1S,2R,4R)-7-azabicyclo[2.2.1]hept-2-yl]-5-(3-hydroxyphenyl)-1H-pyrrole-2-carboxamide;

N-[(1S,2R,4R)-7-azabicyclo[2.2.1]hept-2-yl]-5-(4-hydroxyphenyl)-1H-pyrrole-2-carboxamide;

N-[(1S,2R,4R)-7-azabicyclo[2.2.1]hept-2-yl]-5-(2-methoxyphenyl)-1H-pyrrole-2-carboxamide;

N-[(1S,2R,4R)-7-azabicyclo[2.2.1]hept-2-yl]-5-(3-methoxyphenyl)-1H-pyrrole-2-carboxamide;

N-[(1S,2R,4R)-7-azabicyclo[2.2.1]hept-2-yl]-5-(4-methoxyphenyl)-1H-pyrrole-2-carboxamide;

N-[(1S,2R,4R)-7-azabicyclo[2.2.1]hept-2-yl]-5-(2-methylphenyl)-1H-pyrrole-2-carboxamide;

N-[(1S,2R,4R)-7-azabicyclo[2.2.1]hept-2-yl]-5-(3-methylphenyl)-1H-pyrrole-2-carboxamide;

N-[(1S,2R,4R)-7-azabicyclo[2.2.1]hept-2-yl]-5-(4-methylphenyl)-1H-pyrrole-2-carboxamide;

N-[(1S,2R,4R)-7-azabicyclo[2.2.1]hept-2-yl]-5-(2-methylaminophenyl)-1H-pyrrole-2-carboxamide;

N-[(1S,2R,4R)-7-azabicyclo[2.2.1]hept-2-yl]-5-(3-methylaminophenyl)-1H-pyrrole-2-carboxamide;

N-[(1S,2R,4R)-7-azabicyclo[2.2.1]hept-2-yl]-5-(4-methylaminophenyl)-1H-pyrrole-2-carboxamide;

N-[(1S,2R,4R)-7-azabicyclo[2.2.1]hept-2-yl]-5-(2-nitrophenyl)-1H-pyrrole-2-carboxamide;

N-[(1S,2R,4R)-7-azabicyclo[2.2.1]hept-2-yl]-5-(3-nitrophenyl)-1H-pyrrole-2-carboxamide;

N-[(1S,2R,4R)-7-azabicyclo[2.2.1]hept-2-yl]-5-(4-nitrophenyl)-1H-pyrrole-2-1-carboxamide;

N-[(1S,2R,4R)-7-azabicyclo[2.2.1]hept-2-yl]-5-(2-aminophenyl)-1H-pyrrole-2-carboxamide;

N-[(1S,2R,4R)-7-azabicyclo[2.2.1]hept-2-yl]-5-(3-aminophenyl)-1H-pyrrole-2-carboxamide;

N-[(1S,2R,4R)-7-azabicyclo[2.2.1]hept-2-yl]-5-(4-aminophenyl)-1H-pyrrole-2-carboxamide;

N-[(1S,2R,4R)-7-azabicyclo[2.2.1]hept-2-yl]-5-[2-(acetylamino)phenyl]-1H-pyrrole-2-carboxamide;

N-[(1S,2R,4R)-7-azabicyclo[2.2.1]hept-2-yl]-5-[3-(acetylamino)phenyl]-1H-pyrrole-2-carboxamide;

N-[(1S,2R,4R)-7-azabicyclo[2.2.1]hept-2-yl]-5-[4-(acetylamino)phenyl]-1H-pyrrole-2-carboxamide;

N-[(1S,2R,4R)-7-azabicyclo[2.2.1]hept-2-yl]-5-(pyrid-2-yl)-1H-pyrrole-2-carboxamide;

N-[(1S,2R,4R)-7-azabicyclo[2.2.1]hept-2-yl]-5-(pyrid-3-yl)-1H-pyrrole-2-carboxamide;

N-[(1S,2R,4R)-7-azabicyclo[2.2.1]hept-2-yl]-5-(pyrid-4-yl)-1H-pyrrole-2-carboxamide;

N-[(1S,2R,4R)-7-azabicyclo[2.2.1]hept-2-yl]-5-(3-fluoropyrid-2-yl)-1H-pyrrole-2-carboxamide;

N-[(1S,2R,4R)-7-azabicyclo[2.2.1]hept-2-yl]-5-(4-fluoropyrid-2-yl)-1H-pyrrole-2-carboxamide;

N-[(1S,2R,4R)-7-azabicyclo[2.2.1]hept-2-yl]-5-(5-fluoropyrid-2-yl)-1H-pyrrole-2-carboxamide;

N-[(1S,2R,4R)-7-azabicyclo[2.2.1]hept-2-yl]-5-(6-fluoropyrid-2-yl)-1H-pyrrole-2-carboxamide;

N-[(1S,2R,4R)-7-azabicyclo[2.2.1]hept-2-yl]-5-(2-fluoropyrid-3-yl)-1H-pyrrole-2-carboxamide;

N-[(1S,2R,4R)-7-azabicyclo[2.2.1]hept-2-yl]-5-(4-fluoropyrid-3-yl)-1H-pyrrole-2-carboxamide;

N-[(1S,2R,4R)-7-azabicyclo[2.2.1]hept-2-yl]-5-(5-fluoropyrid-3-yl)-1H-pyrrole-2-carboxamide;

N-[(1S,2R,4R)-7-azabicyclo[2.2.1]hept-2-yl]-5-(6-fluoropyrid-3-yl)-1H-pyrrole-2-carboxamide;

N-[(1S,2R,4R)-7-azabicyclo[2.2.1]hept-2-yl]-5-(2-fluoropyrid-4-yl)-1H-pyrrole-2-carboxamide;

N-[(1S,2R,4R)-7-azabicyclo[2.2.1]hept-2-yl]-5-(3-fluoropyrid-4-yl)-1H-pyrrole-2-carboxamide;

N-[(1S,2R,4R)-7-azabicyclo[2.2.1]hept-2-yl]-5-(2-cyanophenyl)-1H-pyrrole-2-carboxamide;

N-[(1S,2R,4R)-7-azabicyclo[2.2.1]hept-2-yl]-5-(3-cyanophenyl)-1H-pyrrole-2-carboxamide;

N-[(1S,2R,4R)-7-azabicyclo[2.2.1]hept-2-yl]-5-(4-cyanophenyl)-1H-pyrrole-2-carboxamide;

N-[(1S,2R,4R)-7-azabicyclo[2.2.1]hept-2-yl]-3-phenyl-1,2,4-oxadiazole-5-carboxamide.

The compound of Formula I, where (b) is any one or more or combination of the following: 1,3-thiazole-4-yl, 1,3-oxazole-4-yl, 1H-1,2,4-triazole-3-yl, or isoxazole-3-yl, any of which is optionally substituted on carbon (e.g., V or Y is independently $CR_5$) with H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —OR$_8$, —SR$_8$, —N(R$_8$)$_2$, —C(O)R$_8$, —C(S)R$_8$, —C(O)OR$_8$, —C(O)N(R$_8$)$_2$, —NR$_8$C(O)R$_8$, —S(O)$_2$N(R$_8$)$_2$, —OS(O)$_2$R$_8$, —S(O)$_2$R$_8$, —S(O)R$_8$, —NR$_8$S(O)$_2$R$_8$, —N(R$_8$)C(O)N(R$_8$)$_2$, —CN, —NO$_2$, R$_7$, or R$_9$; and further optionally substituted on nitrogen (e.g., U is N-R$_3$) with alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, R$_7$, R$_9$, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—R$_7$, —C(O)—R$_9$, or —C(O)—aryl.

The compound of Formula I or formula A—L—B, where the compound is any one or more or combination of the following as the free base or a pharmaceutically acceptable salt thereof: N-[(1S,2R,4R)-7-azabicyclo[2.2.1]hept-2-yl]-2-pyridin-3-yl-1,3-thiazole-4-carboxamide; N-[(1S,2R,4R)-7-azabicyclo[2.2.1]hept-2-yl]-2-phenyl-1,3-oxazole-4-carboxamide; N-[(1S,2R,4R)-7-azabicyclo[2.2.1]hept-2-yl]-5-phenyl-1H-1,2,4-triazole-3-carboxamide; or N-[(1S,2R,4R)-7-azabicyclo[2.2.1]hept-2-yl]-5-phenylisoxazole-3-carboxamide.

The present invention also includes a pharmaceutical composition comprising a compound of Formula I or formula A—L—B or a pharmaceutically acceptable salt thereof and a pharmaceutically acceptable excipient. The pharmaceutical composition is administered rectally, topically, orally, sublingually, or parenterally for a therapeutically effective interval. The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

A pharmaceutical composition comprising a compound of Formula I or formula A—L—B or a pharmaceutically acceptable salt thereof and an anti-psychotic agent. The pharmaceutical composition is administered to independently administer said compound and said agent rectally, topically, orally, sublingually, or parenterally for a therapeutically effective interval. The pharmaceutical composition is administered to deliver a compound of the present invention in an amount of from bout 0.001 to about 100 mg/kg of body weight of said mammal per day. The pharmaceutical composition is also administered to deliver a compound of the present invention in an amount of from about 0.1 to about 50 mg/kg of body weight of said mammal per day.

The present invention also includes a use of a compound according to Formula I or formula A—L—B or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist.

The present invention also includes a use of a compound according to Formula I or formula A—L—B or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist, wherein the disease, or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The present invention also includes a method for treating a disease or condition in a mammal in need thereof, wherein the mammal would receive symptomatic relief from the administration of an α7 nicotinic acetylcholine receptor agonist comprising administering to the mammal a therapeutically effective amount of a compound according to Formula I or formula A—L—B or pharmaceutically acceptable salt thereof.

The present invention also includes a method for treating a disease or condition in a mammal in need thereof comprising administering to the mammal a therapeutically effective amount of a compound according to Formula I or formula A—L—B or pharmaceutically acceptable salt thereof, wherein the disease or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The compounds of formula A—L—B or Formula I have optically active centers on the 7-azabicyclo[2.2.1]heptane ring which can exhibit a number of stereochemical configurations. The terms exo and endo are stereochemical prefixes that describe the relative configuration of a substituent on a bridge (not a bridgehead) of a bicyclic system. If a substituent is oriented toward the larger of the other bridges, it is endo. If a substituent is oriented toward the smaller bridge it is exo. Depending on the substitution on the carbon atoms, the endo and exo orientations can give rise to different stereoisomers. For instance, when carbons 1 and 4 are substituted with hydrogen and carbon 2 is bonded to a nitrogen containing species, the endo orientation gives rise to the possibility of a pair of enantiomers: either the 1S, 2S, 4R isomer or its enantiomer, the 1R, 2R, 4S isomer. Likewise, the exo orientation gives rise to the possibility of another pair of stereoisomers which are diastereomeric and C-2 epimeric with respect to the endo isomers: either the 1R, 2S, 4S isomer or its enantiomer, the 1S, 2R, 4R isomer. The compounds of this invention exist in the exo orientation. For example, when $R_2=R_4=H$, the absolute stereochemistry is exo-(2R) for the compounds in Formula I.

Stereoselective syntheses and/or subjecting the reaction product to appropriate purification steps produces substantially optically pure materials. Suitable stereoselective synthetic procedures for producing optically pure materials are well known in the art, as are procedures for purifying racemic mixtures into optically pure fractions.

The compounds of the present invention have the exo orientation at the C-2 carbon and S configuration at the C-1 carbon and the R configuration at the C-2 and the C-4 carbons of the 7-azabicyclo[2.2.1]heptane ring. Unexpectedly, the inventive compounds exhibit much higher activity relative to compounds lacking the 1S,2R, and 4R stereochemistry within the 7-azabicyclo[2.2.1]heptane ring system. For example, the ratio of activities for compounds having the 1S,2R, and 4R configuration to other stereochemical configurations of the 7-azabicyclo[2.2.1] heptane ring system may be greater than about 100. Although it is desirable that the stereochemical purity be as high as possible, absolute purity is not required. For example, pharmaceutical compositions can include one or more compounds, each having an exo 2R configuration, or mixtures of compounds having exo 2R and other configurations. In mixtures of compounds, those species possessing stereochemical configurations other than exo 2R act as diluents and tend to lower the activity of the pharmaceutical composition. Typically, pharmaceutical compositions including mixtures of compounds possess a larger percentage of species having the exo 2R configuration relative to other configurations.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

Surprisingly, we have found that compounds of the Formula I:

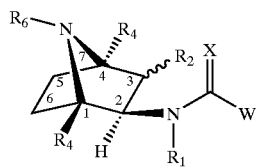

Formula I wherein the stereochemistry of the of the 7-azabicyclo [2.2.1]heptane ring is 1S,4R and the nitrogen substituent at the C-2 carbon has the exo orientation and is R;

X is O or S;

$R_1$ is H, alkyl, halogenated alkyl, cycloalkyl, or aryl;

$R_2$ is H, alkyl, halogenated alkyl, substituted alkyl, cycloalkyl, or aryl;

Alkyl is both straight- and branched-chain moieties having from 1–6 carbon atoms;

Substituted alkyl is an alkyl moiety having from 1–6 carbon atoms and having 0–3 substituents independently selected from F, Cl, Br, or I and further having 1 substituent selected from $-OR_{10}$, $-SR_{10}$, $-S(O)_2R_{10}$, $-S(O)R_{10}$, $-OS(O)_2R_{10}$, $-NR_{10}R_{10}$, $-C(O)R_{10}$, $-C(S)R_{10}$, $-C(O)OR_{10}$, $-C(O)NR_{10}R_{10}$, $-CN$, $-NR_{10}C(O)R_{10}$, $-NR_{10}C(O)NR_{10}R_{10}$, $-S(O)_2NR_{10}R_{10}$, $-NR_{10}S(O)_2R_{10}$, $-NO_2$, $R_7$, $R_9$, or phenyl optionally substituted with 1–4 substituents independently selected from F, Cl, Br, I, $R_{13}$, and $R_{15}$;

Halogenated alkyl is an alkyl moiety having from 1–6 carbon atoms and having 1 to (2n+1) substituent(s) independently selected from F, Cl, Br, or I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl having 1–4 substituents independently selected from F, Cl, Br, I, or $R_{13}$, or having 1 substituent selected from $R_{15}$ and 0–3 substituents independently selected from F, Cl, Br, I, or $R_{13}$;

Substituted naphthyl is a naphthalene moiety 1–4 substituents independently selected from F, Cl, Br, I, or $R_{13}$, or having 1 substituent selected from $R_{15}$ and 0–3 substituents independently selected from F, Cl, Br, I, or $R_{13}$, where the substitution can be independently on either the same ring or different rings of said naphthalene moiety;

W is $-Q$, $-C=C-Q$, or $-C\equiv C-Q$;

Q is a cyclic heteroaromatic moiety where the heteroatoms can be from 1–3 atoms selected from oxygen, sulfur, or nitrogen of the following structures:

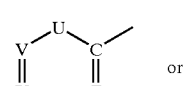

(a)

or

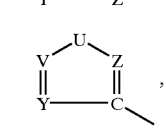

(b)

wherein U is $-O-$, $-S-$, or $-N(R_3)-$;

V and Y are independently selected from $=N-$, and $=C(R_5)-$;

Z is $=N-$, or $=CH-$;

$R_3$ is H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $R_7$, $R_9$, aryl, $-C(O)$-alkyl, $-C(O)$-cycloalkyl, $-C(O)$-heterocycloalkyl, $-C(O)$-halogenated alkyl, $-C(O)$-halogenated cycloalkyl, $-C(O)$-halogenated heterocycloalkyl, $-C(O)$-substituted alkyl, $-C(O)$-substituted cycloalkyl, $-C(O)$-substituted heterocycloalkyl, $-C(O)-R_7$, $-C(O)-R_9$, or $-C(O)$-aryl;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n−1) substituent(s) independently selected from F, Cl, Br, or I where n is the maximum number of carbon atoms in the moiety;

Substituted alkenyl is an unsaturated alkenyl moiety having from 2–6 carbon atoms and having 0–3 substituents independently selected from F, Cl, Br, or I, and further having 1 substituent selected from $R_7$, $R_9$, —$OR_{10}$, —$SR_{10}$, —$S(O)R_{10}$, —$S(O)_2R_{10}$, —$OS(O)_2R_{10}$, —$N(R_{10})_2$, —$C(O)R_{10}$, —$C(S)R_{10}$, —$C(O)OR_{10}$, —$C(O)N(R_{10})_2$, —CN, —$NO_2$, —$NR_{10}C(O)R_{10}$, —$NR_{10}C(O)N(R_{10})_2$, —$S(O)_2N(R_{10})_2$, —$NR_{10}S(O)_2R_{10}$, and phenyl optionally substituted with 1–4 substituents independently selected from F, Cl, Br, I, $R_{13}$, and $R_{15}$;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n−3) substituent(s) independently selected from F, Cl, Br, or I where n is the maximum number of carbon atoms in the moiety;

Substituted alkynyl is an unsaturated alkynyl moiety having from 3–6 carbon atoms and having 0–3 substituents independently selected from F, Cl, Br, or I, and further having 1 substituent selected from $R_7$, $R_9$, —$OR_{10}$, —$SR_{10}$, —$S(O)_2R_{10}$, —$S(O)R_{10}$ —$OS(O)_2R_{10}$, —$N(R_{10})_2$, —$C(O)R_{10}$, —$C(S)R_{10}$, —$C(O)OR_{10}$, —$C(O)N(R_{10})_2$, —CN, —$NO_2$, —$NR_{10}C(O)R_{10}$, —$NR_{10}C(O)N(R_{10})_2$, —$S(O)_2N(R_{10})_2$, —$NR_{10}S(O)_2R_{10}$, and phenyl optionally substituted with 1–4 substituents independently selected from F, Cl, Br, I, $R_{13}$, and $R_{15}$;

Halogenated cycloalkyl is a cyclic moiety having from 3–6 carbon atoms and having 1–4 substituents independently selected from F, Cl, Br, or I;

Substituted cycloalkyl is a cyclic moiety having from 3–6 carbon atoms and having 0–3 substituents independently selected from F, Cl, Br, or I, and further having 1 substituent selected from =O, =S, $R_7$, $R_9$, —$OR_{10}$, —$SR_{10}$, —$S(O)R_{10}$, —$S(O)_2R_{10}$, —$OS(O)_2R_{10}$, —$NR_{10}R_{10}$, —$C(O)R_{10}$, —$C(S)R_{10}$, —$C(O)OR_{10}$, —$C(O)N(R_{10})_2$, —CN, —$NO_2$, —$NR_{10}C(O)R_{10}$, —$NR_{10}C(O)N(R_{10})_2$, —$S(O)_2N(R_{10})_2$, —$NR_{10}S(O)_2R_{10}$, and phenyl optionally substituted with 1–4 substituents independently selected from F, Cl, Br, I, $R_{13}$, and $R_{15}$;

Heterocycloalkyl is a cyclic moiety having 4–7 atoms with 1–2 atoms within the ring being —S—, —N($R_{20}$)—, or —O—;

Halogenated heterocycloalkyl is a cyclic moiety having from 4–7 atoms with 1–2 atoms within the ring being —S—, —N($R_{20}$)—, or —O—, and having 1–4 substituents independently selected from F, Cl, Br, or I;

Substituted heterocycloalkyl is a cyclic moiety having from 4–7 atoms with 1–2 atoms within the ring being —S—, —N($R_{20}$)—, or —O— and having 0–3 substituents independently selected from F, Cl, Br, or I, and further having 1 substituent selected from =O, =S, —$R_7$, —$R_9$, —$OR_{10}$, —$SR_{10}$, —$S(O)R_{10}$, —$S(O)_2R_{10}$, —$OS(O)_2R_{10}$, —$N(R_{10})_2$, —$C(O)R_{10}$, —$C(S)R_{10}$, —$C(O)OR_{10}$, —$C(O)N(R_{10})_2$, —CN, —$NO_2$, —$NR_{10}C(O)R_{10}$, —$NR_{10}C(O)N(R_{10})_2$, —$S(O)_2N(R_{10})_2$, —$NR_{10}S(O)_2R_{10}$, and phenyl optionally substituted with 1–4 substituents independently selected from F, Cl, Br, I, $R_{13}$, and $R_{15}$;

Each $R_4$ is independently H, alkyl, or substituted alkyl;

Each $R_5$ is independently H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —$OR_8$, —$SR_8$, —$N(R_8)_2$, —$C(O)R_8$, —$C(S)R_8$, —$C(O)OR_8$, —$C(O)N(R_8)_2$, —$NR_8C(O)R_8$, —$S(O)_2N(R_8)_2$, —$OS(O)_2R_8$, —$S(O)_2R_8$, —$S(O)R_8$, —$NR_8S(O)_2R_8$, —$N(R_8)C(O)N(R_8)_2$, —CN, —$NO_2$, $R_7$, or $R_9$;

Lactam heterocycloalkyl is a cyclic moiety having from 4–7 atoms with one atom being only nitrogen with the bond to the lactam heterocycloalkyl thru said atom being only nitrogen and having a =O on a carbon adjacent to said nitrogen, and having up to 1 additional ring atom being oxygen, sulfur, or nitrogen and further having 0–2 substituents selected from F, Cl, Br, I, or $R_{18}$ where valency allows;

$R_6$ is H, alkyl, an amino protecting group, or an alkyl group having 1–3 substituents selected from F, Cl, Br, I, —OH, —CN, —$NH_2$, —NH(alkyl), or —N(alkyl)$_2$;

$R_7$ is 5-membered heteroaromatic mono-cyclic moieties containing within the ring 1–3 heteroatoms independently selected from the group consisting of =N—, —N($R_{20}$)—, —O—, and —S—, and having 0–1 substituent selected from $R_{17}$ and further having 0–3 substituents independently selected from F, Cl, Br, or I, or $R_7$ is 9-membered fused-ring moieties having a 6-membered ring fused to a 5-membered ring including the formula

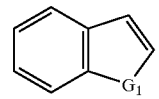

wherein $G_1$ is O, S or $NR_{20}$,

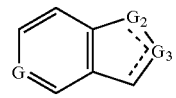

wherein G is C($R_{14}$) or N, and each $G_2$ and $G_3$ is independently selected from C($R_{14}$)$_2$, C($R_{14}$), O, S, N, and N($R_{20}$), provided that both $G_2$ and $G_3$ are not simultaneously O or S, or

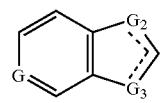

wherein G is C($R_{14}$) or N, and each $G_2$ and $G_3$ is independently selected from C($R_{14}$)$_2$, C($R_{14}$), O, S, N, and N($R_{20}$), each 9-membered bicyclic ring having 0–1 substituent selected from $R_{17}$ and 0–3 substituents independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl optionally substituted with 1–4 substituents independently selected from F, Cl, Br, I, $R_{13}$, and $R_{15}$, or naphthyl optionally substituted with 1–4 substituents independently selected from F, Cl, Br, I, $R_{13}$, and $R_{15}$;

$R_9$ is 6-membered heteroaromatic mono-cyclic moieties containing within the ring 1–3 heteroatoms selected from =N— and having 0–1 substituent selected from $R_{17}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{17}$ and 0–3 substituent(s) independently selected from F, Cl, Br, or I, wherein the $R_9$ moiety attaches to other substituents as defined in formula I at any position on either ring as valency allows;

Each $R_{10}$ is independently H, alkyl, cycloalkyl, heterocycloalkyl, $R_7$, $R_9$, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, or phenyl optionally substituted with 1–4 substituents independently selected from F, Cl, Br, I, $R_{13}$, and $R_{15}$;

Each $R_{11}$ is independently H, alkyl, cycloalkyl, heterocycloalkyl, halogenated alkyl, halogenated cycloalkyl, or halogenated heterocycloalkyl;

$R_{12}$ is alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$S(O)_2R_{11}$, —$S(O)R_{11}$, —$OS(O)_2R_{11}$, —$N(R_{11})_2$, —$C(O)R_{11}$, —$C(S)R_{11}$, —$C(O)OR_{11}$, —$NO_2$, —$C(O)N(R_{11})_2$, —CN, —$NR_{11}C(O)R_{11}$, —$NR_{11}C(O)N(R_{11})_2$, —$S(O)_2N(R_{11})_2$, or —$NR_{11}S(O)_2R_{11}$;

$R_{13}$ is —$OR_{11}$, —$SR_{11}$, —$SOR_{11}$, —$SO_2R_{11}$, —$OSO_2R_{11}$, —$N(R_{11})_2$, —$C(O)R_{11}$, —$C(O)OR_{11}$, —$C(S)R_{11}$, —$C(O)N(R_{11})_2$, —$NO_2$—CN, —$CF_3$, —$NR_{11}C(O)R_{11}$, —$NR_{11}C(O)N(R_{11})_2$, —$S(O)_2N(R_{11})_2$, or —$NR_{11}S(O)_2R_{11}$;

$R_{14}$ is H or $R_{19}$;

$R_{15}$ is $R_7$, $R_9$, $R_9$, or lactam heterocycloalkyl;

Each $R_{16}$ is independently H, alkyl, cycloalkyl, halogenated alkyl, or halogenated cycloalkyl;

$R_{17}$ is alkyl, cycloalkyl, or heterocycloalkyl, each optionally substituted with 1–4 substituents independently selected from F, Cl, Br, I, —$NO_2$, —CN, —$OR_{16}$, —$SR_{16}$, —$S(O)_2R_{16}$, —$S(O)R_{16}$, —$OS(O)_2R_{16}$, —$N(R_{16})_2$, —$C(O)R_{16}$, —$C(S)R_{16}$, —$C(O)OR_{16}$, —$C(O)N(R_{16})_2$, —$NR_{16}C(O)R_{16}$, —$NR_{16}C(O)N(R_{16})_2$, —$S(O)_2N(R_{16})_2$, and —$NR_{16}S(O)_2R_{16}$, and the cycloalkyl and heterocycloalkyl also being further optionally substituted with =O or =S;

$R_{18}$ is alkyl, substituted alkyl, halogenated alkyl, —$OR_{11}$, —CN, —$NO_2$, —$N(R_{10})_2$;

$R_{19}$ is alkyl, cycloalkyl, heterocycloalkyl, phenyl, or naphthyl, each optionally substituted with 1–4 substituents independently selected from F, Cl, Br, I, —CN, —$NO_2$, —$OR_{16}$, —$SR_{16}$, —$S(O)_2R_{16}$, —$S(O)R_{16}$, —$OS(O)_2R_{16}$, —$N(R_{16})_2$, —$C(O)R_{16}$, —$C(S)R_{16}$, —$C(O)OR_{16}$, —$C(O)N(R_{16})_2$, —$NR_{16}C(O)R_{16}$, —$NR_{16}C(O)N(R_{16})_2$, —$S(O)_2N(R_{16})_2$, or —$NR_{16}S(O)_2R_{16}$, and the cycloalkyl and heterocycloalkyl also being further optionally substituted with =O or =S;

$R_{20}$ is H, alkyl, halogenated alkyl, substituted alkyl, cycloalkyl, halogenated cycloalkyl, substituted cycloalkyl, phenyl, —$SO_2R_8$, or phenyl having 1 substituent selected from $R_{12}$ and further having 0–3 substituents independently selected from F, Cl, Br, or I;

or pharmaceutical composition, pharmaceutically acceptable salt, racemic mixture, or pure enantiomer thereof useful to treat any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Another group of compounds of formula A—L—B or Formula I includes any one or more or combination of the following compounds or a pharmaceutically acceptable salt or pharmaceutical composition thereof:

Abbreviations which are well known to one of ordinary skill in the art may be used (e.g., "Ph" for phenyl, "Me" for methyl, "Et" for ethyl, "h" or "hr" for hour or hours, min for minute or minutes, and "rt" or "RT" for room temperature).

All temperatures are in degrees Centigrade.

Room temperature is within the range of 15–25 degrees Celsius.

AChR refers to acetylcholine receptor.

nAChR refers to nicotinic acetylcholine receptor.

Pre-senile dementia is also known as mild cognitive impairment.

$5HT_3R$ refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.

DMF refers to N,N-dimethylformamide.

EtOAc refers to ethyl acetate.

TMS refers to tetramethylsilane.

TEA refers to triethylamine.

DIEA refers to N,N-diisopropylethylamine.

MLA refers to methyllycaconitine.

Ether refers to diethyl ether.

HATU refers to O-(7-azabenzotriazol-1-yl)—N,N,N', N'-tetramethyluronium hexafluorophosphate.

CDI refers to carbonyl diimidazole.

NMO refers to N-methylmorpholine—N-oxide.

TPAP refers to tetrapropylammonium perruthenate.

Halogen is F, Cl, Br, or I.

Amino protecting group includes, but is not limited to, carbobenzyloxy (CBz), 1,1 dimethylcarbamate, tert butoxy carbonyl (BOC) and the like. Examples of other suitable amino protecting groups are known to person skilled in the art and can be found in "Protective Groups in Organic synthesis," 3rd Edition, authored by Theodora Greene and Peter Wuts.

Acrylamide or acrylthioamide is a moiety having the general structure —N(H)C(X)C=C—, where X is O or S, respectively, so A—L—B includes A—N($R_1$)C(X)—C=C—B.

Propiolamide or propiolthioamide is a moiety having the general structure —N(H)C(X)C≡C—, where X is O or S, respectively, so A—L—B includes A—N($R_1$)C(X)—C≡C—B.

One of the most conventionally accepted ways of naming the compound pictured below is 5-(2-aminophenyl)-N-[(1S,2R,4R)-7-azabicyclo[2.2.1]hept-2-yl]-thiophene-2-carboxamide, but for one ordinarily skilled in the art, the following name also describes the same compound, N-[(1S,2R,4R)-7-azabicyclo[2.2.1]hept-2-yl]-5-(2-aminophenyl)-thiophene-2-carboxamide. The two are used interchangeably in this patent.

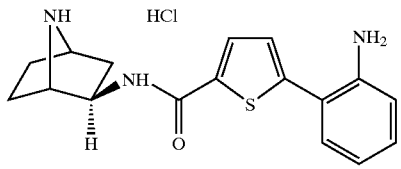

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

Lower alkyl is both straight- and branched-chain moieties having 1–4 carbon atoms.

Halogenated lower alkyl is lower alkyl having 1 to (2n+1) substituent(s) independently selected from F, Cl, Br, or I where n is the maximum number of carbon atoms in the moiety.

Substituted lower alkyl is lower alkyl having 0–3 substituents independently selected from F, Cl, Br, or I and further having 1 substituent selected from $R_7$, $R_9$, —CN, —$NO_2$, —$OR_{10}$, —$SR_{10}$, —S(O)$R_{10}$, —S(O)$_2R_{10}$, —OS(O)$_2R_{10}$, —$NR_{10}R_{10}$, —C(O)$R_{10}$, —C(O)O$R_{10}$, —C(S)$R_{10}$, —C(O)N$R_{10}R_{10}$, —$NR_{10}$C(O)$R_{10}$, —$NR_{10}$C(O)N$R_{10}R_{10}$, —S(O)$_2NR_{10}R_{10}$, —$NR_{10}$S(O)$_2R_{10}$, or phenyl optionally substituted with 1–4 substituents independently selected from F, Cl, Br, I, $R_{13}$, and $R_{15}$.

Non-inclusive examples of heteroaryl compounds that fall within the definition of $R_7$ and $R_9$ include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, furopyridinyl, pyrrolopyridinyl, or thienopyridinyl. All isomeric forms of the non-inclusive named moieties are included, e.g., benzofuranyl includes 1-benzofuran-2-yl, 1-benzofuran-3-yl, 1-benzofuran-4-yl, 1-benzofuran-5-yl, 1-benzofuran-6-yl, 1-benzofuran-7-yl, 2-benzofuran-1-yl, 2-benzofuran-2-yl, 2-benzofuran-3-yl, 2-benzofuran-4-yl, or 2-benzofuran-5-yl. The non-inclusive examples of $R_7$ and $R_9$ may be substituted as allowed within the respective definition of $R_7$ and $R_9$ as valency allows. One of ordinary skill in the art can identify the allowed substitution by comparing the non-inclusive examples with the respective definitions of $R_7$ and $R_9$.

Non-inclusive examples of heterocycloalkyl include, but are not limited to, tetrahydrofurano, tetrahydropyrano, morpholino, pyrrolidino, piperidino, piperazine, azetidino, azetidinono, oxindolo, dihydroimidazolo, pyrrolidino, or isoxazolinyl.

Mammal denotes human and other mammals.

Brine refers to an aqueous saturated sodium chloride solution.

Equ means molar equivalents.

IR refers to infrared spectroscopy.

Lv refers to leaving groups within a molecule, including Cl, OH, or mixed anhydride.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. M+H$^+$ refers to the positive ion of a parent plus a hydrogen atom. M+H$^+$ refers to the negative ion of a parent minus a hydrogen atom. M+Na$^+$ refers to the positive ion of a parent plus a sodium atom. M+K$^+$ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of the present invention. The pharmaceutical compositions may contain active ingredient in the range of about 0.001 to 100 mg/kg/day for an adult, preferably in the range of about 0.1 to 50 mg/kg/day for an adult. A total daily dose of about 1 to 1000 mg of active ingredient may be appropriate for an adult. The daily dose can be administered in one to four doses per day.

In addition to the compound(s) of the present invention, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basalis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychopharmacology* (Berl)., 142(4):334–42, March 1999; Wilens, T. E. et. al., *Am. J. Psychiatry*, 156(12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "atypical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencepholographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry*, 157:55–9, 2000). Multiple studies show that nicotine normalizes the sensory deficit of schizophrenia (Adler, L. E. et. al., *Am. J. Psychiatry*, 150:1856–61, 1993). Pharmacological studies indicate that nicotine's effect on sensory gating is via the α7 nAChR (Adler, L. E. et. al., *Schizophr. Bull.*, 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., *Biol. Psychiatry*, 38:22–33, 1995). Interestingly, genetic data indicate that a polymorphism in the promoter region of the α7 nAChR gene is strongly associated with the sensory gating deficit in schizophrenia (Freedman, R. et. al., *Proc. Nat'l Acad. Sci. USA*, 94(2):587–92, 1997; Myles-Worsley, M. et. al., *Am. J. Med. Genet*, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and 5HT$_3$R. To conduct such an assay, one uses cell lines that expressed functional forms of the α7 nAChR using the α7/5-HT$_3$ channel as the drug target and cell lines that expressed functional 5HT$_3$R. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, atypical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the atypical antipsychotic drugs, and thus, these atypical antipsychotic drugs have a lower risk of producing tardive dyskinesia. Finally these atypical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of the present invention and the anti-psychotic drugs can be administered simultaneously or at separate intervals. When administered simultaneously the compounds of the present invention and the anti-psychotic drugs can be incorporated into a single pharmaceutical composition, e.g., a pharmaceutical combination therapy composition. Alternatively, two separate compositions, i.e., one containing compounds of the present invention and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of the present invention, noted above, and a therapeutically effective amount of anti-psychotic drugs (also called anti-psychotic agents). These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of the present invention and anti-psychotic drugs are administered on a different schedule. One may be administered before the other as long as the time between the two administrations falls within a therapeutically effective interval. A therapeutically effective interval is a period of time beginning when one of either (a) the compounds of the present invention, or (b) the anti-psychotic drugs is administered to a human and ending at the limit of the beneficial effect in the treatment of schizophrenia or psychosis of the combination of (a) and (b). The methods of administration of the compounds of the present invention and the anti-psychotic drugs may vary. Thus, either agent or both agents may be administered rectally, topically, orally, sublingually, or parenterally.

As discussed, the compounds of the present invention are α7 nAChR agonists. Therefore, as another aspect of the present invention, the compounds of the present invention may be used to treat a variety of diseases including cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are α7 nAChR agonists. Therefore, yet other diseases to be treated with compounds of the present invention include treating the cognitive and attention deficits as well as the neurodegeneration associated with any one or more or combination of the following: attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Anxiety disorders (disorders with prominent anxiety or phobic avoidance), represent an area of umet medical needs in the treatment of psychiatric illness. See Diagnostic & Statistical Manual of Mental Disorders, IV (1994), pp 393–394, for various disease forms of anxiety.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Anxiety also includes post-traumatic stress disorder (PTSD), which is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat post traumatic stress disorder.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Dysregulation of food intake associated with eating disease, including bulimia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision.

Laser surgery can treat some cases of wet AMD. Therefore, there is a need of a pharmaceutical agent to address AMD.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and atypical antipsychotic drugs (also called an anti-psychotic agent). All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some atypical anti-psychotic drugs include Ziprasidone, Olanzapine, Resperidone, and Quetiapine.

Compounds of Formula I can be prepared as shown in Scheme 1. Starting materials can be prepared by procedures described below or by procedures that would be well known to one of ordinary skill in organic chemistry. The variables used in Scheme 1 are defined below or as in the claims. The key step in the preparation of this class of compounds is the coupling of exo-tert-butyl (1S,2R,4R)-(+)-2-amino-7-azabicyclo[2.2.1]heptane-7-carboxylate (Example 1) with the requisite acid chloride (Lv=Cl), mixed anhydride (e.g., Lv=diphenyl phosphoryl, bis(2-oxo-3-oxazolidinyl) phosphinyl, or acyloxy of the general formula of O—C(O)—R$_{Lv}$, where R$_{Lv}$ includes phenyl or t-butyl), ester (e.g., Lv=alkyl, aryl, or electron deficient aryl), or carboxylic acid (Lv=OH) in the presence of an activating agent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as uronium salt HATU).

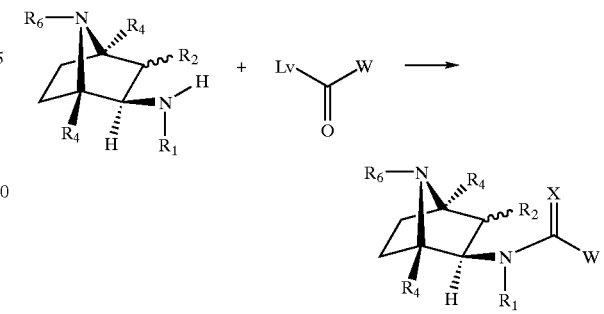

Scheme 1

Preferably, tert-butyl (1S,2R,4R)-(+)-2-amino-7-azabicyclo[2.2.1]heptane-7-carboxylate can be coupled to the acid in the presence of an appropriate base, such as DIEA, and a uronium salt, such as HATU, in an aprotic medium, such as DMF, to give the desired amides. Alternatively, the acid is converted into a mixed anhydride by treatment with bis (2-oxo-3-oxazolidinyl) phosphinic chloride in the presence of TEA with CH$_2$Cl$_2$ or CHCl$_3$ as the solvent. The resulting anhydride solution is directly reacted with tert-butyl (1S,2R,4R)-(+)-2-amino-7-azabicyclo[2.2.1]heptane-7-carboxylate added neat or using CH$_2$Cl$_2$ or CHCl$_3$ as solvent. Furthermore, condensation of the amine with an ester (W—C(O)—O-alkyl or W—C(O)—O-(electron-deficient aryl)) in an alcoholic solvent such as ethanol at an elevated temperature will yield desired amides.

Treatment of the carboxamide with a sulfurating agent such as Lawesson's Reagent (2,4-bis(4-methoxyphenyl)-1,3-dithia-2,4-diphosphetane-2,4-disulfide) in, for instance, dioxane at an appropriate temperature provides the corresponding thioamide, e.g., X in formula I is S. See Lawesson et. al. in *Bull. Soc. Chim. Belg.*, 229 (1978)), or P$_4$S$_{10}$ (see *Chem. Rev.*, 45 (1961). Alternatively, one can react a dithiocarboxylic ester with the corresponding azbicyclo moiety to form the same thioamide.

There are various methods for the construction of the optionally substituted 7-azabicyclo[2.2.1]heptane ring system. For example, the independent work of Trudell (R$_4$=H, Zhang, C., Trudell, M. L., *J. Org. Chem.*, 61, 7189–7191, 1996), and Schultz (R$_4$=Me, Schultz, A. G., Shen, M. S., *Tetrahedron Lett.*, 22, 3347–3350, 1981) describes the utility of a Diels-Alder approach toward preparing this ring system with functionality suitable for further elaboration to the desired 2-amino-7-aza-bicyclo[2.2.1]heptane (Scheme 2). For instance, Trudell reports (Zhang, C., Trudell, M. L., *Tetrahedron*, 54, 8349–8354, 1998) that Diels-Alder adduct 1a (where R$_6$=methylcarbamate, R$_4$=H, and Lv=Br) could readily be functionalized at C-3 via reaction with organocopper species to introduce the substituent R$_2$ in 2a,b. Likewise, hydrogenolysis of adduct 1a,b or 2a,b followed by isomerization of the endo products as described by Singh (Singh, S., Basmadjian, G. P., *Tetrahedron Lett.*, 38, 6829–6830, 1997) could provide access to the required exo acid 3a–d. Treatment of 3 with diphenylphosphoryl azide in the presence of a tertiary amine base (e.g., Et$_3$N) in a suitable solvent such as toluene, followed by warming of the intermediate acylazide in the presence of a suitable alcohol (e.g., benzyl alcohol) would effect the well-known Curtius rearrangement to provide a differentially protected bis carbamate which could be cleaved under typical hydrogenolysis conditions (e.g., 10% Pd/C, EtOH, H$_2$, ambient to 50 psi) to give the desired amine 4. Alternatively, the differentially protected bis carbamate might provide an attractive point of intervention for the chromatographic resolution of the individual 2-exo isomers prior to cleavage to amine 4.

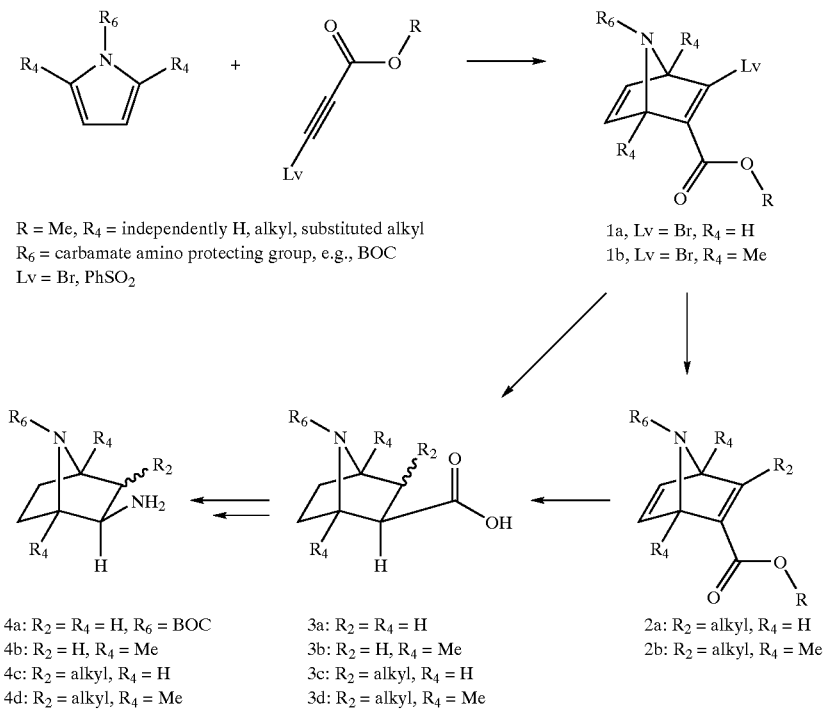

Scheme 2

R = Me, R₄ = independently H, alkyl, substituted alkyl
R₆ = carbamate amino protecting group, e.g., BOC
Lv = Br, PhSO₂

1a, Lv = Br, R₄ = H
1b, Lv = Br, R₄ = Me

2a: R₂ = alkyl, R₄ = H
2b: R₂ = alkyl, R₄ = Me

3a: R₂ = R₄ = H
3b: R₂ = H, R₄ = Me
3c: R₂ = alkyl, R₄ = H
3d: R₂ = alkyl, R₄ = Me 4a: R₂ = R₄ = H, R₆ = BOC
4b: R₂ = H, R₄ = Me
4c: R₂ = alkyl, R₄ = H
4d: R₂ = alkyl, R₄ = Me In the case where $R_6$=tert-butyloxycarbonyl, deprotection of the 7-aza group can be conveniently accomplished under acidic conditions in a suitable solvent such as methanol. After deprotection, the secondary amine may be functionalized with alkyl and substituted alkyl via reductive amination or alkylative procedures.

It will be apparent to those skilled in the art that the requisite carboxylic acids can be obtained through synthesis via literature procedures or through the slight modification thereof.

Preparation of tert-Butyl (1S,2R,4R)-2-amino-7-azabicyclo[2.2.1]heptane-7-carboxylate

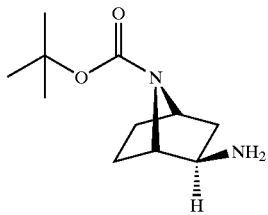

Preparation of methyl-3-bromo-propiolate:

Methyl propiolate (52 ml, 0.583 mol) is combined with recrystallized N-bromo-succinimide (120 g, 0.674 mol) in 1,700 ml acetone under nitrogen. The solution is treated with silver nitrate (9.9 g, 0.0583 mol) neat in a single lot and the reaction is stirred 6 h at RT. The acetone is removed under reduced pressure (25° C., bath temperature) to provide a gray slurry. The slurry is washed with 2×200 ml hexane, the gray solid is removed by filtration, and the filtrate is concentrated in vacuo to provide 95 g of a pale yellow oily residue. The crude material is distilled via short path under reduced pressure (65° C., about 25 mm Hg) into a dry ice/acetone cooled receiver to give 83.7 g (88%) of methyl-3-bromo-propiolate as a pale yellow oil. Anal. calc3 d for $C_4H_3BrO_2$: C, 29.48; H, 1.86. Found: C, 29.09; H, 1.97.

Preparation of 7-tert-butyl 2-methyl 3-bromo-7-azabicyclo[2.2.1]hepta-2,5-diene-2,7-dicarboxylate.

Methyl-3-bromo-propiolate (83.7 g, 0.513 mol) is added to N-t-butyloxy-pyrrole (430 ml, 2.57 mol) under nitrogen. The dark mixture is warmed in a 90° C. bath for 30 h, is cooled, and the bulk of the excess N-t-butyloxy-pyrrole is removed in vacuo using a dry ice/acetone condenser. The dark oily residue is chromatographed over 1 kg silica gel (230–400 mesh) eluting with 0–15% EtOAc/hexane. The appropriate fractions are combined and concentrated to afford 97 g (57%) of 7-tert-butyl 2-methyl 3-bromo-7-azabicyclo[2.2.1]hepta-2,5-diene-2,7-dicarboxylate as a dark yellow oil. HRMS (FAB) calc'd for $C_{13}H_{16}BrNO_4$+H: 330.0341, found 330.0335 (M+H)⁺.

Preparation of (+/−) endo-7-tert-butyl 2-methyl 7-azabicyclo[2.2.1]heptane-2,7-dicarboxylate.

7-tert-Butyl 2-methyl 3-bromo-7-azabicyclo[2.2.1]hepta-2,5-diene-2,7-dicarboxylate (97 g, 0.294 mol) is added to 10% Pd/C (6.8g) in 900 ml absolute EtOH in a PARR bottle. The suspension is diluted with a solution of $NaHCO_3$ (25 g, 0.301 mol) in 250 ml water and the mixture is hydrogenated at 50 PSI for 2.5 h. The catalyst is removed by filtration, is washed with fresh EtOH, and the filtrate is concentrated in vacuo to give a residue. The residue is partitioned between 1×200 ml saturated $NaHCO_3$ and $CH_2Cl_2$ (4×100 ml). The combined organic layer is dried over 1:1 anhydrous $K_2CO_3$/anhydrous $MgSO_4$ and concentrated in vacuo to afford 72.8 g (98%) of (+/−) endo-7-tert-butyl 2-methyl 7-azabicyclo[2.2.1]heptane-2,7-dicarboxylate. MS (EI) for $C_{14}H_{22}O_4$, m/z: 255 (M)⁺.

Preparation of (+/−) exo-7-(tert-butoxycarbonyl)-7-azabicyclo[2.2.1]heptane-2-carboxylic acid.

(+/−)Endo-7-tert-butyl 2-methyl 7-azabicyclo[2.2.1]heptane-2,7-dicarboxylate (72.8 g, 0.285 mol) is dissolved in 1000 ml dry MeOH in a dried flask under nitrogen. The solution is treated with solid NaOMe (38.5 g, 0.713 mol) neat, in a single lot and the reaction is warmed to reflux for 4h. The mixture is cooled to 0° C., is treated with 400 ml water, and the reaction is stirred 1 h as it warms to RT. The mixture is concentrated in vacuo to about 400 ml and the pH of the aqueous residue is adjusted to 4.5 with 12N HCl. The precipitate is collected and dried. The tan, slightly tacky solid is washed with 2×100 ml 60% ether in hexane and is dried to provide 47 g (68%) of (+/−) exo-7-(tert-butoxycarbonyl)-7-azabicyclo[2.2.1]heptane-2-carboxylic acid as an off-white powder. HRMS (FAB) calc'd for $C_{12}H_{19}NO_4$+H: 242.1392, found 242.1390 (M+H)$^+$.

Preparation of (+/−) exo-tert-butyl 2-{[(benzyloxy)carbonyl]amino}-7-azabicyclo[2.2.1]heptane-7-carboxylate.

(+/−)Exo-7-(tert-butoxycarbonyl)-7-azabicyclo[2.2.1]heptane-2-carboxylic acid (103.9 g, 0.430 mol) is combined with TEA (60 ml, 0.430 mol) in 1200 ml dry toluene in a dry flask under nitrogen. The solution is treated drop-wise with diphenylphosphoryl azide (92.8 ml, 0.430 mol), and is allowed to stir for 20 min at RT. The mixture is treated with benzyl alcohol (47.9 ml, 0.463 mol), and the reaction is stirred overnight at 55° C. The mixture is cooled, is extracted successively with 2×500 ml 5% citric acid, 2×500 ml water, 2×500 ml saturated sodium bicarbonate, and 500 ml saturated NaCl. The organic layer is dried over anhydrous $MgSO_4$ and concentrated in vacuo to an amber oil. The crude material is chromatographed over 900 g silica gel (230–400 mesh), eluting with 10–30% EtOAc/hexane. The appropriate fractions are combined and concentrated to give 106 g (71%) of (+/−) exo-tert-butyl 2-{[(benzyloxy)carbonyl]amino }-7-azabicyclo[2.2.1]heptane-7-carboxylate as a pale oil. $^1$H NMR (CDCl$_3$) δ 1.29–1.60, 1.44, 1.62–2.01, 3.76–3.88, 4.10, 4.24, 5.10, 7.36 ppm.

Preparation of (+/−) exo-tert-butyl 2-amino-7-azabicyclo[2.2.1]heptane-7-carboxylate.

(+/−) Exo-tert-Butyl 2-{[(benzyloxy)carbonyl]amino}-7-azabicyclo[2.2.1]heptane-7-carboxylate (1.5 g, 4.33 mmol) is combined with 10% Pd/C (150 mg) in 40 ml EtOH in a 250 ml Parr shaker bottle. The mixture is hydrogenated at 50 PSI for 1.5 h. The catalyst is removed by filtration and the filtrate is concentrated in vacuo. The crude material is chromatographed over 30 g silica gel (230–400 mesh), eluting with 7% MeOH/CH$_2$Cl$_2$+1% conc. NH$_4$OH. The appropriate fractions are combined and concentrated to provide 606 mg (66%) of (+/−) exo-tert-butyl 2-amino-7-azabicyclo[2.2.1]heptane-7-carboxylate. HRMS (FAB) calcd for $C_{11}H_{20}N_2O_2$+H: 213.1603, found 213.1580 (M+H)$^+$. This racemic mixture will be referenced as (+/−)-7-aza-[2.2.1]-Amine.

Resolution of racemic carboxylate mixture:

The isolated (+/−) exo-tert-butyl 2-{[(benzyloxy)carbonyl]amino}-7-azabicyclo[2.2.1]heptane-7-carboxylate is resolved via preparative chiral HPLC (50×500 mm Chiralcel OJ column, 30 deg. C, 70 m/min. 10/90 (v/v) isopropanol/heptane). The resolution affords 40 g of tert-butyl (1S,2R,4R)-(+)-2{[(benzyloxy)carbonyl]amino}-7-azabicyclo[2.2.1]heptane-7-carboxylate and 42 g of tert-butyl-(1R,2S,4S)(−)-2{[(benzyloxy)carbonyl]amino}-7-azabicyclo[2.2.1]heptane-7-carboxylate.

The 2R enantiomer is triturated with 40 ml ether followed by 40 ml hexane (to remove lingering diastereo and enantiomeric impurities) and is dried to afford 30 g (56%) of purified tert-butyl (1S,2R,4R)-(+)-2{[(benzyloxy)carbonyl]amino}-7-azabicyclo[2.2.1]heptane-7-carboxylate with 99% enantiomeric excess. MS (EI) for C)$_{19}H_{26}N_2O_4$, m/z: 346 (M)$^+$. [α]$^{25}{}_D$=22, (c 0.42, chloroform).

The 2S enantiomer is triturated with 40 ml ether followed by 40 ml hexane to give 35 g (66%) of purified tert-butyl (1R,2S,4S)-(−)-2{[(benzyloxy)carbonyl]amino}-7-azabicyclo[2.2.1]heptane-7-carboxylate with 99% enantiomeric excess. MS (EI) for $C_{19}H_{26}N_2O_4$, m/z: 346 (M)$^+$. [α]$^{25}{}_D$=−23, (c 0.39, chloroform).

Preparation of tert-butyl-(1S,2R,4R)-(+)-2-amino-7-azabicyclo[2.2.1]heptane-7-carboxylate ((2R)-7-aza-[2.2.1]-Amine).

tert-Butyl (1S,2R,4R)-(+)-2{[(benzyloxy)carbonyl]amlno}-7-azabicyclo[2.2.1]heptane-7-carboxylate (9.5 g, 27.4 mmol) is combined with 950 mg 10% Pd/C in 75 ml absolute EtOH in a 500 ml Parr bottle. The reaction mixture is hydrogenated at 50 PSI for 3h, the catalyst is removed by filtration, and the filter cake is washed with MeOH. The filtrate is concentrated in vacuo to give 6.4 g of a residue. The crude material is chromatographed over 200 g silica gel (230–400 mesh) eluting with 7% CH$_3$OH/CHCl$_3$ containing 1% conc. NH$_4$OH. The appropriate fractions are combined and concentrated to give 5.61 g (96%) of tert-butyl-(1S,2R,4R)-(+)-2-amino-7-azabicyclo[2.2.1]heptane-7-carboxylate as a pale oil. MS (EI) for $C_{11}H_{20}N_2O_2$, m/z: 212 (M)$^+$. [α]$^{25}$D=9, (c 0.67, CHCl$_3$). This wil referenced as (2R)-7-aza-[2.2.1]-Amine.

Acids

Preferably, when Q is furan, oxazole, oxadiazole, pyrrole, 5-thiazole, thiophene, or triazole, the acid is activated with a uronium salt, preferably HATU (see *J. Am. Chem. Soc.*, 4397 (1993)), in the presence of a base such as DIEA in DMF, and reacted directly with (2R)-7-aza-[2.2.1]-Amine to afford the desired amides. In the case where Q is a 2-thiazole, or 2-oxazole, the amide bond is formed by the reaction of the amine and ester (Lv=OEt) in an alcoholic solvent (see *Liebigs Ann. Chem.*, 1216–1231 (1980)).

It will be apparent to those skilled in the art that the requisite carboxylic acids can be obtained commercially or can be synthesized by known procedures. Certain thiophene acids can be synthesized from the corresponding aldehydes by oxidation with NaClO$_2$ as described in *J. Chem. Soc. Perkin Trans. I.*, 789–794 (1999). The requisite aldehydes can be made as described in *J. Med. Chem.*, 1585–1599 (1997). An aryl boronic acid is reacted with a bromothiophene in the presence of a palladium (0) source, such as tetrakis-(triphenylphosphine)palladium (0), and a base, preferably aqueous sodium carbonate. The reaction works best if heated at reflux in THF/water for 24 hours.

Other thiophene acids are synthesized from the corresponding esters by base catalyzed hydrolysis. Typical hydrolysis procedures are well known in the art. Preferably, the thiophene ester is treated with aqueous lithium hydroxide in a solvent such as dioxane. The esters are either commercially available or synthesized by reaction of a bromothiophene ester with the appropriate thiophenol or phenol as described in *Coll. Czech. Chem. Comm.*, 2360–2363 (1980). Namely, the sodium salt of the thiophenol or phenol is formed by treatment with a strong base like sodium hydride. The sodium salt is then reacted with a bromothiophene in a solvent such as acetone.

Furan examples are prepared in a convergent means by a direct palladium catalyzed Suzuki coupling N-[(2R)-7- azabicyclo[2.2.2]hept-2-yl]-5-bromo-furan-2-carboxamide with the requisite boronic acid by the method described in *Org. Lett.* 965–7 (1999), to yield directly the desired aryl amides.

The 1,3-oxazole-2-carboxylate intermediates can be prepared by the method described in *J. Pharm. Sci. Japan* 305–7, (1956).

Coupling

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. The invention includes the following examples in pure stereoisomeric form or as racemic mixtures.

EXAMPLE 1

N-[(1S,2R,4R)-7-Azabicyclo[2.2.1]hept-2-yl)-5-bromo-2-thiophenecarboxamide Hydrochloride

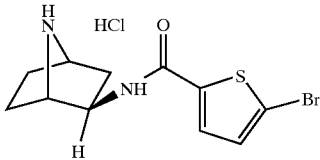

5-Bromothiophene-2-carboxylic acid (388 mg, 1.9 mmol) is combined with 10 ml $CH_2Cl_2$ in a dried flask under nitrogen. The solution is treated with TEA (265 µL, 1.9 mmol) followed by bis (2-oxo-3-oxazolidinyl) phosphinic chloride (479 mg, 1.9 mmol) and the reaction is stirred 1 h at rt. The mixture is treated with (2R)-7-aza-(2.2.1]-Amine (320 mg, 1.5 mmol) in 2 ml $CH_2Cl_2$ and the reaction is stirred 18 h at rt. The mixture is washed with 1×10 ml saturated $NaHCO_3$, the organic layer is dried over anhydrous $K_2CO_3$, and is concentrated in vacuo to a residue. The crude material is chromatographed over 25 g silica gel (230–400 mesh) eluting with 20% EtOAc/hexane. The appropriate fractions are combined and concentrated to afford 400 mg (65%) of the intermediate tert-butyl (1S,2R,4R)-(+)-2-{[(5-bromo-2-thienyl)carbonyl]amino}-7-azabicyclo[2.2.1]heptane-7-carboxylate.

tert-Butyl (1S,2R,4R)-(+)-2-[{(5-bromo-2-thienyl)carbonyl]amino}-7-azabicyclo[2.2.1]heptane-7-carboxylate (222 mg, 0.55 mmol) is combined with 5 ml 2N methanolic HCl acid in 5 ml MeOH under nitrogen. The reaction is warmed in a 60° C. bath for 2 h, is cooled, and is concentrated in vacuo to a residue. The residue is dissolved in 1 ml IPA, is diluted with 2 ml diethyl ether, and is allowed to crystallize. The white solid is washed with ether and is dried to give 165 mg (88%) of Example 1 as a white solid. MS for $C_{11}H_{13}BrN_2OS$, (EI) m/z: 300 $(M-H)^-$. $[\alpha]^{25}D=-5$ (c 0.33, water).

EXAMPLE 2

(+/−) exo-N-[7-Azabicyclo[2.2.1]hept-2-yl]-5-bromo-2-thiophenecarboxamide Hydrochloride 5-Bromothiophene-2-carboxylic acid (738 mg, 3.6 mmol) is combined with 20 ml $CH_2Cl_2$ in an oven-dried flask under nitrogen. The solution is treated with TEA (496 µL, 3.6 mmol) followed by bis (2-oxo-3-oxazolidinyl) phosphinic chloride (906 mg, 3.6 mmol) and the reaction is stirred 1 h at rt. The mixture is treated with (+/−)-7-aza-[2.2.1]-Amine (606 mg, 2.9 mmol) in 5 ml $CH_2Cl_2$, and the reaction is stirred 24 h at rt. The mixture is washed with 1×10 ml saturated sodium bicarbonate, the organic layer is dried over anhydrous potassium carbonate, and is concentrated in vacuo to a pale oily residue. The crude material is chromatographed over 50 g silica gel (230–400 mesh) eluting with 25% ethyl acetate/hexane. The appropriate fractions are combined and concentrated to afford 733 mg (64%) of (+/−) exo-tert-butyl-2-{[(5-bromo-2-thienyl)carbonyl]amino}-7-azabicyclo[2.2.1]heptane-7-carboxylate. HRMS (FAB) calcd for $C_{16}H_{21}BrN_2O_3S$ +H: 401.0535, found 401.0533 $(M+H)^+$.

(+/−) Exo-tert-butyl (2-{[(5-bromo-2-thienyl)carbonyl]amino}-7-azabicyclo[2.2.1]heptane-7-carboxylate (210 mg, 0.52 mmol) is combined with 5 ml 2N methanolic HCl in 5 ml MeOH in a flask under nitrogen. The reaction is warmed to 60° C. for 2 h, is cooled, and the volatiles are removed in vacuo. The residue is dissolved in 1 ml IPA, is diluted with 2 ml $Et_2O$, and is allowed to crystallize. The white solid is washed with ether and is dried to give 154 mg (88%) of Example 2 as a white solid. MS for $C_{11}H_{13}BrN_2OS$, (EI) m/z: 300 $(M)^+$.

EXAMPLE 3

N-[(1S,2S,4R)-7-Azabicyclo[2.2.1]hept-2-yl]-5-bromo-2-hiophenecarboxamide Hydrochloride

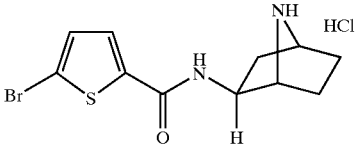

Resolution of (+/−) Exo-tert-butyl-2-{[(5-bromo-2-thienyl)carbonyl]amino}-7-azabicyclo[2.2.1]heptane-7-carboxylate (+/−) Exo-tert-butyl-2-{[(5-bromo-2-thienyl)carbonyl]amino}-7-azabicyclo[2.2.1]heptane-7-carboxylate (500 mg) is resolved via preparative chiral HPLC resolution (Chiralpak AD, IPA/heptane) to provide 175 mg (70%) of tert-butyl-(1S,2R,4R)-{[(5-bromo-2-thienyl)carbonyl]amino}-7-azabicyclo[2.2.1]heptane-7-carboxylate as a white solid (MS for $C_{16}H_{21}BrN_2O_3S$, (EI) m/z: 400 $(M)^+$; the structure is confirmed by x-ray crystallography on crystals obtained from $Et_2O$), and 195 mg (78%) of tert-butyl-(1S,2S,4R)-{[(5-bromo-2-thienyl)carbonyl]amino}-7-azabicyclo[2.2.1]heptane-7-carboxylate as a white solid (MS for $C_{16}H_{21}BrN_2O_3S$, (EI) m/z: 400 (M)+).

tert-Butyl-(1S,2S,4R)-{[(5-bromo-2-thienyl)carbonyl]amino}-7-azabicyclo[2.2.1]heptane-7-carboxylate (165 mg, 0.41 mmol) is deprotected, and the product is isolated as its HCl salt as described in Example 1 to afford 134 mg (97%) of Example 3 as a white solid. MS for $C_{11}H_{13}BrN_2OS$, (EI) m/z: 300 $(M)^+$. $[\alpha]^{25}_D=5°$ (c 0.30, water).

EXAMPLE 5

N-[(1S,2R,4R)-7-Azabicyclo[2.2.1]hept-2-yl]-5-(methylthio)thiophene-2-carboxamide Hydrochloride

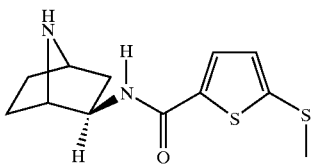

5-Methylthio-thiophene-2-carboxylic acid (192 mg, 1.1 mmol) is coupled with (2R)-7-aza-[2.2.1]-Amine (212 mg, 1.0 mmol) and deprotected as described in Example 1 with non-critical variations to provide 192 mg (63%) of Example 5 as a white solid. MS for $C_{12}H_{16}N_2OS_2$, (EI) m/z: 268 $(M)^+$.

EXAMPLE 6

N-[(1S,2R,4R)-7-Azabicyclo[2.2.1]hept-2-yl]-5-phenylthiophene-2-5 carboxamide Hydrochloride

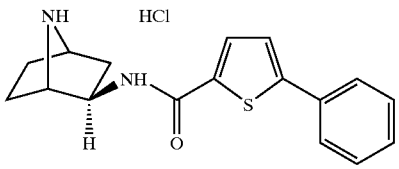

5-Bromothiophene-2-carboxaldehyde (1.0 g, 5.2 mmol) is added to a solution of tetrakis(triphenylphosphine)palladium (0) (180 mg, 0.16 mol) in degassed THF (10 mL). The resulting solution is stirred for 5 minutes and then a solution of phenylboronic acid (760 mg, 6.2 mmol) in THF (10 mL) is added followed by aqueous $Na_2CO_3$ (2M, 5.2 mL). The mixture is heated at reflux for 24 h. The reaction mixture is allowed to cool, poured into ether, and washed twice with water. The ether layer is dried over $Na_2SO_4$ and concentrated in vacuo. The crude product is purified by flash column chromatography (1:1 hexanes/$CH_2Cl_2$) to yield 900 mg (91%) of 5-phenylthiophene-2-carboxaldehyde. $^1$H NMR (300MHz, $CDCl_3$)δ7.38–7.45, 7.65–7.68, 7.73, 9.88.

5-Phenylthiophene-2-carboxaldehyde (750 mg, 4 mmol) is dissolved in a mixture of THF, tBuOH, and water (2:1:1, 60miL). $KH_2PO_4$ (1.36 g, 10 mmol) is added followed by $NaClO_2$ (900 mg, 10 mmol). The mixture is stirred at rt for 5 days. Aqueous NaOH (2M, 10 mL) is added and a majority of the organic solvents are removed in vacuo yielding an aqueous suspension. This suspension is diluted with water and washed with three times with $CH_2Cl_2$. The aqueous layer is acidified to pH<2 with 25% $H_2SO_4$ and the product is extracted three times with $CH_2Cl_2$. The combined organic washes are dried over $Na_2SO_4$, filtered and concentrated in vacuo to yield 417 mg (51%) of 5-phenylthiophene-2-carboxylic acid. MS for $C_{11}H_8O_2S$, (ES) m/z: 203 $(M-H)^-$.

5-Phenyl-thiophene-2-carboxylic acid (224 mg, 1.1 mmol) is coupled with (2R)-7-aza-[2.2.1]-Amine (212 mg, 1.0 mmol) and deprotected as described in Example 1 with non critical variations to provide 258 mg (77%) of Example 6 as a white solid. MS for $C_{17}H_{18}N_2OS$, (EI) m/z: 298 $(M)^+$. HRMS (FAB) calcd for $C_{17}H_{18}N_2OS+H$: 299.1218, found 299.1220 $(M+H)^+$.

EXAMPLE 7

N-[(1S,2R,4R)-7-Azabicyclo[2.2.1]hept-2-yl]-5-(2-chlorophenyl)thiophene-2-carboxamide Hydrochloride

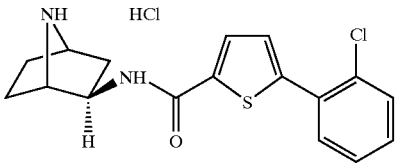

5-(2—Chlorophenyl)-thiophene-2-carboxylic acid is prepared as outlined in Example 3 by starting with 2-chlorophenylboronic acid and 3-bromothiophene-2-carboxaldehyde.

5-(2-Chlorophenyl)-thiophene-2-carboxylic acid (263 mg, 1.1 mmol) is coupled with (2R)-7-aza-[2.2.1]-Amine (212 mg, 1.0 mmol) and deprotected as described in Example 1 with non-critical variations to provide 258 mg (70%) of Example 7 as a white solid. MS for $C_{17}H_{17}ClN_2OS$, (EI) m/z: 332 $(M)^+$.

EXAMPLE 8

N-[(1S,2R,4R)-7-Azabicyclo[2.2.1]hept-2-yl]-5-[(4-chlorophenyl)thio]thiophene-2-carboxamide Hydrochloride

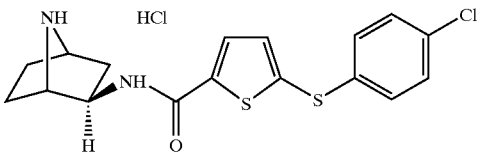

Sodium hydride (60%, 1.2 g, 30 mmol) is added to a solution of 4-chlorothiophenol (4.3 g, 30 mmol) in THF (30 mL). The resulting solution is stirred for 10 minutes then the solvent is removed in vacuo. Acetone (60 mL) is added followed by 5-bromothiophene-2-carboxaldehyde (3.0 mL, 25 mmol). The mixture is stirred at rt for 2 h. The solvent is removed in vacuo and the resulting slurry diluted with $CH_2Cl_2$. This solution is washed three times with 1N NaOH then dried over $MgSO_4$, filtered and concentrated in vacuo. The crude product is purified by flash column chromatography (gradient of 1 to 5% EtOAc in heptane) to give 6.2 g (98%) of 5-(4-chlorophenylsulfanyl)thiophene-2-carboxaldehyde. $^1$H NMR (300 MHz, $CDCl_3$)δ7.13, 7.31–7.39, 7.63, 9.78.

5-(4-Chlorophenylsulfanyl)thiophene-2-carboxaldehyde (6.1 g, 24 mmol) is dissolved in a mixture of THF, tBuOH, and water (3:3:1, 255 mL). 2-methyl-2-butene (20.3 mL, 192 mmol) is added followed by $KH_2PO_4$ (9.8 g, 72 mmol) and then $NaClO_2$ (80%, 8.17 g, 72.3 mmol). The mixture is stirred at rt for 2 hours. Aqueous $KHSO_4$ (0.5M, 200 mL) is added and the organic solvents are removed in vacuo to produce an aqueous suspension of the product. The precipitate is collected by filtration, dissolved in 1N NaOH and washed two times with ether. The aqueous solution is then acidified to pH<2 with concentrated HCl and a precipitate formed. The precipitate is collected by filtration and washed with 0.5M $NaHSO_4$ then water. The solid is dried in vacuo to give 5.7 g (87%) of 5-(4-chlorophenylsulfanyl)thiophene-2-carboxylic acid. MS for $C_{11}H_7ClO_2S_2$, (ES) m/z: 269 $(M-H)^-$.

5-(4-Chlorophenylsulfanyl)thiophene-2-carboxylic acid (290 mg, 1.07 mmol) is added to 10 ml $CH_2Cl_2$ in a dried flask under nitrogen. The solution is treated with TEA (153 μL, 1.1 mmol) followed by bis (2-oxo-3-oxazolidinyl) phosphinic chloride (280 mg, 1.1 mmol) and the reaction is stirred 1 h at rt. The mixture is treated with (2R)-7-aza-[2.2.1]-Amine (212 mg, 1.0 mmol) in 2 ml $CH_2Cl_2$ and the reaction is stirred 4 h at rt. The mixture is washed with 1×10 ml saturated $NaHCO_3$, the organic layer is dried over anhydrous $K_2CO_3$, and is concentrated in vacuo to a residue. The crude material is chromatographed over 25 g silica gel (230–400 mesh) eluting with 35% EtOAc/hexanes. The appropriate fractions are combined and concentrated to afford of the intermediate exo-tert-butyl (1S,2R,4R)-2-{[5-(4-chlorophenylsulfanyl)thiophene-2-carbonyl]amino}-7-azabicyclo[2.2.1]heptane-7-carboxylate as a residue. The residue is combined with 5 ml 2N methanolic HCl acid in 5 ml MeOH in a flask under nitrogen. The reaction is warmed in a 60° C. bath for 2 h, is cooled, and is concentrated in vacuo to a residue. The residue is dissolved in 1 ml IPA, is diluted with 2 ml diethyl ether, and is allowed to crystallize. The white solid is washed with ether and is dried to give 238 mg (59%) of Example 8 as a white solid. MS for $C_{17}H_{17}ClN_2OS_2$, (EI) m/z: 364 (M)$^+$.

EXAMPLE 9

N-[(1S,2R,4R)-7-Azabicyclo[2.2.1]hept-2-yl]-5-methylthiophene-2-carboxamide Hydrochloride

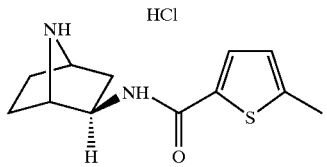

5-Methyl-thiophene-2-carboxylic acid (156mg, 1.1 mmol) is coupled with (2R)-7-aza-[2.2.1]-Amine (212 mg, 1.0 mmol) and deprotected as described in Example 1 with non critical variations to provide 199 mg (73%) of Example 9 as a white solid. HRMS (FAB) calcd for $Cl_{12}H_{16}N_2OS+H$: 237.1062, found 237.1065 for (M+H)$^+$.

EXAMPLE 10

N-[(1S,2R,4R)-7-azabicyclo[2.2.1]hept-2-yl]-5-pyridin-2-ylthiophene-2-carboxamide Dihydrochloride

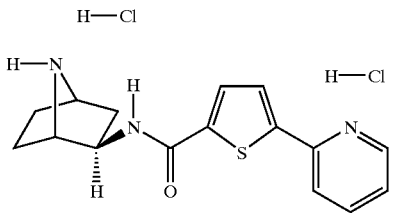

5-(Pyridin-2-yl)thiophene-2-carboxylic acid (226 mg, 1.1 nimol) is coupled with (2R)-7-aza-[2.2.1]-Amine (212 mg, 1.0 mmol) and deprotected as described in Example 1 with non-critical variations to provide 243 mg (65%) of Example 10 as an off-white solid. HRMS (FAB) calcd for $C_{16}H_{17}N_3OS+H$: 300.1170, found 300.1172 (M+H)$^+$.

EXAMPLE 11

N-[(1S,2R,4R)-7-azabicyclo[2.2.1]hept-2-yl]-5-(3-nitrophenyl)-2-furamide Hydrochloride

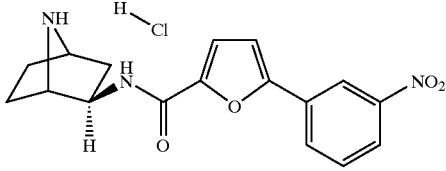

5-(3-Nitrophenyl)furan-2-carboxylic acid (226 mg, 1.1 mmol) is coupled with (2R)-7-aza-[2.2.1]-Amine (212 mg, 1.0 mmol) and deprotected as described in Example 1 with non-critical variations to provide 232 mg (64%) of Example 11 as a yellow solid. HRMS (FAB) calcd for $C_{17}H_{17}N_3O_4+$H: 328.1297, found 328.1292 (M+H)$^+$.

EXAMPLE 12

N-[(1S,2R,4R)-7-Azabicyclo[2.2.1]hept-2-yl]-5-(4-nitrophenyl)-2-furamide Hydrochloride

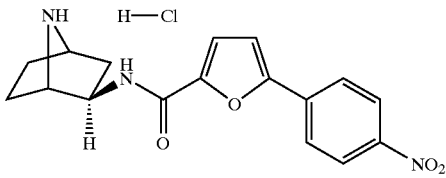

5-(4-Nitrophenyl)furan-2-carboxylic acid (226 mg, 1.1 mmol) is coupled with 2(R)-7-aza-[2.2.1]Amine (212 mg, 1.0 mmol) and deprotected as described in Example 1 with non critical variations to provide 256 mg (71%) of Example 12 as a yellow solid. HRMS (FAB) calcd for $C_{17}H_{17}N_3O_4+$H: 328.1297, found 328.1303 (M+H)$^+$.

EXAMPLE 13

N-[(1S,2R,4R)-7-Azabicyclo[2.2.1]hept-2-yl]-5-(4-chlorophenyl)-2-furamide Hydrochloride

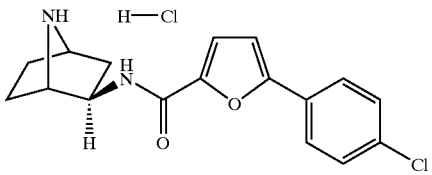

5-(4-Chlorophenyl)furan-2-carboxylic acid (226 mg, 1.1 mmol) is coupled with (2R)-7-aza-[2.2.1]-Amine (212 mg, 1.0 mmol) and deprotected as described in Example 1 with non-critical variations to provide 110 mg (31%) of Example 13 as a white solid. MS for $C_{17}H_{17}ClN_2O_2$, (EI) n/z: 316 (M)$^+$.

EXAMPLE 14

N-[(1S,2R,4R)-7-Azabicyclo[2.2.1]hept-2-yl]-5-chlorothiophene-2-carboxamide Hydrochloride

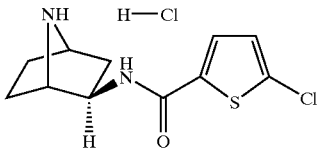

5-Chlorothiophene-2-carboxylic acid (226 mg, 1.1 mmol) is coupled with (2R)-7-aza-[2.2.1]-Amine (212 mg, 1.0 mmol) and deprotected as described in Example 1 with non critical variations to provide 357 mg (46%) of Example 14 as a white solid. MS for $C_{11}H_{14}ClN_2OS$, (EI) m/z: 256 (M)$^+$.

EXAMPLE 15

N-[(1S,2R,4R)-7-Azabicyclo[2.2.1]hept-2-yl]-5-(2-nitrophenyl)-2-furamide Hydrochloride

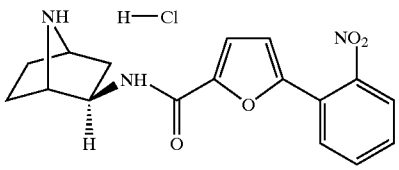

5-(2-Nitrophenyl)furan-2-carboxylic acid (226 mg, 1.1 mmol) is coupled with (2R)-7-aza-[2.2.1]-Amine (212 mg, 1.0 mmol) and deprotected as described in Example 1 with non-critical variations to provide 243 mg (63%) of Example 15 as a yellow solid. Anal. Calcd for $C_{17}H_{17}N_3O_4 \cdot HCl$: C, 56.13; H, 4.99; N, 11.55 @ 0.34% $H_2O$ found. Found: C, 55.84; H, 5.09; N, 11.38.

EXAMPLE 16

N-[(1S,2R,4R)-7-Azabicyclo[2.2.1]hept-2-yl]-5-(4-aminophenyl)-2-furamide Dihydrochloride

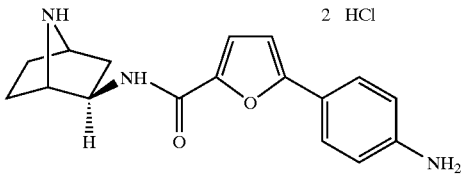

Example 12 (120 mg, 0.33 mmol) is dissolved in EtOH (20 ml) with 2M NaOH (0.17 ml, 0.34 mmol) and hydrogenated at 35 psi for 2 h. The catalyst is filtered off, and the mother liquor is concentrated to an oil. The yellow oil is dissolved in 1M HCl in MeOH (10 ml) and stirred at rt over night. The volatiles are removed in vacuo and the blue-green residue is treated with IPA (2 ml), forming a yellow precipitate. The slurry is filtered, and the cake is washed with ether, affording 104 mg (85%) of Example 16 as a dull yellow solid. HRMS (FAB) calcd for $C_{17}H_{19}N_3O_2$+H: 298.1555, found 298.1554 (M+H)$^+$.

EXAMPLE 17

N-[(1S,2R,4R)-7-Azabicyclo[2.2.1]hept-2-yl]-5-(2-fluorophenyl)-2-furamide Hydrochloride

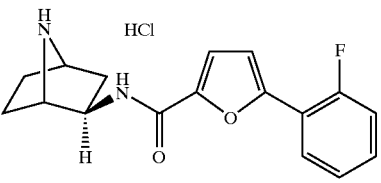

5-(2-Fluorophenyl)-2-furoic acid (140 mg, 0.68 mmol) is dissolved in DMF (5 ml) with DIEA (0.36 ml, 2.05 mmol) and (2R)-7-aza-[2.2.1]-Amine (159 mg, 0.75 mmol) and cooled to 0° C. HATU (259 mg, 0.68 mmol) is added portionwise, and the reaction is stirred overnight at rt, allowing the ice bath to expire. Volatiles are removed in vacuo, and the crude material is chromatographed over 25 g slurry-packed silica, eluting with 40% EtOAc/hexane. The appropriate fractions are collected and concentrated. The residue is dissolved in 1M HCl in MeOH (5 ml) and stirred overnight. Volatiles are removed in vacuo, and the residue is treated with IPA (2 ml). The resulting precipitate is isolated via filtration, rinsed with $Et_2O$, and dried to afford 111 mg (48%) of Example 17 as a white solid. HRMS (FAB) calcd for $C_{17}H_{17}FN_2O_2$+H: 301.1352, found 301.1343 (M+H)$^+$.

EXAMPLE 18

N-[(1S,2R,4R)-7-Azabicyclo[2.2.1]hept-2-yl]-5-(3-fluorophenyl)-2-furamide Hydrochloride

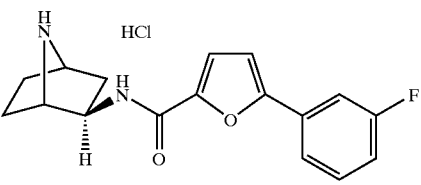

5-(3-Fluorophenyl)-2-furoic acid (140 mg, 0.68 mmol) is coupled with (2R)-7-aza-[2.2.1]-Amine (159 mg, 0.75 mmol) and subsequently deprotected as described in Example 17 with non-critical changes to give 102 mg (45%) of Example 18. HRMS (FAB) calcd for $C_{17}H_{17}FN_2O_2$+H: 301.1352, found 301.1353 (M+H)$^+$.

Example 19

N-[(1S,2R,4R)-7-Azabicyclo[2.2.1]hept-2-yl]-5-(4-fluorophenyl)-2-furamide Hydrochloride

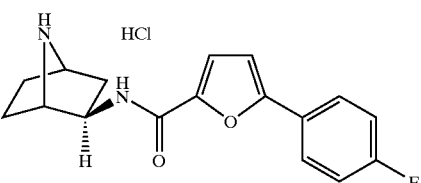

5-(4-Fluorophenyl)-2-furoic acid (140 mg, 0.68 mmol) is coupled with (2R)-7-aza-[2.2.1]-Amine (159 mg, 0.75 mmol) and subsequently deprotected as described in Example 17 with non-critical changes to give 150 mg (66%) of Example 19. HRMS (FAB) calcd for $C_{17}H_{17}FN_2O_2$+H: 301.1352, found 301.1357 (M+H)$^+$.

EXAMPLE 20

N-[(1S,2R,4R)-7-Azabicyclo[2.2.1]hept-2-yl]-5-(4-methylphenyl)-2-furamide Hydrochloride

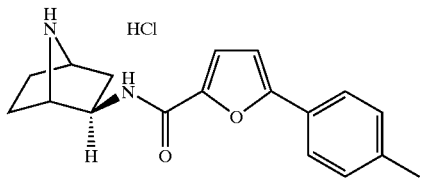

5-(4-Methylphenyl)-2-furoic acid (138 mg, 0.68 mmol) is coupled with (2R)-7-aza-[2.2.1]-Amine (159 mg, 0.75 mmol) and subsequently deprotected as described in Example 17 with non-critical changes to give 147 mg (65%) of Example 20. HRMS (FAB) calcd for $C_{16}H_{17}N_3OS$+H: 300.1170, found 300.1165 (M+H)$^+$.

EXAMPLE 21

N-[(1S,2R,4R)-7-Azabicyclo[2.2.1]hept-2-yl]-2-phenyl-1,3-thiazole-5-to carboxamide Dihydrochloride

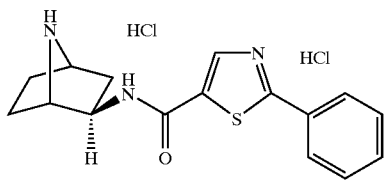

2-Phenyl-1,3-thiazole-5-carboxylic acid (140 mg, 0.68 mmol) is coupled with (2R)-7-aza-[2.2.1]-Amine (159 mg, 0.75 mmol) and subsequently deprotected as described in Example 17 with non-critical changes to give 138 mg (55%) of Example 21. HRMS (FAB) calcd for $C_{16}H_{17}N_3OS$+H: 300.1170, found 300.1165 (M+H)$^+$.

EXAMPLE 22

N-[(1S,2R,4R)-7-Azabicyclo[2.2.1]hept-2-yl]-2-(2-fluorophenyl)-1,3-thiazole-5-carboxamide Hydrochloride

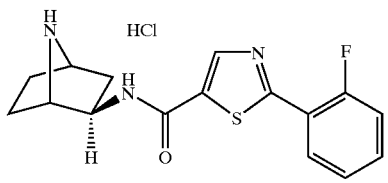

2-(2-Fluorophenyl)-1,3-thiazole-5-carboxylic acid (167 mg, 0.68 mmol) is coupled with (2R)-7-aza-[2.2.1]-Amine (159 mg, 0.75 mmol) and subsequently deprotected as described in Example 17 with non-critical changes to give 176 mg (66%) of Example 22. HRMS (FAB) calcd for $C_{16}H_{16}FN_3OS$+H: 318.1076, found 318.1080 (M+H)$^+$.

EXAMPLE 23

N-[(1S,2R,4R)-7-Azabicyclo[2.2.1]hept-2-yl]-5-phenyl-2-furamide Hydrochloride

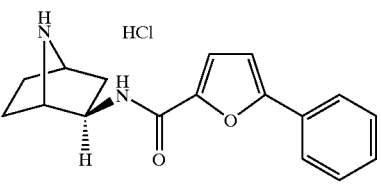

A solution of 5-bromo-furan-2-carbaldehyde (1.08 g, 6.16 mmol, 1 eq), phenylboronic acid (0.90 g, 7.39 mmol, 1.1 eq), tetrabutylanumonium bromide (1.99 g, 6.16 mmol, 1 eq), palladium acetate (30 mg, 0.0.12 mmol 0.02 eq), $K_2CO_3$ (2.13 g, 15.4 mmol, 2.5 eq) in water (10 mL) is stirred under nitrogen at rt overnight. The reaction is diluted with 40 mL water and extracted with EtOAc (3×100 mL). The organic layers are combined and stirred with charcoal for 30 min, then dried over $MgSO_4$ and filtered. The solvent is removed under reduced pressure to give an oil. The intermediate is purified by silica gel chromatography using a Biotage Flash 40M column (10% EtOAc/heptane). Yield 70.1%. HRMS (FAB) calculated for $C_{11}H_8O_2$+H 173.0603, found 173.0607.

To a solution of the intermediate (0.650 g, 3.78 mmol, 1 eq) in water (5.5 mL), t-BuOH (18.0 mL), and THF (18.0 mL) is added 2-methyl-2-butene (3.2 mL, 30.2 mmol, 8 eq), potassium phosphate monobasic (1.54 g, 11.3 mmol, 3 eq), then $NaClO_2$ (1.03 g, 11.3 mmol, 3 eq) in that order. After four hours, the reaction is complete and diluted with 1 N NaOH (100 mL). The aqueous solution is extracted with ether (2×100 mL), and the aqueous layer is acidified with conc. HCl. The resulting solution is extracted with $CH_2Cl_2$ (3×100 mL). The organic layers are dried over $MgSO_4$, and the solvent removed. 5-Phenyl-2-furoic acid is purified by silica gel chromatography using a Biotage Flash 40M column (10% EtOAc/1% formic acid/heptane). The solid remaining after removal of the solvent is filtered and recrystallized from EtOH and water to give the acid as a white crystalline solid (0.499 g, 70.2%). HRMS (FAB) calculated for $C_{11}H_8O_3$+H 189.0473, found 189.0403.

5-Phenyl-2-furoic acid (167 mg, 0.68 mmol) is coupled with (2R)-7-aza-[2.2.1]-Amine (159 mg, 0.75 mmol) and subsequently deprotected as described in Example 17 with non-critical changes to give 92 mg (42%) of Example 23. HRMS (FAB) calcd for $C_{17}H_{18}N_2O_2$+H: 283.1446, found 283.1452 (M+H)$^+$.

EXAMPLE 24

N-[(1S,2R,4R)-7-Azabicyclo[2.2.1]hept-2-yl]-5-bromo-2-furamide Hydrochloride

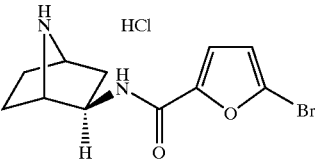

2-Bromofuroic acid (143 mg, 0.75 mmol) is coupled with (2R)-7-aza-[2.2.1]-Amine (159 mg, 0.75 mmol) and subsequently deprotected as described in Example 17 with non-critical changes to give 166 mg (69%) of Example 24. HRMS (FAB) calcd for $C_{11}H_{13}BrN_2O_2$+H: 285.0239, found 285.0241 (M+H)$^+$.

EXAMPLE 25

N-[(1S,2R,4R)-7-Azabicyclo[2.2.1]hept-2-yl]-5-phenyl-1,3-oxazole-2-carboxamide Hydrochloride

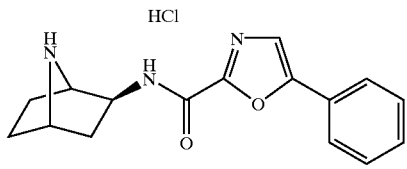

Ethyl 5-phenyl-1,3-oxazole-2-carboxylate (217 mg, 1.0 mmol) is combined with (2R)-7-aza-[2.2.1]-Amine (212 mg, 1.0 mmol) in absolute EtOH (5 ml) in a sealed tube. The reaction is heated to 100° C. for 10 days. Volatiles are removed in vacuo, and the crude material is chromatographed over 25 g slurry-packed silica, fluting with 30% EtOAc/hexane. The appropriate fractions are collected and concentrated to a white solid. The solid is treated with 1M HCl in MeOH (10 ml) and stirred overnight. Volatiles are removed in vacuo, and the resulting foam is triturated with $Et_2O$ (3 ml). The slurry is filtered, and the cake washed with ether and dried overnight, affording 153 mg (48%) of Example 25. HRMS (FAB) calcd for $C_{16}H_{17}N_3O_2$+H: 284.1399, found 284.1391 (M+H)$^+$.

EXAMPLE 26

N-[(1S,2R,4R)-7-Azabicyclo[2.2.1]hept-2-yl]-5-phenylisoxazole-3-carboxamide

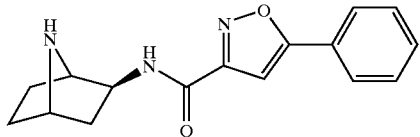

See Vaughan, W. R.; Spencer, J. L. *J. Org. Chem.*; 25; 1960; 1160–1164) for the synethesis of 5-phenylisoxazole-3-carboxylic acid. The amide is obtained using coupling conditions discussed herein to give Example 26.

MATERIALS AND METHODS FOR DETERMINING α7 nAChR AGONIST ACTIVITY

Cell-based Assay for Measuring the $EC_{50}$ of α7 nAChR Agonists

Construction and Expression of the α7-5HT$_3$ Receptor:

The cDNA encoding the N-terminal 201 amino acids from the human α7 nAChR that contain the ligand binding domain of the ion channel was fused to the cDNA encoding the pore forming region of the mouse 5HT$_3$ receptor as described by Eisele J L, et al., Chimaeric nicotinic-serotonergic receptor combines distinct ligand binding and channel specificities, Nature (1993), December 2;366(6454):479–83, and modified by Groppi, et al., WO 00/73431. The chimeric α7-5HT$_3$ ion channel was inserted into pGS175 and pGS179 which contain the resistance genes for G-418 and hygromycin B, respectively. Both plasmids were simultaneously transfected into SH-EP1 cells and cell lines were selected that were resistant to both G-418 and hyrgromycin B. Cell lines expressing the chimeric ion channel were identified by their ability to bind fluorescent a-bungarotoxin on their cell surface. The cells with the highest amount of fluorescent a-bungarotoxin binding were isolated using a Fluorescent Activated Cell Sorter (FACS). Cell lines that stably expressed the chimeric α7-5HT$_3$ were identified by measuring fluorescent α-bungarotoxin binding after growing the cells in minimal essential medium containing non-essential amino acids supplemented with 10% fetal bovine serum, L-glutamine, 100 units/ml penicillin/streptomycin, 250 ng/mg fungizone, 400 μg/ml hygromycin B, and 400 μg/ml G-418 at 37° C. with 6% $CO_2$ in a standard mammalian cell incubator for at least 4 weeks in continuous culture.

Assay of the Activity of the Chimeric α7-5HT$_3$ Receptor

To assay the activity of the α7-5HT$_3$ ion channel, cells expressing the channel were plated into each well of either a 96 or 384 well dish (Corning #3614) and grown to confluence prior to assay. On the day of the assay, the cells were loaded with a 1:1 mixture of 2 mM Calcium Green 1, AM (Molecular Probes) dissolved in anhydrous MSO and 20% pluronic F-127 (Molecular Probes). This solution was added directly to the growth media of each well to achieve a final concentration 2 μM. The cells were incubated with the dye for 60 min at 37° C. and then washed with a modified version of Earle's balanced salt solution (MMEBSS) as described in WO 00/73431. The ion conditions of the MMEBSS was adjusted to maximize the flux of calcium ion through the chimeric α7-5HT$_3$ ion channel as described in WO 00/73431. The activity of compounds on the chimeric α7-5HT$_3$ ion channel was analyzed on FLIPR. The instrument was set up with an excitation wavelength of 488 nanometers using 500 milliwatts of power. Fluorescent emission was measured above 525 nanometers with an appropriate F-stop to maintain a maximal signal to noise ratio. Agonist activity of each compound was measured by directly adding the compound to cells expressing the chimeric α7-5HT$_3$ ion channel and measuring the resulting increase in intracellular calcium that is caused by the agonist-induced activation of the chimeric ion channel. The assay is quantitative such that concentration-dependent increase in intracelluar calcium is measured as concentration-dependent change in Calcium Green fluorescence. The effective concentration needed for a compound to cause a 50% maximal increase in intracellular calcium is termed the $EC_{50}$. The (1S,2R,4R) examples of the present invention have $EC_{50}$ values between 29 nM and 1 1,421 nM.

Binding Constants

Another way for measuring α7 nAChR agonist activity is to determine binding constants of a potential agonist in a competition binding assay. For α7 nAChR agonists, there is good correlation between functional $EC_{50}$ values using the chimeric α7-5HT$_3$ ion channel as a drug target and binding affinity of compounds to the endogenous α7 nAChR.

Membrane Preparation.

Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4°

C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at rt and diluted with Kreb's −20 mM Hepes buffer pH 7.0 (at rt) containing 4.16 mM $NaHCO_3$, 0.44 mM $KH_2PO_4$, 127 mM NaCl, 5.36 mM KCl, 1.26 mM $CaCl_2$, and 0.98 mM $MgCl_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay.

For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 0.05 mls MLA for a final concentration of 1 μM, added before the radioligand. In competition studies, drugs are added in increasing concentrations to the test tubes before addition of 0.05 mls [$^3$H]-MLA for a final concentration 3.0 to 4.0 nM. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis.

In competition binding studies, the inhibition constant (Ki) was calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

What is claimed:

1. A compound of Formula I:

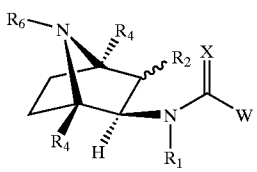

Formula I wherein the stereochemistry of the of the 7-azabicyclo [2.2.1]heptane ring is 1S,4R and the nitrogen substituent at the C-2 carbon has the exo orientation and is R;

X is O or S;

$R_1$ is H, alkyl, halogenated alkyl, cycloalkyl, or aryl;

$R_2$ is H, alkyl, halogenated alkyl, substituted alkyl, cycloalkyl, or aryl;

W is —Q, —C=C—Q, or —C≡C—Q;

Q is a cyclic heteroaromatic moiety where the heteroatoms can be from 1–3 atoms selected from oxygen, sulfur, or nitrogen of the following structures:

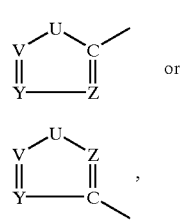

wherein U is —O—, —S—, or —N($R_3$)—;

V and Y are independently selected from =N—, and =C($R_5$)—;

Z is =N—, or =CH—;

$R_3$ is H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $R_7$, $R_9$, aryl, —C(O)—alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—$R_7$, —C(O)—$R_9$, or —C(O)-aryl;

Each $R_4$ is independently H, alkyl, or substituted alkyl;

Each $R_5$ is independently H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —$OR_8$, —$SR_8$, —$N(R_8)_2$, —C(O)$R_8$, —C(S)$R_8$, —C(O)O$R_8$, —C(O)N($R_8)_2$, —$NR_8$C(O)$R_8$, —S(O)$_2$N($R_8)_2$, —OS(O)$_2R_8$, —S(O)$_2R_8$, —S(O)$R_8$, —$NR_8$S(O)$_2R_8$, —N($R_8$)C(O)N($R_8)_2$, —CN, —$NO_2$, $R_7$, or $R_9$;

$R_6$ is H, alkyl, an amino protecting group, or an alkyl group having 1–3 substituents selected from F, Cl, Br, I, —OH, —CN, —$NH_2$, —NH(alkyl), or —N(alkyl)$_2$;

$R_7$ is 5-membered heteroaromatic mono-cyclic moieties containing within the ring 1–3 heteroatoms independently selected from the group consisting of =N—, —N($R_{20}$)—, —O—, and —S—, and having 0–1 substituent selected from $R_{17}$ and further having 0–3 substituents independently selected from F, Cl, Br, or I, or $R_7$ is 9-membered fused-ring moieties having a 6-membered ring fused to a 5-membered ring including the formula

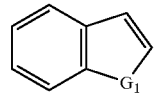

wherein $G_1$ is O, S or $NR_{20}$,

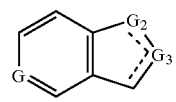

wherein G is C($R_{14}$) or N, and each $G_2$ and $G_3$ is independently selected from C($R_{14})_2$, C($R_{14}$), O, S, N, and N($R_{20}$), provided that both $G_2$ and $G_3$ are not simultaneously O or S, or

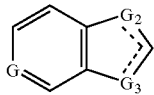

wherein G is $C(R_{14})$ or N, and each $G_2$ and $G_3$ is independently selected from $C(R_{14})_2$, $C(R_{14})$, O, S, N, and $N(R_{20})$, each 9-membered bicyclic ring having 0–1 substituent selected from $R_{17}$ and 0–3 substituents independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl optionally substituted with 1–4 substituents independently selected from F, Cl, Br, I, $R_{13}$, and $R_{15}$, or naphthyl optionally substituted with 1–4 substituents independently selected from F, Cl, Br, I, $R_{13}$, and $R_{15}$;

$R_9$ is 6-membered heteroaromatic mono-cyclic moieties containing within the ring 1–3 heteroatoms selected from =N— and having 0–1 substituent selected from $R_{17}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{17}$ and 0–3 substituent(s) independently selected from F, Cl, Br, or I, wherein the $R_9$ moiety attaches to other substituents as defined in formula I at any position on either ring as valency allows;

Each $R_{10}$ is independently H, alkyl, cycloalkyl, heterocycloalkyl, $R_7$, $R_9$, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, or phenyl optionally substituted with 1–4 substituents independently selected from F, Cl, Br, I, $R_{13}$, and $R_{15}$;

Each $R_{11}$ is independently H, alkyl, cycloalkyl, heterocycloalkyl, halogenated alkyl, halogenated cycloalkyl, or halogenated heterocycloalkyl;

$R_{12}$ is alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $-OR_{11}$, $-SR_{11}$, $-S(O)_2R_{11}$, $-S(O)R_{11}$, $-OS(O)_2R_{11}$, $-N(R_{11})_2$, $-C(O)R_{11}$, $-C(S)R_{11}$, $-C(O)OR_{11}$, $-NO_2$, $-C(O)N(R_{11})_2$, $-CN$, $-NR_{11}C(O)R_{11}$, $-NR_{11}C(O)N(R_{11})_2$, $-S(O)_2N(R_{11})_2$, or $-NR_{11}S(O)_2R_{11}$;

$R_{13}$ is $-OR_{11}$, $-SR_{11}$, $-SOR_{11}$, $-SO_2R_{11}$, $-OSO_2R_{11}$, $-N(R_{11})_2$, $-C(O)R_{11}$, $-C(O)OR_{11}$, $-C(S)R_{11}$, $-C(O)N(R_{11})_2$, $-NO_2$—$CN$, $-CF_3$, $-NR_{11}C(O)R_{11}$, $-NR_{11}C(O)N(R_{11})_2$, $-S(O)_2N(R_{11})_2$, or $-NR_{11})S(O)_2R_{11}$;

$R_{14}$ is H or $R_{19}$;

$R_{15}$ is $R_7$, $R_9$, $R_{19}$, or lactam heterocycloalkyl;

Each $R_{16}$ is independently H, alkyl, cycloalkyl, halogenated alkyl, or halogenated cycloalkyl;

$R_{17}$ is alkyl, cycloalkyl, or heterocycloalkyl, each optionally substituted with 1–4 substituents independently selected from F, Cl, Br, I, $-NO_2$, $-CN$, $-OR_{16}$, $-SR_{16}$, $-S(O)_2R_{16}$, $-S(O)R_{16}$, $-OS(O)_2R_{16}$, $-N(R_{16})_2$, $-C(O)R_{16}$, $-C(S)R_{16}$, $-C(O)OR_{16}$, $-C(O)N(R_{16})_2$, $-NR_{16}C(O)R_{16}$, $-NR_{16}C(O)N(R_{16})_2$, $-S(O)_2N(R_{16})_2$, and $-NR_{16}S(O)_2R_{16}$, and the cycloalkyl and heterocycloalkyl also being further optionally substituted with =O or =S;

$R_{19}$ is alkyl, cycloalkyl, heterocycloalkyl, phenyl, or naphthyl, each optionally substituted with 1–4 substituents independently selected from F, Cl, Br, I, $-CN$, $-NO_2$, $-OR_{16}$, $-SR_{16}$, $-S(O)_2R_{16}$, $-S(O)R_{16}$, $-OS(O)_2R_{16}$, $-N(R_{16})_2$, $-C(O)R_{16}$, $-C(S)R_{16}$, $-C(O)OR_{16}$, $-C(O)N(R_{16})_2$, $-NR_{16}C(O)R_{16}$, $-NR_{16}C(O)N(R_{16})_2$, $-S(O)_2N(R_{16})_2$, or $-NR_{16}S(O)_2R_{16}$, and the cycloalkyl and heterocycloalkyl also being further optionally substituted with =O or =S;

$R_{20}$ is H, alkyl, halogenated alkyl, substituted alkyl, cycloalkyl, halogenated cycloalkyl, substituted cycloalkyl, phenyl, $-SO_2R_8$, or phenyl having 1 substituent selected from $R_{12}$ and further having 0–3 substituents independently selected from F, Cl, Br, or I;

or a pharmaceutically acceptable salt thereof.

2. The compound of claim 1, wherein X is O.

3. The compound of claim 2, wherein $R_1$ is H, alkyl, or cycloalkyl, and $R_2$ is H, alkyl, substituted alkyl, cycloalkyl, halogenated alkyl, or aryl.

4. The compound of claim 3, wherein W is Q.

5. The compound of claim 4, wherein each $R_4$ is independently H, lower alkyl, or substituted lower alkyl.

6. The compound according to claim 5, wherein $R_6$ is an amino protecting group.

7. The compound according to claim 5, wherein $R_6$ is H, or lower alkyl optionally substituted with up to 3 substituents independently selected from F, Cl, Br, I, $-OH$, $-CN$, $-NH_2$, $-NH(alkyl)$, or $-N(alkyl)_2$.

8. The compound of claim 7, wherein at least one $R_4$ is H and one $R_4$ is H or lower alkyl optionally substituted with 1 substituent selected from $-OR_{10}$, $-SR_{10}$, $-S(O)R_{10}$, $-S(O)_2R_{10}$, $-OS(O)_2R_{10}$, $-NR_{10}R_{10}$, $-C(O)R_{10}$, $-C(O)OR_{10}$, $-C(S)R_{10}$, $-C(O)NR_{10}R_{10}$, $-CN$, $-NR_{10}C(O)R_{10}$, $-NR_{10}C(O)NR_{10}R_{10}$, $-S(O)_2NR_{10}R_{10}$, $-NR_{10}S(O)_2R_{10}$, $-NO_2$, or phenyl optionally substituted with up to 4 substituents independently selected from F, Cl, Br, I, $R_{13}$, and $R_{15}$, provided that when lower alkyl is substituted it is further optionally substituted with up to 3 substituents independently selected from F, Cl, Br, and I, wherein $R_{10}$ is H, lower alkyl, or halogenated lower alkyl.

9. The compound according to claim 8, wherein $R_1$, $R_2$, and each $R_4$ are H.

10. The compound of claim 9, wherein $R_1$ is H or lower alkyl, and wherein $R_2$ is H or lower alkyl.

11. The compound of claim 10, wherein Q is (a).

12. The compound of claim 11, wherein (a) is thiophen-2-yl, furan-2-yl, 1,3-thiazol-5-yl, or 1,3-oxazol-2-yl, 1,3-thiazole-2-yl, 1,3,4-oxadiazole-2-yl, 1,3-oxazole-5-yl, 1H-pyrrole-2-yl, or 1,2,4-oxadiazole-5-yl, optionally substituted on carbon independently with H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, $-OR_8$, $-SR_8$, $-N(R_8)_2$, $-C(O)R_8$, $-C(S)R_8$, $-C(O)OR_8$, $-C(O)N(R_8)_2$, —NR₈C(O)R₈, —S(O)₂N(R₈)₂, —OS(O)₂R₈, —S(O)₂R₈, —S(O)R₈, —NR₈S(O)₂R₈—N(R₈)C(O)N(R₈)₂, —CN, —NO₂, R₇, or R₉; and further optionally substituted on nitrogen with alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, R₇, R₉, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—R₇, —C(O)—R₉, or —C(O)-aryl.

13. The compound according to claim 12, wherein the compound is

N-[(1S,2R,4R)-7-azabicyclo[2.2.1]hept-2-yl]-5-bromo-2-thiophenecarboxamide; (+/−) exo-N-[7-azabicyclo[2.2.1]hept-2-yl]-5-bromo-2-thiophenecarboxamide;

N-[(1S,2R,4R)-7-azabicyclo[2.2.1]hept-2-yl]-5-(methylthio)thiophene-2-carboxamide;

N-[(1S,2R,4R)-7-azabicyclo[2.2.1]hept-2-yl]-5-phenylthiophene-2-carboxamide;

N-[(1S,2R,4R)-7-azabicyclo[2.2.1]hept-2-yl]-5-(2-chlorophenyl)thiophene-2-carboxamide;

N-[(1S,2R,4R)-7-azabicyclo[2.2.1]hept-2-yl]-5-[(4-chlorophenyl)thio]thiophene-2-carboxamide;

N-[(1S,2R,4R)-7-azabicyclo[2.2.1]hept-2-yl]-5-methylthiophene-2-carboxamide;

N-[(1S,2R,4R)-7-azabicyclo[2.2.1]hept-2-yl]-5-pyridin-2-ylthiophene-2-carboxamide;

N-[(1S,2R,4R)-7-azabicyclo[2.2.1]hept-2-yl]-5-(3-nitrophenyl)-2-furamide;

N-[(1S,2R,4R)-7-azabicyclo[2.2.1]hept-2-yl]-5-(4-nitrophenyl)-2-furamide;

N-[(1S,2R,4R)-7-azabicyclo[2.2.1]hept-2-yl]-5-(4-chlorophenyl)-2-furamide;

N-[(1S,2R,4R)-7-azabicyclo[2.2.1]hept-2-yl]-5-chlorothiophene-2-carboxamide;

N-[(1S,2R,4R)-7-azabicyclo[2.2.1]hept-2-yl]-5-(2-nitrophenyl)-2-furamide;

N-[(1S,2R,4R)-7-azabicyclo[2.2.1]hept-2-yl]-5-(4-aminophenyl)-2-furamide;

N-[(1S,2R,4R)-7-azabicyclo[2.2.1]hept-2-yl]-5-(2-fluorophenyl)-2-furamide;

N-[(1S,2R,4R)-7-azabicyclo[2.2.1]hept-2-yl]-5-(3-fluorophenyl)-2-furamide;

N-[(1S,2R,4R)-7-azabicyclo[2.2.1]hept-2-yl]-5-(4-fluorophenyl)-2-furamide;

N-[(1S,2R,4R)-7-azabicyclo[2.2.1]hept-2-yl]-5-(4-methylphenyl)-2-furamide;

N-[(1S,2R,4R)-7-azabicyclo[2.2.1]hept-2-yl]-5-bromo-2-furamide;

N-[(1S,2R,4R)-7-azabicyclo[2.2.1]hept-2-yl]-2-phenyl-1,3-thiazole-5-carboxamide;

N-[(1S,2R,4R)-7-azabicyclo[2.2.1]hept-2-yl]-2-(2-fluorophenyl)-1,3-thiazole-5-carboxamide;

N-[(1S,2R,4R)-7-azabicyclo[2.2.1]hept-2-yl]-5-pheny,-2-furamide;

N-[(1S,2R,4R)-7-azabicyclo[2.2.1]hept-2-yl]-5-phenyl-1,3-oxazole-2-carboxamide;

or a pharmaceutically acceptable salt thereof.

14. The compound of claim 12, wherein the compound is N-[(1S,2R, 4R)-7-azabicyclo[2.2.1]hept-2-yl]-5-(4-chlorophenyl)-thiophene-2-carboxamide;

N-[(1S,2R,4R)-7-azabicyclo[2.2.1]hept-2-yl]-5-(3-chlorophenyl)-thiophene-2-carboxamide;

N-[(1S,2R,4R)-7-azabicyclo[2.2.1]hept-2-yl]-2,3'-bithiophene-5-carboxamide;

N-[(1S,2R,4R)-7-azabicyclo[2.2.1]hept-2-yl]-5-(2-nitrophenyl)-thiophene-2-carboxamide;

N-[(1S,2R,4R)-7-azabicyclo[2.2.1]hept-2-yl]-5-(3-nitrophenyl)-thiophene-2-carboxamide;

N-[(1S,2R,4R)-7-azabicyclo[2.2.1]hept-2-yl]-4-phenyl-thiophene-2-carboxamide;

N-[(1S,2R,4R)-7-azabicyclo[2.2.1]hept-2-yl]-5-(3-benzyloxyphenyl)-thiophene-2-carboxamide;

N-[(1S,2R,4R)-7-azabicyclo[2.2.1]hept-2-yl]-5-(4-benzyloxyphenyl)-thiophene-2-carboxamide;

N-[(1S,2R,4R)-7-azabicyclo[2.2.1]hept-2-yl]-5-(3-fluoro-4-benzyloxyphenyl)-thiophene-2-carboxamide;

5-(2-aminophenyl)-N-[(1S,2R,4R)-7-azabicyclo[2.2.1]hept-2-yl]-thiophene-2-carboxamide;

N-[(1S,2R,4R)-7-azabicyclo[2.2.1]hept-2-yl]-5-pyridin-3-yl-thiophene-2-carboxamide;

N-[(1S,2R,4R)-7-azabicyclo[2.2.1]hept-2-yl]-5'-methyl-2,2'-bithiophene-5-carboxamide;

N-[(1S,2R,4R)-7-azabicyclo[2.2.1]hept-2-yl]-5'-chloro-2,2'-bithiophene-5-carboxamide;

N-[(1S,2R,4R)-7-azabicyclo[2.2.1]hept-2-yl]-5-nitro-thiophene-2-carboxamide;

5-(aminomethyl)-N-[(1S,2R,4R)-7-azabicyclo[2.2.1]hept-2-yl]-thiophene-2-carboxamide;

N-[(1S,2R,4R)-7-azabicyclo[2.2.1]hept-2-yl]-5-cyano-thiophene-2-carboxamide;

N-[(1S,2R,4R)-7-azabicyclo[2.2.1]hept-2-yl]-5-methoxy-thiophene-2-carboxamide;

N-[(1S,2R,4R)-7-azabicyclo[2.2.1]hept-2-yl]-[2,2]bithiophene-5-carboxamide;

N-[(1S,2R,4R)-7-azabicyclo[2.2.1]hept-2-yl]-5-acetyl-thiophene-2-carboxamide;

N-[(1S,2R,4R)-7-azabicyclo[2.2.1]hept-2-yl]-5-(phenylsulfanyl)-thiophene-2-carboxamide;

N-[(1S,2R,4R)-7-azabicyclo[2.2.1]hept-2-yl]-5-phenyl-thiophene-2-carbothioamide;

N-[(1S,2R,4R)-7-azabicyclo[2.2.1]hept-2-yl]-5-(2-acetamidophenyl)-thiophene-2-carboxamide;

N-[(1S,2R,4R)-7-azabicyclo[2.2.1]hept-2-yl]-5-(3-acetamidophenyl)-thiophene-2-carboxamide;

N-[(1S,2R,4R)-7-azabicyclo[2.2.1]hept-2-yl]-5-(4-acetarnidophenyl)-thiophene-2-carboxamide;

N-[(1S,2R,4R)-7-azabicyclo[2.2.1]hept-2-yl]-5-(2-trifluoroacetamidophenyl)-thiophene-2-carboxamide;

N-[(1S,2R,4R)-7-azabicyclo[2.2.1]hept-2-yl]-5-(3-trifluoroacetamidophenyl)-thiophene-2-carboxamide;

N-[(1S,2R,4R)-7-azabicyclo[2.2.1]hept-2-yl]-5-(4-trifluoroacetamidophenyl)-thiophene-2-carboxamide;

N-[(1S,2R,4R)-7-azabicyclo[2.2.1]hept-2-yl]-5-(2-methanesulfonylaminophenyl)-thiophene-2-carboxamide;

N-[(1S,2R,4R)-7-azabicyclo[2.2.1]hept-2-yl]-5-(3-methanesulfonylaminophenyl)-thiophene-2-carboxamide;

N-[(1S,2R,4R)-7-azabicyclo[2.2.1]hept-2-yl]-5-(4-methanesulfonylaminophenyl)-thiophene-2-carboxamide;

N-[(1S,2R,4R)-7-azabicyclo[2.2.1]hept-2-yl]-5-(2-trifluoromethanesulfonylaminophenyl)-thiophene-2-carboxamide;

N-[(1S,2R,4R)-7-azabicyclo[2.2.1]hept-2-yl]-5-(3-trifluoromethanesulfonylaminophenyl)-thiophene-2-carboxamide;
N-[(1S,2R,4R)-7-azabicyclo[2.2.1]hept-2-yl]-5-(4-trifluoromethanesulfonylaminophenyl)-thiophene-2-carboxamide;
N-[(1S,2R,4R)-7-azabicyclo[2.2.1]hept-2-yl]-5-(2-difluoroacetamidophenyl)-thiophene-2-carboxamide;
N-[(1S,2R,4R)-7-azabicyclo[2.2.1]hept-2-yl]-5-(3-difluoroacetamidophenyl)-thiophene-2-carboxamide;
N-[(1S,2R,4R)-7-azabicyclo[2.2.1]hept-2-yl]-5-(4-difluoroacetamridophenyl)-thiophene-2-carboxamide;
N-[(1S,2R,4R)-7-azabicyclo[2.2.1]hept-2-yl]-5-(2-carbamoylphenyl)-thiophene-2-carboxamide;
N-[(1S,2R,4R)-7-azabicyclo[2.2.1]hept-2-yl]-5-(3-carbamoylphenyl)-thiophene-2-carboxamide;
N-[(1S,2R,4R)-7-azabicyclo[2.2.1]hept-2-yl]-5-(4-carbamoylphenyl)-thiophene-2-carboxamide;
N-[(1S,2R,4R)-7-azabicyclo[2.2.1]hept-2-yl]-5-(2-sulfamoylphenyl)-thiophene-2-carboxamide;
N-[(1S,2R,4R)-7-azabicyclo[2.2.1]hept-2-yl]-5-(3-sulfamoylphenyl)-thiophene-2-carboxamide;
N-[(1S,2R,4R)-7-azabicyclo[2.2.1]hept-2-yl]-5-(4-sulfamoylphenyl)-thiophene-2-carboxamide;
N-[(1S,2R,4R)-7-azabicyclo[2.2.1]hept-2-yl]-5-(2-acetamidophenylsulfanyl)-thiophene-2-carboxamide;
N-[(1S,2R,4R)-7-azabicyclo[2.2.1]hept-2-yl]-5-(3-acetamidophenylsulfanyl)-thiophene-2-carboxamide;
N-[(1S,2R,4R)-7-azabicyclo[2.2.1]hept-2-yl]-5-(4-acetamidophenylsulfanyl)-thiophene-2-carboxamide;
N-[(1S,2R,4R)-7-azabicyclo[2.2.1]hept-2-yl]-5-(2-trifluoroacetamidophenylsulfanyl)-thiophene-2-carboxamide;
N-[(1S,2R,4R)-7-azabicyclo[2.2.1]hept-2-yl]-5-(3-trifluoroacetamidophenylsulfanyl)-thiophene-2-carboxamide;
N-[(1S,2R,4R)-7-azabicyclo[2.2.1]hept-2-yl]-5-(4-trifluoroacetamidophenylsulfanyl)-thiophene-2-carboxamide;
N-[(1S,2R,4R)-7-azabicyclo[2.2.1]hept-2-yl]-5-(2-methanesulfonylaminophenylsulfanyl)-thiophene-2-carboxamide;
N-[(1S,2R,4R)-7-azabicyclo[2.2.1]hept-2-yl]-5-(3-methanesulfonylaminophenylsulfanyl)-thiophene-2-carboxamide;
N-[(1S,2R,4R)-7-azabicyclo[2.2.1]hept-2-yl]-5-(4-methanesulfonylaminophenylsulfanyl)-thiophene-2-carboxamide;
N-[(1S,2R,4R)-7-azabicyclo[2.2.1]hept-2-yl]-5-(2-trifluoromethanesulfonylaminophenylsulfanyl)-thiophene-2-carboxamide;
N-[(1S,2R,4R)-7-azabicyclo[2.2.1]hept-2-yl]-5-(3-trifluoromethanesulfonylaminophenylsulfanyl)-thiophene-2-carboxamide;
N-[(1S,2R,4R)-7-azabicyclo[2.2.1]hept-2-yl]-5-(4-trifluoromethanesulfonylaminophenylsulfanyl)-thiophene-2-carboxamide;
N-[(1S,2R,4R)-7-azabicyclo[2.2.1]hept-2-yl]-5-(2-difluoroacetamidophenylsulfanyl)-thiophene-2-carboxamide;
N-[(1S,2R,4R)-7-azabicyclo[2.2.1]hept-2-yl]-5-(3-difluoroacetamidophenylsulfanyl)-thiophene-2-carboxamide;
N-[(1S,2R,4R)-7-azabicyclo[2.2.1]hept-2-yl]-5-(4-difluoroacetamidophenylsulfanyl)-thiophene-2-carboxamide;
N-[(1S,2R,4R)-7-azabicyclo[2.2.1]hept-2-yl]-5-(2-carbamoylphenylsulfanyl)-thiophene-2-carboxamide;
N-[(1S,2R,4R)-7-azabicyclo[2.2.1]hept-2-yl]-5-(3-carbamoylphenylsulfanyl)-thiophene-2-carboxamide;
N-[(1S,2R,4R)-7-azabicyclo[2.2.1]hept-2-yl]-5-(4-carbamoylphenylsulfanyl)-thiophene-2-carboxamide;
N-[(1S,2R,4R)-7-azabicyclo[2.2.1]hept-2-yl]-5-(2-sulfamoylphenylsulfanyl)-thiophene-2-carboxamide;
N-[(1S,2R,4R)-7-azabicyclo[2.2.1]hept-2-yl]-5-(3-sulfamoylphenylsulfanyl)-thiophene-2-carboxamide;
N-[(1S,2R,4R)-7-azabicyclo[2.2.1]hept-2-yl]-5-(4-sulfamoylphenylsulfanyl)-thiophene-2-carboxamide;
N-[(1S,2R,4R)-7-azabicyclo[2.2.1]hept-2-yl]-5-(2-hydroxyphenylsulfanyl)-thiophene-2-carboxamide;
N-[(1S,2R,4R)-7-azabicyclo[2.2.1]hept-2-yl]-5-(3-hydroxyphenylsulfanyl)-thiophene-2-carboxamide;
N-[(1S,2R,4R)-7-azabicyclo[2.2.1]hept-2-yl]-5-(4-hydroxyphenylsulfanyl)-thiophene-2-carboxamide;
N-[(1S,2R,4R)-7-azabicyclo[2.2.1]hept-2-yl]-5-(2-aminophenylsulfanyl)-thiophene-2-carboxamide;
N-[(1S,2R,4R)-7-azabicyclo[2.2.1]hept-2-yl]-5-(3-aminophenylsulfanyl)-thiophene-2-carboxamide;
N-[(1S,2R,4R)-7-azabicyclo[2.2.1]hept-2-yl]-5-(4-aminophenylsulfanyl)-thiophene-2-carboxamide;
N-[(1S,2R,4R)-7-azabicyclo[2.2.1]hept-2-yl]-5-(2-acetamidophenoxy)-thiophene-2-carboxamide;
N-[(1S,2R,4R)-7-azabicyclo[2.2.1]hept-2-yl]-5-(3-acetamidophenoxy)-thiophene-2-carboxamide;
N-[(1S,2R,4R)-7-azabicyclo[2.2.1]hept-2-yl]-5-(4-acetamidophenoxy)-thiophene-2-carboxamide;
N-[(1S,2R,4R)-7-azabicyclo[2.2.1]hept-2-yl]-5-(2-trifluoroacetamidophenoxy)-thiophene-2-carboxamide;
N-[(1S,2R,4R)-7-azabicyclo[2.2.1]hept-2-yl]-5-(3-trifluoroacetamidophenoxy)-thiophene-2-carboxamide;
N-[(1S,2R,4R)-7-azabicyclo[2.2.1]hept-2-yl]-5-(4-trifluoroacetamidophenoxy)-thiophene-2-carboxamide;
N-[(1S,2R,4R)-7-azabicyclo[2.2.1]hept-2-yl]-5-(2-methanesulfonylaminophenoxy)-thiophene-2-carboxamide;
N-[(1S,2R,4R)-7-azabicyclo[2.2.1]hept-2-yl]-5-(3-methanesulfonylaminophenoxy)-thiophene-2-carboxamide;
N-[(1S,2R,4R)-7-azabicyclo[2.2.1]hept-2-yl]-5-(4-methanesulfonylaminophenoxy)-thiophene-2-carboxamide;
N-[(1S,2R,4R)-7-azabicyclo[2.2.1]hept-2-yl]-5-(2-trifluoromethanesulfonylaminophenoxy)-thiophene-2-carboxamide;
N-[(1S,2R,4R)-7-azabicyclo[2.2.1]hept-2-yl]-5-(3-trifluoromethanesulfonylaminophenoxy)-thiophene-2-carboxamide;
N-[(1S,2R,4R)-7-azabicyclo[2.2.1]hept-2-yl]-5-(4-trifluoromethanesulfonylaminophenoxy)-thiophene-2-carboxamide;
N-[(1S,2R,4R)-7-azabicyclo[2.2.1]hept-2-yl]-5-(2-difluoroacetamidophenoxy)-thiophene-2-carboxamide;

N-[(1S,2R,4R)-7-azabicyclo[2.2.1]hept-2-yl]-5-(3-difluoroacetamidophenoxy)-thiophene-2-carboxamide;
N-[(1S,2R,4R)-7-azabicyclo[2.2.1]hept-2-yl]-5-(4-difluoroacetamidophenoxy)-thiophene-2-carboxamide;
N-[(1S,2R,4R)-7-azabicyclo[2.2.1]hept-2-yl]-5-(2-carbamoylphenoxy)-thiophene-2-carboxamide;
N-[(1S,2R,4R)-7-azabicyclo[2.2.1]hept-2-yl]-5-(3-carbamoylphenoxy)-thiophene-2-carboxamide;
N-[(1S,2R,4R)-7-azabicyclo[2.2.1]hept-2-yl]-5-(4-carbamoylphenoxy)-thiophene-2-carboxamide;
N-[(1S,2R,4R)-7-azabicyclo[2.2.1]hept-2-yl]-5-(2-sulfamoylphenoxy)-thiophene-2-carboxamide;
N-[(1S,2R,4R)-7-azabicyclo[2.2.1]hept-2-yl]-5-(3-sulfamoylphenoxy)-thiophene-2-carboxamide;
N-[(1S,2R,4R)-7-azabicyclo[2.2.1]hept-2-yl]-5-(4-sulfamoylphenoxy)-thiophene-2-carboxamide;
N-[(1S,2R,4R)-7-azabicyclo[2.2.1]hept-2-yl]-5-(2-hydroxyphenoxy)-thiophene-2-carboxamide;
N-[(1S,2R,4R)-7-azabicyclo[2.2.1]hept-2-yl]-5-(3-hydroxyphenoxy)-thiophene-2-carboxamide;
N-[(1S,2R,4R)-7-azabicyclo[2.2.1]hept-2-yl]-5-(4-hydroxyphenoxy)-thiophene-2-carboxamide;
N-[(1S,2R,4R)-7-azabicyclo[2.2.1]hept-2-yl]-5-(2-aminophenoxy)-thiophene-2-carboxamide;
N-[(1S,2R,4R)-7-azabicyclo[2.2.1]hept-2-yl]-5-(3-aminophenoxy)-thiophene-2-carboxamide;
N-[(1S,2R,4R)-7-azabicyclo[2.2.1]hept-2-yl]-5-(4-aminophenoxy)-thiophene-2-carboxamide;
N-[(1S,2R,4R)-7-azabicyclo[2.2.1]hept-2-yl]-5-(2-chlorophenoxy)-thiophene-2-carboxamide;
N-[(1S,2R,4R)-7-azabicyclo[2.2.1]hept-2-yl]-5-(3-chlorophenoxy)-thiophene-2-carboxamide;
N-[(1S,2R,4R)-7-azabicyclo[2.2.1]hept-2-yl]-5-(4-chlorophenoxy)-thiophene-2-carboxamide;
N-[(1S,2R,4R)-7-azabicyclo[2.2.1]hept-2-yl]-5-(2-cyanophenoxy)-thiophene-2-carboxamide;
N-[(1S,2R,4R)-7-azabicyclo[2.2.1]hept-2-yl]-5-(3-cyanophenoxy)-thiophene-2-carboxamide;
N-[(1S,2R,4R)-7-azabicyclo[2.2.1]hept-2-yl]-5-(4-cyanophenoxy)-thiophene-2-carboxamide;
N-[(1S,2R,4R)-7-azabicyclo[2.2.1]hept-2-yl]-5-(2-methoxyphenyl)-thiophene-2-carboxamide;
N-[(1S,2R,4R)-7-azabicyclo[2.2.1]hept-2-yl]-5-(3-methoxyphenyl)-thiophene-2-carboxamide;
N-[(1S,2R,4R)-7-azabicyclo[2.2.1]hept-2-yl]-5-(4-methoxyphenyl)-thiophene-2-carboxamide;
N-[(1S,2R,4R)-7-azabicyclo[2.2.1]hept-2-yl]-5-(2-methylphenyl)-thiophene-2-carboxamide;
N-[(1S,2R,4R)-7-azabicyclo[2.2.1]hept-2-yl]-5-(3-methylphenyl)-thiophene-2-carboxamide;
N-[(1S,2R,4R)-7-azabicyclo[2.2.1]hept-2-yl]-5-(4-methylphenyl)-thiophene-2-carboxamide;
N-[(1S,2R,4R)-7-azabicyclo[2.2.1]hept-2-yl]-5-(2-trifluoromethylphenyl)-thiophene-2-carboxamide;
N-[(1S,2R,4R)-7-azabicyclo[2.2.1]hept-2-yl]-5-(3-trifluoromethylphenyl)-thiophene-2-carboxamide;
N-[(1S,2R,4R)-7-azabicyclo[2.2.1]hept-2-yl]-5-(4-trifluoromethylphenyl)-thiophene-2-carboxamide;
N-[(1S,2R,4R)-7-azabicyclo[2.2.1]hept-2-yl]-5-(2-acetylphenyl)-thiophene-2-carboxamide;
N-[(1S,2R,4R)-7-azabicyclo[2.2.1]hept-2-yl]-5-(3-acetylphenyl)-thiophene-2-carboxamide;
N-[(1S,2R,4R)-7-azabicyclo[2.2.1]hept-2-yl]-5-(4-acetylphenyl)-thiophene-2-carboxamide;
N-[(1S,2R,4R)-7-azabicyclo[2.2.1]hept-2-yl]-5-(2-cyanophenyl)-thiophene-2-carboxamide;
N-[(1S,2R,4R)-7-azabicyclo[2.2.1]hept-2-yl]-5-(3-cyanophenyl)-thiophene-2-carboxamide;
N-[(1S,2R,4R)-7-azabicyclo[2.2.1]hept-2-yl]-5-(4-cyanophenyl)-thiophene-2-carboxamide;
N-[(1S,2R,4R)-7-azabicyclo[2.2.1]hept-2-yl]-5-(2-morpholin-4-yl-phenyl)-thiophene-2-carboxamide;
N-[(1S,2R,4R)-7-azabicyclo[2.2.1]hept-2-yl]-5-(3-morpholin-4-yl-phenyl)-thiophene-2-carboxamide;
N-[(1S,2R,4R)-7-azabicyclo[2.2.1]hept-2-yl]-5-(4-morpholin4-yl-phenyl)-thiophene-2-carboxamide;
N-[(1S,2R,4R)-7-azabicyclo[2.2.1]hept-2-yl]-5-(2-methoxyphenoxy)-thiophene-2-carboxamide;
N-[(1S,2R,4R)-7-azabicyclo[2.2.1]hept-2-yl]-5-(3-methoxyphenoxy)-thiophene-2-carboxamide;
N-[(1S,2R,4R)-7-azabicyclo[2.2.1]hept-2-yl]-5-(4-methoxyphenoxy)-thiophene-2-carboxamide;
N-[(1S,2R,4R)-7-azabicyclo[2.2.1]hept-2-yl]-5-(2-methylphenoxy)-thiophene-2-carboxamide;
N-[(1S,2R,4R)-7-azabicyclo[2.2.1]hept-2-yl]-5-(3-methylphenoxy)-thiophene-2-carboxamide;
N-[(1S,2R,4R)-7-azabicyclo[2.2.1]hept-2-yl]-5-(4-methylphenoxy)-thiophene-2-carboxamide;
N-[(1S,2R,4R)-7-azabicyclo[2.2.1]hept-2-yl]-5-(2-trifluoromethylphenoxy)-thiophene-2-carboxamide;
N-[(1S,2R,4R)-7-azabicyclo[2.2.1]hept-2-yl]-5-(3-trifluoromethylphenoxy)-thiophene-2-carboxamide;
N-[(1S,2R,4R)-7-azabicyclo[2.2.1]hept-2-yl]-5-(4-trifluoromethylphenoxy)-thiophene-2-carboxamide;
N-[(1S,2R,4R)-7-azabicyclo[2.2.1]hept-2-yl]-5-(2-acetylphenoxy)-thiophene-2-carboxamide;
N-[(1S,2R,4R)-7-azabicyclo[2.2.1]hept-2-yl]-5-(3-acetylphenoxy)-thiophene-2-carboxamide;
N-[(1S,2R,4R)-7-azabicyclo[2.2.1]hept-2-yl]-5-(4-acetylphenoxy)-thiophene-2-carboxamide;
N-[(1S,2R,4R)-7-azabicyclo[2.2.1]hept-2-yl]-5-(2-cyanophenoxy)-thiophene-2-carboxamide;
N-[(1S,2R,4R)-7-azabicyclo[2.2.1]hept-2-yl]-5-(3-cyanophenoxy)-thiophene-2-carboxamide;
N-[(1S,2R,4R)-7-azabicyclo[2.2.1]hept-2-yl]-5-(4-cyanophenoxy)-thiophene-2-carboxamide;
N-[(1S,2R,4R)-7-azabicyclo[2.2.1]hept-2-yl]-5-(2-morpholin-4-yl-phenoxy)-thiophene-2-carboxamide;
N-[(1S,2R,4R)-7-azabicyclo[2.2.1]hept-2-yl]-5-(3-morpholin-4-yl-phenoxy)-thiophene-2-carboxamide;
N-[(1S,2R,4R)-7-azabicyclo[2.2.1]hept-2-yl]-5-(4-morpholin-4-yl-phenoxy)-thiophene-2-carboxamide;
N-[(1S,2R,4R)-7-azabicyclo[2.2.1]hept-2-yl]-5-(2-methoxyphenylsulfanyl)-thiophene-2-carboxamide;
N-[(1S,2R,4R)-7-azabicyclo[2.2.1]hept-2-yl]-5-(3-methoxyphenylsulfanyl)-thiophene-2-carboxamide;
N-[(1S,2R,4R)-7-azabicyclo[2.2.1]hept-2-yl]-5-(4-methoxyphenylsulfanyl)-thiophene-2-carboxamide;
N-[(1S,2R,4R)-7-azabicyclo[2.2.1]hept-2-yl]-5-(2-methylphenylsulfanyl)-thiophene-2-carboxamide;
N-[(1S,2R,4R)-7-azabicyclo[2.2.1]hept-2-yl]-5-(3-methylphenylsulfanyl)-thiophene-2-carboxamide;
N-[(1S,2R,4R)-7-azabicyclo[2.2.1]hept-2-yl]-5-(4-methylphenylsulfanyl)-thiophene-2-carboxamide;

N-[(1S,2R,4R)-7-azabicyclo[2.2.1]hept-2-yl]-5-(2-trifluoromethylphenylsulfanyl)-thiophene-2-carboxamide;
N-[(1S,2R,4R)-7-azabicyclo[2.2.1]hept-2-yl]-5-(3-trifluoromethylphenylsulfanyl)-thiophene-2-carboxamide;
N-[(1S,2R,4R)-7-azabicyclo[2.2.1]hept-2-yl]-5-(4-trifluoromethylphenylsulfanyl)-thiophene-2-carboxamide;
N-[(1S,2R,4R)-7-azabicyclo[2.2.1]hept-2-yl]-5-(2-acetylphenylsulfanyl)-thiophene-2-carboxamide;
N-[(1S,2R,4R)-7-azabicyclo[2.2.1]hept-2-yl]-5-(3-acetylphenylsulfanyl)-thiophene-2-carboxamide;
N-[(1S,2R,4R)-7-azabicyclo[2.2.1]hept-2-yl]-5-(4-acetylphenylsulfanyl)-thiophene-2-carboxamide;
N-[(1S,2R,4R)-7-azabicyclo[2.2.1]hept-2-yl]-5-(2-cyanophenylsulfanyl)-thiophene-2-carboxamide;
N-[(1S,2R,4R)-7-azabicyclo[2.2.1]hept-2-yl]-5-(3-cyanophenylsulfanyl)-thiophene-2-carboxamide;
N-[(1S,2R,4R)-7-azabicyclo[2.2.1]hept-2-yl]-5-(4-cyanophenylsulfanyl)-thiophene-2-carboxamide;
N-[(1S,2R,4R)-7-azabicyclo[2.2.1]hept-2-yl]-5-(2-morpholin-4-yl-phenylsulfanyl)-thiophene-2-carboxamide;
N-[(1S,2R,4R)-7-azabicyclo[2.2.1]hept-2-yl]-5-(3-morpholin-4-yl-phenylsulfanyl)-thiophene-2-carboxamide;
N-[(1S,2R,4R)-7-azabicyclo[2.2.1]hept-2-yl]-5-(4-morpholin-4-yl-phenylsulfanyl)-thiophene-2-carboxamide;
N-[(1S,2R,4R)-7-azabicyclo[2.2.1]hept-2-yl]-5-(pyridin-4-yl)-thiophene-2-carboxamide;
N-[(1S,2R,4R)-7-azabicyclo[2.2.1]hept-2-yl]-5-(2-methylpyridin-4-yl)-thiophene-2-carboxamide;
N-[(1S,2R,4R)-7-azabicyclo[2.2.1]hept-2-yl]-5-(6-methylpyridin-3-yl)-thiophene-2-carboxamide;
N-[(1S,2R,4R)-7-azabicyclo[2.2.1]hept-2-yl]-5-(5-methylpyridin-2-yl)-thiophene-2-carboxamide;
N-[(1S,2R,4R)-7-azabicyclo[2.2.1]hept-2-yl]-5-(2-methoxypyridin-4-yl)-thiophene-2-carboxamide;
N-[(1S,2R,4R)-7-azabicyclo[2.2.1]hept-2-yl]-5-(6-methoxypyridin-3-yl)-thiophene-2-carboxamide;
N-[(1S,2R,4R)-7-azabicyclo[2.2.1]hept-2-yl]-5-(5-methoxypyridin-2-yl)-thiophene-2-carboxamide;
N-[(1S,2R,4R)-7-azabicyclo[2.2.1]hept-2-yl]-5-(2-chloropyridin-4-yl)-thiophene-2-carboxamide;
N-[(1S,2R,4R)-7-azabicyclo[2.2.1]hept-2-yl]-5-(6-chloropyridin-3-yl)-thiophene-2-carboxamide;
N-[(1S,2R,4R)-7-azabicyclo[2.2.1]hept-2-yl]-5-(5-chloropyridin-2-yl)-thiophene-2-carboxamide;
N-[(1S,2R,4R)-7-azabicyclo[2.2.1]hept-2-yl]-5-(5-chloropyridin-3-yl)-thiophene-2-carboxamide;
N-[(1S,2R,4R)-7-azabicyclo[2.2.1]hept-2-yl]-5-(6-chloropyridin-2-yl)-thiophene-2-carboxamide;
N-[(1S,2R,4R)-7-azabicyclo[2.2.1]hept-2-yl]-5-(4-chloropyridin-2-yl)-thiophene-2-carboxamide;
N-[(1S,2R,4R)-7-azabicyclo[2.2.1]hept-2-yl]-5-(pyridin-4-yloxy)-thiophene-2-carboxamide;
N-[(1S,2R,4R)-7-azabicyclo[2.2.1]hept-2-yl]-5-(pyridin-3-yloxy)-thiophene-2-carboxamide;
N-[(1S,2R,4R)-7-azabicyclo[2.2.1]hept-2-yl]-5-(pyridin-2-yloxy)-thiophene-2-carboxamide;
N-[(1S,2R,4R)-7-azabicyclo[2.2.1]hept-2-yl]-5-(2-methylpyridin-4-yloxy)-thiophene-2-carboxamide;
N-[(1S,2R,4R)-7-azabicyclo[2.2.1]hept-2-yl]-5-(6-methylpyridin-3-yloxy)-thiophene-2-carboxamide;
N-[(1S,2R,4R)-7-azabicyclo[2.2.1]hept-2-yl]-5-(5-methylpyridin-2-yloxy)-thiophene-2-carboxamide;
N-[(1S,2R,4R)-7-azabicyclo[2.2.1]hept-2-yl]-5-(2-methoxypyridin-4-yloxy)-thiophene-2-carboxamide;
N-[(1S,2R,4R)-7-azabicyclo[2.2.1]hept-2-yl]-5-(6-methoxypyridin-3-yloxy)-thiophene-2-carboxamide;
N-[(1S,2R,4R)-7-azabicyclo[2.2.1]hept-2-yl]-5-(5-methoxypyridin-2-yloxy)-thiophene-2-carboxamide;
N-[(1S,2R,4R)-7-azabicyclo[2.2.1]hept-2-yl]-5-(2-chloropyridin-4-yloxy)-thiophene-2-carboxamide;
N-[(1S,2R,4R)-7-azabicyclo[2.2.1]hept-2-yl]-5-(6-chloropyridin-3-yloxy)-thiophene-2-carboxamide;
N-[(1S,2R,4R)-7-azabicyclo[2.2.1]hept-2-yl]-5-(5-chloropyridin-2-yloxy)-thiophene-2-carboxamide;
N-[(1S,2R,4R)-7-azabicyclo[2.2.1]hept-2-yl]-5-(2-chloropyridin-4-yloxy)-thiophene-2-carboxamide;
N-[(1S,2R,4R)-7-azabicyclo[2.2.1]hept-2-yl]-5-(6-chloropyridin-3-yloxy)-thiophene-2-carboxamide;
N-[(1S,2R,4R)-7-azabicyclo[2.2.1]hept-2-yl]-5-(5-chloropyridin-2-yloxy)-thiophene-2-carboxamide;
N-[(1S,2R,4R)-7-azabicyclo[2.2.1]hept-2-yl]-5-(5-chloropyridin-3-yloxy)-thiophene-2-carboxamide;
N-[(1S,2R,4R)-7-azabicyclo[2.2.1]hept-2-yl]-5-(6-chloropyridin-2-yloxy)-thiophene-2-carboxamide;
N-[(1S,2R,4R)-7-azabicyclo[2.2.1]hept-2-yl]-5-(4-chloropyridin-2-yloxy)-thiophene-2-carboxamide;
N-[(1S,2R,4R)-7-azabicyclo[2.2.1]hept-2-yl]-5-(pyridin-4-ylsulfanyl)-thiophene-2-carboxamide;
N-[(1S,2R,4R)-7-azabicyclo[2.2.1]hept-2-yl]-5-(pyridin-3-ylsulfanyl)-thiophene-2-carboxamide;
N-[(1S,2R,4R)-7-azabicyclo[2.2.1]hept-2-yl]-5-(pyridin-2-ylsulfanyl)-thiophene-2-carboxamide;
N-[(1S,2R,4R)-7-azabicyclo[2.2.1]hept-2-yl]-5-(2-methylpyridin-4-ylsulfanyl)-thiophene-2-carboxamide;
N-[(1S,2R,4R)-7-azabicyclo[2.2.1]hept-2-yl]-5-(6-methylpyridin-3-ylsulfanyl)-thiophene-2-carboxamide;
N-[(1S,2R,4R)-7-azabicyclo[2.2.1]hept-2-yl]-5-(5-methylpyridin-2-ylsulfanyl)-thiophene-2-carboxamide;
N-[(1S,2R,4R)-7-azabicyclo[2.2.1]hept-2-yl]-5-(2-methoxypyridin-4-ylsulfanyl)-thiophene-2-carboxamide;
N-[(1S,2R,4R)-7-azabicyclo[2.2.1]hept-2-yl]-5-(6-methoxypyridin-3-ylsulfanyl)-thiophene-2-carboxamide;
N-[(1S,2R,4R)-7-azabicyclo[2.2.1]hept-2-yl]-5-(5-methoxypyridin-2-ylsulfanyl)-thiophene-2-carboxamide;
N-[(1S,2R,4R)-7-azabicyclo[2.2.1]hept-2-yl]-5-(2-chloropyridin-4-ylsulfanyl)-thiophene-2-carboxamide;
N-[(1S,2R,4R)-7-azabicyclo[2.2.1]hept-2-yl]-5-(6-chloropyridin-3-ylsulfanyl)-thiophene-2-carboxamide;
N-[(1S,2R,4R)-7-azabicyclo[2.2.1]hept-2-yl]-5-(5-chloropyridin-2-ylsulfanyl)-thiophene-2-carboxamide;
N-[(1S,2R,4R)-7-azabicyclo[2.2.1]hept-2-yl]-5-(2-chloropyridin-4-ylsulfanyl)-thiophene-2-carboxamide;

N-[(1S,2R,4R)-7-azabicyclo[2.2.1]hept-2-yl]-5-(6-chloropyridin-3-ylsulfanyl)-thiophene-2-carboxamide;
N-[(1S,2R,4R)-7-azabicyclo[2.2.1]hept-2-yl]-5-(5-chloropyridin-2-ylsulfanyl)-thiophene-2-carboxamide;
N-[(1S,2R,4R)-7-azabicyclo[2.2.1]hept-2-yl]-5-(5-chloropyridin-3-ylsulfanyl)-thiophene-2-carboxamide;
N-[(1S,2R,4R)-7-azabicyclo[2.2.1]hept-2-yl]-5-(6-chloropyridin-2-ylsulfanyl)-thiophene-2-carboxamide;
N-[(1S,2R,4R)-7-azabicyclo[2.2.1]hept-2-yl]-5-(4-chloropyridin-2-ylsulfanyl)-thiophene-2-carboxamide;
N-[(1S,2R,4R)-7-azabicyclo[2.2.1]hept-2-yl]-5-(thiophen-4-yl)-thiophene-2-carboxamide;
N-[(1S,2R,4R)-7-azabicyclo[2.2.1]hept-2-yl]-5-(5-methylthiophen-2-yl)-thiophene-2-carboxamide;
N-[(1S,2R,4R)-7-azabicyclo[2.2.1]hept-2-yl]-5-(5-methoxythiophen-2-yl)-thiophene-2-carboxamide;
N-[(1S,2R,4R)-7-azabicyclo[2.2.1]hept-2-yl]-5-(5-chlorothiophen-2-yl)-thiophene-2-carboxamide;
N-[(1S,2R,4R)-7-azabicyclo[2.2.1]hept-2-yl]-5-(2-methyl-5-trifluoromethyl-2H-pyrazole-3-yl)-thiophene-2-carboxamide;
N-[(1S,2R,4R)-7-azabicyclo[2.2.1]hept-2-yl]-5-(2-methylthiazol-4-yl)-thiophene-2-carboxamide;
N-[(1S,2R,4R)-7-azabicyclo[2.2.1]hept-2-yl]-5-[2-(3-chlorophenyl)-vinyl]-thiophene-2-carboxamide;
N-[(1S,2R,4R)-7-azabicyclo[2.2.1]hept-2-yl]-5-(2,4-difluorophenyl-sulfanyi)-thiophene-2-carboxamide;
N-[(1S,2R,4R)-7-azabicyclo[2.2.1]hept-2-yl]-5-(3-chlorophenyl-sulfanyl)-thiophene-2-carboxamide;
N-[(1S,2R,4R)-7-azabicyclo[2.2.1]hept-2-yl]-5-(3-chloro-4-fluoro-phenylsulfanyl)-thiophene-2-carboxamide;
N-[(1S,2R,4R)-7-azabicyclo[2.2.1]hept-2-yl]-5-(2,3-dichlorophenyl-sulfanyl)-thiophene-2-carboxamide;
N-[(1S,2R,4R)-7-azabicyclo[2.2.1]hept-2-yl]-5-(2,4,5-trichlorophenyl-sulfanyl)-thiophene-2-carboxamide;
N-[(1S,2R,4R)-7-azabicyclo[2.2.1]hept-2-yl]-5-(3,4-dichlorophenyl-sulfanyl)-thiophene-2-carboxamide;
N-[(1S,2R,4R)-7-azabicyclo[2.2.1]hept-2-yl]-5-phenoxy-thiophene-2-carboxamide;
N-[(1S,2R,4R)-7-azabicyclo[2.2.1]hept-2-yl]-5-(2-hydroxyphenyl)-thiophene-2-carboxamide;
N-[(1S,2R,4R)-7-azabicyclo[2.2.1]hept-2-yl]-5-(3-hydroxyphenyl)-thiophene-2-carboxamide;
N-[(1S,2R,4R)-7-azabicyclo[2.2.1]hept-2-yl]-5-(3-fluoro-4-hydroxyphenyl)-thiophene-2-carboxamide;
N-[(1S,2R,4R)-7-azabicyclo[2.2.1]hept-2-yl]-5-(furan-4-yl)-thiophene-2-carboxamide;
N-[(1S,2R,4R)-7-azabicyclo[2.2.1]hept-2-yl]-5-(5-methylfuran-2-yl)-thiophene-2-carboxamide;
N-[(1S,2R,4R)-7-azabicyclo[2.2.1]hept-2-yl]-5-(5-methoxyfuran-2-yl)-thiophene-2-carboxamide;
N-[(1S,2R,4R)-7-azabicyclo[2.2.1]hept-2-yl]-5-(5-chlorofuran-2-yl)-thiophene-2-carboxamide;
N-[(1S,2R,4R)-7-azabicyclo[2.2.1]hept-2-yl]-5-(oxazol-2-yl)-thiophene-2-carboxamide;
N-[(1S,2R,4R)-7-azabicyclo[2.2.1]hept-2-yl]-5-(5-methyloxazol-2-yl)-thiophene-2-carboxamide;
N-[(1S,2R,4R)-7-azabicyclo[2.2.1]hept-2-yl]-5-(5-methoxyoxazol-2-yl)-thiophene-2-carboxamide;
N-[(1S,2R,4R)-7-azabicyclo[2.2.1]hept-2-yl]-5-(5-chlorooxazol-2-yl)-thiophene-2-carboxamide;
N-[(1S,2R,4R)-7-azabicyclo[2.2.1]hept-2-yl]-5-(oxazol-5-yl)-thiophene-2-carboxamide;
N-[(1S,2R,4R)-7-azabicyclo[2.2.1]hept-2-yl]-5-(2-methyloxazol-5-yl)-thiophene-2-carboxamide;
N-[(1S,2R,4R)-7-azabicyclo[2.2.1]hept-2-yl]-5-(2-methoxyoxazol-5-yl)-thiophene-2-carboxamide;
N-[(1S,2R,4R)-7-azabicyclo[2.2.1]hept-2-yl]-5-(2-chlorooxazol-5-yl)-thiophene-2-carboxamide;
N-[(1S,2R,4R)-7-azabicyclo[2.2.1]hept-2-yl]-5-(thiazol-2-yl)-thiophene-2-carboxamide;
N-[(1S,2R,4R)-7-azabicyclo[2.2.1]hept-2-yl]-5-(5-methylthiazol-2-yl)-thiophene-2-carboxamide;
N-[(1S,2R,4R)-7-azabicyclo[2.2.1]hept-2-yl]-5-(5-methoxythiazol-2-yl)-thiophene-2-carboxamide;
N-[(1S,2R,4R)-7-azabicyclo[2.2.1]hept-2-yl]-5-(5-chlorothiazol-2-yl)-thiophene-2-carboxamide;
N-[(1S,2R,4R)-7-azabicyclo[2.2.1]hept-2-yl]-5-(thiazol-5-yl)-thiophene-2-carboxamide;
N-[(1S,2R,4R)-7-azabicyclo[2.2.1]hept-2-yl]-5-(2-methylthiazol-5-yl)-thiophene-2-carboxamide;
N-[(1S,2R,4R)-7-azabicyclo[2.2.1]hept-2-yl]-5-(2-methoxythiazol-5-yl)-thiophene-2-carboxamide;
N-[(1S,2R,4R)-7-azabicyclo[2.2.1]hept-2-yl]-5-(2-chlorothiazol-5-yl)-thiophene-2-carboxamide;
N-[(1S,2R,4R)-7-azabicyclo[2.2.1]hept-2-yl]-5-(4-methylthiazol-2-yl)-thiophene-2-carboxamide;
N-[(1S,2R,4R)-7-azabicyclo[2.2.1]hept-2-yl]-5-(4-methoxythiazol-2-yl)-thiophene-2-carboxamide;
N-[(1S,2R,4R)-7-azabicyclo[2.2.1]hept-2-yl]-5-(4-chlorothiazol-2-yl)-thiophene-2-carboxamide;
N-[(1S,2R,4R)-7-azabicyclo[2.2.1]hept-2-yl]-5-(4-methyloxazol-2-yl)-thiophene-2-carboxamide;
N-[(1S,2R,4R)-7-azabicyclo[2.2.1]hept-2-yl]-5-(4-methoxyoxazol-2-yl)-thiophene-2-carboxamide;
N-[(1S,2R,4R)-7-azabicyclo[2.2.1]hept-2-yl]-5-(4-chlorooxazol-2-yl)-thiophene-2-carboxamide;
N-[(1S,2R,4R)-7-azabicyclo[2.2.1]hept-2-yl]-5-([1,3,4]thiadiazol-2-yl)-thiophene-2-carboxamide;
N-[(1S,2R,4R)-7-azabicyclo[2.2.1]hept-2-yl]-5-(5-methyl[1,3,4]thiadiazol-2-yl)-thiophene-2-carboxamide;
N-[(1S,2R,4R)-7-azabicyclo[2.2.1]hept-2-yl]-5-(5-methoxy[1,3,4]thiadiazol-2-yl)-thiophene-2-carboxamide;
N-[(1S,2R,4R)-7-azabicyclo[2.2.1]hept-2-yl]-5-(5-chloro[1,3,4]thiadiazol-2-yl)-thiophene-2-carboxamide;
N-[(1S,2R,4R)-7-azabicyclo[2.2.1]hept-2-yl]-5-([1,3,4]oxadiazol-2-yl)-thiophene-2-carboxamide;
N-[(1S,2R,4R)-7-azabicyclo[2.2.1]hept-2-yl]-5-(5-methyl[1,3,4]oxadiazol-2-yl)-thiophene-2-carboxamide;
N-[(1S,2R,4R)-7-azabicyclo[2.2.1]hept-2-yl]-5-(5-methoxy[1,3,4]oxadiazol-2-yl)-thiophene-2-carboxamide;
N-[(1S,2R,4R)-7-azabicyclo[2.2.1]hept-2-yl]-5-(5-chloro[1,3,4]oxadiazol-2-yl)-thiophene-2-carboxamide;
N-[(1S,2R,4R)-7-azabicyclo[2.2.1]hept-2-yl]-5-(thiophen-4-yloxy)-thiophene-2-carboxamide;
N-[(1S,2R,4R)-7-azabicyclo[2.2.1]hept-2-yl]-5-(5-methylthiophen-2-yloxy)-thiophene-2-carboxamide;
N-[(1S,2R,4R)-7-azabicyclo[2.2.1]hept-2-yl]-5-(5-methoxythiophen-2-yloxy)-thiophene-2-carboxamide;

N-[(1S,2R,4R)-7-azabicyclo[2.2.1]hept-2-yl]-5-(5-chlorothiophen-2-yloxy)-thiophene-2-carboxamide;
N-[(1S,2R,4R)-7-azabicyclo[2.2.1]hept-2-yl]-5-(furan-4-yloxy)-thiophene-2-carboxamide;
N-[(1S,2R,4R)-7-azabicyclo[2.2.1]hept-2-yl]-5-(5-methylfuran-2-yloxy)-thiophene-2-carboxamide;
N-[(1S,2R,4R)-7-azabicyclo[2.2.1]hept-2-yl]-5-(5-methoxyfuran-2-yloxy)-thiophene-2-carboxamide;
N-[(1S,2R,4R)-7-azabicyclo[2.2.1]hept-2-yl]-5-(5-chlorofuran-2-yloxy)-thiophene-2-carboxamide;
N-[(1S,2R,4R)-7-azabicyclo[2.2.1]hept-2-yl]-5-(oxazol-2-yloxy)-thiophene-2-carboxamide;
N-[(1S,2R,4R)-7-azabicyclo[2.2.1]hept-2-yl]-5-(5-methyloxazol-2-yloxy)-thiophene-2-carboxamide;
N-[(1S,2R,4R)-7-azabicyclo[2.2.1]hept-2-yl]-5-(5-methoxyoxazol-2-yloxy)-thiophene-2-carboxamide;
N-[(1S,2R,4R)-7-azabicyclo[2.2.1]hept-2-yl]-5-(5-chlorooxazol-2-yloxy)-thiophene-2-carboxamide;
N-[(1S,2R,4R)-7-azabicyclo[2.2.1]hept-2-yl]-5-(oxazol-5-yloxy)-thiophene-2-carboxamide;
N-[(1S,2R,4R)-7-azabicyclo[2.2.1]hept-2-yl]-5-(2-methyloxazol-5-yloxy)-thiophene-2-carboxamide;
N-[(1S,2R,4R)-7-azabicyclo[2.2.1]hept-2-yl]-5-(2-methoxyoxazol-5-yloxy)-thiophene-2-carboxamide;
N-[(1S,2R,4R)-7-azabicyclo[2.2.1]hept-2-yl]-5-(2-chlorooxazol-5-yloxy)-thiophene-2-carboxamide;
N-[(1S,2R,4R)-7-azabicyclo[2.2.1]hept-2-yl]-5-(thiazol-2-yloxy)-thiophene-2-carboxamide;
N-[(1S,2R,4R)-7-azabicyclo[2.2.1]hept-2-yl]-5-(5-methylthiazol-2-yloxy)-thiophene-2-carboxamide;
N-[(1S,2R,4R)-7-azabicyclo[2.2.1]hept-2-yl]-5-(5-methoxythiazol-2-yloxy)-thiophene-2-carboxamide;
N-[(1S,2R,4R)-7-azabicyclo[2.2.1]hept-2-yl]-5-(5-chlorothiazol-2-yloxy)-thiophene-2-carboxamide;
N-[(1S,2R,4R)-7-azabicyclo[2.2.1]hept-2-yl]-5-(thiazol-5-yloxy)-thiophene-2-carboxamide;
N-[(1S,2R,4R)-7-azabicyclo[2.2.1]hept-2-yl]-5-(2-methylthiazol-5-yloxy)-thiophene-2-carboxamide;
N-[(1S,2R,4R)-7-azabicyclo[2.2.1]hept-2-yl]-5-(2-methoxythiazol-5-yloxy)-hiophene-2-carboxamide;
N-[(1S,2R,4R)-7-azabicyclo[2.2.1]hept-2-yl]-5-(2-chlorothiazol-5-yloxy)-thiophene-carboxamide;
N-[(1S,2R,4R)-7-azabicyclo[2.2.1]hept-2-yl]-5-(4-methylthiazol-2-yloxy)-thiophene-2-carboxamide;
N-[(1S,2R,4R)-7-azabicyclo[2.2.1]hept-2-yl]-5-(4-methoxythiazol-2-yloxy)-thiophene-2-carboxamide;
N-[(1S,2R,4R)-7-azabicyclo[2.2.1]hept-2-yl]-5-(4-chlorothiazol-2-yloxy)-thiophene-2-carboxamide;
N-[(1S,2R,4R)-7-azabicyclo[2.2.1]hept-2-yl]-5-(4-methyloxazol-2-yloxy)-thiophene-2-carboxamide;
N-[(1S,2R,4R)-7-azabicyclo[2.2.1]hept-2-yl]-5-(4-methoxyoxazol-2-yloxy)-thiophene-2-carboxamide;
N-[(1S,2R,4R)-7-azabicyclo[2.2.1]hept-2-yl]-5-(4-chlorooxazol-2-yloxy)-thiophene-2-carboxamide;
N-[(1S,2R,4R)-7-azabicyclo[2.2.1]hept-2-yl]-5-([1,3,4]thiadiazol-2-yloxy)-thiophene-2-carboxamide;
N-[(1S,2R,4R)-7-azabicyclo[2.2.1]hept-2-yl]-5-(5-methyl[1,3,4]thiadiazol-2-yloxy)-thiophene-2-carboxamide;
N-[(1S,2R,4R)-7-azabicyclo[2.2.1]hept-2-yl]-5-(5-methoxy[1,3,4]thiadiazol-2-yloxy)-thiophene-2-carboxamide;
N-[(1S,2R,4R)-7-azabicyclo[2.2.1]hept-2-yl]-5-(5-chloro[1,3,4]thiadiazol-2-yloxy)-thiophene-2-carboxamide;
N-[(1S,2R,4R)-7-azabicyclo[2.2.1]hept-2-yl]-5-([1,3,4]oxadiazol-2-yloxy)-thiophene-2-carboxamide;
N-[(1S,2R,4R)-7-azabicyclo[2.2.1]hept-2-yl]-5-(5-methyl [1,3,4]oxadiazol-2-yloxy)-thiophene-2-carboxamide;
N-[(1S,2R,4R)-7-azabicyclo[2.2.1]hept-2-yl]-5-(5-methoxy[1,3,4]oxadiazol-2-yloxy)-thiophene-2-carboxamide;
N-[(1S,2R,4R)-7-azabicyclo[2.2.1]hept-2-yl]-5-(5-chloro[1,3,4]oxadiazol-2-yloxy)-thiophene-2-carboxamide;
N-[(1S,2R,4R)-7-azabicyclo[2.2.1]hept-2-yl]-5-(thiophen-4-ylsulfanyl)-thiophene-2-carboxamide;
N-[(1S,2R,4R)-7-azabicyclo[2.2.1]hept-2-yl]-5-(5-methylthiophen-2-ylsulfanyl)-thiophene-2-carboxamide;
N-[(1S,2R,4R)-7-azabicyclo[2.2.1]hept-2-yl]-5-(5-methoxythiophen-2-ylsulfanyl)-thiophene-2-carboxamide;
N-[(1S,2R,4R)-7-azabicyclo[2.2.1]hept-2-yl]-5-(5-chlorothiophen-2-ylsulfanyl)-thiophene-2-carboxamide;
N-[(1S,2R,4R)-7-azabicyclo[2.2.1]hept-2-yl]-5-(furan-4-ylsulfanyl)-thiophene-2-carboxamide;
N-[(1S,2R,4R)-7-azabicyclo[2.2.1]hept-2-yl]-5-(5-methylfuran-2-ylsulfanyl)-thiophene-2-carboxamide;
N-[(1S,2R,4R)-7-azabicyclo[2.2.1]hept-2-yl]-5-(5-methoxyfuran-2-ylsulfanyl3-thiophene-2-carboxamide;
N-[(1S,2R,4R)-7-azabicyclo[2.2.1]hept-2-yl]-5-(5-chlorofuran-2-ylsulfanyl)-thiophene-2-carboxamide;
N-[(1S,2R,4R)-7-azabicyclo[2.2.1]hept-2-yl]-5-(oxazol-2-ylsulfanyl)-thiophene-2-carboxamide;
N-[(1S,2R,4R)-7-azabicyclo[2.2.1]hept-2-yl]-5-(5-methyloxazol-2-ylsulfanyl)-thiophene-2-carboxamide;
N-[(1S,2R,4R)-7-azabicyclo[2.2.1]hept-2-yl]-5-(5-methoxyoxazol-2-ylsulfanyl)-thiophene-2-carboxamide;
N-[(1S,2R,4R)-7-azabicyclo[2.2.1]hept-2-yl]-5-(5-chlorooxazol-2-ylsulfanyl)-thiophene-2-carboxamide;
N-[(1S,2R,4R)-7-azabicyclo[2.2.1]hept-2-yl]-5-(oxazol-5-ylsulfanyl)-thiophene-2-carboxamide;
N-[(1S,2R,4R)-7-azabicyclo[2.2.1]hept-2-yl]-5-(2-methyloxazol-5-ylsulfanyl)-thiophene-2-carboxamide;
N-[(1S,2R,4R)-7-azabicyclo[2.2.1]hept-2-yl]-5-(2-methoxyoxazol-5-ylsulfanyl)-thiophene-2-carboxamide;
N-[(1S,2R,4R)-7-azabicyclo[2.2.1]hept-2-yl]-5-(2-chlorooxazol-5-ylsulfanyl)-thiophene-2-carboxamide;
N-[(1S,2R,4R)-7-azabicyclo[2.2.1]hept-2-yl]-5-(thiazol-2-ylsulfanyl)-thiophene-2-carboxamide;
N-[(1S,2R,4R)-7-azabicyclo[2.2.1]hept-2-yl]-5-(5-methylthiazol-2-ylsulfanyl)-thiophene-2-carboxamide;
N-[(1S,2R,4R)-7-azabicyclo[2.2.1]hept-2-yl]-5-(5-methoxythiazol-2-ylsulfanyl)-thiophene-2-carboxamide;
N-[(1S,2R,4R)-7-azabicyclo[2.2.1]hept-2-yl]-5-(5-chlorothiazol-2-ylsulfanyl)-thiophene-2-carboxamide;
N-[(1S,2R,4R)-7-azabicyclo[2.2.1]hept-2-yl]-5-(thiazol-5-ylsulfanyl)-thiophene-2-carboxamide;
N-[(1S,2R,4R)-7-azabicyclo[2.2.1]hept-2-yl]-5-(2-methylthiazol-5-ylsulfanyl)-thiophene-2-carboxamide;

N-[(1S,2R,4R)-7-azabicyclo[2.2.1]hept-2-yl]-5-(2-methoxythiazol-5-ylsulfanyl)-thiophene-2-carboxamide;

N-[(1S,2R,4R)-7-azabicyclo[2.2.1]hept-2-yl]-5-(2-chlorothiazol-5-ylsulfanyl)-thiophene-2-carboxamide;

N-[(1S,2R,4R)-7-azabicyclo[2.2.1]hept-2-yl]-5-(4-methylthiazol-2-ylsulfanyl)-thiophene-2-carboxamide;

N-[(1S,2R,4R)-7-azabicyclo[2.2.1]hept-2-yl]-5-(4-methoxythiazol-2-ylsulfanyl)-thiophene-2-carboxamide;

N-[(1S,2R,4R)-7-azabicyclo[2.2.1]hept-2-yl]-5-(4-chlorothiazol-2-ylsulfanyl)-thiophene-2-carboxamide;

N-[(1S,2R,4R)-7-azabicyclo[2.2.1]hept-2-yl]-5-(4-methyloxazol-2-ylsulfanyl)-thiophene-2-carboxamide;

N-[(1S,2R,4R)-7-azabicyclo[2.2.1]hept-2-yl]-5-(4-methoxyoxazol-2-ylsulfanyl)-thiophene-2-carboxamide;

N-[(1S,2R,4R)-7-azabicyclo[2.2.1]hept-2-yl]-5-(4-chlorooxazol-2-ylsulfanyl)-thiophene-2-carboxamide;

N-[(1S,2R,4R)-7-azabicyclo[2.2.1]hept-2-yl]-5-([1,3,4]thiadiazol-2-ylsulfanyl)-thiophene-2-carboxamide;

N-[(1S,2R,4R)-7-azabicyclo[2.2.1]hept-2-yl]-5-(5-methyl[1,3,4]thiadiazol-2-ylsulfanyl)-thiophene-2-carboxamide;

N-[(1S,2R,4R)-7-azabicyclo[2.2.1]hept-2-yl]-5-(5-methoxy[1,3,4]thiadiazol-2-ylsulfanyl)-thiophene-2-carboxamide;

N-[(1S,2R,4R)-7-azabicyclo[2.2.1]hept-2-yl]-5-(5-chloro[1,3,4]thiadiazol-2-ylsulfanyl)-thiophene-2-carboxamide;

N-[(1S,2R,4R)-7-azabicyclo[2.2.1]hept-2-yl]-5-([1,3,4]oxadiazol-2-ylsulfanyl)-thiophene-2-carboxamide;

N-[(1S,2R,4R)-7-azabicyclo[2.2.1]hept-2-yl]-5-(5-methyl[1,3,4]oxadiazol-2-ylsulfanyl)-thiophene-2-carboxamide;

N-[(1S,2R,4R)-7-azabicyclo[2.2.1]hept-2-yl]-5-(5-methoxy[1,3,4]oxadiazol-2-ylsulfanyl)-thiophene-2-carboxamide;

N-[(1S,2R,4R)-7-azabicyclo[2.2.1]hept-2-yl]-5-(5-chloro[1,3,4]oxadiazol-2-ylsulfanyl)-thiophene-2-carboxamide;

N-[(1S,2R,4R)-7-azabicyclo[2.2.1]hept-2-yl]-5-(pyrrole-2-yl)-thiophene-2-carboxamide;

N-[(1S,2R,4R)-7-azabicyclo[2.2.1]hept-2-yl]-5-(isothiazol-3-yl)-thiophene-2-carboxamide;

N-[(1S,2R,4R)-7-azabicyclo[2.2.1]hept-2-yl]-5-(isoxazol-3-yl)-thiophene-2-carboxamide;

N-[(1S,2R,4R)-7-azabicyclo[2.2.1]hept-2-yl]-5-(3H-imidazol-4-yl)-thiophene-2-carboxamide;

N-[(1S,2R,4R)-7-azabicyclo[2.2.1]hept-2-yl]-4-(4-hydroxyphenylsulfanyl)-thiophene-2-carboxamide;

N-[(1S,2R,4R)-7-azabicyclo[2.2.1]hept-2-yl]-4-(3-acetamidophenylsulfanyl)-thiophene-2-carboxamide;

N-[(1S,2R,4R)-7-azabicyclo[2.2.1]hept-2-yl]-4-(2-methanesulfonylaminophenyl)-thiophene-2-carboxamide;

N-[(1S,2R,4R)-7-azabicyclo[2.2.1]hept-2-yl]-4-(pyridin-2-yloxy)-thiophene-2-carboxamide;

N-[(1S,2R,4R)-7-azabicyclo[2.2.1]hept-2-yl]-4-(2-methylpyridin-4-yloxy)-thiophene-2-carboxamide;

N-[(1S,2R,4R)-7-azabicyclo[2.2.1]hept-2-yl]-4-(4-trifluoromethylphenyl)-thiophene-2-carboxamide;

N-[(1S,2R,4R)-7-azabicyclo[2.2.1]hept-2-yl]-4-(2-acetylphenyl)-thiophene-2-carboxamide;

N-[(1S,2R,4R)-7-azabicyclo[2.2.1]hept-2-yl]-4-chloro-5-phenyl-thiophene-2-carboxamide;

N-[(1S,2R,4R)-7-azabicyclo[2.2.1]hept-2-yl]-4-methyl-5-phenyl-thiophene-2-carboxamide;

N-[(1S,2R,4R)-7-azabicyclo[2.2.1]hept-2-yl]-4-cyano-5-phenyl-thiophene-2-carboxamide;

N-[(1S,2R,4R)-7-azabicyclo[2.2.1]hept-2-yl]-4-methoxy-5-phenyl-thiophene-2-carboxamide;

N-[(1S,2R,4R)-7-azabicyclo[2.2.1]hept-2-yl]-5-chloro-4-phenyl-thiophene-2-carboxamide;

N-[(1S,2R,4R)-7-azabicyclo[2.2.1]hept-2-yl]-5-methyl-4-phenyl-thiophene-2-carboxamide;

N-[(1S,2R,4R)-7-azabicyclo[2.2.1]hept-2-yl]-5-cyano-4-phenyl-thiophene-2-carboxamide;

N-[(1S,2R,4R)-7-azabicyclo[2.2.1]hept-2-yl]-5-methoxy-4-phenyl-thiophene-2-carboxamide;

N-[(1S,2R,4R)-7-azabicyclo[2.2.1]hept-2-yl]-4-chloro-5-bromo-thiophene-2-carboxamide;

N-[(1S,2R,4R)-7-azabicyclo[2.2.1]hept-2-yl]-4-chloro-5-methylsulfanyl-thiophene-2-carboxamide;

N-[(1S,2R,4R)-7-azabicyclo[2.2.1]hept-2-yl]-4-chloro-5-methyl-thiophene-2-carboxamide;

N-[(1S,2R,4R)-7-azabicyclo[2.2.1]hept-2-yl]-4-chloro-5-cyano-thiophene-2-carboxamide;

N-[(1S,2R,4R)-7-azabicyclo[2.2.1]hept-2-yl]-5-chloro-4-bromo-thiophene-2-carboxamide;

N-[(1S,2R,4R)-7-azabicyclo[2.2.1]hept-2-yl]-5-chloro-4-methylsulfanyl-thiophene-2-carboxamide;

N-[(1S,2R,4R)-7-azabicyclo[2.2.1]hept-2-yl]-5-chloro-4-methyl-thiophene-2-carboxamide;

N-[(1S,2R,4R)-7-azabicyclo[2.2.1]hept-2-yl]-5-chloro-4-cyano-thiophene-2-carboxamide;

N-[(1S,2R,4R)-7-azabicyclo[2.2.1]hept-2-yl]-5-(acetylamino)-furan-2-carboxamide;

N-[(1S,2R,4R)-7-azabicyclo[2.2.1]hept-2-yl]-5-trifluoromethyl-furan-2-carboxamide;

N-[(1S,2R,4R)-7-azabicyclo[2.2.1]hept-2-yl]-5-(2-bromophenyl)-furan-2-carboxamide;

N-[(1S,2R,4R)-7-azabicyclo[2.2.1]hept-2-yl]-5-(3-bromophenyl)-furan-2-carboxamide;

N-[(1S,2R,4R)-7-azabicyclo[2.2.1]hept-2-yl]-5-(2,3-dichlorophenyl)-furan-2-carboxamide;

N-[(1S,2R,4R)-7-azabicyclo[2.2.1]hept-2-yl]-5-(2,4-dichlorophenyl)-furan-2-carboxamide;

N-[(1S,2R,4R)-7-azabicyclo[2.2.1]hept-2-yl]-5-(2,5-dichlorophenyl)-furan-2-carboxamide;

N-[(1S,2R,4R)-7-azabicyclo[2.2.1]hept-2-yl]-5-(2,6-dichlorophenyl)-furan-2-carboxamide;

N-[(1S,2R,4R)-7-azabicyclo[2.2.1]hept-2-yl]-5-(3,4-dichlorophenyl)-furan-2-carboxamide;

N-[(1S,2R,4R)-7-azabicyclo[2.2.1]hept-2-yl]-5-(3,5-dichlorophenyl)-furan-2-carboxamide;

N-[(1S,2R,4R)-7-azabicyclo[2.2.1]hept-2-yl]-5-(4-amino-2-fluorophenyl)-furan-2-carboxamide;

N-[(1S,2R,4R)-7-azabicyclo[2.2.1]hept-2-yl]-5-(3-amino-2-fluorophenyl)-furan-2-carboxamide;

N-[(1S,2R,4R)-7-azabicyclo[2.2.1]hept-2-yl]-5-(4-amino-2-chlorophenyl)-furan-2-carboxamide;

N-[(1S,2R,4R)-7-azabicyclo[2.2.1]hept-2-yl]-5-(3-amino-2-chlorophenyl)-furan-2-carboxamide;

N-[(1S,2R,4R)-7-azabicyclo[2.2.1]hept-2-yl]-5-(3-aminophenyl)-furan-2-carboxamide;
N-[(1S,2R,4R)-7-azabicyclo[2.2.1]hept-2-yl]-5-(2-cyanophenyl)-furan-2-carboxamide;
N-[(1S,2R,4R)-7-azabicyclo[2.2.1]hept-2-yl]-5-(3-cyanophenyl)-furan-2-carboxamide;
N-[(1S,2R,4R)-7-azabicyclo[2.2.1]hept-2-yl]-5-(2-hydroxyphenyl)-furan-2-carboxamide;
N-[(1S,2R,4R)-7-azabicyclo[2.2.1]hept-2-yl]-5-(3-hydroxyphenyl)-furan-2-carboxamide;
N-[(1S,2R,4R)-7-azabicyclo[2.2.1]hept-2-yl]-5-(4-hydroxyphenyl)-furan-2-carboxamide;
N-[(1S,2R,4R)-7-azabicyclo[2.2.1]hept-2-yl]-5-(2-fluoro-4-methylphenyl)-furan-2-carboxamide;
N-[(1S,2R,4R)-7-azabicyclo[2.2.1]hept-2-yl]-5-(2-fluoro-3-methoxyphenyl)-furan-2-carboxamide;
N-[(1S,2R,4R)-7-azabicyclo[2.2.1]hept-2-yl]-5-(2-fluoro-4-methoxyphenyl)-furan-2-carboxamide;
N-[(1S,2R,4R)-7-azabicyclo[2.2.1]hept-2-yl]-5-(2-[(methylsulfonyl)amino]phenyl)-furan-2-carboxamide;
N-[(1S,2R,4R)-7-azabicyclo[2.2.1]hept-2-yl]-5-(3-[(methylsulfonyl)amino]phenyl)-furan-2-carboxamide;
N-[(1S,2R,4R)-7-azabicyclo[2.2.1]hept-2-yl]-5-(4-[(methylsulfonyl)amino]phenyl)-furan-2-carboxamide;
N-[(1S,2R,4R)-7-azabicyclo[2.2.1]hept-2-yl]-5-(2-([(trifluoromethyl)sulfonyl]amino)phenyl)-furan-2-carboxamide;
N-[(1S,2R,4R)-7-azabicyclo[2.2.1]hept-2-yl]-5-(3-([(trifluoromethyl)sulfonyl]amino)phenyl)-furan-2-carboxamide;
N-[(1S,2R,4R)-7-azabicyclo[2.2.1]hept-2-yl]-5-(4-([(trifluoromethyl)sulfonyl]amino)phenyl)-furan-2-carboxamide;
N-[(1S,2R,4R)-7-azabicyclo[2.2.1]hept-2-yl]-5-(2-[(phenylsulfonyl)amino]phenyl)-furan-2-carboxamide;
N-[(1S,2R,4R)-7-azabicyclo[2.2.1]hept-2-yl]-5-(3-[(phenylsulfonyl)amino]phenyl)-furan-2-carboxamide;
N-[(1S,2R,4R)-7-azabicyclo[2.2.1]hept-2-yl]-5-(4-[(phenylsulfonyl)amino]phenyl)-furan-2-carboxamide;
N-[(1S,2R,4R)-7-azabicyclo[2.2.1]hept-2-yl]-5-(2-[(methylamino)carbonyl]phenyl)-furan-2-carboxamide;
N-[(1S,2R,4R)-7-azabicyclo[2.2.1]hept-2-yl]-5-(3-[(methylamino)carbonyl]phenyl)-furan-2-carboxamide;
N-[(1S,2R,4R)-7-azabicyclo[2.2.1]hept-2-yl]-5-(4-[(methylamino)carbonyl]phenyl)-furan-2-carboxamide;
N-[(1S,2R,4R)-7-azabicyclo[2.2.1]hept-2-yl]-5-(2-[(methylamino)sulfonyl]phenyl)-furan-2-carboxamide;
N-[(1S,2R,4R)-7-azabicyclo[2.2.1]hept-2-yl]-5-(3-[(methylamino)sulfonyl]phenyl)-furan-2-carboxamide;
N-[(1S,2R,4R)-7-azabicyclo[2.2.1]hept-2-yl]-5-(4-[(methylamino)sulfonyl]phenyl)-furan-2-carboxamide;
N-[(1S,2R,4R)-7-azabicyclo[2.2.1]hept-2-yl]-5-[2-(methylamino)phenyl]-furan-2-carboxamide;
N-[(1S,2R,4R)-7-azabicyclo[2.2.1]hept-2-yl]-5-[3-(methylamino)phenyl]-furan-2-carboxamide;
N-[(1S,2R,4R)-7-azabicyclo[2.2.1]hept-2-yl]-5-[4-(methylamino)phenyl]-furan-2-carboxamide;
N-[(1S,2R,4R)-7-azabicyclo[2.2.1]hept-2-yl]-5-[2-(ethylamino)phenyl]-furan-2-carboxamide;
N-[(1S,2R,4R)-7-azabicyclo[2.2.1]hept-2-yl]-5-[3-(ethylarmino)phenyl]-furan-2-carboxamide;
N-[(1S,2R,4R)-7-azabicyclo[2.2.1]hept-2-yl]-5-[4-(ethylamino)phenyl]-furan-2-carboxamide;
N-[(1S,2R,4R)-7-azabicyclo[2.2.1]hept-2-yl]-5-(2-acetylphenyl)-furan-2-carboxamide;
N-[(1S,2R,4R)-7-azabicyclo[2.2.1]hept-2-yl]-5-(3-acetylphenyl)-furan-2-carboxamide;
N-[(1S,2R,4R)-7-azabicyclo[2.2.1]hept-2-yl]-5-(4-acetylphenyl)-furan-2-carboxamide;
N-[(1S,2R,4R)-7-azabicyclo[2.2.1]hept-2-yl]-5-[2-(methylthio)phenyl]-furan-2-carboxamide;
N-[(1S,2R,4R)-7-azabicyclo[2.2.1]hept-2-yl]-5-[3-(methylthio)phenyl]-furan-2-carboxamide;
N-[(1S,2R,4R)-7-azabicyclo[2.2.1]hept-2-yl]-5-[4-(methylthio)phenyl]-furan-2-carboxamide;
N-[(1S,2R,4R)-7-azabicyclo[2.2.1]hept-2-yl]-5-[2-(phenylthio)phenyl]-furan-2-carboxamide;
N-[(1S,2R,4R)-7-azabicyclo[2.2.1]hept-2-yl]-5-[3-(phenylthio)phenyl]-furan-2-carboxamide;
N-[(1S,2R,4R)-7-azabicyclo[2.2.1]hept-2-yl]-5-[4-(phenylthio)phenyl]-furan-2-carboxamide;
N-[(1S,2R,4R)-7-azabicyclo[2.2.1]hept-2-yl]-5-(2-phenoxyphenyl)-furan-2-20 carboxamide;
N-[(1S,2R,4R)-7-azabicyclo[2.2.1]hept-2-yl]-5-(3-phenoxyphenyl)-furan-2-carboxamide;
N-[(1S,2R,4R)-7-azabicyclo[2.2.1]hept-2-yl]-5-(4-phenoxyphenyl)-furan-2-carboxamide;
N-[(1S,2R,4R)-7-azabicyclo[2.2.1]hept-2-yl]-5-(2-anilinophenyl)-furan-2-carboxamide;
N-[(1S,2R,4R)-7-azabicyclo[2.2.1]hept-2-yl]-5-(3-anilinophenyl)-furan-2-carboxamide;
N-[(1S,2R,4R)-7-azabicyclo[2.2.1]hept-2-yl]-5-(4-anilinophenyl)-furan-2-carboxamide;
N-[(1S,2R,4R)-7-azabicyclo[2.2.1]hept-2-yl]-5-(phenylthio)-furan-2-carboxamide;
N-[(1S,2R,4R)-7-azabicyclo[2.2.1]hept-2-yl]-5-[(2-fluorophenyl)thio]-furan-2-carboxamide;
N-[(1S,2R,4R)-7-azabicyclo[2.2.1]hept-2-yl]-5-[(3-fluorophenyl)thio]-furan-2-carboxamide;
N-[(1S,2R,4R)-7-azabicyclo[2.2.1]hept-2-yl]-5-[(4-fluorophenyl)thio]-furan-2-carboxamide;
N-[(1S,2R,4R)-7-azabicyclo[2.2.1]hept-2-yl]-5-[(2-chlorophenyl)thio]-furan-2-carboxamide;
N-[(1S,2R,4R)-7-azabicyclo[2.2.1]hept-2-yl]-5-[(3-chlorophenyl)thio]-furan-2-carboxamide;
N-[(1S,2R,4R)-7-azabicyclo[2.2.1]hept-2-yl]-5-[(4-chlorophenyl)thio]-furan-2-carboxamide;
N-[(1S,2R,4R)-7-azabicyclo[2.2.1]hept-2-yl]-5-(2-fluorophenoxy)-furan-2-carboxamide;
N-[(1S,2R,4R)-7-azabicyclo[2.2.1]hept-2-yl]-5-(3-fluorophenoxy)-furan-2-carboxamide;
N-[(1S,2R,4R)-7-azabicyclo[2.2.1]hept-2-yl]-5-(4-fluorophenoxy)-furan-2-carboxamide;
N-[(1S,2R,4R)-7-azabicyclo[2.2.1]hept-2-yl]-5-(2-chlorophenoxy)-furan-2-carboxamide;
N-[(1S,2R,4R)-7-azabicyclo[2.2.1]hept-2-yl]-5-(3-chlorophenoxy)-furan-2-carboxamide;
N-[(1S,2R,4R)-7-azabicyclo[2.2.1]hept-2-yl]-5-(4-chlorophenoxy)-furan-2-carboxamide;
N-[(1S,2R,4R)-7-azabicyclo[2.2.1]hept-2-yl]-5-pyridin-2-yl-furan-2-carboxamide;

N-[(1S,2R,4R)-7-azabicyclo[2.2.1]hept-2-yl]-5-pyridin-3-yl-furan-2-carboxamide;
N-[(1S,2R,4R)-7-azabicyclo[2.2.1]hept-2-yl]-5-pyridin-4-yl-furan-2-carboxamide;
N-[(1S,2R,4R)-7-azabicyclo[2.2.1]hept-2-yl]-5-(3-fluoropyridin-2-yl)-furan-2-carboxamide;
N-[(1S,2R,4R)-7-azabicyclo[2.2.1]hept-2-yl]-5-(4-fluoropyridin-2-yl)-furan-2-carboxamide;
N-[(1S,2R,4R)-7-azabicyclo[2.2.1]hept-2-yl]-5-(5-fluoropyridin-2-yl)-furan-2-carboxamide;
N-[(1S,2R,4R)-7-azabicyclo[2.2.1]hept-2-yl]-5-(6-fluoropyridin-2-yl)-furan-2-carboxamide;
N-[(1S,2R,4R)-7-azabicyclo[2.2.1]hept-2-yl]-5-(2-fluoropyridin-3-yl)-furan-2-carboxamide;
N-[(1S,2R,4R)-7-azabicyclo[2.2.1]hept-2-yl]-5-(4-fluoropyridin-3-yl)-furan-2-carboxamide;
N-[(1S,2R,4R)-7-azabicyclo[2.2.1]hept-2-yl]-5-(5-fluoropyridin-3-yl)-furan-2-carboxamide;
N-[(1S,2R,4R)-7-azabicyclo[2.2.1]hept-2-yl]-5-(6-fluoropyridin-3-yl)-furan-2-carboxamide;
N-[(1S,2R,4R)-7-azabicyclo[2.2.1]hept-2-yl]-5-(2-fluoropyridin-4-yl)-furan-2-carboxamide;
N-[(1S,2R,4R)-7-azabicyclo[2.2.1]hept-2-yl]-5-(3-fluoropyridin-4-yl)-furan-2-carboxamide;
N-[(1S,2R,4R)-7-azabicyclo[2.2.1]hept-2-yl]-5-(3-chloropyridin-2-yl)-furan-2-carboxamide;
N-[(1S,2R,4R)-7-azabicyclo[2.2.1]hept-2-yl]-5-(4-chloropyridin-2-yl)-furan-2-carboxamide;
N-[(1S,2R,4R)-7-azabicyclo[2.2.1]hept-2-yl]-5-(5-chloropyridin-2-yl)-furan-2-carboxamide;
N-[(1S,2R,4R)-7-azabicyclo[2.2.1]hept-2-yl]-5-(6-chloropyridin-2-yl)-furan-2-carboxamide;
N-[(1S,2R,4R)-7-azabicyclo[2.2.1]hept-2-yl]-5-(2-chloropyridin-3-yl)-furan-2-carboxamide;
N-[(1S,2R,4R)-7-azabicyclo[2.2.1]hept-2-yl]-5-(4-chloropyridin-3-yl)-furan-2-carboxamide;
N-[(1S,2R,4R)-7-azabicyclo[2.2.1]hept-2-yl]-5-(5-chloropyridin-3-yl)-furan-2-carboxamide;
N-[(1S,2R,4R)-7-azabicyclo[2.2.1]hept-2-yl]-5-(6-chloropyridin-3-yl)-furan-2-carboxamide;
N-[(1S,2R,4R)-7-azabicyclo[2.2.1]hept-2-yl]-5-(2-chloropyridin-4-yl)-furan-2-carboxamide;
N-[(1S,2R,4R)-7-azabicyclo[2.2.1]hept-2-yl]-5-(3-chloropyridin-4-yl)-furan-2-carboxamide;
N-[(1S,2R,4R)-7-azabicyclo[2.2.1]hept-2-yl]-5-(2-piperidin-1-ylphenyl)-furan-2-carboxamide;
N-[(1S,2R,4R)-7-azabicyclo[2.2.1]hept-2-yl]-5-(3-piperidin-1-ylphenyl)-furan-2-carboxamide;
N-[(1S,2R,4R)-7-azabicyclo[2.2.1]hept-2-yl]-5-(4-piperidin-1-ylphenyl)-furan-2-carboxamide;
N-[(1S,2R,4R)-7-azabicyclo[2.2.1]hept-2-yl]-5-(2-morpholin-4-ylphenyl)-furan-2-carboxamide;
N-[(1S,2R,4R)-7-azabicyclo[2.2.1]hept-2-yl]-5-(3-morpholin-4-ylphenyl)-furan-2-carboxamide;
N-[(1S,2R,4R)-7-azabicyclo[2.2.1]hept-2-yl]-5-(4-morpholin-4-ylphenyl)-furan-2-carboxamide;
N-[(1S,2R,4R)-7-azabicyclo[2.2.1]hept-2-yl]-5-(2-pyrrolidin-1-ylphenyl)-furan-2-carboxamide;
N-[(1S,2R,4R)-7-azabicyclo[2.2.1]hept-2-yl]-5-(3-pyrrolidin-1-ylphenyl)-furan-2-carboxamide;
N-[(1S,2R,4R)-7-azabicyclo[2.2.1]hept-2-yl]-5-(4-pyrrolidin-1-ylphenyl)-furan-2-carboxamide;
N-[(1S,2R,4R)-7-azabicyclo[2.2.1]hept-2-yl]-5-[2-(1H-pyrrol-2-yl)phenyl]-furan-2-carboxamide;
N-[(1S,2R,4R)-7-azabicyclo[2.2.1]hept-2-yl]-5-[3-(1H-pyrrol-2-yl)phenyl]-furan-2-carboxamide;
N-[(1S,2R,4R)-7-azabicyclo[2.2.1]hept-2-yl]-5-[4-(1H-pyrrol-2-yl)phenyl]-furan-2-carboxamide;
N-[(1S,2R,4R)-7-azabicyclo[2.2.1]hept-2-yl]-5-[2-(2-furyl)phenyl]-furan-2-carboxamide;
N-[(1S,2R,4R)-7-azabicyclo[2.2.1]hept-2-yl]-5-[2-(3-furyl)phenyl]-furan-2-carboxamide;
N-[(1S,2R,4R)-7-azabicyclo[2.2.1]hept-2-yl]-5-[2-(5-methyl-2-furyl)phenyl]-furan-2-carboxamide;
N-[(1S,2R,4R)-7-azabicyclo[2.2.1]hept-2-yl]-5-[3-(2-furyl)phenyl]-furan-2-carboxamide;
N-[(1S,2R,4R)-7-azabicyclo[2.2.1]hept-2-yl]5-[3-(3-furyl)phenyl]-furan-2-carboxamide;
N-[(1S,2R,4R)-7-azabicyclo[2.2.1]hept-2-yl]-5-[3-(5-methyl-2-furyl)phenyl]-furan-2-carboxamide;
N-[(1S,2R,4R)-7-azabicyclo[2.2.1]hept-2-yl]-5-[4-(2-furyl)phenyl]-furan-2-carboxamide;
N-[(1S,2R,4R)-7-azabicyclo[2.2.1]hept-2-yl]-5-[4-(3-furyl)phenyl]-furan-2-carboxamide;
N-[(1S,2R,4R)-7-azabicyclo[2.2.1]hept-2-yl]-5-[4-(5-methyl-2-furyl)phenyl]-furan-2-carboxamide;
N-[(1S,2R,4R)-7-azabicyclo[2.2.1]hept-2-yl]-5-[2-(1,3-thiazol-2-yl)phenyl]-furan-2-carboxamide;
N-[(1S,2R,4R)-7-azabicyclo[2.2.1]hept-2-yl]-5-[3-(1,3-thiazol-2-yl)phenyl]-furan-2-carboxamide;
N-[(1S,2R,4R)-7-azabicyclo[2.2.1]hept-2-yl]-5-[4-(1,3-thiazol-2-yl)phenyl]-furan-2-carboxamide;
N-[(1S,2R,4R)-7-azabicyclo[2.2.1]hept-2-yl]-5-[2-(1,3-oxazol-2-yl)phenyl]-furan-2-carboxamide;
N-[(1S,2R,4R)-7-azabicyclo[2.2.1]hept-2-yl]-5-[3-(1,3-oxazol-2-yl)phenyl]-furan-2-carboxamide;
N-[(1S,2R,4R)-7-azabicyclo[2.2.1]hept-2-yl]-5-[4-(1,3-oxazol-2-yl)phenyl]-furan-2-carboxamide;
N-[(1S,2R,4R)-7-azabicyclo[2.2.1]hept-2-yl]-5-(2-isothiazol-5-ylphenyl)-furan-2-carboxamide;
N-[(1S,2R,4R)-7-azabicyclo[2.2.1]hept-2-yl]-5-(3-isothiazol-5-ylphenyl)-furan-2-carboxamide;
N-[(1S,2R,4R)-7-azabicyclo[2.2.1]hept-2-yl]-5-(4-isothiazol-5-ylphenyl)-furan-2-carboxamide;
N-[(1S,2R,4R)-7-azabicyclo[2.2.1]hept-2-yl]-5-[4-(1H-indol-2-yl)phenyl]-furan-2-carboxamide;
N-[(1S,2R,4R)-7-azabicyclo[2.2.1]hept-2-yl]-5-[4-(1H-indol-3-yl)phenyl]-furan-2-carboxamide;
N-[(1S,2R,4R)-7-azabicyclo[2.2.1]hept-2-yl]-5-(1H-indol-5-yl)-furan-2-carboxamide;
N-[(1S,2R,4R)-7-azabicyclo[2.2.1]hept-2-yl]-5-(1H-indol-6-yl)-furan-2-carboxamide;
N-[(1S,2R,4R)-7-azabicyclo[2.2.1]hept-2-yl]-5-(2-chlorophenyl)-furan-2-carboxamide;
N-[(1S,2R,4R)-7-azabicyclo[2.2.1]hept-2-yl]-5-(3-chlorophenyl)-furan-2-carboxamide;
N-[(1S,2R,4R)-7-azabicyclo[2.2.1]hept-2-yl]-5-(4-bromophenyl)-furan-2-carboxamide;
N-[(1S,2R,4R)-7-azabicyclo[2.2.1]hept-2-yl]-5-[2-(trifluoromethyl)-phenyl]-furan-2-carboxamide;
N-[(1S,2R,4R)-7-azabicyclo[2.2.1]hept-2-yl]-5-[3-(trifluoromethyl)-phenyl]-furan-2-carboxamide;
N-[(1S,2R,4R)-7-azabicyclo[2.2.1]hept-2-yl]-5-(2,4-difluorophenyl)-furan-2-carboxamide;

N-[(1S,2R,4R)-7-azabicyclo[2.2.1]hept-2-yl]-5-(2,5-difluorophenyl)-furan-2-carboxamide;
N-[(1S,2R,4R)-7-azabicyclo[2.2.1]hept-2-yl]-5-(2-methoxyphenyl)-furan-2-carboxamide;
N-[(1S,2R,4R)-7-azabicyclo[2.2.1]hept-2-yl]-5-(3-methoxyphenyl)-furan-2-carboxamide;
N-[(1S,2R,4R)-7-azabicyclo[2.2.1]hept-2-yl]-5-[3-(trifluoromethoxy)phenyl]-furan-2-carboxamide;
N-[(1S,2R,4R)-7-azabicyclo[2.2.1]hept-2-yl]-5-[2-chloro-5-(trifluoromethyl)phenyl]-furan-2-carboxamide;
N-[(1S,2R,4R)-7-azabicyclo[2.2.1]hept-2-yl]-5-(4-fluoro-3-methylphenyl)-furan-2-carboxamide;
N-[(1S,2R,4R)-7-azabicyclo[2.2.1]hept-2-yl]-5-(4-cyanophenyl)-furan-2-carboxamide;
N-[(1S,2R,4R)-7-azabicyclo[2.2.1]hept-2-yl]-5-thien-2-yl-furan-2-carboxamide;
N-[(1S,2R,4R)-7-azabicyclo[2.2.1]hept-2-yl]-5-thien-3-yl-furan-2-carboxamide;
N-[(1S,2R,4R)-7-azabicyclo[2.2.1]hept-2-yl]-5-nitro-furan-2-carboxamide;
N-[(1S,2R,4R)-7-azabicyclo[2.2.1]hept-2-yl]-4,5-dimethyl-furan-2-carboxamide;
N-[(1S,2R,4R)-7-azabicyclo[2.2.1]hept-2-yl]-5-(4-chloro-2-nitrophenyl)-furan-2-carboxamide;
N-[(1S,2R,4R)-7-azabicyclo[2.2.1]hept-2-yl]-5-(4-methyl-2-nitrophenyl)-furan-2-carboxamide;
N-[(1S,2R,4R)-7-azabicyclo[2.2.1]hept-2-yl]-5-(2,3-difluorophenyl)-furan-2-carboxamide;
N-[(1S,2R,4R)-7-azabicyclo[2.2.1]hept-2-yl]-5-(3,4-difluorophenyl)-furan-2-carboxamide;
N-[(1S,2R,4R)-7-azabicyclo[2.2.1]hept-2-yl]-5-(3,5-difluorophenyl)-furan-2-carboxamide;
N-[(1S,2R,4R)-7-azabicyclo[2.2.1]hept-2-yl]-5-(4-methoxy-phenyl)-furan-2-carboxamide;
N-[(1S,2R,4R)-7-azabicyclo[2.2.1]hept-2-yl]-5-(2-methylphenyl)-furan-2-carboxamide;
N-[(1S,2R,4R)-7-azabicyclo[2.2.1]hept-2-yl]-5-(3-methylphenyl)-furan-2-carboxamide;
N-[(1S,2R,4R)-7-azabicyclo[2.2.1]hept-2-yl]-5-[2-(trifluoromethoxy)phenyl]-furan-2-carboxamide;
N-[(1S,2R,4R)-7-azabicyclo[2.2.1]hept-2-yl]-5-[4-(trifluoromethoxy)phenyl]-furan-2-carboxamide;
N-[(1S,2R,4R)-7-azabicyclo[2.2.1]hept-2-yl]-5-(4-tert-butylphenyl)-furan-2-carboxamide;
N-[(1S,2R,4R)-7-azabicyclo[2.2.1]hept-2-yl]-5-(1-benzothien-2-yl)-furan-2-carboxamide;
N-[(1S,2R,4R)-7-azabicyclo[2.2.1]hept-2-yl]-5-quinolin-3-yl-furan-2-carboxamide;
N-[(1S,2R,4R)-7-azabicyclo[2.2.1]hept-2-yl]-5-(4-ethylphenyl)-furan-2-carboxamide;
N-[(1S,2R,4R)-7-azabicyclo[2.2.1]hept-2-yl]-5-(4-isopropylphenyl)-furan-2-carboxamide;
N-[(1S,2R,4R)-7-azabicyclo[2.2.1]hept-2-yl]-5-(3-fluoro-4-methoxyphenyl)-furan-2-carboxamide;
N-[(1S,2R,4R)-7-azabicyclo[2.2.1]hept-2-yl]-5-(1-benzofuran-2-yl)-furan-2-carboxamide;
5-(2-aminophenyl)-N-[(1S,2R,4R)-7-azabicyclo[2.2.1]hept-2-yl]-furan-2-carboxamide;
5-(2-amino-4-methylphenyl)-N-[(1S,2R,4R)-7-azabicyclo[2.2.1]hept-2-yl]-furan-2-carboxamide;
N-[(1S,2R,4R)-7-azabicyclo[2.2.1]hept-2-yl]-5-(phenylethynyl)-furan-2-carboxamide;

N-[(1S,2R,4R)-7-azabicyclo[2.2.1]hept-2-yl]-5-phenoxy-furan-2-carboxamide;
N-[(1S,2R,4R)-7-azabicyclo[2.2.1]hept-2-yl]-5-(methylthio)-1,3-thiazole-2-carboxamide;
N-[(1S,2R,4R)-7-azabicyclo[2.2.1]hept-2-yl]-5-chloro-1,3-thiazole-2-carboxamide;
N-[(1S,2R,4R)-7-azabicyclo[2.2.1]hept-2-yl]-5-bromo-1,3-thiazole-2-carboxamide;
N-[(1S,2R,4R)-7-azabicyclo[2.2.1]hept-2-yl]-5-(phenylthio)-1,3-thiazole-2-carboxamide;
N-[(1S,2R,4R)-7-azabicyclo[2.2.1]hept-2-yl]-5-[(2-fluorophenyl)thio]-1,3-thiazole-2-carboxamide;
N-[(1S,2R,4R)-7-azabicyclo[2.2.1]hept-2-yl]-5-[(3-fluorophenyl)thio]-1,3-thiazole-2-carboxamide;
N-[(1S,2R,4R)-7-azabicyclo[2.2.1]hept-2-yl]-5-[(4-fluorophenyl)thio]-1,3-thiazole-2-carboxamide;
N-[(1S,2R,4R)-7-azabicyclo[2.2.1]hept-2-yl]-5-[(2-chlorophenyl)thio]-1,3-thiazole-2-carboxamide;
N-[(1S,2R,4R)-7-azabicyclo[2.2.1]hept-2-yl]-5-[(3-chlorophenyl)thio]-1,3-thiazole-2-carboxamide;
N-[(1S,2R,4R)-7-azabicyclo[2.2.1]hept-2-yl]-5-[(4-chlorophenyl)thio]-1,3-thiazole-2-carboxamide;
N-[(1S,2R,4R)-7-azabicyclo[2.2.1]hept-2-yl]-5-phenoxy-1,3-thiazole-2-carboxamide;
N-[(1S,2R,4R)-7-azabicyclo[2.2.1]hept-2-yl]-5-(2-fluorophenoxy)-1,3-thiazole-2-carboxamide;
N-[(1S,2R,4R)-7-azabicyclo[2.2.1]hept-2-yl]-5-(3-fluorophenoxy)-1,3-thiazole-2-carboxamide;
N-[(1S,2R,4R)-7-azabicyclo[2.2.1]hept-2-yl]-5-(4-fluorophenoxy)-1,3-thiazole-2-carboxamide;
N-[(1S,2R,4R)-7-azabicyclo[2.2.1]hept-2-yl]-5-(2-chlorophenoxy)-1,3-thiazole-2-carboxamide;
N-[(1S,2R,4R)-7-azabicyclo[2.2.1]hept-2-yl]-5-(3-chlorophenoxy)-1,3-thiazole-2-carboxamide;
N-[(1S,2R,4R)-7-azabicyclo[2.2.1]hept-2-yl]-5-(4-chlorophenoxy)-1,3-thiazole-2-carboxamide;
N-[(3R)-1-azabicyclo[2.2.2]oct-3-yl)]-5-thien-3-yl-1,3-thiazole-2-carboxamide;
N-[(1S,2R,4R)-7-azabicyclo[2.2.1]hept-2-yl]-5-(2,4-difluorophenyl)-1,3-thiazole-2-carboxamide;
N-[(1S,2R,4R)-7-azabicyclo[2.2.1]hept-2-yl]-5-(3,5-difluorophenyl)-1,3-thiazole-2-carboxamide;
N-[(1S,2R,4R)-7-azabicyclo[2.2.1]hept-2-yl]-5-(2,4-dichlorophenyl)-1,3-thiazole-2-carboxamide;
N-[(1S,2R,4R)-7-azabicyclo[2.2.1]hept-2-yl]-5-(3,5-dichlorophenyl)-1,3-thiazole-2-carboxamide;
N-[(1S,2R,4R)-7-azabicyclo[2.2.1]hept-2-yl]-5-(2-bromophenyl)-1,3-thiazole-2-carboxamide;
N-[(1S,2R,4R)-7-azabicyclo[2.2.1]hept-2-yl]-5-(3-bromophenyl)-1,3-thiazole-2-carboxamide;
N-[(1S,2R,4R)-7-azabicyclo[2.2.1]hept-2-yl]-5-(2-cyanophenyl)-1,3-thiazole-2-carboxamide;
N-[(1S,2R,4R)-7-azabicyclo[2.2.1]hept-2-yl]-5-(3-cyanophenyl)-1,3-thiazole-2-carboxamide;
N-[(1S,2R,4R)-7-azabicyclo[2.2.1]hept-2-yl]-5-(4-cyanophenyl)-1,3-thiazole-2-carboxamide;
N-[(1S,2R,4R)-7-azabicyclo[2.2.1]hept-2-yl]-5-(2-hydroxyphenyl)-1,3-thiazole-2-carboxamide;
N-[(1S,2R,4R)-7-azabicyclo[2.2.1]hept-2-yl]-5-(3-hydroxyphenyl)-1,3-thiazole-2-carboxamide;
N-[(1S,2R,4R)-7-azabicyclo[2.2.1]hept-2-yl]-5-(4-hydroxyphenyl)-1,3-thiazole-2-carboxamide;

N-[(1S,2R,4R)-7-azabicyclo[2.2.1]hept-2-yl]-5-(2-nitrophenyl)-1,3-thiazole-2-carboxamide;
N-[(1S,2R,4R)-7-azabicyclo[2.2.1]hept-2-yl]-5-(4-nitrophenyl)-1,3-thiazole-2-carboxamide;
N-[(1S,2R,4R)-7-azabicyclo[2.2.1]hept-2-yl]-5-(2-methylphenyl)-1,3-thiazole-2-carboxamide;
N-[(1S,2R,4R)-7-azabicyclo[2.2.1]hept-2-yl]-5-(3-methylphenyl)-1,3-thiazole-2-carboxamide;
N-[(1S,2R,4R)-7-azabicyclo[2.2.1]hept-2-yl]-5-(4-methylphenyl)-1,3-thiazole-2-carboxamide;
N-[(1S,2R,4R)-7-azabicyclo[2.2.1]hept-2-yl]-5-(2-aminophenyl)-1,3-thiazole-2-carboxamide;
N-[(1S,2R,4R)-7-azabicyclo[2.2.1]hept-2-yl]-5-(3-aminophenyl)-1,3-thiazole-2-carboxamide;
N-[(1S,2R,4R)-7-azabicyclo[2.2.1]hept-2-yl]-5-(4-aminophenyl)-1,3-thiazole-2-carboxamide;
N-[(1S,2R,4R)-7-azabicyclo[2.2.1]hept-2-yl]-5-[(2-(acetylamino)phenyl]-1,3-thiazole-2-carboxamide;
N-[(1S,2R,4R)-7-azabicyclo[2.2.1]hept-2-yl]-5-[3-(acetylamino)phenyl]-1,3-thiazole-2-carboxamide;
N-[(1S,2R,4R)-7-azabicyclo[2.2.1]hept-2-yl]-5-[4-(acetylamino)phenyl]-1,3-thiazole-2-carboxamide;
N-[(1S,2R,4R)-7-azabicyclo[2.2.1]hept-2-yl]-5-(pyridin-2-yl)-1,3-thiazole-2-carboxamide;
N-[(1S,2R,4R)-7-azabicyclo[2.2.1]hept-2-yl]-5-(pyridin-3-yl)-1,3-thiazole-2-carboxamide;
N-[(1S,2R,4R)-7-azabicyclo[2.2.1]hept-2-yl]-5-(pyridin-4-yl)-1,3-thiazole-2-carboxamide;
N-[(1S,2R,4R)-7-azabicyclo[2.2.1]hept-2-yl]-5-(3-fluoropyridin-2-yl)-1,3-thiazole-2-carboxamide;
N-[(1S,2R,4R)-7-azabicyclo[2.2.1]hept-2-yl]-5-(4-fluoropyridin-2-yl)-1,3-thiazole-2-carboxamide;
N-[(1S,2R,4R)-7-azabicyclo[2.2.1]hept-2-yl]-5-(5-fluoropyridin-2-yl)-1,3-thiazole-2-carboxamide;
N-[(1S,2R,4R)-7-azabicyclo[2.2.1]hept-2-yl]-5-(6-fluoropyridin-2-yl)-1,3-thiazole-2-carboxamide;
N-[(1S,2R,4R)-7-azabicyclo[2.2.1]hept-2-yl]-5-(2-fluoropyridin-3-yl)-1,3-thiazole-2-carboxamide;
N-[(1S,2R,4R)-7-azabicyclo[2.2.1]hept-2-yl]-5-(4-fluoropyridin-3-yl)-1,3-thiazole-2-carboxamide;
N-[(1S,2R,4R)-7-azabicyclo[2.2.1]hept-2-yl]-5-(5-fluoropyridin-3-yl)-1,3-thiazole-2-carboxamide;
N-[(1S,2R,4R)-7-azabicyclo[2.2.1]hept-2-yl]-5-(6-fluoropyridin-3-yl)-1,3-thiazole-2-carboxamide;
N-[(1S,2R,4R)-7-azabicyclo[2.2.1]hept-2-yl]-5-(2-fluoropyridin-4-yl)-1,3-thiazole-2-carboxamide;
N-[(1S,2R,4R)-7-azabicyclo[2.2.1]hept-2-yl]-5-[(2-methoxyphenyl)thio]-1,3-thiazole-2-carboxamide;
N-[(1S,2R,4R)-7-azabicyclo[2.2.1]hept-2-yl]-5-[(3-methoxyphenyl)thio]-1,3-thiazole-2-carboxamide;
N-[(1S,2R,4R)-7-azabicyclo[2.2.1]hept-2-yl]-5-[(4-methoxyphenyl)thio]-1,3-thiazole-2-carboxamide;
N-[(1S,2R,4R)-7-azabicyclo[2.2.1]hept-2-yl]-5-[(2-methylphenyl)thio]-1,3-thiazole-2-carboxamide;
N-[(1S,2R,4R)-7-azabicyclo[2.2.1]hept-2-yl]-5-[(3-methylphenyl)thio]-1,3-thiazole-2-carboxamide;
N-[(1S,2R,4R)-7-azabicyclo[2.2.1]hept-2-yl]-5-[(4-methylphenyl)thio]-1,3-thiazole-2-carboxamide;
N-[(1S,2R,4R)-7-azabicyclo[2.2.1]hept-2-yl]-5-([4-(acetylamino)phenyl]thio)-1,3-thiazole-2-carboxamide;
N-[(1S,2R,4R)-7-azabicyclo[2.2.1]hept-2-yl]-5-[(4-aminophenyl)thio]-1,3-thiazole-2-carboxamide;
N-[(1S,2R,4R)-7-azabicyclo[2.2.1]hept-2-yl]-5-[(4-hydroxyphenyl)thio]-1,3-thiazole-2-carboxamide;
N-[(1S,2R,4R)-7-azabicyclo[2.2.1]hept-2-yl]-5-(2-methylphenoxy)-1,3-thiazole-2-carboxamide;
N-[(1S,2R,4R)-7-azabicyclo[2.2.1]hept-2-yl]-5-(3-methylphenoxy)-1,3-thiazole-2-carboxamide;
N-[(1S,2R,4R)-7-azabicyclo[2.2.1]hept-2-yl]-5-(4-methylphenoxy)-1,3-thiazole-2-carboxamide;
N-[(1S,2R,4R)-7-azabicyclo[2.2.1]hept-2-yl]-5-(2-methoxyphenoxy)-1,3-thiazole-2-carboxamide;
N-[(1S,2R,4R)-7-azabicyclo[2.2.1]hept-2-yl]-5-(3-methoxyphenoxy)-1,3-thiazole-2-carboxamide;
N-[(1S,2R,4R)-7-azabicyclo[2.2.1]hept-2-yl]-5-(4-methoxyphenoxy)-1,3-thiazole-2-carboxamide;
N-[(1S,2R,4R)-7-azabicyclo[2.2.1]hept-2-yl]-5-(4-hydroxyphenoxy)-1,3-thiazole-2-carboxamide;
N-[(1S,2R,4R)-7-azabicyclo[2.2.1]hept-2-yl]-5-(4-aminophenoxy)-1,3-thiazole-2-carboxamide;
N-[(1S,2R,4R)-7-azabicyclo[2.2.1]hept-2-yl]-5-[4-(acetylamino)phenoxy]-1,3-thiazole-2-carboxamide;
N-[(1S,2R,4R)-7-azabicyclo[2.2.1]hept-2-yl]-5-(2-fluorophenyl)-4-methyl-1,3-thiazole-2-carboxamide;
N-[(1S,2R,4R)-7-azabicyclo[2.2.1]hept-2-yl]-5-(3-fluorophenyl)-4-methyl-1,3-thiazole-2-carboxamide;
N-[(1S,2R,4R)-7-azabicyclo[2.2.1]hept-2-yl]-5-(2-chlorophenyl)-4-methyl-1,3-thiazole-2-carboxamide;
N-[(1S,2R,4R)-7-azabicyclo[2.2.1]hept-2-yl]-5-(3-chlorophenyl)-4-methyl-1,3-thiazole-2-carboxamide;
N-[(1S,2R,4R)-7-azabicyclo[2.2.1]hept-2-yl]-5-(2-methoxyphenyl)-4-methyl-1,3-thiazole-2-carboxamide;
N-[(1S,2R,4R)-7-azabicyclo[2.2.1]hept-2-yl]-5-(3-methoxyphenyl)-4-methyl-1,3-thiazole-2-carboxamide;
N-[(1S,2R,4R)-7-azabicyclo[2.2.1]hept-2-yl]-4-methyl-5-thien-2-yl-1,3-thiazole-2-carboxamide;
N-[(1S,2R,4R)-7-azabicyclo[2.2.1]hept-2-yl]-4-methyl-5-phenyl-1,3-thiazole-2-carboxamide;
N-[(1S,2R,4R)-7-azabicyclo[2.2.1]hept-2-yl]-5-phenyl-1,3-thiazole-2-carboxamide;
N-[(1S,2R,4R)-7-azabicyclo[2.2.1]hept-2-yl]-5-(4-bromophenyl)-1,3-thiazole-2-carboxamide;
N-[(1S,2R,4R)-7-azabicyclo[2.2.1]hept-2-yl]-5-(3-nitrophenyl)-1,3-thiazole-2-carboxamide;
N-[(1S,2R,4R)-7-azabicyclo[2.2.1]hept-2-yl]-5-(3-methoxyphenyl)-1,3-thiazole-2-carboxamide;
N-[(1S,2R,4R)-7-azabicyclo[2.2.1]hept-2-yl]-5-(2-chlorophenyl)-1,3-thiazole-2-carboxamide;
N-[(1S,2R,4R)-7-azabicyclo[2.2.1]hept-2-yl]-5-(4-fluorophenyl)-1,3-thiazole-2-carboxamide;
N-[(1S,2R,4R)-7-azabicyclo[2.2.1]hept-2-yl]-5-(2-methoxyphenyl)-1,3-thiazole-2-carboxamide;
N-[(1S,2R,4R)-7-azabicyclo[2.2.1]hept-2-yl]-5-(4-chlorophenyl)-1,3-thiazole-2-carboxamide;
N-[(1S,2R,4R)-7-azabicyclo[2.2.1]hept-2-yl]-5-methyl-1,3-thiazole-2-carboxamide;
N-[(1S,2R,4R)-7-azabicyclo[2.2.1]hept-2-yl]-5-(3-chlorophenyl)-1,3-thiazole-2-carboxamide;
N-[(1S,2R,4R)-7-azabicyclo[2.2.1]hept-2-yl]-5-(2-fluorophenyl)-1,3-thiazole-2-carboxamide;
N-[(1S,2R,4R)-7-azabicyclo[2.2.1]hept-2-yl]-5-(3-fluorophenyl)-1,3-thiazole-2-carboxamide;

N-[(1S,2R,4R)-7-azabicyclo[2.2.1]hept-2-yl]-5-thien-2-yl-1,3-thiazole-2-carboxamide;
N-[(1S,2R,4R)-7-azabicyclo[2.2.1]hept-2-yl]-2-(phenylsulfanyl)-1,3-thiazole-5-carboxamide;
N-[(1S,2R,4R)-7-azabicyclo[2.2.1]hept-2-yl]-2-[(4-chlorophenyl)-sulfanyl]-1,3-thiazole-5-carboxamide;
N-[(1S,2R,4R)-7-azabicyclo[2.2.1]hept-2-yl]-2-phenoxy-1,3-thiazole-5-carboxamide;
N-[(1S,2R,4R)-7-azabicyclo[2.2.1]hept-2-yl]-2-[(4-fluorophenyl)-sulfanyl]-1,3-thiazole-5-carboxamide;
N-[(1S,2R,4R)-7-azabicyclo[2.2.1]hept-2-yl]-2-(methylsulfanyl)-1,3-thiazole-5-carboxamide;
N-[(1S,2R,4R)-7-azabicyclo[2.2.1]hept-2-yl]-2-(4-chlorophenoxy)-1,3-thiazole-5-carboxamide;
N-[(1S,2R,4R)-7-azabicyclo[2.2.1]hept-2-yl]-2,4-dimethyl-1,3-thiazole-5-carboxamide;
N-[(1S,2R,4R)-7-azabicyclo[2.2.1]hept-2-yl]-2-(3-fluorophenyl)-1,3-thiazole-5-carboxamide;
N-[(1S,2R,4R)-7-azabicyclo[2.2.1]hept-2-yl]-2-(4-fluorophenyl)-1,3-thiazole-5-carboxamide;
N-[(1S,2R,4R)-7-azabicyclo[2.2.1]hept-2-yl]-2-(2-hydroxyphenyl)-1,3-thiazole-5-carboxamide;
N-[(1S,2R,4R)-7-azabicyclo[2.2.1]hept-2-yl]-2-(4-methylphenyl)-1,3-thiazole-5-carboxamide;
N-[(1S,2R,4R)-7-azabicyclo[2.2.1]hept-2-yl]-2-[4-(benzyloxy)phenyl]-1,3-thiazole-5-carboxamide;
N-[(1S,2R,4R)-7-azabicyclo[2.2.1]hept-2-yl]-4-methyl-2-phenyl-1,3-thiazole-5-carboxamide;
N-[(1S,2R,4R)-7-azabicyclo[2.2.1]hept-2-yl]-2-(4-chlorophenyl)-4-methyl-1,3-thiazole-5-carboxamide;
N-[(1S,2R,4R)-7-azabicyclo[2.2.1]hept-2-yl]-4-methyl-2-pyridin-2-yl-1,3-thiazole-5-carboxamide;
N-[(1S,2R,4R)-7-azabicyclo[2.2.1]hept-2-yl]-4-methyl-2-pyridin-4-yl-1,3-thiazole-5-carboxamide;
N-[(1S,2R,4R)-7-azabicyclo[2.2.1]hept-2-yl]-2-(methylamino)-1,3-thiazole-5-carboxamide;
N-[(1S,2R,4R)-7-azabicyclo[2.2.1]hept-2-yl]-2-(2,3-difluorophenyl)-1,3-thiazole-5-carboxamide;
N-[(1S,2R,4R)-7-azabicyclo[2.2.1]hept-2-yl]-2-(2,4-difluorophenyl)-1,3-thiazole-5-carboxamide;
N-[(1S,2R,4R)-7-azabicyclo[2.2.1]hept-2-yl]-2-(2,5-difluorophenyl)-1,3-thiazole-5-carboxamide;
N-[(1S,2R,4R)-7-azabicyclo[2.2.1]hept-2-yl]-2-(2,6-difluorophenyl)-1,3-thiazole-5-carboxamide;
N-[(1S,2R,4R)-7-azabicyclo[2.2.1]hept-2-yl]-2-(3,4-difluorophenyl)-1,3-thiazole-5-carboxamide;
N-[(1S,2R,4R)-7-azabicyclo[2.2.1]hept-2-yl]-2-(3,5-difluorophenyl)-1,3-thiazole-5-carboxamide;
N-[(1S,2R,4R)-7-azabicyclo[2.2.1]hept-2-yl]-2-(2-chlorophenyl)-1,3-thiazole-5-carboxamide;
N-[(1S,2R,4R)-7-azabicyclo[2.2.1]hept-2-yl]-2-(3-chlorophenyl)-1,3-thiazole-5-carboxamide;
N-[(1S,2R,4R)-7-azabicyclo[2.2.1]hept-2-yl]-2-(4-chlorophenyl)-1,3-thiazole-5-carboxamide;
N-[(1S,2R,4R)-7-azabicyclo[2.2.1]hept-2-yl]-2-(2-bromophenyl)-1,3-thiazole-5-carboxamide;
N-[(1S,2R,4R)-7-azabicyclo[2.2.1]hept-2-yl]-2-(3-bromophenyl)-1,3-thiazole-5-carboxamide;
N-[(1S,2R,4R)-7-azabicyclo[2.2.1]hept-2-yl]-2-(4-bromophenyl)-1,3-thiazole-5-carboxamide;
N-[(1S,2R,4R)-7-azabicyclo[2.2.1]hept-2-yl]-2-(2-cyanophenyl)-1,3-thiazole-5-carboxamide;
N-[(1S,2R,4R)-7-azabicyclo[2.2.1]hept-2-yl]-2-(3-cyanophenyl)-1,3-thiazole-5-carboxamide;
N-[(1S,2R,4R)-7-azabicyclo[2.2.1]hept-2-yl]-2-(4-cyanophenyl)-1,3-thiazole-5-carboxamide;
N-[(1S,2R,4R)-7-azabicyclo[2.2.1]hept-2-yl]-2-(2-nitrophenyl)-1,3-thiazole-5-carboxamide;
N-[(1S,2R,4R)-7-azabicyclo[2.2.1]hept-2-yl]-2-(3-nitrophenyl)-1,3-thiazole-5-carboxamide;
N-[(1S,2R,4R)-7-azabicyclo[2.2.1]hept-2-yl]-2-(4-nitrophenyl)-1,3-thiazole-5-carboxamide;
N-[(1S,2R,4R)-7-azabicyclo[2.2.1]hept-2-yl]-2-(2-methylphenyl)-1,3-thiazole-5-carboxamide;
N-[(1S,2R,4R)-7-azabicyclo[2.2.1]hept-2-yl]-2-(3-methylphenyl)-1,3-thiazole-5-carboxamide;
N-[(1S,2R,4R)-7-azabicyclo[2.2.1]hept-2-yl]-2-(2-aminophenyl)-1,3-thiazole-5-carboxamide;
N-[(1S,2R,4R)-7-azabicyclo[2.2.1]hept-2-yl]-2-(3-aminophenyl)-1,3-thiazole-5-carboxamide;
N-[(1S,2R,4R)-7-azabicyclo[2.2.1]hept-2-yl]-2-(4-aminophenyl)-1,3-thiazole-5-carboxamide;
N-[(1S,2R,4R)-7-azabicyclo[2.2.1]hept-2-yl]-2-[2-(methylamino)phenyl]-1,3-thiazole-5-carboxamide;
N-[(1S,2R,4R)-7-azabicyclo[2.2.1]hept-2-yl]-2-[3-(methylamino)phenyl]-1,3-thiazole-5-carboxamide;
N-[(1S,2R,4R)-7-azabicyclo[2.2.1]hept-2-yl]-2-[4-(methylamino)phenyl]-1,3-thiazole-5-carboxamide;
N-[(1S,2R,4R)-7-azabicyclo[2.2.1]hept-2-yl]-2-[2-(acetylamino)phenyl]-1,3-thiazole-5-carboxamide;
N-[(1S,2R,4R)-7-azabicyclo[2.2.1]hept-2-yl]-2-[3-(acetylamino)phenyl]-1,3-thiazole-5-carboxamide;
N-[(1S,2R,4R)-7-azabicyclo[2.2.1]hept-2-yl]-2-[4-(acetylamino)phenyl]-1,3-thiazole-5-carboxamide;
N-[(1S,2R,4R)-7-azabicyclo[2.2.1]hept-2-yl]-2-(2-[(trifluoroacetyl)amino]phenyl]-1,3-thiazole-5-carboxamide;
N-[(1S,2R,4R)-7-azabicyclo[2.2.1]hept-2-yl]-2-(3-[(trifluoroacetyl)amino]phenyl]-1,3-thiazole-5-carboxamide;
N-[(1S,2R,4R)-7-azabicyclo[2.2.1]hept-2-yl]-2-(4-[(trifluoroacetyl)amino]phenyl)-1,3-thiazole-5-carboxamide;
N-[(1S,2R,4R)-7-azabicyclo[2.2.1]hept-2-yl]-2-(2-[(methylsulfonyl)amino]phenyl)-1,3-thiazole-5-carboxamide;
N-[(1S,2R,4R)-7-azabicyclo[2.2.1]hept-2-yl]-2-(3-[(methylsulfonyl)amino]phenyl)-1,3-thiazole-5-carboxamide;
N-[(1S,2R,4R)-7-azabicyclo[2.2.1]hept-2-yl]-2-(4-[(methylsulfonyl)amino]phenyl)-1,3-thiazole-5-carboxamide;
N-[(1S,2R,4R)-7-azabicyclo[2.2.1]hept-2-yl]-2-(3-hydroxyphenyl)-1,3-thiazole-5-carboxamide;
N-[(1S,2R,4R)-7-azabicyclo[2.2.1]hept-2-yl]-2-(4-hydroxyphenyl)-1,3-thiazole-5-carboxamide;
N-[(1S,2R,4R)-7-azabicyclo[2.2.1]hept-2-yl]-2-(2-methoxyphenyl)-1,3-thiazole-5-carboxamide;
N-[(1S,2R,4R)-7-azabicyclo[2.2.1]hept-2-yl]-2-(3-methoxyphenyl)-1,3-thiazole-5-carboxamide;
N-[(1S,2R,4R)-7-azabicyclo[2.2.1]hept-2-yl]-2-(4-methoxyphenyl)-1,3-thiazole-5-carboxamide;
N-[(1S,2R,4R)-7-azabicyclo[2.2.1]hept-2-yl]-2-[2-(trifluoromethoxy)phenyl]-1,3-thiazole-5-carboxamide;

N-[(1S,2R,4R)-7-azabicyclo[2.2.1]hept-2-yl]-2-[3-(trifluoromethoxy)phenyl]-1,3-thiazole-5-carboxamide;
N-[(1S,2R,4R)-7-azabicyclo[2.2.1]hept-2-yl]-2-[4-(trifluoromethoxy)phenyl]-1,3-thiazole-5-carboxamide;
N-[(1S,2R,4R)-7-azabicyclo[2.2.1]hept-2-yl]-2-pyridin-2-yl-1,3-thiazole-5-carboxamide;
N-[(1S,2R,4R)-7-azabicyclo[2.2.1]hept-2-yl]-2-pyridin-3-yl-1,3-thiazole-5-carboxamide;
N-[(1S,2R,4R)-7-azabicyclo[2.2.1]hept-2-yl]-2-pyridin-4-yl-1,3-thiazole-5-carboxamide;
N-[(1S,2R,4R)-7-azabicyclo[2.2.1]hept-2-yl]-2-(6-fluoropyridin-2-yl)-1,3-thiazole-5-carboxamide;
N-[(1S,2R,4R)-7-azabicyclo[2.2.1]hept-2-yl]-2-(5-fluoropyridin-2-yl)-1,3-thiazole-5-carboxamide;
N-[(1S,2R,4R)-7-azabicyclo[2.2.1]hept-2-yl]-2-(4-fluoropyridin-2-yl)-1,3-thiazole-5-carboxamide;
N-[(1S,2R,4R)-7-azabicyclo[2.2.1]hept-2-yl]-2-(3-fluoropyridin-2-yl)-1,3-thiazole-5-carboxamide;
N-[(1S,2R,4R)-7-azabicyclo[2.2.1]hept-2-yl]-2-(2-fluoropyridin-2-yl)-1,3-thiazole-5-carboxamide;
N-[(1S,2R,4R)-7-azabicyclo[2.2.1]hept-2-yl]-2-(6-fluoropyridin-3-yl)-1,3-thiazole-5-carboxamide;
N-[(1S,2R,4R)-7-azabicyclo[2.2.1]hept-2-yl]-2-(5-fluoropyridin-3-yl)-1,3-thiazole-5-carboxamide;
N-[(1S,2R,4R)-7-azabicyclo[2.2.1]hept-2-yl]-2-(4-fluoropyridin-3-yl)-1,3-thiazole-5-carboxamide;
N-[(1S,2R,4R)-7-azabicyclo[2.2.1]hept-2-yl]-2-(2-fluoropyridin-3-yl)-1,3-thiazole-5-carboxamide;
N-[(1S,2R,4R)-7-azabicyclo[2.2.1]hept-2-yl]-2-(2-fluoropyridin-4-yl)-1,3-thiazole-5-carboxamide;
N-[(1S,2R,4R)-7-azabicyclo[2.2.1]hept-2-yl]-2-(3-fluoropyridin-4-yl)-1,3-thiazole-5-carboxamide;
N-[(1S,2R,4R)-7-azabicyclo[2.2.1]hept-2-yl]-5-(phenylsulfanyl)-1,3,4-thiadiazole-2-carboxamide;
N-[(1S,2R,4R)-7-azabicyclo[2.2.1]hept-2-yl]-5-phenoxy-1,3,4-thiadiazole-2-carboxamide;
N-[(1S,2R,4R)-7-azabicyclo[2.2.1]hept-2-yl]-5-[(4-chlorophenyl)-sulfanyl]-1,3,4-thiadiazole-2-carboxamide;
N-[(1S,2R,4R)-7-azabicyclo[2.2.1]hept-2-yl]-5-(4-fluorophenoxy)-1,3,4-thiadiazole-2-carboxamide;
N-[(1S,2R,4R)-7-azabicyclo[2.2.1]hept-2-yl]-5-(4-chlorophenoxy)-1,3,4-thiadiazole-2-carboxamide;
N-[(1S,2R,4R)-7-azabicyclo[2.2.1]hept-2-yl]-5-[(3-fluorophenyl)-sulfanyl]-1,3,4-thiadiazole-2-carboxamide;
N-[(1S,2R,4R)-7-azabicyclo[2.2.1]hept-2-yl]-5-[(2-chlorophenyl)-sulfanyl]-1,3,4-thiadiazole-2-carboxamide;
N-[(1S,2R,4R)-7-azabicyclo[2.2.1]hept-2-yl]-5-[(4-fluorophenyl)-sulfanyl]-1,3,4-thiadiazole-2-carboxamide;
N-[(1S,2R,4R)-7-azabicyclo[2.2.1]hept-2-yl]-5-[(3-chlorophenyl)-sulfanyl]-1,3,4-thiadiazole-2-carboxamide;
N-[(1S,2R,4R)-7-azabicyclo[2.2.1]hept-2-yl]-5-phenyl-1,3,4-oxadiazole-2-carboxamide;
N-[(1S,2R,4R)-7-azabicyclo[2.2.1]hept-2-yl]-5-(methylthio)-1,3,4-oxadiazole-2-carboxamide;
N-[(1S,2R,4R)-7-azabicyclo[2.2.1]hept-2-yl]-5-(3-chlorophenyl)-1,3-oxazole-2-carboxamide;
N-[(1S,2R,4R)-7-azabicyclo[2.2.1]hept-2-yl]-5-(3-methoxyphenyl)-1,3-oxazole-2-carboxamide;
N-[(1S,2R,4R)-7-azabicyclo[2.2.1]hept-2-yl]-5-(3-nitrophenyl)-1,3-oxazole-2-carboxamide;
N-[(1S,2R,4R)-7-azabicyclo[2.2.1]hept-2-yl]-5-(4-methoxyphenyl)-1,3-oxazole-2-carboxamide;
N-[(1S,2R,4R)-7-azabicyclo[2.2.1]hept-2-yl]-5-(2-nitrophenyl)-1,3-oxazole-2-carboxamide;
N-[(1S,2R,4R)-7-azabicyclo[2.2.1]hept-2-yl]—S-(2-methoxyphenyl)-1,3-oxazole-2-carboxamide;
N-[(1S,2R,4R)-7-azabicyclo[2.2.1]hept-2-yl]-5-(4-fluorophenyl)-1,3-oxazole-2-carboxamide;
N-[(1S,2R,4R)-7-azabicyclo[2.2.1]hept-2-yl]-5-(2-chlorophenyl)-1,3-oxazole-2-carboxamide;
N-[(1S,2R,4R)-7-azabicyclo[2.2.1]hept-2-yl]-5-(3-cyanophenyl)-1,3-oxazole-2-carboxamide;
N-[(1S,2R,4R)-7-azabicyclo[2.2.1]hept-2-yl]-5-(4-bromophenyl)-1,3-oxazole-2-carboxamide;
N-[(1S,2R,4R)-7-azabicyclo[2.2.1]hept-2-yl]-5-phenylsulfanyl-1,3-oxazole-2-carboxamide;
N-[(1S,2R,4R)-7-azabicyclo[2.2.1]hept-2-yl]-5-(2-fluorophenylsulfanyl)-1,3-oxazole-2-carboxamide;
N-[(1S,2R,4R)-7-azabicyclo[2.2.1]hept-2-yl]-5-(3-fluorophenylsulfanyl)-1,3-oxazole-2-carboxamide;
N-[(1S,2R,4R)-7-azabicyclo[2.2.1]hept-2-yl]-5-(4-fluorophenylsulfanyl)-1,3-oxazole-2-carboxamide;
N-[(1S,2R,4R)-7-azabicyclo[2.2.1]hept-2-yl]-5-(3,4-difluorophenylsulfanyl)-1,3-oxazole-2-carboxamide;
N-[(1S,2R,4R)-7-azabicyclo[2.2.1]hept-2-yl]-5-(2,4-difluorophenylsulfanyl)-1,3-oxazole-2-carboxamide;
N-[(1S,2R,4R)-7-azabicyclo[2.2.1]hept-2-yl]-5-(3,5-difluorophenylsulfanyl)-1,3-oxazole-2-carboxamide;
N-[(1S,2R,4R)-7-azabicyclo[2.2.1]hept-2-yl]-5-(2-chlorophenylsulfanyl)-1,3-oxazole-2-carboxamide;
N-[(1S,2R,4R)-7-azabicyclo[2.2.1]hept-2-yl]-5-(3-chlorophenylsulfanyl)-1,3-oxazole-2-carboxamide;
N-[(1S,2R,4R)-7-azabicyclo[2.2.1]hept-2-yl]-5-(4-chlorophenylsulfanyl)-1,3-oxazole-2-carboxamide;
N-[(1S.2R,4R)-7-azabicyclo[2.2.1]hept-2-yl]-5-(3,4-dichlorophenylsulfanyl)-1,3-oxazole-2-carboxamide;
N-[(1S,2R,4R)-7-azabicyclo[2.2.1]hept-2-yl]-5-(2,4-dichlorophenylsulfanyl)-1,3-oxazole-2-carboxamide;
N-[(1S,2R,4R)-7-azabicyclo[2.2.1]hept-2-yl]-5-(3,5-dichlorophenylsulfanyl)-1,3-oxazole-2-carboxamide;
N-[(1S,2R,4R)-7-azabicyclo[2.2.1]hept-2-yl]-5-(2-fluorophenyl)-1,3-oxazole-2-carboxamide;
N-[(1S,2R,4R)-7-azabicyclo[2.2.1]hept-2-yl]-5-(3-fluorophenyl)-1,3-oxazole-2-carboxamide;
N-[(1S,2R,4R)-7-azabicyclo[2.2.1]hept-2-yl]-5-(3,4-difluorophenyl)-1,3-oxazole-2-carboxamide;
N-[(1S,2R,4R)-7-azabicyclo[2.2.1]hept-2-yl]-5-(2,4-difluorophenyl)-1,3-oxazole-2-carboxamide;
N-[(1S,2R,4R)-7-azabicyclo[2.2.1]hept-2-yl]-5-(3,5-difluorophenyl)-1,3-oxazole-2-carboxamide;
N-[(1S,2R,4R)-7-azabicyclo[2.2.1]hept-2-yl]-5-(4-chlorophenyl)-1,3-oxazole-2-carboxamide;
N-[(1S,2R,4R)-7-azabicyclo[2.2.1]hept-2-yl]-5-(3,4-dichlorophenyl)-1,3-oxazole-2-carboxamide;
N-[(1S,2R,4R)-7-azabicyclo[2.2.1]hept-2-yl]5-(2,4-dichlorophenyl)-1,3-oxazole-2-carboxamide;
N-[(1S,2R,4R)-7-azabicyclo[2.2.1]hept-2-yl]-5-(3,5-dichlorophenyl)-1,3-oxazole-2-carboxamide;

N-[(1S,2R,4R)-7-azabicyclo[2.2.1]hept-2-yl]-5-(2-bromophenyl)-1,3-oxazole-2-carboxamide;
N-[(1S,2R,4R)-7-azabicyclo[2.2.1]hept-2-yl]-5-(3-bromophenyl)-1,3-oxazole-2-carboxamide;
N-[(1S,2R,4R)-7-azabicyclo[2.2.1]hept-2-yl]-5-(2-cyanophenyl)-1,3-oxazole-2-carboxamide;
N-[(1S,2R,4R)-7-azabicyclo[2.2.1]hept-2-yl]-5-(4-cyanophenyl)-1,3-oxazole-2-carboxamide;
N-[(1S,2R,4R)-7-azabicyclo[2.2.1]hept-2-yl]-5-(2-hydroxyphenyl)-1,3-oxazole-2-carboxamide;
N-[(1S,2R,4R)-7-azabicyclo[2.2.1]hept-2-yl]-5-(3-hydroxyphenyl)-1,3-oxazole-2-carboxamide;
N-[(1S,2R,4R)-7-azabicyclo[2.2.1]hept-2-yl]-5-(4-hydroxyphenyl)-1,3-oxazole-2-carboxamide;
N-[(1S,2R,4R)-7-azabicyclo[2.2.1]hept-2-yl]-5-(4-nitrophenyl)-1,3-oxazole-2-carboxamide;
N-[(1S,2R,4R)-7-azabicyclo[2.2.1]hept-2-yl]-5-(2-methylphenyl)-1,3-oxazole-2-carboxamide;
N-[(1S,2R,4R)-7-azabicyclo[2.2.1]hept-2-yl]-5-(3-methylphenyl)-1,3-oxazole-2-carboxamide;
N-[(1S,2R,4R)-7-azabicyclo[2.2.1]hept-2-yl]-5-(4-methylphenyl)-1,3-oxazole-2-carboxamide;
N-[(1S,2R,4R)-7-azabicyclo[2.2.1]hept-2-yl]-5-(2-methylarminophenyl)-1,3-oxazole-2-carboxamide;
N-[(1S,2R,4R)-7-azabicyclo[2.2.1]hept-2-yl]-5-(3-methylaminophenyl)-1,3-oxazole-2-carboxamide;
N-[(1S,2R,4R)-7-azabicyclo[2.2.1]hept-2-yl]-5-(4-methylaminophenyl)-1,3-oxazole-2-carboxamide;
N-[(1S,2R,4R)-7-azabicyclo[2.2.1]hept-2-yl]-5-(2-aminophenyl)-1,3-oxazole-2-carboxamide;
N-[(1S,2R,4R)-7-azabicyclo[2.2.1]hept-2-yl]-5-(3-aminophenyl)-1,3-oxazole-2-carboxamide;
N-[(1S,2R,4R)-7-azabicyclo[2.2.1]hept-2-yl]-5-(4-aminophenyl)-1,3-oxazole-2-carboxamide;
N-[(1S,2R,4R)-7-azabicyclo[2.2.1]hept-2-yl]-5-[2-(acetylamino)phenyl]-1,3-oxazole-2-carboxamide;
N-[(1S,2R,4R)-7-azabicyclo[2.2.1]hept-2-yl]-5-[3-(acetylamino)phenyl]-1,3-oxazole-2-carboxamide;
N-[(1S,2R,4R)-7-azabicyclo[2.2.1]hept-2-yl]-5-[4-(acetylamino)phenyl]-1,3-oxazole-2-carboxamide;
N-[(1S,2R,4R)-7-azabicyclo[2.2.1]hept-2-yl]-5-(pyridin-2-yl)-1,3-oxazole-2-carboxamide;
N-[(1S,2R,4R)-7-azabicyclo[2.2.1]hept-2-yl]-5-(pyridin-3-yl)-1,3-oxazole-2-carboxamide;
N-[(1S,2R,4R)-7-azabicyclo[2.2.1]hept-2-yl]-5-(pyridin-4-yl)-1,3-oxazole-2-carboxamide;
N-[(1S,2R,4R)-7-azabicyclo[2.2.1]hept-2-yl]-5-(3-fluoropyridin-2-yl)-1,3-oxazole-2-carboxamide;
N-[(1S,2R,4R)-7-azabicyclo[2.2.1]hept-2-yl]-5-(4-fluoropyridin-2-yl)-1,3-oxazole-2-carboxamide;
N-[(1S,2R,4R)-7-azabicyclo[2.2.1]hept-2-yl]-5-(5-fluoropyridin-2-yl)-1,3-oxazole-2-carboxamide;
N-[(1S,2R,4R)-7-azabicyclo[2.2.1]hept-2-yl]-5-(6-fluoropyridin-2-yl)-1,3-oxazole-2-carboxamide;
N-[(1S,2R,4R)-7-azabicyclo[2.2.1]hept-2-yl]-5-(2-fluoropyridin-3-yl)-1,3-oxazole-2-carboxamide;
N-[(1S,2R,4R)-7-azabicyclo[2.2.1]hept-2-yl]-5-(4-fluoropyridin-3-yl)-1,3-oxazole-2-carboxamide;
N-[(1S,2R,4R)-7-azabicyclo[2.2.1]hept-2-yl]-5-(5-fluoropyridin-3-yl)-1,3-oxazole-2-carboxamide;
N-[(1S,2R,4R)-7-azabicyclo[2.2.1]hept-2-yl]-5-(6-fluoropyridin-3-yl)-1,3-oxazole-2-carboxamide;
N-[(1S,2R,4R)-7-azabicyclo[2.2.1]hept-2-yl]-5-(2-fluoropyridin-4-yl)-1,3-oxazole-2-carboxamide;
N-[(1S,2R,4R)-7-azabicyclo[2.2.1]hept-2-yl]-5-(2-fluoropyridin-3-yl)-1,3-oxazole-2-carboxamide;
N-[(1S,2R,4R)-7-azabicyclo[2.2.1]hept-2-yl]-5-phenoxy-1,3-oxazole-2-carboxamide;
N-[(1S,2R,4R)-7-azabicyclo[2.2.1]hept-2-yl]-5-(2-fluorophenoxy)-1,3-oxazole-2-carboxamide;
N-[(1S,2R,4R)-7-azabicyclo[2.2.1]hept-2-yl]-5-(3-fluorophenoxy)-1,3-oxazole-2-carboxamide;
N-[(1S,2R,4R)-7-azabicyclo[2.2.1]hept-2-yl]-5-(4-fluorophenoxy)-1,3-oxazole-2-carboxamide;
N-[(1S,2R,4R)-7-azabicyclo[2.2.1]hept-2-yl]-5-(3,4-difluorophenoxy)-1,3-oxazole-2-carboxamide;
N-[(1S,2R,4R)-7-azabicyclo[2.2.1]hept-2-yl]-5-(2,4-difluorophenoxy)-1,3-oxazole-2-carboxamide;
N-[(1S,2R,4R)-7-azabicyclo[2.2.1]hept-2-yl]-5-(3,5-difluorophenoxy)-1,3-oxazole-2-carboxamide;
N-[(1S,2R,4R)-7-azabicyclo[2.2.1]hept-2-yl]-5-(2-chlorophenoxy)-1,3-oxazole-2-carboxamide;
N-[(1S,2R,4R)-7-azabicyclo[2.2.1]hept-2-yl]-5-(3-chlorophenoxy)-1,3-oxazole-2-carboxamide;
N-[(1S,2R,4R)-7-azabicyclo[2.2.1]hept-2-yl]-5-(4-chlorophenoxy)-1,3-oxazole-2-carboxamide;
N-[(1S,2R,4R)-7-azabicyclo[2.2.1]hept-2-yl]-5-(3,4-dichlorophenoxy)-1,3-oxazole-2-carboxamide;
N-[(1S,2R,4R)-7-azabicyclo[2.2.1]hept-2-yl]-5-(2,4-dichlorophenoxy)-1,3-oxazole-2-carboxamide;
N-[(1S,2R,4R)-7-azabicyclo[2.2.1]hept-2-yl]-5-(3,5-dichlorophenoxy)-1,3-oxazole-2-carboxamide;
N-[(1S,2R,4R)-7-azabicyclo[2.2.1]hept-2-yl]-2-phenyl-1,3-oxazole-5-carboxamide;
N-[(1S,2R,4R)-7-azabicyclo[2.2.1]hept-2-yl-]-1-methyl-5-phenyl-1H-pyrrole-2-carboxamide;
N-[(1S,2R,4R)-7-azabicyclo[2.2.1]hept-2-yl]-5-bromo-1-methyl-1H-pyrrole-2-carboxamide;
N-[(1S,2R,4R)-7-azabicyclo[2.2.1]hept-2-yl]-5-[2-(methylthio)phenyl]-1-methyl-1H-pyrrole-2-carboxamide;
N-[(1S,2R,4R)-7-azabicyclo[2.2.1]hept-2-yl]-5-[4-(methylthio)phenyl]1-methyl-1H-pyrrole-2-carboxamide;
N-[(1S,2R,4R)-7-azabicyclo[2.2.1]hept-2-yl]-5-phenyl-1H-pyrrole-2-carboxamide;
N-[(1S,2R,4R)-7-azabicyclo[2.2.1]hept-2-yl]-5-(2-fluorophenyl)-1-methyl-1H-pyrrole-2-carboxamide;
N-[(1S,2R,4R)-7-azabicyclo[2.2.1]hept-2-yl]-5-(3-fluorophenyl)-1-methyl-1H-pyrrole-2-carboxamide;
N-[(1S,2R,4R)-7-azabicyclo[2.2.1]hept-2-yl]-5-(4-fluorophenyl)-1-methyl-1H-pyrrole-2-carboxamide;
N-[(1S,2R,4R)-7-azabicyclo[2.2.1]hept-2-yl]-5-(2,3-difluorophenyl)-1-methyl-1H-pyrrole-2-carboxamide;
N-[(1S,2R,4R)-7-azabicyclo[2.2.1]hept-2-yl]-5-(2,4-difluorophenyl)-1-methyl-1H-pyrrole-2-carboxamide;
N-[(1S,2R,4R)-7-azabicyclo[2.2.1]hept-2-yl]-5-(2,6-difluorophenyl)-1-methyl-1H-pyrrole-2-carboxamide;
N-[(1S,2R,4R)-7-azabicyclo[2.2.1]hept-2-yl]-5-(3,4-difluorophenyl)-1-methyl-1H-pyrrole-2-carboxamide;
N-[(1S,2R,4R)-7-azabicyclo[2.2.1]hept-2-yl]-5-(3,5-difluorophenyl)-1-methyl-1H-pyrrole-2-carboxamide;
N-[(1S,2R,4R)-7-azabicyclo[2.2.1]hept-2-yl]-5-(2,4,6-trifluorophenyl)-1-methyl-1H-pyrrole-2-carboxamide;

N-[(1S,2R,4R)-7-azabicyclo[2.2.1]hept-2-yl]-5-(2-chlorophenyl)-1-methyl-1H-pyrrole-2-carboxamide;
N-[(1S,2R,4R)-7-azabicyclo[2.2.1]hept-2-yl]-5-(3-chlorophenyl)-1-methyl-1H-pyrrole-2-carboxamide;
N-[(1S,2R,4R)-7-azabicyclo[2.2.1]hept-2-yl]-5-(4-chlorophenyl)-1-methyl-1H-pyrrole-2-carboxamide;
N-[(1S,2R,4R)-7-azabicyclo[2.2.1]hept-2-yl]-5-(2,4-dichlorophenyl)-1-methyl-1H-pyrrole-2-carboxamide;
N-[(1S,2R,4R)-7-azabicyclo[2.2.1]hept-2-yl]-5-(3,4-dichlorophenyl)-1-methyl-1H-pyrrole-2-carboxamide;
N-[(1S,2R,4R)-7-azabicyclo[2.2.1]hept-2-yl]-5-(3,5-dichlorophenyl)-1-methyl-1H-pyrrole-2-carboxamide;
N-[(1S,2R,4R)-7-azabicyclo[2.2.1]hept-2-yl]-5-(2-bromophenyl)-1-methyl-1H-pyrrole-2-carboxamide;
N-[(1S,2R,4R)-7-azabicyclo[2.2.1]hept-2-yl]-5-(3-bromophenyl)-1-methyl-1H-pyrrole-2-carboxamide;
N-[(1S,2R,4R)-7-azabicyclo[2.2.1]hept-2-yl]-5-(4-bromophenyl)-1-methyl-1H-pyrrole-2-carboxamide;
N-[(1S,2R,4R)-7-azabicyclo[2.2.1]hept-2-yl]-5-(2-hydroxyphenyl)-1-methyl-1H-pyrrole-2-carboxamide;
N-[(1S,2R,4R)-7-azabicyclo[2.2.1]hept-2-yl]-5-(3-hydroxyphenyl)-1-methyl-1H-pyrrole-2-carboxamide;
N-[(1S,2R,4R)-7-azabicyclo[2.2.1]hept-2-yl]-5-(4-hydroxyphenyl)-1-methyl-1H-pyrrole-2-carboxamide;
N-[(1S,2R,4R)-7-azabicyclo[2.2.1]hept-2-yl]-5-(2-methoxyphenyl)-1-methyl-1H-pyrrole-2-carboxamide;
N-[(1S,2R,4R)-7-azabicyclo[2.2.1]hept-2-yl]-5-(3-methoxyphenyl)-1-methyl-1H-pyrrole-2-carboxamide;
N-[(1S,2R,4R)-7-azabicyclo[2.2.1]hept-2-yl]-5-(4-methoxyphenyl)-1-methyl-1H-pyrrole-2-carboxamide;
N-[(1S,2R,4R)-7-azabicyclo[2.2.1]hept-2-yl]-5-(2-methylphenyl)-1-methyl-1H-pyrrole-2-carboxamide;
N-[(1S,2R,4R)-7-azabicyclo[2.2.1]hept-2-yl]-5-(3-methylphenyl)-1-methyl-1H-pyrrole-2-carboxamide;
N-[(1S,2R,4R)-7-azabicyclo[2.2.1]hept-2-yl]-5-(4-methylphenyl)-1-methyl-1H-pyrrole-2-carboxamide;
N-[(1S,2R,4R)-7-azabicyclo[2.2.2 1]hept-2-yl]-5-(2-methylaminophenyl)-1-methyl-1H-pyrrole-2-carboxamide;
N-[(1S,2R,4R)-7-azabicyclo[2.2.1]hept-2-yl]-5-(3-methylaminophenyl)-1-methyl-1H-pyrrole-2-carboxamide;
N-[(1S,2R,4R)-7-azabicyclo[2.2.1]hept-2-yl]-5-(4-methylaminophenyl)-1-methyl-1H-pyrrole-2-carboxamide;
N-[(1S,2R,4R)-7-azabicyclo[2.2.1]hept-2-yl]-5-(2-nitrophenyl)-1-methyl-1H-pyrrole-2-carboxamide;
N-[(1S,2R,4R)-7-azabicyclo[2.2.1]hept-2-yl]-5-(3-nitrophenyl)-1-methyl-1H-pyrrole-2-carboxamide;
N-[(1S,2R,4R)-7-azabicyclo[2.2.1]hept-2-yl]-5-(4-nitrophenyl)-1-methyl-1H-pyrrole-2-carboxamide;
N-[(1S,2R,4R)-7-azabicyclo[2.2.1]hept-2-yl]-5-(2-aminophenyl)-1-methyl-1H-pyrrole-2-carboxamide;
N-[(1S,2R,4R)-7-azabicyclo[2.2.1]hept-2-yl]-5-(3-aminophenyl)-1-methyl-1H-pyrrole-2-carboxamide;
N-[(1S,2R,4R)-7-azabicyclo[2.2.1]hept-2-yl]-5-(4-aminophenyl)-1-methyl-1H-pyrrole-2-carboxamide;
N-[(1S,2R,4R)-7-azabicyclo[2.2.1]hept-2-yl]-5-[2-(acetylamino)phenyl]-1-methyl-1H-pyrrole-2-carboxamide;
N-[(1S,2R,4R)-7-azabicyclo[2.2.1]hept-2-yl]-5-[3-(acetylamino)phenyl]-1-methyl-1H-pyrrole-2-carboxamide;
N-[(1S,2R,4R)-7-azabicyclo[2.2.1]hept-2-yl]-5-[4-(acetylamino)phenyl]-1-methyl-1H-pyrrole-2-carboxamide;
N-[(1S,2R,4R)-7-azabicyclo[2.2.1]hept-2-yl]-5-(pyrid-2-yl)-1-methyl-1H-pyrrole-2-carboxamide;
N-[(1S,2R,4R)-7-azabicyclo[2.2.1]hept-2-yl]-5-(pyrid-3-yl)-1-methyl-1H-pyrrole-2-carboxamide;
N-[(1S,2R,4R)-7-azabicyclo[2.2.1]hept-2-yl]-5-(pyridin-4-yl)-1-methyl-1H-pyrrole-2-carboxamide;
N-[(1S,2R,4R)-7-azabicyclo[2.2.1]hept-2-yl]-5-(3-fluoropyrid-2-yl)-1-methyl-1H-pyrrole-2-carboxamide;
N-[(1S,2R,4R)-7-azabicyclo[2.2.1]hept-2-yl]-5-(4-fluoropyrid-2-yl)-1-methyl-1H-pyrrole-2-carboxamide;
N-[(1S,2R,4R)-7-azabicyclo[2.2.1]hept-2-yl]-5-(5-fluoropyrid-2-yl)-1-methyl-1H-pyrrole-2-carboxamide;
N-[(1S,2R,4R)-7-azabicyclo[2.2.1]hept-2-yl]-5-(6-fluoropyrid-2-yl)-1-methyl-1H-pyrrole-2-carboxamide;
N-[(1S,2R,4R)-7-azabicyclo[2.2.1]hept-2-yl]-5-(2-fluoropyrid-3-yl)-1-methyl-1H-pyrrole-2-carboxamide;
N-[(1S,2R,4R)-7-azabicyclo[2.2.1]hept-2-yl]-5-(4-fluoropyrid-3-yl)-1-methyl-1H-pyrrole-2-carboxamide;
N-[(1S,2R,4R)-7-azabicyclo[2.2.1]hept-2-yl]-5-(5-fluoropyrid-3-yl)-1-methyl-1H-pyrrole-2-carboxamide;
N-[(1S,2R,4R)-7-azabicyclo[2.2.1]hept-2-yl]-5-(6-fluoropyrid-3-yl)-1-methyl-1H-pyrrole-2-carboxamide;
N-[(1S,2R,4R)-7-azabicyclo[2.2.1]hept-2-yl]-5-(2-fluoropyrid-4-yl)-1-methyl-1H-pyrrole-2-carboxamide;
N-[(1S,2R,4R)-7-azabicyclo[2.2.1]hept-2-yl]-5-(3-fluoropyrid-4-yl)-1-methyl-1H-pyrrole-2-carboxamide;
N-[(1S,2R,4R)-7-azabicyclo[2.2.1]hept-2-yl]-5-(2-cyanophenyl)-1-methyl-1H-pyrrole-2-carboxamide;
N-[(1S,2R,4R)-7-azabicyclo[2.2.1]hept-2-yl]-5-(3-cyanophenyl)-1-methyl-1H-pyrrole-2-carboxamide;
N-[(1S,2R,4R)-7-azabicyclo[2.2.1]hept-2-yl]-5-(4-cyanophenyl)-1-methyl-1H-pyrrole-2-carboxamide;
N-[(1S,2R,4R)-7-azabicyclo[2.2.1]hept-2-yl]-5-(2-fluorophenyl)-1H-pyrrole-2-carboxamide;
N-[(1S,2R,4R)-7-azabicyclo[2.2.1]hept-2-yl]-5-(3-fluorophenyl)-1H-pyrrole-2-carboxamide;
N-[(1S,2R,4R)-7-azabicyclo[2.2.1]hept-2-yl]-5-(4-fluorophenyl)-1H-pyrrole-2-carboxamide;
N-[(1S,2R,4R)-7-azabicyclo[2.2.1]hept-2-yl]-5-(3,5-difluorophenyl)-1H-pyrrole-2-carboxamide;
N-[(1S,2R,4R)-7-azabicyclo[2.2.1]hept-2-yl]-5-(3,4-difluorophenyl)-1H-pyrrole-2-carboxamide;
N-[(1S,2R,4R)-7-azabicyclo[2.2.1]hept-2-yl]-5-(2,4-difluorophenyl)-1H-pyrrole-2-carboxamide;
N-[(1S,2R,4R)-7-azabicyclo[2.2.1]hept-2-yl]-5-(2-chlorophenyl)-1H-pyrrole-2-carboxamide;
N-[(1S,2R,4R)-7-azabicyclo[2.2.1]hept-2-yl]-5-(3-chlorophenyl)-1H-pyrrole-2-carboxamide;
N-[(1S,2R,4R)-7-azabicyclo[2.2.1]hept-2-yl]-5-(4-chlorophenyl)-1H-pyrrole-2-carboxamide;

N-[(1S,2R,4R)-7-azabicyclo[2.2.1]hept-2-yl]-5-(3,5-dichlorophenyl)-1H-pyrrole-2-carboxamide;
N-[(1S,2R,4R)-7-azabicyclo[2.2.1]hept-2-yl]-5-(3,4-dichlorophenyl)-1H-pyrrole-2-carboxamide;
N-[(1S,2R,4R)-7-azabicyclo[2.2.1]hept-2-yl]-5-(2,4-dichlorophenyl)-1H-pyrrole-2-carboxamide;
N-[(1S,2R,4R)-7-azabicyclo[2.2.1]hept-2-yl]-5-(2-bromophenyl)-1H-pyrrole-2-carboxamide;
N-[(1S,2R,4R)-7-azabicyclo[2.2.1]hept-2-yl]-5-(3-bromophenyl)-1H-pyrrole-2-carboxamide;
N-[(1S,2R,4R)-7-azabicyclo[2.2.1]hept-2-yl]-5-(4-bromophenyl)-1H-pyrrole-2-carboxamide;
N-[(1S,2R,4R)-7-azabicyclo[2.2.1]hept-2-yl]-5-(2-hydroxyphenyl)-1H-pyrrole-2-carboxamide;
N-[(1S,2R,4R)-7-azabicyclo[2.2.1]hept-2-yl]-5-(3-hydroxyphenyl)-1H-pyrrole-2-carboxamide;
N-[(1S,2R,4R)-7-azabicyclo[2.2.1]hept-2-yl]-5-(4-hydroxyphenyl)-1H-pyrrole-2-carboxamide;
N-[(1S,2R,4R)-7-azabicyclo[2.2.1]hept-2-yl]-5-(2-methoxyphenyl)-1H-pyrrole-2-carboxamide;
N-[(1S,2R,4R)-7-azabicyclo[2.2.1]hept-2-yl]-5-(3-methoxyphenyl)-1H-pyrrole-2-carboxamide;
N-[(1S,2R,4R)-7-azabicyclo[2.2.1]hept-2-yl]-5-(4-methoxyphenyl)-1H-pyrrole-2-carboxamide;
N-[(1S,2R,4R)-7-azabicyclo[2.2.1]hept-2-yl]-5-(2-methylphenyl)-1H-pyrrole-2-carboxamide;
N-[(1S,2R,4R)-7-azabicyclo[2.2.1]hept-2-yl]-5-(3-methylphenyl)-1H-pyrrole-2-carboxamide;
N-[(1S,2R,4R)-7-azabicyclo[2.2.1]hept-2-yl]-5-(4-methylphenyl)-1H-pyrrole-2-carboxamide;
N-[(1S,2R,4R)-7-azabicyclo[2.2.1]hept-2-yl]-5-(2-methylaminophenyl)-1H-pyrrole-2-carboxamide;
N-[(1S,2R,4R)-7-azabicyclo[2.2.1]hept-2-yl]-5-(3-methylaminophenyl)-1H-pyrrole-2-carboxamide;
N-[(1S,2R,4R)-7-azabicyclo[2.2.1]hept-2-yl]-5-(4-methylaminophenyl)-1H-pyrrole-2-carboxamide;
N-[(1S,2R,4R)-7-azabicyclo[2.2.1]hept-2-yl]-5-(2-nitrophenyl)-1H-pyrrole-2-carboxamide;
N-[(1S,2R,4R)-7-azabicyclo[2.2.1]hept-2-yl]-5-(3-nitrophenyl)-1H-pyrrole-2-carboxamide;
N-[(1S,2R,4R)-7-azabicyclo[2.2.1]hept-2-yl]-5-(4-nitrophenyl)-1H-pyrrole-2-carboxamide;
N-[(1S,2R,4R)-7-azabicyclo[2.2.1]hept-2-yl]-5-(2-aminophenyl)-1H-pyrrole-2-carboxamide;
N-[(1S,2R,4R)-7-azabicyclo[2.2.1]hept-2-yl]-5-(3-aminophenyl)-1H-pyrrole-2-carboxamide;
N-[(1S,2R,4R)-7-azabicyclo[2.2.1]hept-2-yl]-5-(4-aminophenyl)-1H-pyrrole-2-carboxamide;
N-[(1S,2R,4R)-7-azabicyclo[2.2.1]hept-2-yl]-5-[2-(acetylamino)phenyl]-1H-pyrrole-2-carboxamide;
N-[(1S,2R,4R)-7-azabicyclo[2.2.1]hept-2-yl]-5-[3-(acetylamino)phenyl]-1H-pyrrole-2-carboxamide;
N-[(1S,2R,4R)-7-azabicyclo[2.2.1]hept-2-yl]-5-[4-(acetylamino)phenyl]-1H-pyrrole-2-carboxamide;
N-[(1S,2R,4R)-7-azabicyclo[2.2.1]hept-2-yl]-5-(pyrid-2-yl)-1H-pyrrole-2-carboxamide;
N-[(1S,2R,4R)-7-azabicyclo[2.2.1]hept-2-yl]-5-(pyrid-3-yl)-1H-pyrrole-2-carboxamide;
N-[(1S,2R,4R)-7-azabicyclo[2.2.1]hept-2-yl]-5-(pyrid-4-yl)-1H-pyrrole-2-carboxamide;
N-[(1S,2R,4R)-7-azabicyclo[2.2.1]hept-2-yl]-5-(3-fluoropyrid-2-yl)-1H-pyrrole-2-carboxamide;
N-[(1S,2R,4R)-7-azabicyclo[2.2.1]hept-2-yl]-5-(4-fluoropyrid-2-yl)-1H-pyrrole-2-carboxamide;
N-[(1S,2R,4R)-7-azabicyclo[2.2.1]hept-2-yl]-5-(5-fluoropyrid-2-yl)-1H-pyrrole-2-carboxamide;
N-[(1S,2R,4R)-7-azabicyclo[2.2.1]hept-2-yl]-5-(6-fluoropyrid-2-yl)-1H-pyrrole-2-carboxamide;
N-[(1S,2R,4R)-7-azabicyclo[2.2.1]hept-2-yl]-5-(2-fluoropyrid-3-yl)-1H-pyrrole-2-carboxamide;
N-[(1S,2R,4R)-7-azabicyclo[2.2.1]hept-2-yl]-5-(4-fluoropyrid-3-yl)-1H-pyrrole-2-carboxamide;
N-[(1S,2R,4R)-7-azabicyclo[2.2.1]hept-2-yl]-5-(5-fluoropyrid-3-yl)-1H-pyrrole-2-carboxamide;
N-[(1S,2R,4R)-7-azabicyclo[2.2.1]hept-2-yl]-5-(6-fluoropyrid-3-yl)-1H-pyrrole-2-carboxamide;
N-[(1S,2R,4R)-7-azabicyclo[2.2.1]hept-2-yl]-5-(2-fluoropyrid-4-yl)-1H-pyrrole-2-carboxamide;
N-[(1S,2R,4R)-7-azabicyclo[2.2.1]hept-2-yl]-5-(3-fluoropyrid-4-yl)-1H-pyrrole-2-carboxamide;
N-[(1S,2R,4R)-7-azabicyclo[2.2.1]hept-2-yl]-5-(2-cyanophenyl)-1H-pyrrole-2-carboxamide;
N-[(1S,2R,4R)-7-azabicyclo[2.2.1]hept-2-yl]-5-(3-cyanophenyl)-1H-pyrrole-2-carboxamide;
N-[(1S,2R,4R)-7-azabicyclo[2.2.1]hept-2-yl]-5-(4-cyanophenyl)-1H-pyrrole-2-carboxamide;
N-[(1S,2R,4R)-7-azabicyclo[2.2.1]hept-2-yl]-3-phenyl-1,2,4-oxadiazole-5-carboxamide; or a pharmaceutically acceptable salt thereof.

15. The compound according to claim 10, wherein Q is (b).

16. The compound of claim 15, wherein (b) is 1,3-thiazole-4-yl, 1,3-oxazole-4-yl, 1H-1,2,4-triazole-3-yl, or isoxazole-3-yl, optionally substituted on carbon with H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, lactam heterocycloalkyl, aryl, —$OR_8$, —$SR_8$, —$N(R_8)_2$, —$C(O)R_8$, —$C(S)R_8$, —$C(O)OR_8$, —$C(O)N(R_8)_2$, —$NR_8C(O)R_8$, —$S(O)_2N(R_8)_2$, —$OS(O)_2R_8$, —$S(O)_2R_8$, —$S(O)R_8$, —$NR_8S(O)_2R_8$, —$N(R_8)C(O)N(R_8)_2$, —CN, —$NO_2$, $R_7$, or $R_9$; and further optionally substituted on nitrogen with alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $R_7$, $R_9$, aryl, —C(O)-alkyl, —C(O)-cycloalkyl, —C(O)-heterocycloalkyl, —C(O)-halogenated alkyl, —C(O)-halogenated cycloalkyl, —C(O)-halogenated heterocycloalkyl, —C(O)-substituted alkyl, —C(O)-substituted cycloalkyl, —C(O)-substituted heterocycloalkyl, —C(O)—$R_7$, —C(O)—$R_9$, or —C(O)-aryl.

17. The compound according to claim 16, wherein the compound is N-[(1S,2R,4R)-7-azabicyclo[2.2.1]hept-2-yl]-2-pyridin-3-yl-1,3-thiazole-4-carboxamide; N-[(1S,2R,4R)-7-azabicyclo[2.2.1]hept-2-yl]-2-phenyl-1,3-oxazole-4-carboxamide; N-[(1S,2R,4R)-7-azabicyclo[2.2.1]hept-2-yl]-5-phenyl-1H-1,2,4-triazole-3-carboxamide; N-[(1S,2R,4R)-7-azabicyclo[2.2.1]hept-2-yl]-5-phenylisoxazole-3-carboxamide; or a pharmaceutically acceptable salt thereof.

18. A pharmaceutical composition comprising a compound according to claim 1, an anti-psychotic agent, and a pharmaceutically acceptable excipient.

19. The pharmaceutical composition according to claim 18, wherein said compound and said agent are to be independently administered rectally, topically, orally, sublingually, or parenterally for a therapeutically effective interval.

20. The pharmaceutical composition according to claim 18, wherein said compound is administered in an amount of from about 0.001 to about 100 mg/kg of body weight of said mammal per day.

21. The pharmaceutical composition according to claims 18, wherein said compound is administered in an amount of from about 0.1 to about 50 mg/kg of body weight of said mammal per day.

22. The pharmaceutical composition comprising a compound according to claim 1 and a pharmaceutically acceptable excipient.

23. The pharmaceutical composition according to claim 22, wherein said compound is administered rectally, topically, orally, sublingually, or parenterally for a therapeutically effective interval.

24. The pharmaceutical composition according to claim 22, wherein said compound is administered in an amount of from about 0.001 to about 100 mg/kg of body weight of said mammal per day.

25. The pharmaceutical composition according to claim 23, wherein said compound is administered in an amount of from about 0.1 to about 50 mg/kg of body weight of said mammal per day.

26. A method f or treating a disease or condition in a mammal in need thereof, wherein the mammal would receive symptomatic relief from the administration of an α7 nicotine acetylcholine receptor agonist comprising administering to the mammal a therapeutically effective amount of a compound according to claim 1.

27. The method according to claim 26, wherein the disease or condition is cognitive and attention deficit symptoms of Alzheimer's, neurodegeneration associated with diseases such as Alzheimer's disease, pre-senile dementia (mild cognitive impairment), or senile dementia.

28. The method according to claim 26, wherein the disease or condition is schizophrenia or psychosis.

29. The method of claim 28, wherein an anti-psychotic agent is added for a therapeutically effective interval.

30. The method according to claim 26, wherein the disease or condition is depression, anxiety, general anxiety disorders, post traumatic stress disorder.

31. The method according to claim 26, wherein the disease or condition is attention deficit disorder, or attention deficit hyperactivity disorder.

32. The method according to claim 26, wherein the disease or condition is mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourettes Syndrome, age-related macular degeneration, glaucoma, neurodegeneration associated with glaucoma, or symptoms associated with pain.

* * * * *